(12) United States Patent
Kanes et al.

(10) Patent No.: US 11,554,125 B2
(45) Date of Patent: Jan. 17, 2023

(54) NEUROACTIVE STEROIDS, COMPOSITIONS, AND USES THEREOF

(71) Applicant: Sage Therapeutics, Inc., Cambridge, MA (US)

(72) Inventors: Stephen Jay Kanes, Brynlawn, PA (US); Helen Colquhoun, Arlington, MA (US)

(73) Assignee: Sage Therapeutics, Inc., Cambridge, MA (US)

( * ) Notice: Subject to any disclaimer, the term of this patent is extended or adjusted under 35 U.S.C. 154(b) by 5 days.

(21) Appl. No.: 17/195,129

(22) Filed: Mar. 8, 2021

(65) Prior Publication Data

US 2022/0023313 A1      Jan. 27, 2022

Related U.S. Application Data

(63) Continuation of application No. 16/718,430, filed on Dec. 18, 2019, now Pat. No. 10,940,156, which is a continuation of application No. 16/083,339, filed as application No. PCT/US2017/021325 on Mar. 8, 2017, now abandoned.

(Continued)

(51) Int. Cl.
| | |
|---|---|
| *A61K 31/57* | (2006.01) |
| *A61P 25/24* | (2006.01) |
| *A61K 9/00* | (2006.01) |
| *A61K 9/08* | (2006.01) |
| *A61K 47/40* | (2006.01) |

(Continued)

(52) U.S. Cl.
CPC ............ *A61K 31/57* (2013.01); *A61K 9/0019* (2013.01); *A61K 9/08* (2013.01); *A61K 31/58* (2013.01); *A61K 47/40* (2013.01); *A61P 25/22* (2018.01); *A61P 25/24* (2018.01)

(58) Field of Classification Search
CPC .............................. A61K 31/57; A61K 31/573
See application file for complete search history.

(56) References Cited

U.S. PATENT DOCUMENTS

| | | |
|---|---|---|
| 3,117,142 A | 1/1964 | Candido et al. |
| 3,169,134 A | 2/1965 | Klimstra et al. |

(Continued)

FOREIGN PATENT DOCUMENTS

| | | |
|---|---|---|
| CA | 2443266 A1 | 8/2002 |
| CA | 2443466 A1 | 12/2002 |

(Continued)

OTHER PUBLICATIONS

Eser et al., "Neuropsychopharmacological properties of neuroactive steroids in depression and anxiety disorders", Psychopharmacolody, (2006) 186: pp. 373-387.

(Continued)

*Primary Examiner* — San Ming R Hui
(74) *Attorney, Agent, or Firm* — Honigman LLP; Harold H. Fox; Jonathan P. O'Brien

(57) ABSTRACT

Described herein are methods of treating a disorder, e.g., tremor, e.g., essential tremor; depression, e.g., postpostum depression; and anxiety disorder, the method comprising administering to a human subject suffering from a disorder, e.g., tremor, e.g., essential tremor; depression, e.g., postpostum depression, an anxiety disorder with a neuroactive steroid or a composition comprising a neuroactive steroid (e.g., pregnanolone, allopregnanolone, alphadalone, ganaxolone, or alphaxolone).

10 Claims, 12 Drawing Sheets

Related U.S. Application Data

(60) Provisional application No. 62/360,762, filed on Jul. 11, 2016, provisional application No. 62/360,758, filed on Jul. 11, 2016, provisional application No. 62/355,669, filed on Jun. 28, 2016, provisional application No. 62/355,174, filed on Jun. 27, 2016, provisional application No. 62/305,279, filed on Mar. 8, 2016.

(51) Int. Cl.
*A61P 25/22* (2006.01)
*A61K 31/58* (2006.01)

(56) References Cited

U.S. PATENT DOCUMENTS

| | | |
|---|---|---|
| 3,580,937 A | 5/1971 | Campbell et al. |
| 3,865,939 A | 2/1975 | Jandacek |
| 3,943,124 A | 3/1976 | Philipps et al. |
| 3,983,111 A | 9/1976 | Philipps et al. |
| 4,071,625 A | 1/1978 | Grunwell et al. |
| 4,192,871 A | 3/1980 | Philipps et al. |
| 5,719,197 A | 2/1998 | Kanios et al. |
| 5,925,630 A | 7/1999 | Upasani et al. |
| 5,939,545 A | 8/1999 | Upasani et al. |
| 6,143,736 A | 11/2000 | Upasani et al. |
| 6,245,757 B1 | 6/2001 | Chopp et al. |
| 6,277,838 B1 | 8/2001 | Upasani et al. |
| 6,376,531 B1 | 4/2002 | Bell |
| 6,455,516 B1 | 9/2002 | Backstrom et al. |
| 6,603,008 B1 | 8/2003 | Ando et al. |
| 6,780,853 B1 | 8/2004 | Upasani et al. |
| 7,060,255 B2 | 6/2006 | Rabinowitz et al. |
| 7,064,116 B2 | 6/2006 | Calogeropoulou et al. |
| 7,090,830 B2 | 8/2006 | Hale et al. |
| 7,630,757 B2 | 12/2009 | Dorfmeister et al. |
| 7,816,074 B2 | 10/2010 | Smith et al. |
| 7,858,609 B2 | 12/2010 | Shaw et al. |
| 7,998,971 B2 | 8/2011 | Barlow et al. |
| 8,012,958 B2 | 9/2011 | Sabnani et al. |
| 8,618,087 B2 | 12/2013 | Shaw et al. |
| 8,697,678 B2 | 4/2014 | Goodchild et al. |
| 8,969,329 B2 | 3/2015 | Brinton et al. |
| 9,056,116 B2 | 6/2015 | Shaw et al. |
| 9,084,797 B2 | 7/2015 | Caufriez et al. |
| 9,339,508 B2 | 5/2016 | Baulieu et al. |
| 9,365,611 B2 | 6/2016 | Martinez Botella et al. |
| 9,512,165 B2 | 12/2016 | Martinez Botella et al. |
| 9,630,986 B2 | 4/2017 | Covey et al. |
| 9,676,812 B2 | 6/2017 | Covey et al. |
| 9,765,110 B2 | 9/2017 | Covey |
| 2002/0072509 A1 | 6/2002 | Stein et al. |
| 2002/0183293 A1 | 12/2002 | Banerjee et al. |
| 2002/0198174 A1 | 12/2002 | Lyons |
| 2003/0032638 A1 | 2/2003 | Kim et al. |
| 2005/0201888 A1 | 9/2005 | Amar et al. |
| 2006/0063707 A1 | 3/2006 | Baudry et al. |
| 2006/0198896 A1 | 9/2006 | Liversidge et al. |
| 2007/0014719 A1 | 1/2007 | Reading et al. |
| 2007/0020299 A1 | 1/2007 | Pipkin et al. |
| 2007/0081948 A1 | 4/2007 | Morton et al. |
| 2007/0287931 A1 | 12/2007 | Dilorenzo |
| 2008/0195160 A1 | 8/2008 | Wingeier et al. |
| 2008/0269183 A1 | 10/2008 | Mellon et al. |
| 2009/0074677 A1 | 3/2009 | Marx et al. |
| 2009/0130216 A1 | 5/2009 | Cartt et al. |
| 2009/0162441 A1 | 6/2009 | Bartus et al. |
| 2009/0198145 A1 | 8/2009 | Chow |
| 2009/0203658 A1 | 8/2009 | Marx et al. |
| 2009/0221544 A1 | 9/2009 | Stein et al. |
| 2009/0239942 A1 | 9/2009 | Cloyd |
| 2009/0325920 A1 | 12/2009 | Hoffman et al. |
| 2010/0136105 A1 | 6/2010 | Chen et al. |
| 2010/0234335 A1 | 9/2010 | Gravanis et al. |
| 2010/0297181 A1 | 11/2010 | Hanada et al. |
| 2010/0316678 A1 | 12/2010 | Goodchild |
| 2010/0317638 A1 | 12/2010 | Covey et al. |
| 2010/0331762 A1 | 12/2010 | Wingeier et al. |
| 2011/0054038 A1 | 3/2011 | Glozman |
| 2011/0152840 A1 | 6/2011 | Lee et al. |
| 2011/0288059 A1 | 11/2011 | Marx et al. |
| 2011/0306579 A1 | 12/2011 | Stein |
| 2011/0319386 A1 | 12/2011 | Barlow et al. |
| 2012/0142645 A1 | 6/2012 | Marx |
| 2012/0302535 A1 | 11/2012 | Caufriez et al. |
| 2012/0316146 A1 | 12/2012 | Goodchild et al. |
| 2013/0210783 A1 | 8/2013 | Marx et al. |
| 2013/0309306 A1 | 11/2013 | Rogawski et al. |
| 2014/0050789 A1 | 2/2014 | Rogawski et al. |
| 2014/0057885 A1 | 2/2014 | Reddy et al. |
| 2014/0058079 A1 | 2/2014 | Mensah-Nyagan et al. |
| 2014/0148412 A1 | 5/2014 | Hogenkamp |
| 2014/0322198 A1 | 10/2014 | Buchwald-Werner et al. |
| 2014/0343027 A1 | 11/2014 | Rogawski |
| 2015/0018327 A1 | 1/2015 | Reddy |
| 2015/0158903 A1 | 6/2015 | Upasani et al. |
| 2015/0175651 A1 | 6/2015 | Salituro et al. |
| 2015/0265632 A1 | 9/2015 | Goodchild et al. |
| 2015/0290181 A1 | 10/2015 | Lee et al. |
| 2015/0291654 A1 | 10/2015 | Upasani et al. |
| 2015/0313915 A1 | 11/2015 | Rogawski et al. |
| 2016/0068563 A1 | 3/2016 | Martinez Botella et al. |
| 2016/0083418 A1 | 3/2016 | Martinez Botella et al. |
| 2016/0108080 A1 | 4/2016 | Martinez Botella et al. |
| 2018/0050005 A1 | 2/2018 | DiMauro et al. |
| 2018/0050107 A1 | 2/2018 | DiMauro et al. |
| 2018/0064728 A1 | 3/2018 | Chang et al. |
| 2018/0071315 A1 | 3/2018 | Cashman et al. |
| 2018/0133229 A1 | 5/2018 | Rogawski et al. |
| 2018/0153906 A1 | 6/2018 | Rogawski et al. |
| 2018/0193357 A1 | 7/2018 | Rogawski et al. |
| 2018/0235916 A1 | 8/2018 | Kaufman et al. |
| 2018/0256726 A1 | 9/2018 | Rogawski |
| 2018/0296487 A1 | 10/2018 | Saporito et al. |
| 2018/0369171 A1 | 12/2018 | Pinna et al. |
| 2019/0160078 A1 | 5/2019 | Masuoka et al. |
| 2019/0337975 A1 | 11/2019 | Bryson et al. |
| 2020/0147071 A1 | 5/2020 | Jindal |
| 2020/0155522 A1 | 5/2020 | Osten et al. |
| 2020/0179350 A1 | 6/2020 | During |
| 2020/0179351 A1 | 6/2020 | During |
| 2020/0179403 A1 | 6/2020 | Aimetti et al. |
| 2020/0188412 A1 | 6/2020 | Bryson et al. |

FOREIGN PATENT DOCUMENTS

| | | |
|---|---|---|
| CN | 1190404 A | 8/1998 |
| CN | 104136452 A | 11/2014 |
| EP | 0233849 A1 | 8/1987 |
| EP | 0656365 A1 | 6/1995 |
| EP | 0808325 A1 | 11/1997 |
| EP | 1038880 A2 | 9/2000 |
| GB | 1430942 A | 4/1976 |
| GB | 1570394 A | 7/1980 |
| GB | 1581234 A | 12/1980 |
| WO | 1991011172 A1 | 8/1991 |
| WO | 1991016897 A1 | 11/1991 |
| WO | 9303732 A1 | 3/1993 |
| WO | 9305786 A1 | 4/1993 |
| WO | 9318053 A1 | 9/1993 |
| WO | 9427608 A1 | 12/1994 |
| WO | 1995021617 A1 | 8/1995 |
| WO | 9526325 A2 | 10/1995 |
| WO | 1996003421 A1 | 2/1996 |
| WO | 1996016076 A1 | 5/1996 |
| WO | 9640043 A2 | 12/1996 |
| WO | 1997003677 A1 | 2/1997 |
| WO | 9805337 A1 | 2/1998 |
| WO | 1999045931 A1 | 9/1999 |
| WO | 2002030409 A1 | 4/2002 |
| WO | 2004019953 A1 | 3/2004 |
| WO | 2005105822 A2 | 11/2005 |
| WO | 2006102644 A2 | 9/2006 |
| WO | 2007062266 A2 | 5/2007 |

(56) References Cited

FOREIGN PATENT DOCUMENTS

| WO | 2008128049 A2 | 10/2008 |
|---|---|---|
| WO | 2008157460 A1 | 12/2008 |
| WO | 2009088530 A1 | 7/2009 |
| WO | 2010003391 A2 | 1/2010 |
| WO | 2010042925 A2 | 4/2010 |
| WO | 2010063030 A2 | 6/2010 |
| WO | 2010107815 A1 | 9/2010 |
| WO | 2011088503 A1 | 7/2011 |
| WO | 2012059456 A1 | 5/2012 |
| WO | 2012075286 A2 | 6/2012 |
| WO | 2012110010 A1 | 8/2012 |
| WO | 2012116290 A2 | 8/2012 |
| WO | 2013036835 A1 | 3/2013 |
| WO | 2013043985 A1 | 3/2013 |
| WO | 2013056181 A1 | 4/2013 |
| WO | 2013112605 A2 | 8/2013 |
| WO | 2013188792 A2 | 12/2013 |
| WO | 2014028398 A2 | 2/2014 |
| WO | 2014031792 A2 | 2/2014 |
| WO | 2014085668 A1 | 6/2014 |
| WO | 2014108808 A2 | 7/2014 |
| WO | 2015195962 A1 | 12/2015 |
| WO | 2016040322 A1 | 3/2016 |
| WO | 2016127170 A1 | 8/2016 |
| WO | 2017021325 A1 | 2/2017 |
| WO | 2017066240 A1 | 4/2017 |
| WO | 2017156103 A1 | 9/2017 |
| WO | 2018035095 A1 | 2/2018 |
| WO | 2018048789 A1 | 3/2018 |
| WO | 2018169798 A1 | 9/2018 |
| WO | 2018195186 A1 | 10/2018 |
| WO | 2018236955 A1 | 12/2018 |
| WO | 2018237282 A1 | 12/2018 |
| WO | 2019094724 A1 | 5/2019 |

OTHER PUBLICATIONS

Evans, et al. "Allopregnanolone regulates neurogensis and depressive/anxiety-like behaviour in social isolation rodent model of chronic stress", Neuropharmacology 63 (2012) 1315-1326.
Extended European Search Report for application PCT/CN2014075593 dated Aug. 26, 2016.
Extended European Search Report for application PCT/CN2014075594 dated Aug. 26, 2016.
Extended European Search Report for European Application No. 13740743.3 dated Jan. 14, 2016.
Extended European Search Report for European Application No. 13830765.7 dated Jan. 12, 2016.
Extended European Search Report for European Application No. 13857993.3 dated May 2, 2016.
Finn et al., "The Estrus Cycle, Sensitivity to Convulsants and the Anticonvulsant Effect of Neuroactive Steroid", The Journal of Pharmacology and Experimental Therapeutics (1994), vol. 271, pp. 164-170.
Fitelson et al., "Treatment of postpartum despression: clinical, psychological and pharmacological options", International Journal of Women's Health, 2011, pp. 1-14.
Foster, "Deuterium isotope effects in studies of drug metablosim". Trends in Pharmacological Sciences, vol. 5, pp. 524-527 (Abstract) (1984).
Frank et al., "Neuroprotective effects of allopregnenolone on hippocampal irreversible neurotoxicity in vitro", Prog. Neuro-psychopharmacol. & Biol Psychiat. 2000, vol. 24, pp. 1117-1126.
Freeman et al., "Alopregnanolone levels and symptom improvement in severe premenstrual syndrome", J. Clin. Psychopharmacol 2002; 22:516-520.
Frye et al. "Hippocampal 3a,5a-THP may alter depressive behavior of pregnant an lactating rats", Pharmacology, Biochemistry and Behavior 78 (2004) 531-540.
Frye et al., "Changes in Progesterone metabolites in the hippocampus can modulate open field and forced swim test behavior of proestrous rats", Hormones and Behavior 41, 306-315 (2002).
Frye et al., "Infusion of 3a,5a-THP to the pontine reticular formation attenuates PTZ-induced seizures". Brain Research (2000), vol. 881, pp. 98-102.
Frye, "The neurosteroid 3-a, 5 a-THP has antiseizure and possible neuroproteclive effects in an animal model of epilepsy," Brain Research, (1995), 696:113-120.
Frye, et al., "Effects and mechanism of 3a,5a,-THP on emotion, motivation, and reward functions involving pregnane xenobiotic receptor", Frontiers in Neuroscience (2012), vol. 5, Article 136, pp. 1-18.
Galvin et al., "Midazolam: an effective intravenous agent for seizure control," Archives of emergency medicine, (1987), 4:169-172.
Gasior et al., "Anticonvulsant and behaviorial effects of neuroactive steroids alone and in conjunction with diazepam", The Journal of Pharmacology and Experimental Therapeutics (1997), vol. 282, No. 2, pp. 543-553.
Gasior et al., "Neuroactive steroids: potential therapeutic use in neurological and psychiatric disorders", Trends in Pharmacological Science, (1999), vol. 20, No. 3, pp. 107-112.
Gaynes et al., "Perinatal Depression: Prevalence, Screening Accuracy, and Screening Outcomes", Evidence Report/Technology Assessment, (2005), No. 119, pp. 1-8.
Gilbert et al., "3a-reduced neuroactive steroids and their precursors during pregnancy and the postpartum period", Gynecol Endocrinol., (2005), 21(5): pp. 268-279.
Girdler et al. "Neurosteroids in the context of stress: Implications for depressive disorders", Pharmacology & Therapeutics 116 (2007) 125-139.
Griffin et al., "Current perspectives on the role of neurosteroids in PMS and depression", International Review of Neurobiology, vol. 46, 2001, pp. 479-492.
Guidotti et al., "The socially-isolated mouse: a model to study the putative role of allopregnanolone and 5a-dihydroprogesterone in psychiatric disorders", Brain Research Reviews 37 (2001) 110-115.
Gul et al., "Sterols and the phytosterol content in oilseed rape (*Brassica napus* L.)", Journal of Cell and Molecular Biology (2006), 5:71-79.
Haas et al., "Ketamine: A Review of its Pharmacologic Properties and Use in Ambulatory Anesthesia", Anesthesia, Anesthesia Progress, The American Dental Society of Anesthesiology (1992), vol. 39, pp. 61-68.
Hanley et al., "Use of midazolam in the treatment of refractory status epilepticus", Clinical Therapeutics, (1998), 20(6):1093-1105.
Hardoy et al. "The link between neurosteroids and syndromic/syndromal components of the mood spectrum disorders in women during the premenstrual phase", Clinical Practice and Epidemiology in Mental Health 2008, 4:3.
Hardoy, et al., "Increased neuroactive steroids concentrations in women with bipolar disorder or major depressive disorder", J. Clin Psychopharmacol 2006;26:379-384.
Harrison et al., "Structure-Activity Relationships for Steroid Interaction with the y-Aminobutyric AcidA Receptor Complex" The Journal of Pharmacology and Experimental Therapeutics (1987) vol. 241, No. 1, pp. 346-353.
Haut et al., "Seizure clustering during epilepsy monitoring", Epilepsia, (2002), 43(7): 711-715.
Haut, "Seizure clustering", Epilepsy & Behavior, (2006), 8:50-55.
Haut, "Seizure Clusters: characteristics and treatment," Current Opin. Neurol., (2015), 28(2):143-150, Abstract only.
Hawkinson et al., "3a-Hydroxy-3b-trifluoromethyl-5a-pregnan-20-one (Co Feb. 1970): A Partial Agonist at the Neuroactive Steroid Site of the y-Aminobutyric acidA Receptor" Molecular Pharmacology (1996) vol. 49, pp. 897-906.
Hawkinson et al., "Correlation of Neuroactive Steroid Modulation of [35S]t-Butylbicyclophosphorothionate and [3H] Flunitrazepam Binding and y-Aminobutyric AcidA Receptor Function", Molecular Pharmacology (1994) vol. 46, pp. 977-985.
Hawkinson et al., "Substituted 3b-Phenylethynyl Derivatives of 3a-Hydroxy-5a-pregnan-20-one: Remarkably Potent Neuroactive Steroid Modulators of y-Aminobutyric AcidA Receptors", The Journal of Pharmacology and Experimental Therapeutics(1998), vol. 287, No. 1, pp. 198-207.

(56) References Cited

OTHER PUBLICATIONS

Hay et al., "Pathways to Violence in the Children of Mothers Who Were Depressed Postpartum", Developmental Psychology, 2003, vol. 39, No. 6, pp. 1083-1094.
He J et al., "Allopregnanolone facilitates spatial learning after traumatic brain injury", Abstracts of the Annual Meeting of the Society for Neuroscience (2000) p. 2296.
Hellgren et al., "Low serum allopregnanolone is associated with symptoms of depression in late pregnancy," Neuropsychobiology, (2014), 69:147-153.
Hincal, "Recent advances in drug delivery using amphiphilic cyclodextrin nanoparticles", European Journal of pharmaceutical Sciences (2005), vol. 23S1, pp. S3-S4.
Hogenkamp et al., "Synthesis and in Vitro Activity of 3b-Substituted-3a-hydroxypregnan-20-ones: Allosteric Modulators of the GABAA Receptor", Journal of Medicinal Chemistry, (1997), vol. 40, pp. 61-72.
Hu et al., "Neurosteroid Analogues: Structure-Activity Studies of Benz(e) indene Modulators of GABAA Receptor-Function. 1. The Effect of 6-Melhyl Substitution on the Electrophysiological Activity of 7-Substituted Benz[e]indene-3-carbonitriles". Journal of Medicinal Chemistry, (1993), pp. 3956-3967.
Huber, et al. "Effect of an oral contrceptive with chlormadinone Acetate on depressive mood", Clin Drug Invest 2008: 28(12): 783-791.
Hunter et al., "Status Epilepticus: A Review, With Emphasis on Refractory Cases" Can. J. Neurol. Sci. (2012), vol. 39, pp. 157-169.
International Search Report and Written Opinion (Declaration of non-establishment of International Search Report) for corresponding International Application No. PCT/US2011/062888 dated Jun. 15, 2012.
International Search Report and Written Opinion for corresponding International Application No. PCT/US13/56062 dated Jan. 29, 2014.
International Search Report and Written Opinion for corresponding International Application No. PCT/US2012/056509 dated Dec. 27, 2012.
International Search Report and Written Opinion for corresponding International Application No. PCT/US2013/054562 dated Jan. 13, 2014.
International Search Report and Written Opinion for corresponding International Application No. PCT/US2013/072351 dated Mar. 17, 2014.
International Search Report and Written Opinion for corresponding International Application No. PCT/US2013/22772 dated Mar. 27, 2013.
International Search Report and Written Opinion for corresponding International Application No. PCT/US2013/56062 dated Jan. 29, 2014.
International Search Report and Written Opinion for corresponding International Application No. PCT/US2015/48937 dated Feb. 5, 2016.
International Search Report and Written Opinion for Corresponding International Application No. PCT/US2016/018748 dated Aug. 29, 2016.
International Search Report and Written Opinion for corresponding International Application No. PCT/US2016/026705 dated Aug. 19, 2016.
International Search Report and Written Opinion for corresponding International Application No. PCT/US2016/038195 dated Oct. 20, 2016.
International Search Report and Written Opinion for corresponding International Application No. PCT/US2017/021325 dated May 22, 2017.
International Search Report and Written Opinion for corresponding International Application No. PCT/US2018/050444 dated Dec. 3, 2018.
International Search Report and Written Opinion for International Application No. PCT/CN2013/074312 dated Jan. 23, 2014.
International Search Report and Written Opinion for International Application No. PCT/CN2013/074319 dated Jan. 23, 2014.
International Search Report and Written Opinion for International Application No. PCT/CN2013/074323 dated Jan. 30, 2014.
International Search Report and Written Opinion for International Application No. PCT/CN2013/074325 dated Jan. 23, 2014.
International Search Report and Written Opinion for International Application No. PCT/CN2014/075585 dated Aug. 4, 2014.
International Search Report and Written Opinion for International Application No. PCT/CN2014/075593 dated Jul. 22, 2014.
International Search Report and Written Opinion for International Application No. PCT/CN2014/075594 dated Jul. 16, 2014.
International Search Report and Written Opinion for International Application No. PCT/CN2014/075600 dated Jul. 29, 2014.
International Search Report and Written Opinion for International Application No. PCT/US14/47246, dated Jan. 22, 2015.
International Search Report for International Application No. PCT/US2012/060136 dated Mar. 27, 2013.
Irwin et al., "Allopregnanolone predinical acute pharmacokinetic and pharmacodynamic studies to predict tolerability and efficacy for alzheimer's disease", Plos One, vol. 10, No. 6, 2015, pp. 1-31.
Jain et al., "Hygroscopicity, phase solubility and dissolution of various substituted sulfobutylether b-cydodextrins (SBE) and danazol-Sbe inclusion complexes", International Journal of Pharmaceutics (2001), vol. 212, pp. 177-186.
Jin et al., "A sensitive and selective LC-differential mobility-mass spectrometric analysis of allopregnanolone and pregnanolone in human plasma", Analytical and Bioanalytical Chemistry, vol. 405, No. 29, 2013, pp. 1-23.
Johnson et al., "Deuterium Labelled Steroid Hormones: Syntheses and Applications in Quantitation and Endocrinology", Journal of Steroid Biochemistry, vol. 14, 1981, pp. 793-800.
Jones, "Post-partum depression-a gimpse of light in the darkness?", Published online Jun. 12, 2017, 2 pages.
Kaminski et al., "Allopregnanolone analogs that positively modulate GABAA receptors protect against partial seizures induced by 6-Hz electrical stimulation in mice," Epilepsia, (2004), 45(7):864-867.
Kanes et al., "Brexanolone (SAGE-547 injection) in post partum depression: a randomised controlled trial", The Lancet, 2017; vol. 390, Issue 10093, pp. 480-489.
Kanes et al., "Open-label, proof-of-concept study of brexanbne in the treatment of severe postpartum depression", Hum Psychopharmacol Clin Exp. (2017).
Kanto, "Midazolam: The first water-soluble benzodiazepine pharmacology, pharmacokinetics and efficacy in insomnia and anesthesia", Pharmacotherapy, (1985), 5(3): 138-155.
Kask et al., "Allopregnenolone has no effect on startle response and prepulse inhibition of startle response in patients with premenstrual dysphoric disorder or healthy controls", Pharmacology, Biochemistry and Behavior (2009), vol. 92, pp. 608-613.
Kask et al., "Allopregnanolone impairs episodic memory in healthy women", Psycopharmacology (2008), vol. 199, pp. 161-168.
Kaura et al., "The Progesterone metabolite allopregnanolone potentiates GABAA rceptor-mediated inhibition of 5-Ht neuronal activity", European Neuropsychopharmacology, (2007), 17, pp. 108-115.
Khenna et al., "Nanotoxicity: An interplay of oxidative stress, inflammation and cell death," nanomaterials, (2015), 5:1163-1180.
Khisti et al., "Serotonergic agents modulate anti-depressant-like effect of the neurosteroid 3a-hydroxy-5a-pregnan-20-one in mice" Brain Research 865 (2000) 291-300.
Kim et al., "Modulation of presynaptic GABAA receptors by endogenous neurosteroids", British Journal of Pharmacology (2011), vol. 164, pp. 1698-1710.
Kimmel et al., "Oxytocin receptor DNA methylation inpostpartum depression," Psychoneuroendocrinology, (2016), 69:150-160.
Klatzkin et al. "Associations of histories of depression and PMDD diagnosis with allopregnanolone concentrations following the oral administration of micronized progesterone", Psychoneuroendocrinology (2006) 31, 1208-1219.
Klatzkin et al., "Histories of depression, allopregnanolone responses to stress, and premenstrual symptoms in women:", Biological Psychology 71 (2006) 2-11.

(56) References Cited

OTHER PUBLICATIONS

Kokate et al., "Anticonvulsant Activity of Neurosteroids: Correlation with g-Aminobutyric Acid-Evoked Chloride Current Potentiation", The Journal of Pharmacology and Experimental Therapeutics (1994), vol. 270, No. 3, pp. 1223-1229.
Kokate et al., "Convulsant actions of the neurosteroid pregnenolone sulfate in mice", Brain Research (1999), vol. 831, pp. 119-124.
Kokate et al., "Neuroactive Steroids Protect Against Pilocarpine- and Kainic Acid-induced Limbic Seizures and Status Epilepticus in Mice", Neuropharmacology (1996) vol. 35, No. 8, pp. 1049-1056.
Kramer, "Early Ketamine to Treat Refractory Status Epilepticus" Neuroait. Care (2012), vol. 16, pp. 299-305.
Kushner et al., "Pharmacological uses and perspectives of heavy water and deuterated compounds". Candian Journal Physiology and Pharmacology, vol. 77, pp. 79-88 (1999).
Lahiani-Skiba et al., "Solubility and Dissolution Rate of Progesterone-Cyclodextrin-Polymer Systems", Drug Development and Industrial Pharmacy (2006), vol. 32, pp. 1043-1058.
Larsen et. al., "Phase Solubility and Structure of the Inclusion Complexes of Prednisolone and 6a-Methyl Prednisolone with Various Cyclodextrins", Journal of Pharmaceutical Sciences (2005), vol. 94, No. 3, pp. 507-515.
Leroy et al., "Pharmacological plasticity of GABAA receptors at dentate gyrus synapses in a rat model of temporal lobe epilepsy", J. Physol, (2004), vol. 557, No. 2, pp. 473-487.
Li et al., "Nanoparticle-induced pulmonary toxicity," Experimental Biology and Medicine, (2010), 235:1025-1033.
Lonsdale et al., "The Anticonvulsant effects of allopregnanolone against amygdala-kindled seizures in female rats", Neuroscience Letters (2007), vol. 411, pp. 147-151.
Lossin et al., "Alopregnanolone treatment in a rat pediatric status epilepticus model: Comparison with diazepam", American Epilepsy Society (2012), (Abst. 3.220).
MacKenzie et al., "Neurosleriods and GABAergic signaling in health arid disease", BioMol Concepts 2013; 4(1): 29-42.
Madl et al., "Nanoparticles, lung injury, and the role of oxidant stress," Annu Rev Physiol., (2014), 76:447-465.
Maguire et al., "GABAAR plasticity during pregnancy relevance to postpartum Depression," Neuron, (2008), 59:207-213.
Martini et al., "Nasal and pulmonary drug delivery systems", Exp. Opin. Ther. Patents, (2000), 10(3):315-323.
Marx et al., "Neuroactive steroids are altered in schizophrenia and bipolar disorder: relevance to pathophysiology and therapeutics", Neuropsychopharmacology (2006) 31, 1249-1263.
Matsumoto et al., "GAGAa receptor neutrotransmission dysfunction in a mouse model of social isolation-induced stress: Possible insights into a non-serotonergic mechanism of action of SSRIs in mood and anxiety disorders", Stress, Mar. 2007; 10(1): 3-12.
Mayer et al., "Refractory Status Epilepticus Frequency, Risk Factors, and Impact on Outcome", Archives of Neurology (2002), vol. 59, pp. 205-210.
Meierkord et al., "EFNS Guideline on the Management of Status Epilepticus in Adults", European Journal of Neurology (2010), vol. 17, pp. 348-355.
Meltzer-Brody et al., "Phase 2 and 3 Studies Evaluating Brexanobne iv, a GABAA Receptor Positive Allosteric Modulator, in Postpartum Depression", Presented at the 56th Annual Meeting of the American College of Neuropsychopharmacology; Dec. 3, 2017, 14 pages.
Melville, "New drug shows rapid, robust effect in postpartum", Medscape, (2017), 2 pages.
Merzlikine et al., "Development of machine learning models of b-cydodexhin and sutfobutylether-b-cyclodextrin complexation free energies", International Journal of Pharmaceutics (2011), vol. 418, pp. 207-216.
Miller, "Postpartum Depression", Clinician's Corner, vol. 287, No. 6, (2002), pp. 762-765.
Monagle et al., "A Phase 1c Trial Comparing the Efficacy and Safety of a New Aqueous Formulation of Alphaxalone with Propofol", Anesthesia & Analgesia (2015), vol. 121, No. 4, pp. 914-924.
Morgan, et al. "Neuroactive steroids after estrogen exposure in depressed postmenopausal women treated with sertraline and asymptomatic postmenopausal woman", Arch Womens Ment, Health (2010) 13:91-98.
Moses Kolko et al., "Antepartum and Postpartum Depression: Healthy Mom, Healthy Baby", Journal of the American Medical Women's Association, 2004; 59: pp. 181-191.
Munari et al., "The Use of Althesin in Drug-Resistant Status Epilepticus", Epilepsia (1979), vol. 20, pp. 475-484.
Murayama et al., "Effects of neurosteroid 3a-hydroxy-5a-pregnan-20-one on ethanol-mediated paired-pulse depression of population spikes in the CA1 region of rat hippocampal slices", Neuroscience Letters 394 (2006) 28-32.
Murray et al., "Maternal Postnatal Depression and the Development of Depression in Offspring Up to 16 Years of Age", Journal of the American Academy of Child & Adolescent Psychiatry, 2011; 50 (5), pp. 460-470.
Murray et al., "Prediction, detection, and treatment of post natal depression", Archives of Disease in Childhood, The Journal of the Royal College of Paediatrics and Child Health, 1997, 77: 97-101.
Másson et al., "Cydodextrins and the liquid-liquid phase distribution of progesterone, estrone and prednicarbate", J Incl Phenom Macrocycl Chem (2007), vol. 57, pp. 481-487.
Naert, et al. "Neuroactive steroids modulate HPA axis actiity and cerebral brain-derived neurotrophic factor (BDNF) )protein levels in adult male rats", Psychoneuroendocrinology (2007) 32, 1062-1078.
Nanjwade et al., Pulmonary Drug Delivery: Novel Pharmaceutical Technologies Breathe New Life into the Lungs, PDA JPharm Sci and Tech, (2015), 65: 513-534.
Nappi et al., "Serum Allopregnanolone in women with postpartum blues", Obstetrics & Gynecology, vol. 97, No. 1, 2001: 77-80.
Nin et al. "Neurosteroids reduce social insolation-induced behavioral deficits; a proposed link with neurosteroid-mediated upregulation of BDNF expression", Frontiers in Endocrinology (2011) vol. 2, Article 73.
Nin et al., "The effect of intra-nucleus accumbens administration of allopregnanolone on 6 and y2 GABAA receptor Subunit mRNA expression in the hippocampus and on depressive-like and grooming behaviors in rats," Pharmacology, Biochemistry and Behavior, (2012), 103:359-366.
Northdurfter et al., "Recent Developments in Potential Anxiolytic Agents Targeting GABAA/BzR Complex or the Translocator Protein (18kDa) (TSPO)", Current Topics in Medicinal Chemistry, 2012, 12; 360-370.
Notification of Transmittal of the International Search Report and the Written Opinion of the International Searching authority, or the Declaration, International Application No. PCT/US13/45933, dated Dec. 3, 2013, 5 Pages.
Novy et al., "Refractory Status Epilepticus: A Prospective Observational Study", Epilepsia (2010), vol. 51, No. 2, pp. 251-256.
Oka et al., "A reliable method for intratracheal instillation of materials to the entire lung in rats," J Toxicol Pathol, (2006) 19:107-109.
Osborne et al.,"Replication of epigenetic postpartum depression biomarkers and variation with hormone levels," Neuropsychopharmacology, Accepted Manuscript (2015), pp. 1-32.
Park et al., "Multiple effects of allopregnanolone on GABAergic responses in single hippocampal CA3 pyramidal neurons", European Journal of Pharmacology (2011), vol. 652, pp. 46-54.
Parlzek et al., "Steroid hormones in the development of postpartum depression". Physiological Research, 2014, vol. 63, No. Suppl. 2, pp. S277-S282.
Pearlstein, et al. "Premenstrual dysphoric disorder: burden of illness and treatment update", J Psychiatry Neurosci 2008:33(4):291-301.
Phillipps et al., "A New Series of Steroidal Antidysrhythmic Agents," J. Steroid Biochem. 19(1):759-765 (1983).
Phillipps et al., "Water-soluble Steroidal Anaesthetics", Journal of Steroid Biochemistry 11:79-86 (1979).
Phillipps, "Structure-Activity Relationships in Steroidal Anaesthetics", Journal of Steroid Biochemistry, (1975), vol. 6, pp. 607-613.

(56) References Cited

OTHER PUBLICATIONS

Pieribone et al., "Clinical Evaluation of Ganaxolone in Pediatric and Adolescent Patients with Refractory Epilepsy", Epilepsia (2007), vol. 48, No. 10, pp. 1870-1874.

Pinna, et al., "Up-Regulation of Neutrosteriod Biosynthesis as a Pharmacological Strategy to improve behavioural Deficits in a Putative mouse model of Post-traumatic stress disorder", Journal of Neuroendocrinology 24 (2011), p. 1102-116.

Pires et al., "Intranasal Drug Delivery: How, Why and What for?" Journal of Pharm, Pharmaceut Sci, (2009), 12 (3):288-311.

Poromaa et al., "GABA receptor, progresteron and premenstrual dysphoric disorder", Arch Womens Ment Health (2003) 6:23-41.

Pubchem, CID 92786.

Puia, et al. "Novel modulatory effects of neurosteriods and benzodiazepines on excitatory and inhibitory neurons excitability: a multi-electrode array recording study", Frontiers in Neutral Circuits, (2012) vol. 6, Article 94.

Ramsay, "Treatment of status epilepticus", Epilepsia, 2013, 34 Suppl.:S71-S81.

Rapkin et al., "Progesterone metabolite allopregnanolone in women with premenstrual syndrome", Obstet. Gynecol 1997; 90:709-714.

Rasheed et al., "Cydodextrins as Drug Carrier Molecule: A Review", Scientia Pharmaceutica, Review, (2008), pp. 567-598.

Rasmusson, et al. "Decreased Cerebrospinal Fluid Allopregnanolone levels in women with posttraumatic stress disordei", Biol. Psychiatry 2006;60:704-713.

Reddy "Role of anticonvulsant and antiepileptogenic neurosteroids in the pathophysiology and treatment of epilepsy," Frontiers in Endocrinology, 2:38, (2011).

Reddy "The clinical potentials of endogenous neurosteroids" Drugs of Today 2002, 38 (7): 465-485.

Reddy et al., "Neurosteroids—Endogenous Regulators of Seizure Susceptibility and Role in Treatment of Epilepsy", Jasper's Basic Mechanisms of the Epilepsies Fourth Edition (2012), pp. 1-23.

Reddy, "Neurosteroids: Endogenous role in the human brain and therapeutic potentials", Progress in Brain Research, (2010) vol. 186, pp. 113-137.

Reddy, "Pharmacology of Endogenous Neuroactive Steroids", Critical Reviews in Neurobiology, 15 (3&4)197-234 (2003).

Reddy, "SGE-102: a novel therapy for refractory status epilepticus", Epilepsia, Abstract 34 Suppl 6: 81-82.

Rogawski et al., "Neuroactive Steroids for the Treatment of Status Epilepticus", Epilepsia (2013), vol. 54, No. 6, pp. 93-98.

Romeo, et al. "Effect of antidepressant treatment on neuroactive steroids in major deprssion" Am. J. Psychiatry 1998; 155:910-913.

Rosenthal et al., "Brexanolone as adjunctive therapy in super-refractory status epilepticus," Annals of Neurology, John Kiley & Wiley Sons, (2017), 32pp.

Rossetti et al., "A Randomized Trial for the Treatment of Refractory Status Epilepticus", Neurocritical Care Society (2011) vol. 14, No. 1, pp. 4-10.

Rouge-Pont et al., "The neurosteroid allopregnanolone increases dopamine release and dopaminergic response to morphine in the rat nucleus accumbens", European Journal of Neuroscience, vol. 16, pp. 169-173, 2002.

Runyon et al., "17b-Nitro-5a-androstan-3a-ol and its 3b-methyl derivative: Neurosteroid analogs with potent anticonvulsant and anxiolytic activities", European Journal of Pharmacology 617, (2009), pp. 68-73.

Rupprecht et al.. "Neuroactive steroids; mechanisms of action and neuropsychopharmacological perspectives", Trends Neurosci. (1999) 22, 410-416.

Saady et al., "Case Report: Althesin in Status Epilepticus" Aneasth. Intens. Care (1979), vol. 7, No. 3, pp. 267-270.

Saalmann et al., "Neurosteroids involved in regulating inhibition in the inferior colliculus" J. Neurophysiol 96: 3064-3073, 2006.

Sahin et al., "Outcome of Severe Refractory Status Epilepticus in Children", Epilepsia (2001), vol. 41, No. 11, pp. 1461-1467.

Sanborn et al., "Identifying and managing adverse environmental health effects: 4. Pesticides," CMAJ, (2002) 166 (11)1431-1436.

Santoro et al., "Decreased allopregnanolone induced by hormonal contraceptives is associated with a reduction in social behavior and sexual motivation in female rats," Psychopharmacology, (2014), 14pp.

Saporito et al, Intravenously Administered Ganaxolone Blocks Diazepam-Resislant Lithium-Pilocarpine-Induced Status Epilepticus in Rats: Comparison with Allopregnanolone, Journal of Pharmacology Exp. Ther. 2019, 368(3), pp. 326-327.

Schiller et al., "Allopregnanolone as a mediator of affective switching in reproductive mood disorders," Psychopharmacology, (2014), 11pp.

Schiller et al., "The role of reproductive hormones in postpartum depression," CNS Spectrums, (2015), 20(1):48-59.

Schule et al., "Neuroactive steriods in Affective Disorders: target for Novel antidepressant or anxiolytic drugs", Neuroscience 191 (2011) p. 55-77.

Schule et al., "The role of allopregnanolone in depression and anxiety", Progress in Neurobiology 113 (2014) 79-87.

Shah et al., "Peripheral WBC Count and Serum Prolactin Level in Various Seizure Types and Nonepileptic Events", Epilepsia (2011), vol. 42, No. 11, pp. 1472-1475.

Shimizu et al., "Allopregnanolone increases mature excitatory synapses along dendrites via protein kinase A signaling ," Neuroscience, (2015), 305:139-145.

Shorvon et al., "The Outcome of Therapies in Refractory and Super-Refractory Convulsive Status Epilepticus and Recommendations for Therapy", Brain (2012), vol. 135, No. 8, pp. 2314-2328.

Shorvon et al., "The Proceedings of the First London Colloquium on Status Epilepticus", University College London, Apr. 12-15, Epilepsia (2007), vol. 48, No. 8, pp. 1-3.

Shorvon et al., "The Treatment of Super-Refractory Status Epilepticus: A Critical Review of Available Therapies and a Clinical Treatment Protocol", Brain (2011,) vol. 134, No. 10, pp. 2802-2818.

Shu et al., "Characteristics of concatemeric GABM receptors containing alpha4/d subunits expressed in Xenopus oocytes" British Journal of Phannacology (2012) 165, 2228-2243.

Smith et al., "The influence of stress at puberty on mood and learning: Role of the a4136 GABAA receptor," Neuroscience, (2013), 249:192-213.

Stevens et al., "Hormonal Therapy for Epilepsy", Curr Neurol. Neurosci Rep. 11: 2011, pp. 435-442.

Supplemental European Search Report, European Patent Application No. 14826212.4, dated Feb. 16, 2017.

Timby et al., "Pharmacokinetic and behavioral effects of alopregnanolone in healthy women", Psycopharmacology (2006), vol. 186, pp. 414-424.

Timby et al., "Women with premenstrual dysphoric disorder have altered sensitivity to alopregnanolone over the menstrual cycle compared to controls-a pilot study," Psychopharmacology, (2016), 233:2109-2117.

Tolmacheva et al., "The role of ovarian steroid hormones in the regulation of basal and stress induced absence seizures", Journal of Steroid Biochemistry & Molecular Biology (2007), vol. 104, pp. 281-288.

Tongiani et al., "Sullobutyl Ether-Alkyl Ether Mixed Cyclodextrin Derivatives With Enhanced Inclusion Ability", Journal of Pharmaceutical Sciences (2009), vol. 98, No. 12, pp. 4769-4780.

Turkmen et al., "Tolerance to Allopregnanolone with Focus on the GABA-A Receptor", British Journal of Pharmacology (2011) vol. 162, pp. 311-327.

Ueda et al., "Evaluation of a Sullobutyl Ether b-Cydodextrin as a Aolubilizing/Stabilizing Agent for Several Drugs", Drug Development and Industrial Pharmacy (2008), vol. 24, No. 9, pp. 863-867.

Ungard et al., "Modification of behavioral effects of drugs in mice by neuroactive steroids", Psychopharmacology (2000) 148:336-343.

Upasani et al., "3a-Hydroxy-3β-(phenylethynyl)-5β-pregnan-20-ones: Synthesis and Pharmacological Activity of Neuroactive Steroids with High Affinity for GABAA Receptors", J. Med. Chem. (1997) vol. 40, No. 1, pp. 73-84.

Uzunova et al. "Region-specific dysregulation of allopregnanolone brain contante tin the olfactory bulbectomized rat model of depression", Brain Research 976 (2003) 1-8.

(56) References Cited

OTHER PUBLICATIONS

Uzunova et al., "Relevance of endogenous 3a-reduced neurosteroids to depression and antidepressant action", Psycophaemacology (2006) 186: 351-361.
Vaitkevicius et al., "First-in-man allopregnanolone use in super-refractory stats epilepticus", Annals of Clinical and Translational Neurology, vol. 4, No. 6, 2017, pp. 411-414.
Vaitkevicius et al., "Successful allopregnanolone treatment of new onset refractory status epilepticus (Norse) syndrome: First in man experience," Epilepsia, (2013), Abstract p114.
Van Broekhoven et al., "Neurosteroids in depression: a review", Psychopharmacology (2003) 165:97-110.
Vanlandingham et al., "Progesterone and its metabolite allopregnanolone differentially regulate hemostatic proteins after traumatic brain injury", Journal of Cerebral Blood Flow & Metabolism (2008), vol. 28, pp. 1786-1794.
Vanover et al., "Behavioral characterization of Co 134444 (3a-hydroxy-21-(1'-imidazolyl)-3b-methoxymethyl-5a-)pregnan-20-one), a novel sedative-hypnotic neuroactive steroid", Psychopharmacology (2001), vol. 155, pp. 285-291.
Vanover et al., "Characterization of the Anxiolytic Properties of a Novel Neuroactive Steroid, Co 2-6749 (GMA-839; WAY-141839; 3a, 21-Dihydroxy-3b-trifluoromethyl-19-nor-5b-pregnan-20-one), a Selective Modulator of y-Aminobutyric AcidA Receptors", The Journal of Pharmacology and Experimental Therapeutics, (2000), vol. 295, No. 1, pp. 337-345.
Vanover et al., "Response-Rate Suppression in Operant Paradigm as Predictor of Soporific Potency in Rats and Identification of Three Novel Sedative-Hypnotic Neuroactive Steroids", The Journal of Pharmacology and Experimental Therapeutics, (1999), vol. 291, No. 3, pp. 1317-1323.
Vine et al., "2H-Labelled 3a-Hydroxy-5a-Pregnane-11, 20-Dione and 3a, 21-Dihydroxy-5a-Pregnane-11, 20-Dione 21-Acetate", Journal of Labelled Compounds and Radiopharmaceuticals, vol. IX, No. 4, 1982, pp. 597-604.
Weisberg et al., "Seizure disorders," Essentials of Clinical Neurology, Chapter 11, (1983), pp. 167-175.
Wirth, "Beyond the HPA axis; progesterone-derived neuroactive steroids in human stress and emotion," Frontiers in Endocrinology (2011) vol. 2, Article 19.
Wolkowitz, et al. "Of Sound Mind and Body; depression, disease, and accelerated aging", Dialogues in Clinical Neuroscience, vol. 13, No. 1, 2011, p. 25-39.
Yunes et al., "Postnatal administration of allopregnanolone modifies glutamate release but not BDNF content in striatum samples of rats prenatally exposed to ethanal", Biomed Research International, vol. 2015, 2015, pp. 1-6.
Zeng et al., "Neurosteroid Analogues. 10. The Effect of Methyl Group Substitution at the C-6 and C-7 Positions on the GABA Modulatory and Anesthetic Actions of (3a,5a) -and (3a, 5b)-3-Hydroxypregnan-20-one", Journal of Medicinal Chemistry, (2005). vol. 48, pp. 3051-3059.
Zhu et al., "Evaluation and comparison of the pharmacokinetic and pharmacodynamic properties of allopregnanolone and pregnanolone at induction of anaesthesia in the male rat", British Journal of Anaesthesia (2001,) vol. 86, No. 3, pp. 403-412.
Zia et al., "Effect of Alkyl Chain and Degree of Substitution on the Complexation of Sulfoalkyl Ether b-Cyclodextrins with Steroids", Journal of Pharmaceutical Sciences (1996), vol. 86, No. 2, pp. 220-224.
Zia et al., "Effect of Cydodextrin Charge on Complexation of Neutral and Charged Substrates: Comparison of (SBE) 7M-b-CD to HP-b-CD", Pharmaceutical Research (2001) vol. 18, No. 5, pp. 667-673.
Zia et al., "Thermodynamics of Binding of Neutral Molecules to Sulfobutyl Ether b-Cyclodextrins (SBE-b-CDs):The Effect of Total Degree of Substitution", Pharmaceutical Research (2000), vol. 17, No. 8, pp. 936-941.

Zolkowska et al., "Anticonvulsant Activity of Intravenous and Intramuscular Allopregnenalone". 1-25. 26a-30a. 26b-30b. American Epilepsy Society: 2012 Annual Meeting Abstracts.
Zolkowska et al., "Anticonvulsant activity of intravenous and intramuscular allopregnenalone," American Epilepsy Society, (Poster), UC Davis, University of California, (2012), 1 page.
Zonana et al., "The Neurobiology of Postpartum Depression", CNS Spectrums, (2005), pp. 792-799, 805.
Zsuzsa, "Neurological and psychiatric aspects of some endocrine diseases. The role of neurosteroids and neuroactive steroids", Medical Journal (2007), 148(41): pp. 1929-1937, machine translated into English.
"Alopregnanolone for the Treatment of Traumatic Brain Injury" ClinicalTrials.gov, Updated May 22, 2013, pp. 1-4.
"Sage Therapeutics Announces Brexalone Achieves Primary Endpoints in Both Phase 3 Clinical Trials in Postpartum Depression", Press Release, Nov. 9, 2017.
"Sage Therapeutics Welcome to R&D day 2016", Jan. 1, 2016, pp. 1-143.
"Sage Therapeutics Wins Big in Depression Trial", Press Release, 247Chrislange, Nov. 9, 2017.
Abend et al., "Treatment of refratory status epilepticus: Literature review and a proposed protocol", Pediatric Neurology, vol. 38, No. 6, 2008, pp. 377-390.
Akhondzadeh et al., "Induction of a novel form of hippocampal long-term depression by muscimol: involvement of GABAA but not glutamate receptors", British Journal of Pharmacology (1995) 115, 527-533.
Aladdin et al., "Refractory Status Epleptícus During Pregnancy Secondary to Cavernous Angiona", Epilepsia, vol. 49, No. 9, (2008), pp. 1627-1629.
Allen et al., "Menstrual phase, depressive symptoms, and allopregnanolone during short-term smoking cessation," Experimental and Clinical Psychopharmacology, (2013) 21(6):427-433.
Amin et al., "The interaction of neuroactive steroids and GABA in the development of neuropsychiatric disorders in women", Pharmacology, Biochemistry and Behavior 84 (2006) 635-643.
Anderson et al., "Oxidative/nitrosatrve stress and immuno-inflammatory pathways in depression: Treatment Implications," Current Pharmaceutical Design, (2014) 20(25):4126-4161.
Anovadiya et al., "Epilepsy: Novel Therapeutic Targets", Journal of Pharmacology and Pharmacotherapeutics, 2012, pp. 112-117.
Backstrom et al. "Pathogensis in Menstrual cyde-inked CNS disorders", Ann. N.Y. Acad. Sci. 1007: 42-53 (2003).
Baker et al., "Efficacy of progesterone vaginal suppositories in Alleviation of Nervous Symptoms in Patients with Premenstrual Syndrome", Journal of Assisted Reproduction and Genetics, vol. 12, No. 3 1995, pp. 205-209.
Bali, et al. 'Multifunctional aspects of alopregnanolone in stress and related disorders, Progress in Neuro-Psychopharmacology & Biological Psychiatry 48 (2014) 64-78.
Bancaud et al., (From the Commission on Classification and Terminology of the International League Against Epilepsy) (Aug. 1981) "Proposal for Revised Clinical and Electroencephalographic Classification of Epileptic Seizures," Epilepsia, 22:489-501.
Bandyopadhyaya et al., "Neurosteroid Analogs. 15. A Comparative Study of the Anesthetic and GABAergic Actions of Alphaxalone, D16-Alphaxalone and Their Conesponding 17-Carbonitrile Analogs, "Bioorganic & Medicinal Chemistry Letters 20:6680-6684 (2010).
Beckley et al., "Progesterone receptor antagonist CDB-4124 increases depression-like behavior in mice without affecting locomotor ability," Psychoneuroendocrinology, (2011) 36:824-833.
Bernardi, et al., "Disadaptive disorders in women: allopregnanolone, a sensitive steroid", Gynecol Endocrinol 2004; 19:344-353.
Biagini et al., "Endogenous neurosteroids modulate epileptogenesis in a model of temporal lobe epilepsy", Experimental Neurology, (2006), vol. 201, pp. 519-524.
Bicikova et al., "Serum concentrations of some neuroactive steroids in women suffering from mixed anxiety-depressive disorder", Neurochemical Research, vol. 25, No. 12, 2000, pp. 1623-1627.

(56) References Cited

OTHER PUBLICATIONS

Birzniece et al., "Neuroactive steroid effects of cognitive functions with a focus on the serotonin and GABA systems" Brain Research Reviews 51 (2006) 212-239.

Bleck et al., "Refractory Status Epileptics", Current Opinion in Critical Care, (2005), vol. 11, pp. 117-120.

Bobb et al., "Allopregnanolone to treat refractory status epilepticus," presented at American Clinical Neurophysiology, Society (ACNS) Annual Meeting & Courses, The Westin Peachtree Plaza, Atlanta, Georgia, (Feb. 4-9, 2014) Abstract S26.

Botella et al., "Neuroactive Steroids. 1. Positive Allosteric Modulators of the (g-Aminobutyric Acid)A Receptor: Structure-Activity Relationships of Heterocyclic Substitution at C-21", Journal of Medical Chemistry, 2015, pp. 3500-3511.

Botella et al., "NeuroactiveSteroids. 2. 3a-Hydroxy-3b-methyl-21-(4-cyano-1H-pyrazol-1-yl)-19-nor-5b-pregnan-20-one (SAGE-217): A Clinical Next Generation Neuroactive Steroid Positive Allosteric Modulator of the (g-Aminobutyric Acid) A Receptor" Journal of Medical Chemistry, 2017, 10 pp A-J.

Broomall et al., "Pediatric super-refractory status epilepticus treated with allopregnanolone," Ann. Neurol, (2014), 76: 911-915.

Brown et al., "A randomized, double-blind, placebo-controlled trial of pregnenolone for bipolar depression," Neuropsychopharmacology, (2014) 39:2867-2873.

Brunn et al., "Combined treatment with diazepam and allopregnanolone reverses tetramelhylenedisulfotetramine (TETS)-induced calcium dysregulalion in cultured neurons and protects TETS-intoxicated mice against lethal seizures," Neuropharmacology, (2015), 95:332-342.

Burdock, "Encyclopedia of food additives and coloring," Taylor & Francis, 3 Volume Set, (1997), pp. 2410-2413.

Cao et al., "Tetramethylenedisulfotelramine alters $Ca2^+$ dynamics in cultured hippocampal neurons: Mitigation by NMDA receptor blockade and GABAA receptor-positive modulation," Toxicological Sciences, (2012), 130(2):362-372.

Carta, et al. "GABAergic neuroactive steroids: a new frontier in bipolar disorders", Behavioral and Brain Functions 2012, 8:61.

Chen et al., "Ibogaine block of the NMDA receptor: In vitro and in vivo studies," Neuropharmacology, (1996) 35 (4):423-431.

Chiasar et al., "The Influence of Neuroactive Steroid Lipophilicity on GABA Receptor Modulation: Evidence for a Low-Affinity Interaction", Journal of Neurophysiology (2009), vol. 102, pp. 1254-1264.

Claassen et al., "Treatment of Refractory Status Epilepticus with Pentobarbital, Propofol, or Midazolam: A Systematic Review", Epilepsia (2002), vol. 43, No. 2, pp. 146-153.

D'Aquila, et al. ."Dopamine is involved in the anti-depressant-like effect of allopregnanolone in the forced swimming test in female rats", Behavioural Pharmacology 2010, 21:21-28.

Database CAPLUS in STN, Acc. No. 1995:986323, Upsani et al., WO 9521617 A1 (Aug. 17, 1995) (abstract). [Upasani, Ravindra B. "Androstanes and pregnanes far allosteric modulation of GABA receptor, and preparation and therapeutic uses of compounds".]

Database CAPLUS in STN, Acc. No. 1998:112239, Lan, WO 9805337 A1 (Feb. 12, 1998) (abstract). [Lan, Nancy C., "Use of GABA agonists and NMDA receptor antagonists for the treatment of migraine headache".]

De Crescenzo et al., "Selective serotonin reuptake inhibitors (SSRIs) for postpartum depression (PPD): A systematic review of randomized clinical trials". Journal of Affective Disorders, 152-154 (2014) 39-44.

Deligianndis et al., "Peripartum neuroactive steroid and y-aminobutyric acid profiles in women at-risk for postpartum depression," Psychoneuroendocrinology, Accepted Manuscript (2016), 33p.

Deligiannidis, et al. "GABAergic neuroactive steroids and resting-state functional connectivity in postpartum depression; A preliminary study", Journal of Psychiatric Research 47 (2013) 816-828.

Delorenzo et al., "Epidemiology of Status Epilepticus" Journal of Clinical Neurophysiology (1995), vol. 12, No. 4, pp. 316-325.

Deutsch et al., "Evaluation of in Vivo Interactions in Mice Between Flurazepam and Two Neuroactive Steroids", Pharmacology Biochemistry & Behavior (1996), vol. 55, No. 3, pp. 323-326.

Dhir et al., "Role of neurosteroids in the anticonvulsant activity of midazolam," British Journal of Pharmacology, (2012), 165(8): 2684-2691.

Dhir et al., "Seizure protection by intrapulmonary delivery of midazolam in mice," Neuropharmacology, (2013), 73:425-431.

Dhir et al., "Seizure protection by intrapulmonary delivery of propofol hemisuccinate," The Journal of Pharmacology and Experimental Therapeutics, (2011), 336(1):215-222.

Dorwald, "Side Reactions in Organic Synthesis", 2005, Wiley-VCH, Preface, p. IX.

Drugan et al. "Resilience in shock and swim stress models of depression". Frontiers in Behavorial Neuroscience, Feb. 2013, vol. 7, Article 14.

Dyck et al., "Effects of Deuterium Substitution on the Catabolism of beta-Phenylethylamine: An in Vivo Study". J. Neurochem., vol. 46(2), pp. 399-404 (1986).

Edgar et al., "CCD-3693: An Orally Bioavailable Analog of the Endogenous Neuroactive Steroid, Pregnanolone, Demonstrates Potent Sedalive Hypnotic Actions in the Rat" The Journal of Pharmacology and Experimental Therapeutics (1997) vol. 282, No. 1, pp. 420-429.

Eser et al., "Neuroactive Steroids in Depression and Anxiety Disorders: Clinical Studies", Neuroendocrinology, (2006) 84: pp. 244-254.

| Seizure Model | | mg/kg (IP) |
|---|---|---|
| Mouse | MES * | Active |
| | PTZ (sc) | MED = 0.3 (IP/PO) |
| | 6Hz (32 mA) | $ED_{50}$ = 1.9 |
| | 6Hz (44 mA)* | $ED_{50}$ > 10 |
| | Audiogenic | MED ≤ 0.1 |
| | Corneal Kindling * | $ED_{50}$ = 1.22 |
| | mTLE | MED ≤ 1.0 |
| Rat | MES * | Active |
| | LTG-resistant AMG Kindled* | $ED_{50}$ = 0.47 |
| | Li-pilocarpine SE | MED = 3 (IV) |

NEUROACTIVE STEROIDS, COMPOSITIONS, AND USES THEREOF

CROSS-REFERENCE TO RELATED APPLICATION

This application is a continuation of U.S. Ser. No. 16/718,430, filed Dec. 18, 2019, which is a continuation of U.S. Ser. No. 16/083,339, filed Sep. 7, 2018, which is a national stage application under 35 U.S.C. § 371 of International Application No. PCT/US2017/021325 filed, Mar. 8, 2017, which claims priority under 35 U.S.C. § 119(e) to U.S. Ser. No. 62/305,279 filed Mar. 8, 2016, U.S. Ser. No. 62/355,174 filed Jun. 27, 2016, U.S. Ser. No. 62/355,669 filed Jun. 28, 2016, U.S. Ser. No. 62/360,758 filed Jul. 11, 2016, and U.S. Ser. No. 62/360,762 filed Jul. 11, 2016, all of which are incorporated herein by reference in their entireties.

SUMMARY OF THE INVENTION

Progesterone and its metabolites have been demonstrated to have profound effects on brain excitability (Backstrom, T. et al., *Acta Obstet. Gynecol. Scand. Suppl.* 130:19-24 (1985); Pfaff, D. W and McEwen, B. S., *Science* 219:808-814 (1983); Gyermek et al., *J Med Chem.* 11: 117 (1968); Lambert, J. et al., Trends Pharmacol. Sci. 8:224-227 (1987)). The levels of progesterone and its metabolites vary with the phases of the menstrual cycle. It has been well documented that the levels of progesterone and its metabolites decrease prior to the onset of menses. The monthly recurrence of certain physical symptoms prior to the onset of menses has also been well documented. These symptoms, which have become associated with premenstrual syndrome (PMS), include stress, anxiety, and migraine headaches (Dalton, K., *Premenstrual Syndrome and Progesterone Therapy*, 2nd edition, Chicago Yearbook, Chicago (1984)). Subjects with PMS have a monthly recurrence of symptoms that are present in premenses and absent in postmenses.

A syndrome also related to low progesterone levels is postnatal depression (PND) or postpartum depression (PPD). Immediately after birth, progesterone levels decrease dramatically leading to the onset of PND. The symptoms of PND range from mild depression to psychosis requiring hospitalization. PND is also associated with severe anxiety and irritability. PND-associated depression is not amenable to treatment by classic antidepressants, and women experiencing PND show an increased incidence of PMS (Dalton, K., *Premenstrual Syndrome* and Progesterone Therapy, 2nd edition, Chicago Yearbook, Chicago (1984)).

Additionally, several lines of evidence suggest that cerebellar dysfunction through the cerebello-thalamocortical pathway play a key role in essential tremor (ET) (McAuley 2000; Pinto 2003; Elble 2009; Schnitzler 2009; Deuschl 2009). Activation studies with positron emission tomography (PET) indicate abnormally increased regional cerebral blood flow in the cerebellum both at rest and when tremor is provoked by unilateral arm extension (Boechker 1994, Wills 1996). Post-mortem analysis revealed a 35% reduction of GABAA receptors and a 22-31% reduction of GABAB receptors in the dentate nucleus of cerebella from ET patients (Paris-Robidas 2012).

There is increasing evidence to support the use of neuroactive steroids, e.g., a neuroactive steroid as described herein, e.g., progesterone and its metabolites; in the treatment and prevention of tremor (e.g., essential tremor), depression (e.g., postpartum depression, major depressive disorder), and anxiety disorder.

SUMMARY OF THE INVENTION

The disclosure features, inter alia, a method, the method comprising administering a neuroactive steroid, e.g., a neuroactive steroid as described herein, e.g., pregnanolone, allopregnanolone, alphadalone, ganaxolone, alphaxolone, or Compound 9 as described below, or a pharmaceutical composition comprising a neuroactive steroid (e.g., brexanolone) to a subject, for example to treat a CNS-related disorder such as tremor, depression (e.g., postpartum depression, major depressive disorder), or anxiety disorder. In some embodiments, the neuroactive steroid is formulated for parenteral delivery (e.g., intravenous delivery (IV)). The disclosure features methods of treating a subject having a CNS disorder, e.g., tremor, e.g., essential tremor; depression, e.g., postpartum depression; and anxiety disorder, the methods comprising administering to the subject a composition described herein, e.g., a neuroactive steroid, e.g., pregnanolone, allopregnanolone, alphadalone, ganaxolone, or alphaxolone, and optionally a cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®. The disclosure also features, inter alia, compositions comprising a neuroactive steroid, e.g., pregnanolone, allopregnanolone, alphadalone, ganaxolone, or alphaxolone; and optionally a cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®.

In an aspect, provided is a method for treating a human subject, the method comprising: identifying a subject at risk of suffering from depression (e.g., postpartum depression) or an anxiety disorder; and administering (e.g., orally, intravenously) to the subject a therapeutically effective amount of a therapeutic agent (e.g., a neuroactive steroid as described herein (e.g., allopregnanolone)) or a pharmaceutical composition comprising a therapeutic agent (e.g., a pharmaceutical composition as described herein, e.g., brexanolone). In some embodiments, the therapeutic agent is administered to the subject within 3 days, 2 days, 1 day, or 24 hours of delivery of a baby (e.g., within 12 hours, within 6 hours, within 3 hours, within 2 hours, within 1 hour, within 30 minutes).

In some embodiments, the subject is identified to be at risk through a screening method (e.g., Edinburgh Postnatal Depression Scale (EPDS), e.g., a score of 10 or more on the EPDS, a score of 13 or more on the EPDS). In some embodiments, the subject is identified to be at risk through screening instruments such as Patient Health Questionnaire (PHQ) in various forms or the Hospital Anxiety and Depression Scales or Geriatric Depression Scale.

In some embodiments, the subject has given birth. In some embodiments, the subject has given birth within 3, 2, or 1 days; 24, 20, 16, 12, 8, 6, 4, 3, 2, or 1 hours; or 60, 45, 30, 15, 10, or 5 minutes. In some embodiments, the subject is due to give birth. In some embodiments, the subject is due to give birth in 9, 8, 7, 6, 5, 4, 3, 2, or 1 months; 4, 3, 2, or 1 weeks; or 7, 6, 5, 4, 3, 2, or 1 days. In some embodiments, the subject is in her third trimester of pregnancy. In some embodiments, the subject has an attribute, characteristic, or exposure (that increases the likelihood of developing a disorder as described herein, e.g., neuroactive steroid deficiency). In some embodiments, the subject has a chronic illness (e.g., cancer or cardiovascular disease), other mental health disorders (including substance misuse), or a family history of psychiatric disorders. In some embodiments, the subject is disabled or has poor health status due to medical illness, complicated grief, chronic sleep disturbance, loneliness, or history of depression. In some embodiments, the subject has poor self-esteem, child-care stress, prenatal anxiety, life stress, decreased social support, single/unpartnered relationship status, history of depression, difficult infant temperament, previous postpartum depression, lower socioeconomic status, or unintended pregnancy. In some embodiments, the subject has hyperemesis gravidarum (e.g., severe form of morning sickness, e.g., preventing adequate intake of food and fluids). In some embodiments, the subject has had a complication in pregnancy (e.g., emergency C-sections, pre-eclampsia, hospitalization during pregnancy, concern about fetal distress and admission of the baby to special care (NICU), the baby was in the NICU). In some embodiments, the subject has had emotionally painful or stressful experiences around pregnancy, childbirth, or early parenting (e.g., the subject was treated for infertility, had a previous miscarriage or other pregnancy loss, delivery of muliples, special needs, colic or difficult temperament baby, had difficulty feeding). In some embodiments, the subject has had a history of domestic violence, sexual or other abuse (e.g., abused as a child or as an adult). In some embodiments, the subject has had a traumatic childhood (e.g., loss of a parent, troubling relationship with parent). In some embodiments, the subject has stress (e.g., loss of someone close, job loss, financial hardship, divorce, strain in a relationship, house move). In some embodiments, the subject has lack of social support. In some embodiments, the subject has a perfectionist or controlling personality.

In some embodiments, the therapeutic agent is a Selective Serotonin Reuptake Inhibitor (SSRI).

In some embodiments, the therapeutic agent is a neuroactive steroid described herein (e.g., a neuroactive steroid selected from pregnanolone, ganaxolone, alphadalone, alphaxalone, and allopregnanolone) or a pharmaceutically acceptable salt or isotopologue thereof). In some embodiments, the therapeutic agent is:

(Compound 1)

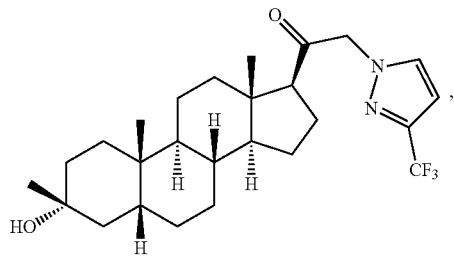

(Compound 2)

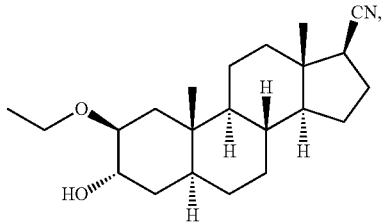

(Compound 3)

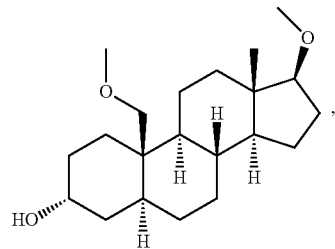

(Compound 4)

(Compound 5)

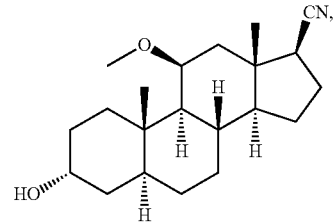

(Compound 6)

(Compound 7)

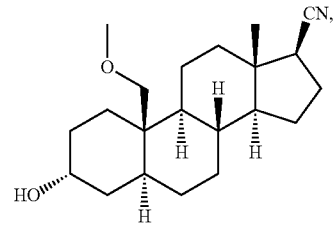

(Compound 8)

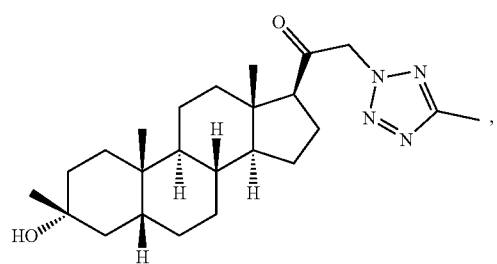

(Compound 9)
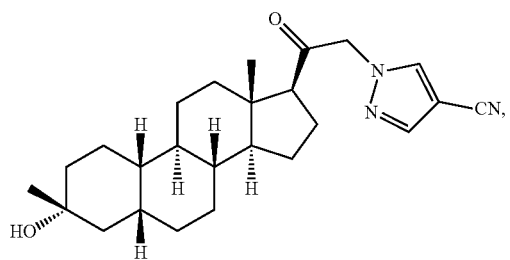
(Compound 10)
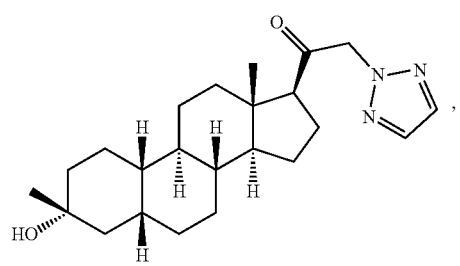
(Compound 11)
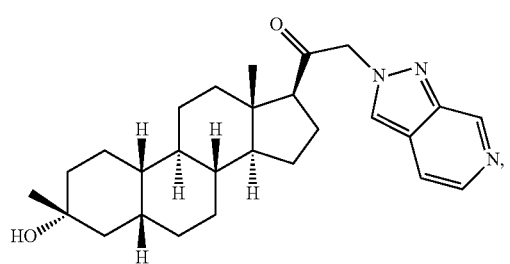
(Compound 12)
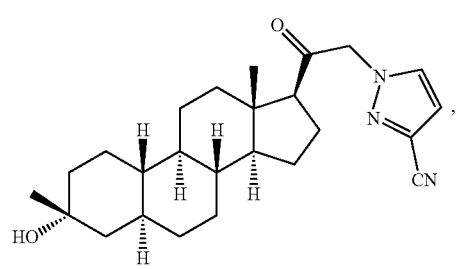
(Compound 13)
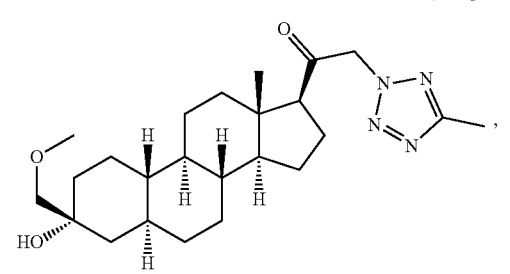
(Compound 14)
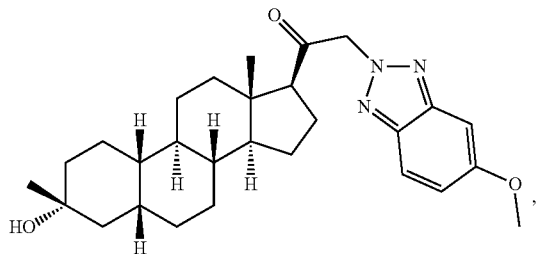
(Compound 15)
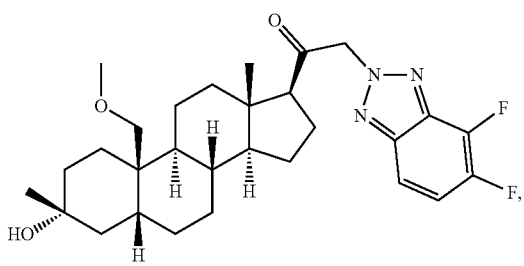
(Compound 16)
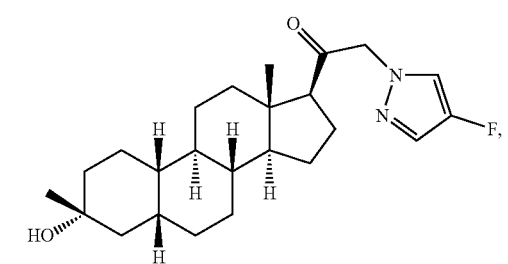
(Compound 17)
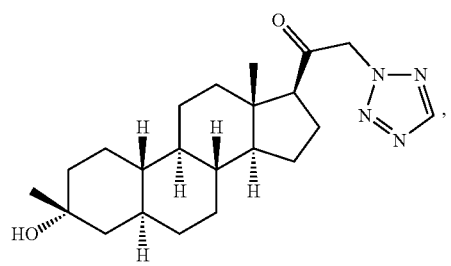
(Compound 18)
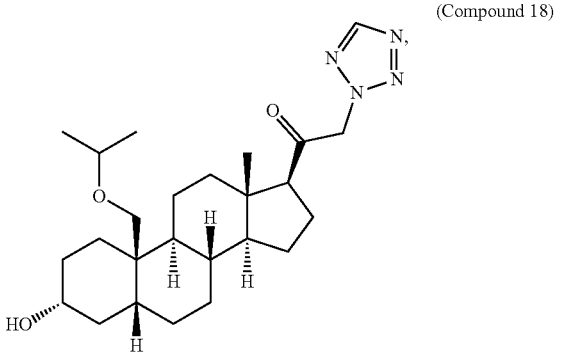

-continued

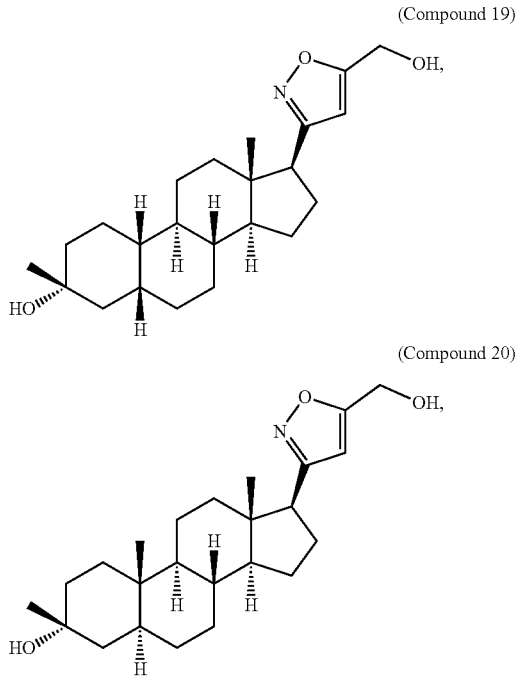

(Compound 19)

(Compound 20)

or a pharmaceutically acceptable salt or isotopologue thereof.

In some embodiments, the pharmaceutical composition is brexanolone. In some embodiments, the therapeutic agent is Compound 9 or a pharmaceutically acceptable salt or isotopologue thereof.

In some embodiments, when the therapeutic agent is allopregnanolone, then the therapeutic agent or pharmaceutical composition comprising the therapeutic agent (e.g., brexanolone) is administered parenterally, wherein administering occurs through an intermittent intravenous infusion or continuous intravenous infusion. In some embodiments, when the therapeutic agent is Compound 9, then the therapeutic agent or pharmaceutical composition comprising the therapeutic agent is administered orally. In some embodiments, the neuroactive steroid or pharmaceutical composition comprising the neuroactive steroid is administered chronically. In some embodiments, the neuroactive steroid or pharmaceutical composition comprising the neuroactive steroid is administered acutely.

In an aspect, provided is a method for treating a human subject suffering from depression (e.g., postpartum depression or major depressive disorder) or an anxiety disorder, the method comprising administering (e.g., orally, intravenously) to the subject a therapeutically effective amount of a neuroactive steroid (e.g., allopregnanolone) or pharmaceutically acceptable salt or isotopologue thereof or a pharmaceutical composition comprising a neuroactive steroid or pharmaceutically acceptable salt or isotopologue thereof (e.g., brexanolone).

In some embodiments, the depression is clinical depression (e.g., severe depression), postnatal or postpartum depression, atypical depression, melancholic depression, Psychotic Major Depression (PMD), catatonic depression, Seasonal Affective Disorder (SAD), dysthymia, double depression, Depressive Personality Disorder (DPD), Recurrent Brief Depression (RBD), minor depressive disorder, bipolar disorder or manic depressive disorder, post-traumatic stress disorders, depression caused by chronic medical conditions, treatment-resistant depression, refractory depression, suicidality, suicidal ideation, or suicidal behavior. In some embodiments, the depression is severe depression. In some embodiments, the depression is postpartum depression. In some embodiments, the depression is major depressive disorder.

In some embodiments, the method provides maintenance treatment or preventative treatment.

In some embodiments, the method provides acute treatment of the depression (e.g., within 72 hours, 60 hours, 48 hours, 24 hours, 12 hours, or less). In some embodiments, the method provides acute treatment of the depression or anxiety disorder (e.g., provides relief from a symptom in less than 1 week (e.g., within 6 days, 5 days, 4 days, 3 days, 2 days, 1 day, or 12 hours).

In some embodiments, the method provides rapid onset of efficacy (e.g., rapid reduction in a symptom of depression or anxiety disorder; rapidly affective to reduce a symptom of depression or anxiety disorder, e.g., a subject experiences relief from a symptom of depression or anxiety disorder described herein within 1 week (e.g., within 6 days, 5 days, 4 days, 3 days, 2 days, 1 day, or 12 hours)).

In some embodiments, the therapeutic effect is sustained (e.g., effectively treats a symptom of depression or anxiety disorder and the efficacy is maintained for at least 1 day (e.g., at least 2 days, 3 days, 4 days, 5 days, 6 days, 1 week, 2 weeks, 3 weeks, 1 month, 2 months, 3 months, 4 months, 5 months, or 6 months, 7 months, 8 months, 9 months, 10 months, 11 months, 1 year, 2 years, or more).

In some embodiments, the efficacy is maintained after a single course of treatment (e.g., single dose, multiple doses, or cycle of treatment) of a compound described herein (e.g., allopregnanolone) or pharmaceutical composition described herein (e.g., brexanolone).

In some embodiments, the therapeutic effect is does not cause an adverse event (e.g., does not cause a severe or moderate adverse event, e.g., during treatment or 3 days, 7 days, 10 days, 20 days, 30 days, 60 days, 90 days, 3 months, 4 months, 5 months, 6 months, 7 months, 8 months, 9 months, 10 months, 11 months, 12 months, or more after treatment).

In some embodiments, the method includes a course of treatment with multiple dosages or cycles of treatment (e.g., a first dose or cycle of treatment is a parenteral dose such as an i.v. dose, and a second dose or cycle of treament is an oral dose). In some embodiments, the first and second dose or cycle of treatment include the same compound. In some embodiments, the first dose or cycle of treatment includes a first compound (e.g., a first compound described herein such as allopregnanolone) and the second dose or cycle of treatment includes a second compound that is different from the first compound.

In some embodiments, the subject is substantially relieved of at least one symptom within 3, 2, 1 days; 24, 20, 16, 12, 10, 8 hours or less of said administration. In some embodiments, the subject is substantially relieved of at least one symptom for 1, 2, 3, 4, 5, 6, or 7 days; 1, 2, 3, or 4 weeks; or 1, 2, 3, 4, 5, 6, 7, 8, 9, 10, 11, 12 months or more.

In some embodiments, the neuroactive steroid is selected from pregnanolone, ganaxolone, alphadalone, alphaxalone, and allopregnanolone. In some embodiments, the neuroactive steroid is deuterated allopregnanolone. In some embodiments, the neuroactive steroid is an estrol. In some embodiments, the neuroactive steroid is:

(Compound 1)
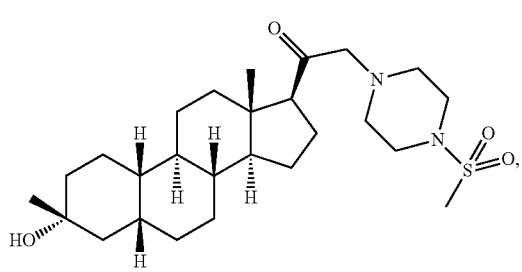
(Compound 2)
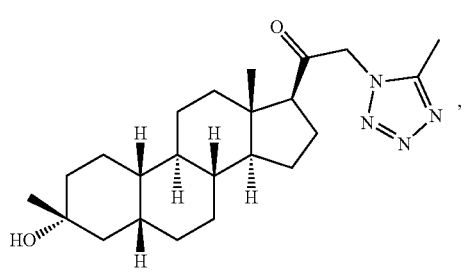
(Compound 3)
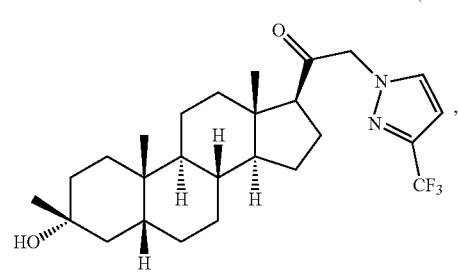
(Compound 4)
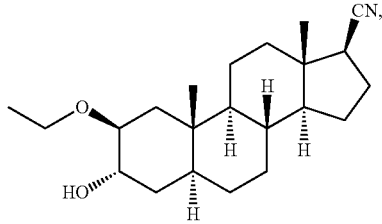
(Compound 5)
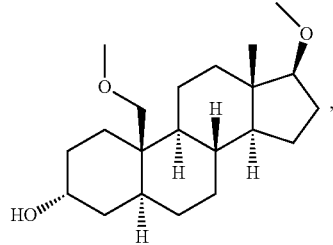
(Compound 6)
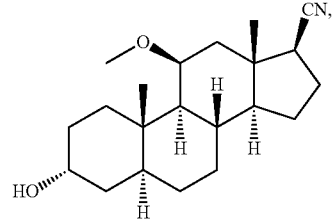
-continued
(Compound 7)
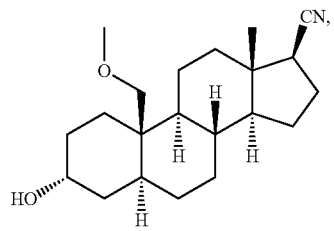
(Compound 8)
(Compound 9)
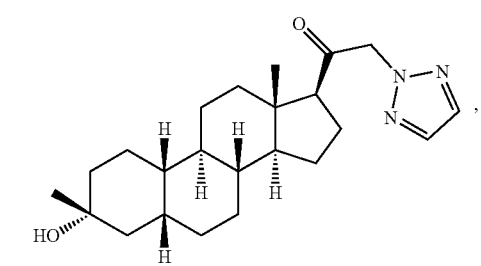
(Compound 10)
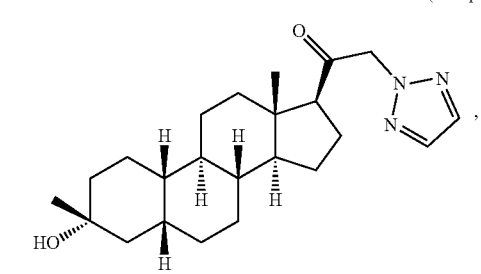
(Compound 11)
(Compound 12)
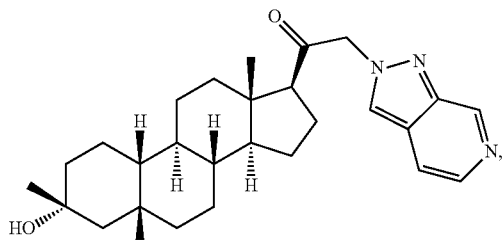

(Compound 13)

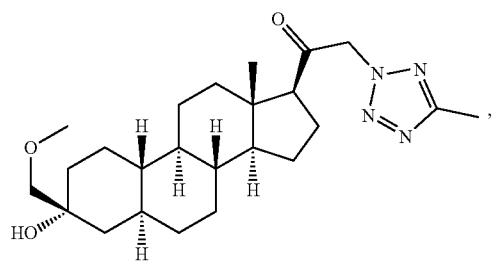

(Compound 14)

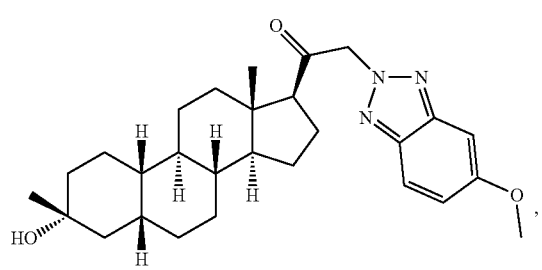

(Compound 15)

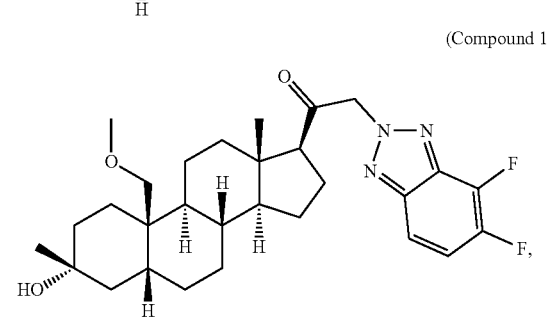

(Compound 16)

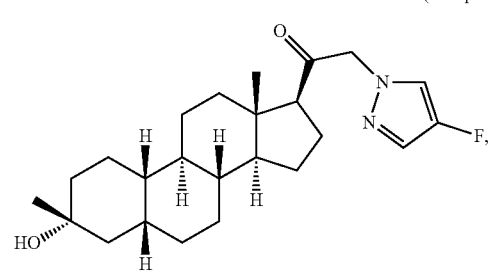

(Compound 17)

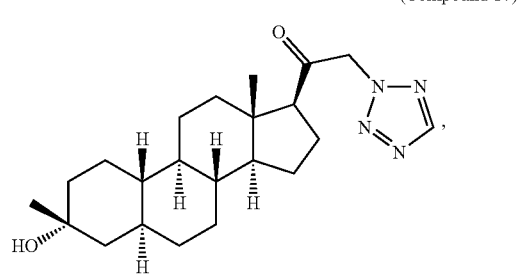

(Compound 18)

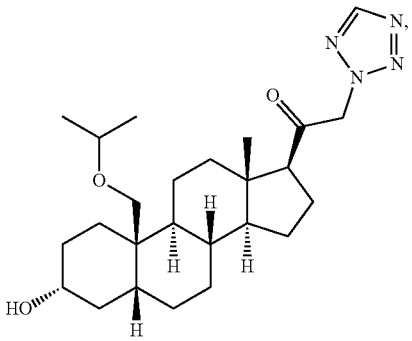

(Compound 19)

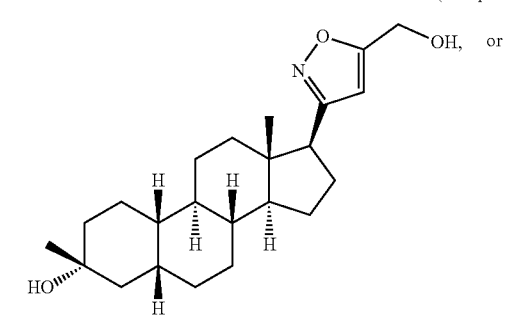

(Compound 20)

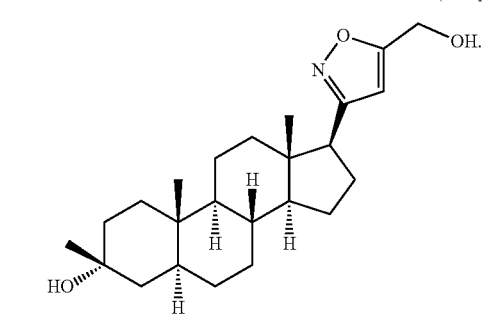

In some embodiments, the pharmaceutical composition is brexanolone.

In some embodiments, the neuroactive steroid is Compound 9 as described herein.

In some embodiments, when the neuroactive steroid is allopregnanolone, then the neuroactive steroid or pharmaceutical composition comprising the neuroactive steroid (e.g., brexanolone) is administered parenterally, wherein administering occurs through an intravenous intermittent infusion. In some embodiments, when the neuroactive steroid is Compound 9, then the neuroactive steroid or pharmaceutical composition comprising the neuroactive steroid is administered orally. In some embodiments, the neuroactive steroid or pharmaceutical composition comprising the neuroactive steroid is administered chronically. In some embodiments, the neuroactive steroid or pharmaceutical composition comprising the neuroactive steroid is administered acutely.

In some embodiments, the neuroactive steroid or pharmaceutically acceptable salt thereof or pharmaceutical composition comprising a neuroactive steroid is administered to the subject within 3 days, 2 days, 1 day, or 24 hours of delivery of a baby (e.g., within 12 hours, within 6 hours, within 3 hours, within 2 hours, within 1 hour, within 30 minutes).

In some embodiments, the subject is identified to be at risk through a screening method (e.g., Edinburgh Postnatal Depression Scale (EPDS), e.g., a score of 10 or more on the EPDS, a score of 13 or more on the EPDS). In some embodiments, the subject is identified to be at risk through screening instruments such as Patient Health Questionnaire (PHQ) in various forms or the Hospital Anxiety and Depression Scales or Geriatric Depression Scale.

In some embodiments, the subject has given birth. In some embodiments, the subject has given birth within 3, 2, or 1 days; 24, 20, 16, 12, 8, 6, 4, 3, 2, or 1 hours; or 60, 45, 30, 15, 10, or 5 minutes. In some embodiments, the subject is due to give birth. In some embodiments, the subject is due to give birth in 9, 8, 7, 6, 5, 4, 3, 2, or 1 months; 4, 3, 2, or 1 weeks; or 7, 6, 5, 4, 3, 2, or 1 days.

In some embodiments, the subject has an attribute, characteristic, or exposure (that increases the likelihood of developing a disorder as described herein, e.g., neuroactive steroid deficiency). In some embodiments, the subject has a chronic illness (e.g., cancer or cardiovascular disease), other mental health disorders (including substance misuse), or a family history of psychiatric disorders. In some embodiments, the subject is disabled or has poor health status due to medical illness, complicated grief, chronic sleep disturbance, loneliness, or history of depression. In some embodiments, the subject has poor self-esteem, child-care stress, prenatal anxiety, life stress, decreased social support, single/unpartnered relationship status, history of depression, difficult infant temperament, previous postpartum depression, lower socioeconomic status, or unintended pregnancy. In some embodiments, the subject has hyperemesis gravidarum (e.g., severe form of morning sickness, e.g., preventing adequate intake of food and fluids). In some embodiments, the subject has had a complication in pregnancy (e.g., emergency C-sections, pre-eclampsia, hospitalization during pregnancy, concern about fetal distress and admission of the baby to special care (NICU), the baby was in the NICU). In some embodiments, the subject has had emotionally painful or stressful experiences around pregnancy, childbirth, or early parenting (e.g., the subject was treated for infertility, had a previous miscarriage or other pregnancy loss, delivery of multiples, special needs, colic or difficult temperament baby, had difficulty feeding). In some embodiments, the subject has had a history of domestic violence, sexual or other abuse (e.g., abused as a child or as an adult). In some embodiments, the subject has had a traumatic childhood (e.g., loss of a parent, troubling relationship with parent). In some embodiments, the subject has stress (e.g., loss of someone close, job loss, financial hardship, divorce, strain in a relationship, house move). In some embodiments, the subject has lack of social support. In some embodiments, the subject has a perfectionist or controlling personality. In some embodiments, the subject is a female. In some embodiments, the female is not breast feeding. In some embodiments, the subject is an adult. In some embodiments, the subject is from 18 to 45 years of age. In some embodiments, the subject is suffering from (e.g., has been diagnosed with) postpartum depression (e.g., severe postpartum depression). In some embodiments, the subject has experienced a Major Depressive Episode in the postpartum period. In some embodiments, the period begins within the first 4 weeks following delivery of a baby.

In an aspect, provided is a method of treating a human subject suffering from tremor, the method comprising administering a therapeutically effective amount of a neuroactive steroid. In some embodiments, the method does not result in sedation. In some embodiments, the tremor is essential tremor.

In some embodiments, the administering is performed parenterally. In some embodiments, the administering is performed intravenously.

In some embodiments, the administering is performed orally.

In some embodiments, the administering comprises administering one or more cycles of treatment, a cycle of treatment comprising: administering a first dose of the neuroactive steroid; administering a second dose of the neuroactive steroid; and administering a third dose of the neuroactive steroid, said neuroactive steroid doses being sufficient to treat said subject.

In some embodiments, the first dose is 20 to 40 µg/kg/hr (e.g., about 30 µg/kg/hr, 29 µg/kg/hr). In some embodiments, the second dose is 45 to 65 µg/kg/hr (e.g., about 60 µg/kg/hr, 58 µg/kg/hr). In some embodiments, the third dose is 80 to 100 µg/kg/hr (e.g., about 90 µg/kg/hr, 86 µg/kg/hr). In some embodiments, each of the first, second, and third doses are 2 to 6 hours (e.g., 4 hours) in duration. In some embodiments, each of the first, second, and third doses are 1, 2, 3, 4, 5, or 6 hours in duration. In some embodiments, each of the first, second, and third doses are administered for equal periods of duration.

In some embodiments, the administering comprises administering two cycles of treatment.

In some embodiments, a rest period follows (e.g., immediately follows, is less than 60, 30, 20, 10, 5, 2, or 1 minute after) the first cycle of treatment. In some embodiments, a rest period precedes the second cycle of treatment. In some embodiments, a rest period follows the first cycle of treatment and precedes the second cycle of treatment. In some embodiments, the rest period is 6 to 8 days (e.g., 7 days) in duration.

In some embodiments, the amount of neuroactive steroid delivered/unit time in the second dose, e.g., as measured in µg/kg/hour, is 1 to 2 times higher than that of the first dose. In some embodiments, the amount of neuroactive steroid delivered/unit time in the third dose, e.g., as measured in µg/kg/hour, is 2 to 4 times higher than that of the first dose.

In some embodiments, said first dose results in a plasma concentration of 10 to 100 nM, 25 to 75 nM, 40 to 60, or 50 nM. In some embodiments, said second dose results in a plasma concentration of 20 to 200 nM, 50 to 150 nM, 80 to 120, or 100 nM. In some embodiments, said third dose results in a plasma concentration of 30 to 300 nM, 100 to 200 nM, 120 to 180, or 150 nM. In some embodiments, said first dose results in a plasma concentration of 50+/−10 nM, 50+/−5 nM, 50+/−2 nM, or 50 nM. In some embodiments, said second dose results in a plasma concentration of 100+/−20 nM, 100+/−10 nM, 100+/−5 nM, or 100 nM. In some embodiments, said third dose results in a plasma concentration of 150+/−30 nM, 150+/−20 nM, 150+/−10 nM, or 150 nM. In some embodiments, said first dose is administered over a period of time that is not longer than 6, 5, 4, or 3 hours. In some embodiments, said first dose is administered over a period of time that is at least 2, 3, or 4 hours in duration. In some embodiments, administration of the second dose occurs immediately after administration of the first dose. In some embodiments, administration of the third dose occurs immediately after administration of the second dose.

In some embodiments, the duration of administration is at least 12, 24, 48, 72, or 96 hours in duration. In some embodiments, the duration of administration is about 40, 50, 60, or 70 hours. In some embodiments, the administration is performed continuously.

In some embodiments, the administering comprises administering one or more cycles of treatment, a cycle of treatment comprising: providing a single infusion of the neuroactive steroid.

In some embodiments, the administering comprises administering one or more cycles of treatment, a cycle of treatment comprising: administering a first infusion of the neuroactive steroid; and administering a second infusion of the neuroactive steroid; said neuroactive steroid infusions being sufficient to treat said subject.

In some embodiments, the administration of the second infusion occurs immediately after administration of the first infusion. In some embodiments, the amount of neuroactive steroid delivered/unit time in the second infusion, e.g., as measured in µg/kg/hour, is higher than that of the first infusion. In some embodiments, the amount of neuroactive steroid delivered/unit time in the second infusion, e.g., as measured in µg/kg/hour, is at least 1 to 2 times higher than that of the first infusion. In some embodiments, the amount of neuroactive steroid delivered/unit time in the second infusion, e.g., as measured in µg/kg/hour, is lower than that of the first infusion. In some embodiments, the amount of neuroactive steroid delivered/unit time in the second infusion, e.g., as measured in µg/kg/hour, is at least 1 to 2 times lower than that of the first infusion.

In some embodiments, the method comprises administering a plurality of infusions. In some embodiments, the method comprises administering a first and second infusion. In some embodiments, the administration of the second infusion begins no longer than 90, 60, 30, 10, or 5 minutes after the beginning or end of the administration of the first infusion. In some embodiments, the second infusion begins 0 to 90, 0 to 60, 0 to 30, 0 to 10, or 0 to 5 minutes after the beginning or end of the administration of the first infusion. In some embodiments, the second infusion begins no more than 60, 30, 20, 10, 5, 4, 3, 2, or 1 minute(s) after the end of administration of the first infusion. In some embodiments, the second infusion begins at the end of administration of the first infusion. In some embodiments, the first infusion and the initiation of the second infusion are performed with the same delivery device, e.g., with the same cannula or reservoir. In some embodiments, the amount of neuroactive steroid delivered/unit time varies during the first infusion.

In some embodiments, the first (step-up) infusion delivers a smaller amount of neuroactive steroid/unit time than the second (maintenance) infusion. In some embodiments, the first (step-up) infusion comprises administering a plurality of step doses, wherein each subsequent step dose delivers a larger amount of neuroactive steroid/unit time than the step dose that precedes it.

In some embodiments, the amount of neuroactive steroid delivered/unit time varies during the second (step-down) infusion. In some embodiments, the second (step-down) infusion delivers a smaller amount of neuroactive steroid/ unit time than the first (maintenance) infusion. In some embodiments, the second (step-down) infusion comprises administering a plurality of step doses, wherein each subsequent step dose delivers a smaller amount of neuroactive steroid/unit time than the step dose that precedes it.

In some embodiments, the subject is 35 to 75 years of age. In some embodiments, the subject has a TETRAS Performance Subscale score of 2 or greater for at least one maneuver selected from forward horizontal reach posture, lateral "wing beating" posture, or finger-nose-finger testing; in the 'upper limb tremor' test.

In some embodiments, the method provides acute treatment of the tremor (e.g., provides relief from a symptom in less than 1 week (e.g., within 6 days, 5 days, 4 days, 3 days, 2 days, 1 day, or 12 hours).

In some embodiments, the method provides rapid onset of efficacy (e.g., rapid reduction in a symptom of tremor; rapidly affective to reduce a symptom of tremor, e.g., a subject experiences relief from a symptom of a tremor within 1 week (e.g., within 6 days, 5 days, 4 days, 3 days, 2 days, 1 day, or 12 hours)).

In some embodiments, the therapeutic effect is sustained (e.g., effectively treats a symptom of tremor and the efficacy is maintained for at least 1 day (e.g., at least 2 days, 3 days, 4 days, 5 days, 6 days, 1 week, 2 weeks, 3 weeks, 1 month, 2 months, 3 months, 4 months, 5 months, or 6 months).

In some embodiments, the efficacy is maintained after a single course of treatment (e.g., single dose, multiple doses, or cycle of treatment) of a compound described herein (e.g., allopregnanolone).

In some embodiments, the therapeutic effect is does not cause an adverse event (e.g., does not cause a severe or moderate adverse event, e.g., during treatment or 3 days, 7 days, 10 days, 20 days, 30 days, 60 days, 90 days, 3 months, 4 months, 5 months, 6 months, 7 months, 8 months, 9 months, 10 months, 11 months, 12 months, or more after treatment).

In some embodiments, the method includes a course of treatment with multiple dosages or cycles of treatment (e.g., a first dose or cycle of treatment is a parenteral dose such as an i.v. dose, and a second dose or cycle of treatment is an oral dose).

In some embodiments, the first and second dose or cycle of treatment include the same compound. In some embodiments, the first dose or cycle of treatment includes a first compound (e.g., a first compound described herein such as allopregnanolone) and the second dose or cycle of treatment includes a second compound that is different from the first compound.

In some embodiments, the subject has been diagnosed with essential tremor. In some embodiments, the subject has suffered from tremor for at least 2 years.

In an aspect, provided is a method of treating a subject suffering from tremor (e.g., essential tremor), comprising: administering a first dose, wherein administration of said first dose; and results in a plasma level of neuroactive steroid of 50 to 300 nM neuroactive steroid; a rest period comprising at least 1, 2, 3, 4, 5, 6, 7, 8, 9, or 10 days; and administering a second dose, wherein administration of said second dose; and results in a plasma level of neuroactive steroid of 50 to 300 nM neuroactive steroid; wherein, collectively, the administrations are provided in sufficient amount to treat said subject. In some embodiments, the method does not result in sedation.

In an aspect, provided is a method of treating a subject suffering from tremor (e.g., essential tremor), comprising: administering a first dose, wherein administration of said first dose lasts for at least 1 day; and results in a plasma level of neuroactive steroid of 100 to 200 nM neuroactive steroid; a rest period comprising at least 5, 6, or 7 days; and administering a second dose, wherein administration of said second dose lasts for at least 1 day; and results in a plasma level of neuroactive steroid of 100 to 200 nM neuroactive steroid; wherein, collectively, the administrations are provided in sufficient amount to treat said subject. In some embodiments, the method does not result in sedation.

In an aspect, provided is a method of treating a subject suffering from tremor (e.g., essential tremor), comprising: administering a first dose, wherein administration of said first dose lasts for 1 day; and results in a plasma level of neuroactive steroid of 150 nM neuroactive steroid; a rest period comprising 7 days; and administering a second dose, wherein administration of said second dose lasts for 1 day; and results in a plasma level of neuroactive steroid of 150 nM neuroactive steroid; wherein, collectively, the administrations are provided in sufficient amount to treat said subject. In some embodiments, the method does not result in sedation.

In some embodiments, the administration of the second dose begins no longer than 1, 2, 3, 4, 5, 6, 7, 8, 9, 10, 11, or 12 days after the beginning or end of the administration of the first dose. In some embodiments, the second dose begins 1 to 14, 3 to 12, 5 to 10, or 7 days after the beginning or end of the administration of the first dose. In some embodiments, the second dose begins no more than 14, 12, 10, 9, 8, 7, 6, 5, 3, 2, or 1 day after the end of administration of the first dose. In some embodiments, the first dose and the initiation of the second dose are performed with the same delivery device, e.g., with the same cannula or reservoir. In some embodiments, the plasma concentration of said third dose is measured at a preselected time, e.g., at 10, 15, 20, 30, 45, or 60 minutes, 2, 3, 4, 5, 6, 8, 10, 12, or 24 hours, or 2, 3, or 4 days after the initiation of said third dose. In some embodiments, said third dose results in a plasma concentration of 150 nM, e.g., as measured at a preselected time, e.g., at 10, 15, 20, 30, 45, or 60 minutes, 2, 3, 4, 5, 6, 8, 10, 12, or 24 hours, or 2, 3, or 4 days after the initiation of said third dose.

In an aspect, provided is a method of treating a subject suffering from tremor (e.g., essential tremor) comprising the steps of: a) receiving information related to the therapeutic effect of a neuroactive steroid (e.g., allopregnanolone or Compound 9) in reducing tremor (e.g., symptoms of tremor) in a subject treated with the neuroactive steroid (e.g., allopregnanolone or Compound 9); and b) administering to the subject a therapeutic agent (e.g., neuroactive steroid) if the information indicates that tremor (e.g., symptoms of tremor) is reduced in the subject as compared to the subject before having received the neuroactive steroid (e.g., allopregnanolone or Compound 9), thereby treating the subject.

In an aspect, provided is a method of selecting a therapeutic agent (e.g., a neuroactive steroid) for treating tremor (e.g., essential tremor) in a human subject treated with a neuroactive steroid (e.g., allopregnanolone or Compound 9) comprising the steps of: a) receiving information related to the therapeutic effect of a neuroactive steroid (e.g., allopregnanolone or Compound 9) in reducing tremor (e.g., symptoms of tremor) in a subject; and b) selecting the therapeutic agent (e.g., neuroactive steroid) if the information indicates that tremor (e.g., symptoms of the depression or anxiety disorder) is reduced in the subject as compared to the subject before having received the neuroactive steroid (e.g., allopregnanolone or Compound 9).

In an aspect, provided is a method of evaluating (e.g., diagnosing, prognosing, and determining a course of treatment in) a subject suffering from tremor (e.g., essential tremor), comprising the steps of: a) receiving information related to the therapeutic effect of a neuroactive steroid (e.g., allopregnanolone) in reducing tremor (e.g., symptoms of tremor) in a subject treated with the neuroactive steroid (e.g., allopregnanolone); and b) determining if tremor (e.g., symptoms of tremor) is reduced in the subject as compared to the subject before receiving the neuroactive steroid (e.g., allopregnanolone), thereby evaluating the subject.

In some embodiments, the information is received, e.g., about 1, 2, 3, 4, 5, or 6 days; about 1, 2, or 3 weeks; about 1, 2, or 3 months after administration of the neuroactive steroid (e.g., allopregnanolone).

In some embodiments, the subject has been administered the neuroactive steroid less than about 3 months (e.g., less than about 2 or 1 month; 3, 2, or 1 weeks; 6, 5, 4, 3, 2, or 1 days) prior to receiving the information. In some embodiments, the subject has been administered the neuroactive steroid (e.g., allopregnanolone) by intravenous infusion.

In some embodiments, the therapeutic agent is administered by oral administration. In some embodiments, the therapeutic agent is administered as a solid composition (e.g., a solid dosage form).

In an aspect, provided is a method of evaluating (e.g., diagnosing, prognosing, or determining a course of treatment in) a subject suffering from tremor (e.g., essential tremor), comprising the steps of: a) administering to the subject a therapeutic agent (e.g., neuroactive steroid); and b) receiving information related to the therapeutic effect of a neuroactive steroid (e.g., allopregnanolone) in reducing tremor (e.g., symptoms of tremor) in a subject treated with the neuroactive steroid (e.g., allopregnanolone), thereby evaluating the subject. In some embodiments, the information is acquired by imaging the subject or a sample from the subject. In some embodiments, the information is acquired by fMRI. In some embodiments, the information is acquired by SPECT.

In an aspect, provided is a method for treating a human subject suffering from depression (e.g., postpartum depression) or an anxiety disorder, the method comprising: administering a first infusion of a neuroactive steroid, wherein said first/step-up infusion is administered for 8-16 hours (e.g., 12 hours); administering a second/maintenance infusion of a neuroactive steroid, wherein said second/maintenance infusion is administered for 24-48 hours (e.g., 36 hours); and administering a third infusion of a neuroactive steroid, wherein said third/downward taper infusion is administered for 8-16 hours (e.g., 12 hours); said neuroactive steroid doses being sufficient to treat said subject.

In some embodiments, the subject is identified to be at risk through a screening method (e.g., Edinburgh Postnatal Depression Scale (EPDS), e.g., a score of 10 or more on the EPDS, a score of 13 or more on the EPDS). In some embodiments, the subject is identified to be at risk through screening instruments such as Patient Health Questionnaire (PHQ) in various forms or the Hospital Anxiety and Depression Scales or Geriatric Depression Scale.

In some embodiments, the subject has given birth. In some embodiments, the subject has given birth within 3, 2, 1 days; 24, 20, 16, 12, 8, 6, 4, 3, 2, 1 hours; 60, 45, 30, 15, 10, 5 minutes. In some embodiments, the subject is due to give birth. In some embodiments, the subject is due to give birth in 9, 8, 7, 6, 5, 4, 3, 2, 1 months; 4, 3, 2, 1 weeks; 7, 6, 5, 4, 3, 2, 1 days.

In some embodiments, the subject has an attribute, characteristic, or exposure (that increases the likelihood of developing a disorder as described herein, e.g., neuroactive steroid deficiency). In some embodiments, the subject has a chronic illness (e.g., cancer or cardiovascular disease), other mental health disorders (including substance misuse), or a family history of psychiatric disorders. In some embodiments, the subject is disabled or has poor health status due to medical illness, complicated grief, chronic sleep disturbance, loneliness, or history of depression. In some embodiments, the subject has poor self-esteem, child-care stress, prenatal anxiety, life stress, decreased social support, single/unpartnered relationship status, history of depression, difficult infant temperament, previous postpartum depression, lower socioeconomic status, or unintended pregnancy.

In some embodiments, the subject has hyperemesis gravidarum (e.g., severe form of morning sickness, e.g., preventing adequate intake of food and fluids). In some embodiments, the subject has had a complication in pregnancy (e.g., emergency C-sections, pre-eclampsia, hospitalization during pregnancy, concern about fetal distress and admission of the baby to special care (NICU), the baby was in the NICU). In some embodiments, the subject has had emotionally painful or stressful experiences around pregnancy, childbirth, or early parenting (e.g., the subject was treated for infertility, had a previous miscarriage or other pregnancy loss, delivery of multiples, special needs, colic or difficult temperament baby, had difficulty feeding). In some embodiments, the subject has had a history of domestic violence, sexual or other abuse (e.g., abused as a child or as an adult). In some embodiments, the subject has had a traumatic childhood (e.g., loss of a parent, troubling relationship with parent). In some embodiments, the subject has stress (e.g., loss of someone close, job loss, financial hardship, divorce, strain in a relationship, house move). In some embodiments, the subject has lack of social support. In some embodiments, the subject has a perfectionist or controlling personality.

In an aspect, provided is a method for treating a human subject suffering from depression (e.g., postpartum depression or major depressive disorder) or an anxiety disorder, the method comprising: administering a first infusion of a neuroactive steroid, said first/step-up infusion comprising administering a continuously increasing amount of neuroactive steroid at an amount of neuroactive steroid/unit time of 5-100 µg/kg/hour, 10-80 µg/kg/hour, 15-70 µg/kg/hour, or 30 µg/kg/hour; administering a second/maintenance infusion of a neuroactive steroid, said second/maintenance infusion comprising administering an amount of neuroactive steroid/unit time of 50-100 µg/kg/hour, 70-100 µg/kg/hour, 86 µg/kg/hour, or 60 µg/kg/hour; and administering a third infusion of a neuroactive steroid, said third/downward taper infusion comprising administering a continuously decreasing amount of neuroactive steroid at an amount of neuroactive steroid/unit time of 5-100 µg/kg/hour, 10-80 µg/kg/hour, 15-70 µg/kg/hour, or 90 µg/kg/hour; said neuroactive steroid doses being sufficient to treat said subject.

In some embodiments, the method provides therapeutic effect (e.g., as measured by reduction in Hamilton Depression Score (HAM-D)) within 4, 3, 2, or 1 days; or 24, 20, 16, 12, 10, or 8 hours or less. In some embodiments, the therapeutic effect is a decrease from baseline in HAM-D score at the end of a treatment period (e.g., 12, 24, or 48 hours after administration; or 24, 48, 60, 72, or 96 hours or more).

In some embodiments, the method provides therapeutic effect (e.g., as measured by reduction in Edinburgh Postnatal Depression Scale (EPDS)) within 4, 3, 2, or 1 days; or 24, 20, 16, 12, 10, or 8 hours or less. In some embodiments, the therapeutic effect is a improvement measured by the EPDS.

In some embodiments, the method provides therapeutic effect (e.g., as measured by reduction in Clinical Global Impression-Improvement Scale (CGI)) within 4, 3, 2, 1 days; 24, 20, 16, 12, 10, 8 hours or less. In some embodiments, the therapeutic effect is a CGI score of 2 or less.

In some embodiments, the subject is identified to be at risk through a screening method (e.g., Edinburgh Postnatal Depression Scale (EPDS), e.g., a score of 10 or more on the EPDS, a score of 13 or more on the EPDS). In some embodiments, the subject is identified to be at risk through screening instruments such as Patient Health Questionnaire (PHQ) in various forms or the Hospital Anxiety and Depression Scales or Geriatric Depression Scale.

In some embodiments, the subject has given birth (e.g., a live birth, stillbirth, miscarriage). In some embodiments, the subject has given birth within 3, 2, 1 days; 24, 20, 16, 12, 8, 6, 4, 3, 2, 1 hours; 60, 45, 30, 15, 10, 5 minutes. In some embodiments, the subject is due to give birth. In some embodiments, the subject is in her third trimester of pregnancy. In some embodiments, the subject has reached term pregnancy (e.g., early term (i.e., between 37 weeks and 38 weeks and 6 days); full term (i.e., between 39 weeks and 40 weeks and 6 days); late term (i.e., between 41 weeks and 41 weeks and 6 days); or postterm (i.e., 42 weeks and beyond)) or has given early term, full term, late term, or postterm birth. In some embodiments, the subject is due to give birth in 9, 8, 7, 6, 5, 4, 3, 2, 1 months; 4, 3, 2, 1 weeks; 7, 6, 5, 4, 3, 2, 1 days. In some embodiments, the subject has terminated her pregnancy. In some embodiments, the subject has had an abortion.

In some embodiments, the subject has an attribute, characteristic, or exposure (that increases the likelihood of developing a disorder as described herein, e.g., neuroactive steroid deficiency). In some embodiments, the subject has a chronic illness (e.g., cancer or cardiovascular disease), other mental health disorders (including substance misuse), or a family history of psychiatric disorders. In some embodiments, the subject is disabled or has poor health status due to medical illness, complicated grief, chronic sleep disturbance, loneliness, or history of depression. In some embodiments, the subject has poor self-esteem, child-care stress, prenatal anxiety, life stress, decreased social support, single/unpartnered relationship status, history of depression, difficult infant temperament, previous postpartum depression, lower socioeconomic status, or unintended pregnancy.

In some embodiments, the subject has hyperemesis gravidarum (e.g., severe form of morning sickness, e.g., preventing adequate intake of food and fluids). In some embodiments, the subject has had a complication in pregnancy (e.g., emergency C-sections, pre-eclampsia, hospitalization during pregnancy, concern about fetal distress and admission of the baby to special care (NICU), the baby was in the NICU). In some embodiments, the subject has had emotionally painful or stressful experiences around pregnancy, childbirth, or early parenting (e.g., the subject was treated for infertility, had a previous miscarriage or other pregnancy loss, delivery of muliples, special needs, colic or difficult temperament baby, had difficulty feeding). In some embodiments, the subject has had a history of domestic violence, sexual or other abuse (e.g., abused as a child or as an adult). In some embodiments, the subject has had a traumatic childhood (e.g., loss of a parent, troubling relationship with parent). In some embodiments, the subject has stress (e.g., loss of someone close, job loss, financial hardship, divorce, strain in a relationship, house move). In some embodiments, the subject has lack of social support. In some embodiments, the subject has a perfectionist or controlling personality.

In an aspect, provided is a method of treating a subject suffering from depression or an anxiety disorder comprising the steps of: a) receiving information related to the therapeutic effect of a neuroactive steroid (e.g., allopregnanolone or Compound 9) in reducing the depression or anxiety disorder (e.g., symptoms of the depression or anxiety disorder) in a subject treated with the neuroactive steroid (e.g., allopregnanolone or Compound 9); and b) administering to the subject a therapeutic agent (e.g., a neuroactive steroid) if the information indicates that the depression or anxiety disorder (e.g., symptoms of the depression or anxiety disorder) is reduced in the subject as compared to the subject before having received the neuroactive steroid (e.g., allopregnanolone or Compound 9), thereby treating the subject. In some embodiments, the depression is major depressive disorder. In some embodiments, the depression is postpartum depression.

In an aspect, provided is a method of selecting a therapeutic agent (e.g., a neuroactive steroid) for treating depression or an anxiety disorder in a human subject treated with a neuroactive steroid (e.g., allopregnanolone or Compound 9) comprising the steps of: a) receiving information related to the therapeutic effect of a neuroactive steroid (e.g., allopregnanolone or Compound 9) in reducing the depression or anxiety disorder (e.g., symptoms of the depression or anxiety disorder) in a subject; and b) selecting the therapeutic agent (e.g., neuroactive steroid) if the information indicates that the depression or anxiety disorder (e.g., symptoms of the depression or anxiety disorder) is reduced in the subject as compared to the subject before having received the neuroactive steroid (e.g., allopregnanolone or Compound 9). In some embodiments, the depression is major depressive disorder. In some embodiments, the depression is postpartum depression.

In an aspect, provided is a method of evaluating (e.g., diagnosing, prognosing, and determining a course of treatment in) a subject suffering from depression or anxiety disorder, comprising the steps of:
a) receiving information related to the therapeutic effect of a neuroactive steroid (e.g., allopregnanolone or Compound 9) in reducing depression or anxiety disorder (e.g., symptoms of the depression or anxiety disorder) in a subject treated with the neuroactive steroid (e.g., allopregnanolone or Compound 9); and b) determining if the depression or anxiety disorder (e.g., symptoms of the depression or anxiety disorder) is reduced in the subject as compared to the subject before receiving the neuroactive steroid (e.g., allopregnanolone), thereby evaluating the subject. In some embodiments, the information is received, e.g., about 1, 2, 3, 4, 5, or 6 days; about 1, 2, or 3 weeks; about 1, 2, or 3 months after administration of the neuroactive steroid (e.g., allopregnanolone). In some embodiments, the subject has been administered the neuroactive steroid less than about 3 months (e.g., less than about 2 or 1 month; 3, 2, or 1 weeks; 6, 5, 4, 3, 2, or 1 days) prior to receiving the information. In some embodiments, the subject has been administered the neuroactive steroid (e.g., allopregnanolone) by intravenous infusion. In some embodiments, the therapeutic agent is administered by oral administration. In some embodiments, the therapeutic agent is administered as a solid composition (e.g., a solid dosage form).

In an aspect, provided is a method of evaluating (e.g., diagnosing, prognosing, or determining a course of treatment in) a subject suffering from depression or anxiety disorder, comprising the steps of:
a) administering to the subject a therapeutic agent (e.g., neuroactive steroid or Compound 9); and b) receiving information related to the therapeutic effect of a neuroactive steroid (e.g., allopregnanolone or Compound 9) in reducing the depression or anxiety disorder (e.g., symptoms of the depression or anxiety disorder) in a subject treated with the neuroactive steroid (e.g., allopregnanolone or Compound 9), thereby evaluating the subject. In some embodiments, the information is acquired by imaging the subject or a sample from the subject. In some embodiments, the information is acquired by fMRI. In some embodiments, the information is acquired by SPECT.

In an aspect, provided is a method of treating a subject suffering from a neuroendocrine disease (or neuroendocrine dysfunction), comprising: intravenously administering to the subject a therapeutically effective amount of a neuroactive steroid (e.g., allopregnanolone), wherein administering occurs by continuous intravenous infusion or intermittent intravenous infusion. In some embodiments, the concentrations of allopregnanolone in plasma is greater than that in a normal subject. In some embodiments, the concentrations of allopregnanolone in plasma is 10 nM in plasma or less.

In an aspect, provided is a method of treating a symptom of a neuroendocrine diseases (or neuroendocrine dysfunction), comprising: intravenously administering to the subject a therapeutically effective amount of a neuroactive steroid (e.g., allopregnanolone), wherein administering occurs by continuous intravenous infusion. In some embodiments, the symptom is reduced at a magnitude or rate different from that observed in a subject without having received treatment.

In an aspect, provided is a method of increasing allopregnanolone levels in a subject (e.g., a subject with low levels of allopregnanolone as compared with a subject with normal levels of allopregnanolone), comprising: intravenously administering to the subject a therapeutically effective amount of a neuroactive steroid (e.g., allopregnanolone), wherein administering occurs by continuous intravenous infusion or intermittent infusion.

In one aspect, provided herein are methods for treating a disease or disorder described herein, comprising administering to a subject a therapeutically effective amount of Compound 9

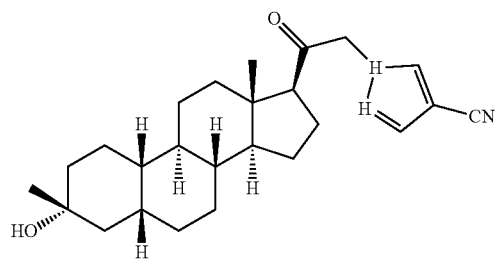

(Compound 9)

or pharmaceutically acceptable salt or isotopologue thereof.

In an aspect, provided is a method for treating or preventing a disorder described herein, comprising orally administering a total daily dose of Compound 9, or pharmaceutically acceptable salt or isotopologue thereof, or pharmaceutical composition thereof of about 10 mg to about 100 mg to a subject in need thereof.

In some embodiments, Compound 9, or a pharmaceutically acceptable salt or isotopologue thereof, or pharmaceutical composition thereof is administered chronically. In some embodiments, Compound 9, or pharmaceutically acceptable salt or isotopologue thereof, or pharmaceutical composition thereof is administered acutely.

In some embodiments, the disease or disorder is a GABA-related disease or disorder. In some embodiments, the GABA receptor is modulated (e.g., as determined by assessment of electrical activity in the brain using an electroencephalogram (EEG)). In some embodiments, the GABA receptor is modulated (e.g., as determined by assessment of electrical activity in the brain by beta-band EEG).

In some embodiments, the subject is administered about 10 mg to about 80 mg (e.g., about 10 mg to about 60 mg) of the compound. In some embodiments, the subject is administered about 10 mg to about 50 mg (e.g., about 35 mg) of the compound. In some embodiments, the subject is administered less than about 100 mg, less than about 80 mg, less than about 60 mg, less than about 50, less than about 40, less than about 20 mg.

In some embodiments, the subject is administered at least once a day. In some embodiments, the subject is administered once a day.

In some embodiments, the subject is administered for at least 1, 2, 3, 4, 5, 6, 7 days. In some embodiments, the subject is administered for 1, 2, 3, 4, 5, 6, 7 days.

In some embodiments, the subject has not had food for 1, 2, 4, 6, 8, 12, 24 hours. In some embodiments, the subject has had food within 1, 2, 4, 6, 8, 12, 24 hours of administration.

In some embodiments, the subject is administered as a pharmaceutical composition. In some embodiments, the subject is administered a solution formulation. In some embodiments, the subject is administered a suspension formulation. In some embodiments, the subject is administered a solid dosage formulation.

In some embodiments, the composition comprises a cyclodextrin (e.g., sulfoalkyl ether β-cyclodextrin (SAEBCD) or hydroxypropyl β-cyclodextrin (HPBCD)).

In some embodiments, the disorder is a seizure or epilepsy disorder (e.g., orphan epilepsies (e.g., Dravet syndrome, Lennox-Gastaut syndrome, Tuberous sclerosis complex, Rett syndrome, PCDH19 epilepsy), seizure associated with a neurological disorder).

In some embodiments, the disorder is depression (e.g., postpartum depression).

In some embodiments, the subject does not experience an adverse effect (e.g., a serious adverse event or severe adverse event as described herein). In some embodiments, the subject does not experience an increase from pre-dose supine blood pressure (e.g., systolic, diastolic) 1, 2, 4, 8, 12, 24 hours or more after administration. In some embodiments, the subject does not experience an increase in heart rate from 1, 2, 4, 8, 12, 24 hours or more after administration. In some embodiments, the subject experiences sedation (e.g., mild, transient, and associated with daily peak exposure). In some embodiments, the subject does not experience sedation (e.g., rate of moderate to deep sedation as defined by a structured rating scale (e.g., MOAA/S) is comparable to placebo (e.g., MOAA/S is less than 3, MOAA/S is less than 2). In some embodiments, the subject is not sedated relative to a reference standard. In some embodiments, the reference standard is the amount of sedation relative to a subject administered a placebo. In some embodiments, the subject does not experience sedation, as measured in a score of 3 or less as measured by MOAA/S (e.g., as measured in a score of 2 or less as measured by MOAA/S. (e.g., rate of moderate to deep sedation as defined by a structured rating scale (e.g., MOAA/S) is comparable to placebo (e.g., MOAA/S is 3 or less, MOAA/S is 2 or less). In some embodiments, the subject does not experience sedation e.g., as measured by a score of 5 or higher as measured by SSS. In some embodiments, the subject does not experience impact on cognition e.g., as measured by testing of psychomotor function, attention, visual learning, or executive function.

In some embodiments, the method further comprises administering an additional therapeutic agent.

In an aspect, provided is a method for treating a human subject, the method comprising: identifying a subject at risk of suffering from depression (e.g., postpartum depression) or an anxiety disorder; and administering (e.g., orally, intravenously) to the subject a therapeutically effective amount of Compound 9.

In some embodiments, the therapeutic agent is administered to the subject within 3 days, 2 days, 1 day, 24 hours of delivery of a baby (e.g., within 12 hours, within 6 hours, within 3 hours, within 2 hours, within 1 hour, within 30 minutes). In some embodiments, Compound 9 or a composition comprising Compound 9 is administered orally.

In some embodiments, the subject is identified to be at risk through a screening method (e.g., Edinburgh Postnatal Depression Scale (EPDS), e.g., a score of 10 or more on the EPDS, a score of 13 or more on the EPDS). In some embodiments, the subject has given birth (e.g., the subject has given birth within 3, 2, 1 days; 24, 20, 16, 12, 8, 6, 4, 3, 2, 1 hours; 60, 45, 30, 15, 10, 5 minutes). In some embodiments, the subject is due to give birth. In some embodiments, the subject is due to give birth in 9, 8, 7, 6, 5, 4, 3, 2, 1 months; 4, 3, 2, 1 weeks; 7, 6, 5, 4, 3, 2, 1 days. In some embodiments, the subject has an attribute, characteristic, or exposure (that increases the likelihood of developing a disorder as described herein, e.g., neuroactive steroid deficiency). In some embodiments, the subject has hyperemesis gravidarum (e.g., severe form of morning sickness, e.g., preventing adequate intake of food and fluids). In some embodiments, the subject has had a complication in pregnancy (e.g., emergency C-sections, pre-eclampsia, hospitalization during pregnancy, concern about fetal distress and admission of the baby to special care (NICU), the baby was in the NICU). In some embodiments, the subject has had emotionally painful or stressful experiences around pregnancy, childbirth, or early parenting (e.g., the subject was treated for infertility, had a previous miscarriage or other pregnancy loss, delivery of multiples, special needs, colic or difficult temperament baby, had difficulty feeding). In some embodiments, the subject has had a history of domestic violence, sexual or other abuse (e.g., abused as a child or as an adult). In some embodiments, the subject has had a traumatic childhood (e.g., loss of a parent, troubling relationship with parent). In some embodiments, the subject has stress (e.g., loss of someone close, job loss, financial hardship, divorce, strain in a relationship, house move). In some embodiments, the subject has lack of social support. In some embodiments, the subject has a perfectionist or controlling personality. In some embodiments, the therapeutic agent is a Selective Serotonin Reuptake Inhibitor (SSRI).

In an aspect, provided is a method for treating a human subject suffering from major depressive disorder (e.g., postpartum depression) or an anxiety disorder, the method comprising administering (e.g., orally, intravenously) to the subject a therapeutically effective amount of Compound 9.

In an aspect, provided is a method for treating a human subject suffering from depression (e.g., postpartum depression) or an anxiety disorder, the method comprising administering (e.g., orally, intravenously) to the subject a therapeutically effective amount of Compound 9.

In some embodiments, the depression is clinical depression (e.g., severe depression), postnatal or postpartum depression, atypical depression, melancholic depression, Psychotic Major Depression (PMD), catatonic depression, Seasonal Affective Disorder (SAD), dysthymia, double depression, Depressive Personality Disorder (DPD), Recurrent Brief Depression (RBD), minor depressive disorder, bipolar disorder or manic depressive disorder, post-traumatic stress disorders, depression caused by chronic medical conditions, treatment-resistant depression, refractory depression, suicidality, suicidal ideation, or suicidal behavior. In some embodiments, the depression is severe depression. In some embodiments, the depression is postpartum depression. In some embodiments, the depression is major depressive disorder.

In some embodiments, the method provides acute treatment of the depression (e.g., within 72 hours, 48 hours, 24 hours, 12 hours, or less). In some embodiments, the method provides maintenance treatment or preventative treatment. In some embodiments, the method provides acute treatment of the depression or anxiety disorder (e.g., provides relief from a symptom in less than 1 week (e.g., within 6 days, 5 days, 4 days, 3 days, 2 days, 1 day, or 12 hours). In some embodiments, the method provides rapid onset of efficacy (e.g., rapid reduction in a symptom of depression or anxiety disorder; rapidly affective to reduce a symptom of depression or anxiety disorder, e.g., a subject experiences relief from a symptom of depression or anxiety disorder described herein within 1 week (e.g., within 6 days, 5 days, 4 days, 3 days, 2 days, 1 day, or 12 hours)). In some embodiments, the therapeutic effect is sustained (e.g., effectively treats a symptom of depression or anxiety disorder and the efficacy is maintained for at least 1 day (e.g., at least 2 days, 3 days, 4 days, 5 days, 6 days, 1 week, 2 weeks, 3 weeks, 1 month, 2 months, 3 months, 4 months, 5 months, or 6 months, 7 months, 8 months, 9 months, 10 months, 11 months, 1 year, 2 years, or more). In some embodiments, the efficacy is maintained after a single course of treatment (e.g., single dose, multiple doses, or cycle of treatment) of Compound 9.

In some embodiments, the therapeutic effect is does not cause an adverse event (e.g., does not cause a severe or moderate adverse event, e.g., during treatment or 3 days, 7 days, 10 days, 20 days, 30 days, 60 days, 90 days, 3 months, 4 months, 5 months, 6 months, 7 months, 8 months, 9 months, 10 months, 11 months, 12 months, or more after treatment).

In some embodiments, the subject is substantially relieved of at least one symptom within 3, 2, 1 days; 24, 20, 16, 12, 10, 8 hours or less of said administration. In some embodiments, the subject is substantially relieved of at least one symptom for 1, 2, 3, 4, 5, 6, 7 days; 1, 2, 3, 4 weeks; 1, 2, 3, 4, 5, 6, 7, 8, 9, 10, 11, 12 months or more.

In some embodiments, Compound 9 is administered to a pregnant subject. In some embodiments, the subject is pregnant. In some embodiments, Compound 9 is administered to the subject in a pregnant subject in the third trimester of the pregnancy.

In some embodiments, Compound 9 is administered to the subject within 3 days, 2 days, 1 day, 24 hours of delivery of a baby (e.g., within 12 hours, within 6 hours, within 3 hours, within 2 hours, within 1 hour, within 30 minutes).

In some embodiments, the subject is identified to be at risk through a screening method (e.g., Edinburgh Postnatal Depression Scale (EPDS), e.g., a score of 10 or more on the EPDS, a score of 13 or more on the EPDS). In some embodiments, the subject has given birth (e.g., the subject has given birth within 3, 2, 1 days; 24, 20, 16, 12, 8, 6, 4, 3, 2, 1 hours; 60, 45, 30, 15, 10, 5 minutes). In some embodiments, the subject is due to give birth. In some embodiments, the subject is due to give birth in 9, 8, 7, 6, 5, 4, 3, 2, 1 months; 4, 3, 2, 1 weeks; 7, 6, 5, 4, 3, 2, 1 days. In some embodiments, the subject has an attribute, characteristic, or exposure (that increases the likelihood of developing a disorder as described herein, e.g., neuroactive steroid deficiency). In some embodiments, the subject has hyperemesis gravidarum (e.g., severe form of morning sickness, e.g., preventing adequate intake of food and fluids). In some embodiments, the subject has had a complication in pregnancy (e.g., emergency C-sections, pre-eclampsia, hospitalization during pregnancy, concern about fetal distress and admission of the baby to special care (NICU), the baby was in the NICU). In some embodiments, the subject has had emotionally painful or stressful experiences around pregnancy, childbirth, or early parenting (e.g., the subject was treated for infertility, had a previous miscarriage or other pregnancy loss, delivery of multiples, special needs, colic or difficult temperament baby, had difficulty feeding) In some embodiments, the subject has had a history of domestic violence, sexual or other abuse (e.g., abused as a child or as an adult). In some embodiments, the subject has had a traumatic childhood (e.g., loss of a parent, troubling relationship with parent). In some embodiments, the subject has stress (e.g., loss of someone close, job loss, financial hardship, divorce, strain in a relationship, house move). In some embodiments, the subject has lack of social support. In some embodiments, the subject has a perfectionist or controlling personality. In some embodiments, the subject is a female. In some embodiments, the female is not breast feeding. In some embodiments, the subject is an adult. In some embodiments, the subject is from 18 to 45 years of age. In some embodiments, the subject is suffering from (e.g., has been diagnosed with) postpartum depression (e.g., severe postpartum depression). In some embodiments, the subject has experienced a Major Depressive Episode in the postpartum period. In some embodiments, the period begins within the first 4 weeks following delivery of a baby.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75th Ea inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, $5^{th}$ Edition, John Wiley & Sons, Inc., New York, 2001; Larock, *Comprehensive Organic Transformations*, VCH Publishers, Inc., New York, 1989; and Carruthers, Some Modern Methods of Organic Synthesis, $3^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Car-* bon *Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

The articles "a" and "an" may be used herein to refer to one or to more than one (i.e. at least one) of the grammatical objects of the article. By way of example "an analogue" means one analogue or more than one analogue.

As used herein, the term "modulation" refers to the inhibition or potentiation of GABA receptor function. A "modulator" (e.g., a modulator compound) may be, for example, an agonist, partial agonist, antagonist, or partial antagonist of the GABA receptor.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like. The term "pharmaceutically acceptable cation" refers to an acceptable cationic counterion of an acidic functional group. Such cations are exemplified by sodium, potassium, calcium, magnesium, ammonium, tetraalkylammonium cations, and the like. See, e.g., Berge, et al., *J. Pharm. Sci.* (1977) 66(1): 1-79.

"Solvate" refers to forms of the compound that are associated with a solvent or water (also referred to as "hydrate"), usually by a solvolysis reaction. This physical association includes hydrogen bonding. Conventional solvents include water, ethanol, acetic acid, and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

"Stereoisomers": It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base. Tautomeric forms may be relevant to the attainment of the optimal chemical reactivity and biological activity of a compound of interest.

"Brexanolone" refers to a sterile solution of 5 mg/mL allopregnanolone in 250 mg/mL sulfobutylether-β-cyclodextrin (SBECD) buffered with citrate, which is diluted with sterile water for injection to render it isotonic for W infusion.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

As used herein, and unless otherwise specified, a "cycle of treatment" comprises administering a first dose of a neuroactive steroid, administering a second dose of the neuroactive steroid, and administering a third dose of the neuroactive steroid, said neuroactive steroid doses being sufficient to treat said subject.

In general, the "effective amount" of a compound refers to an amount sufficient to elicit the desired biological response, e.g., to treat a CNS-related disorder, e.g., a disorder as described herein (e.g., tremor (e.g., essential tremor); depression (e.g., postpartum depression); or an anxiety disorder). As will be appreciated by those of ordinary skill in this art, the effective amount of a compound of the invention may vary depending on such factors as the desired biological endpoint, the pharmacokinetics of the compound, the disease being treated, the mode of administration, and the age, weight, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

BRIEF DESCRIPTION OF THE DRAWINGS

(FIG. 2A) PTZ threshold following subchronic dosing for 7d; and (FIG. 2B) Pharmacoresistant SE model.

(FIG. 4A) Exposure levels of allopregnanolone and Compound 9 following a single oral dose in rat; (FIG. 4B) Exposure levels of Compound 9 in the plasma and brain of rat.

DETAILED DESCRIPTION OF CERTAIN EMBODIMENTS OF THE INVENTION

Methods of Use and Treatment

Figure 1A:
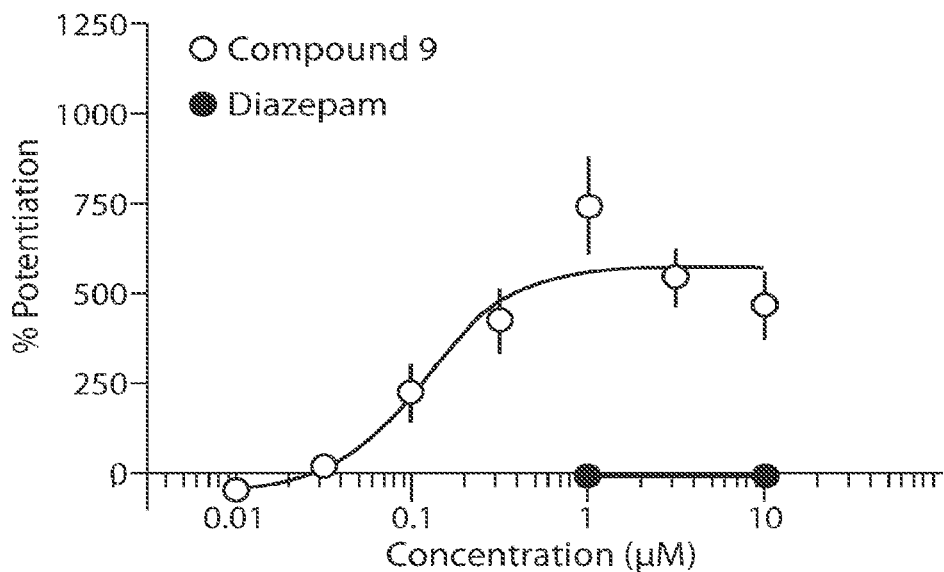
FIGS. 1A-1B depict an exemplary effect of Compound 9 and diazepam on (FIG. 1A) extrasynaptic or (FIG. 1B) synaptic electrical activity in the brain.
Figure 1B:
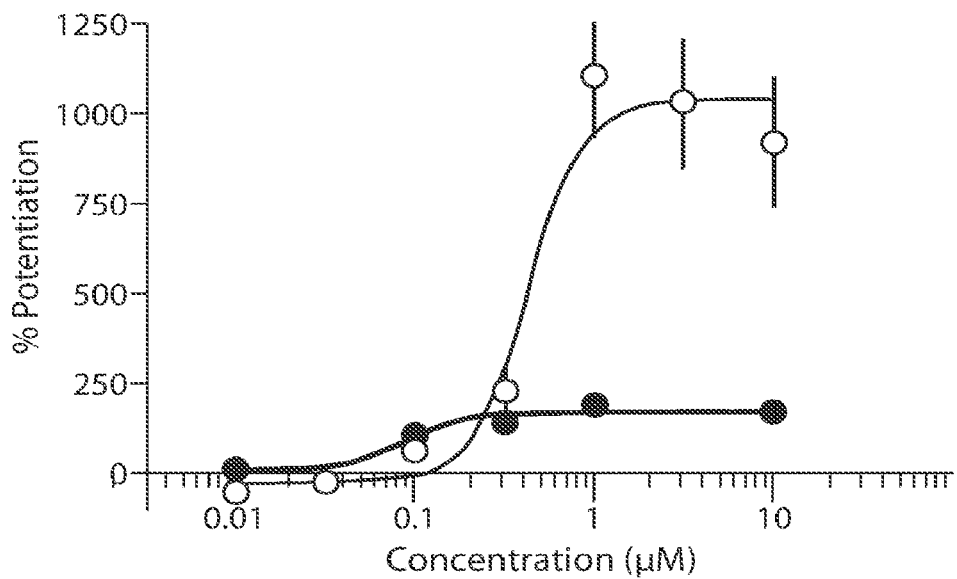
Figure 2A:
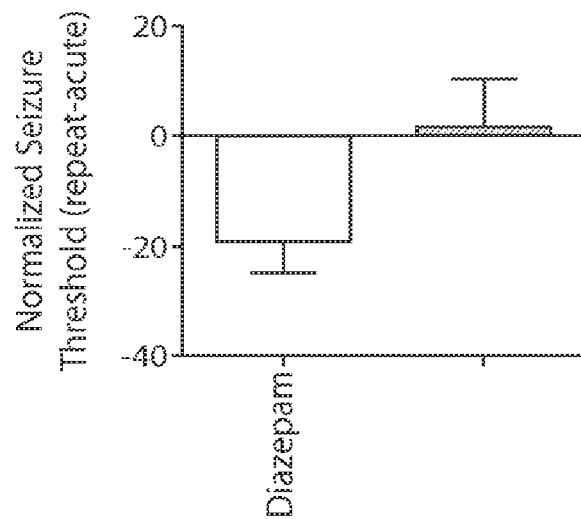
FIGS. 2A-2B depict an exemplary comparative effect of Compound 9 and diazepam.
Figure 2B:
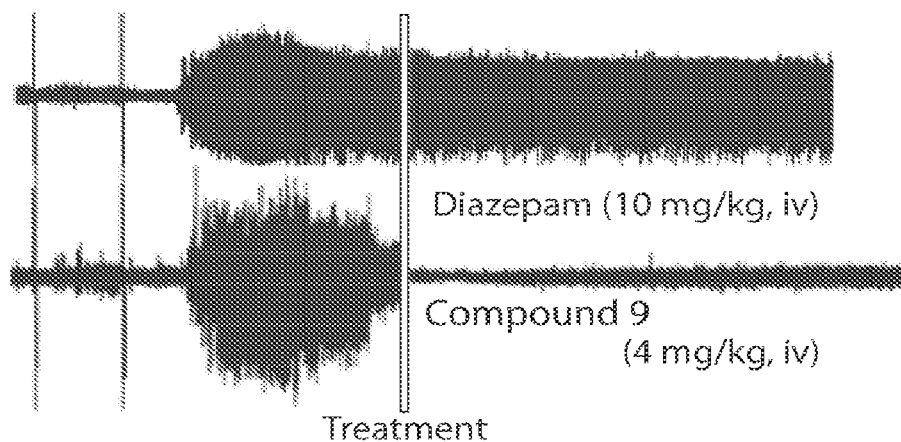
Figures 3A, 3B:
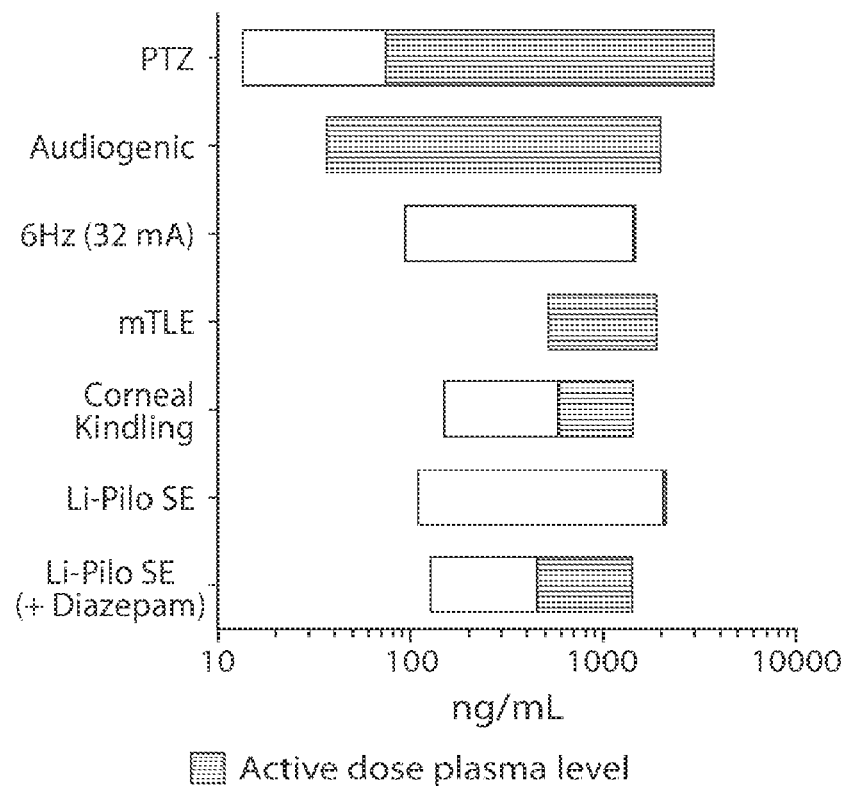
FIGS. 3A-3B depict exemplary preclinical anticonvulsant efficacy in rodents.
Figure 4A:
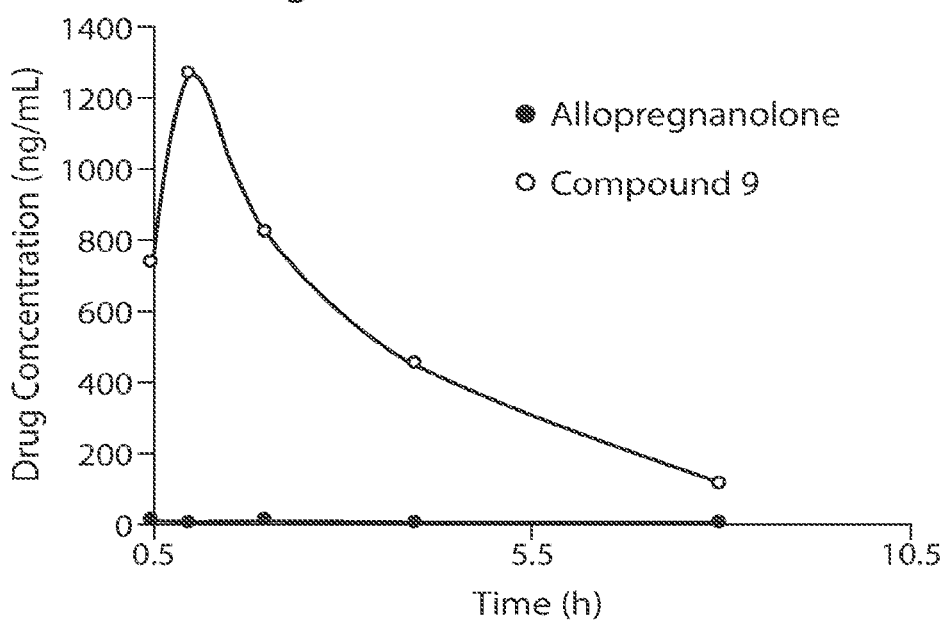
FIGS. 4A-4B depict exemplary PK/PD Profile and Brain Exposure for Compound 9.
Figure 4B:
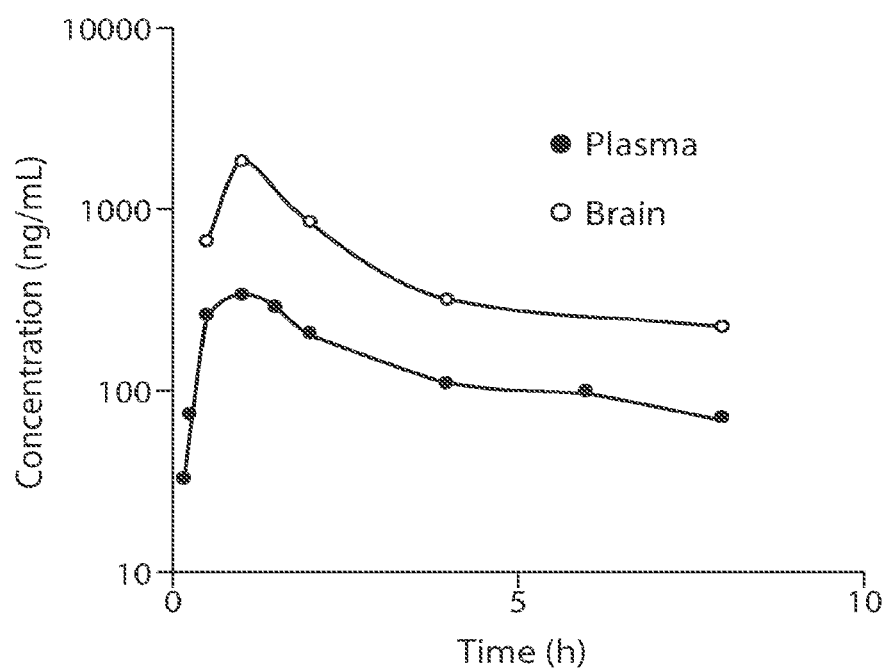
Figure 5:
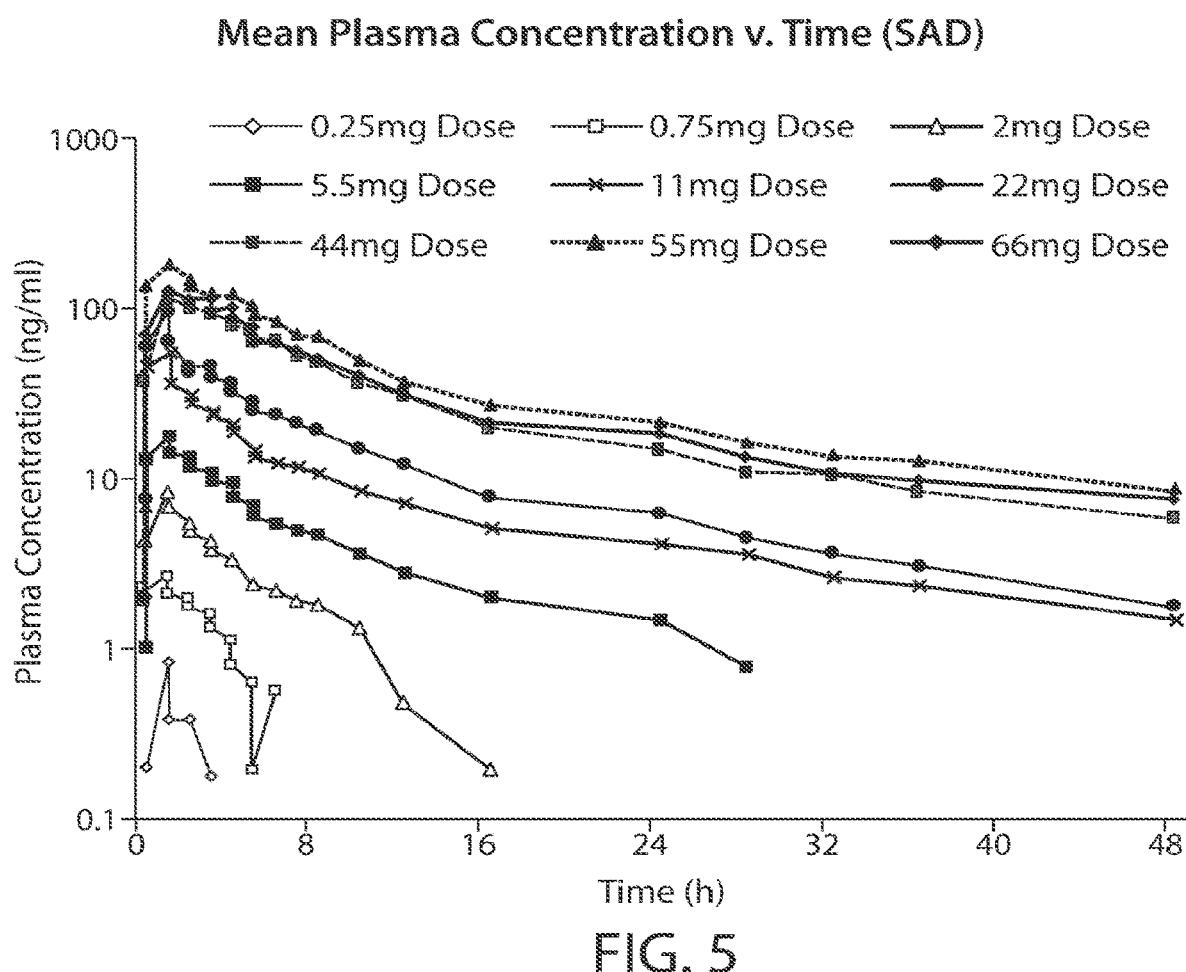
FIG. 5 shows exemplary pharmacokinetics of Compound 9 during Single Ascending Dose Study.
Figure 6:
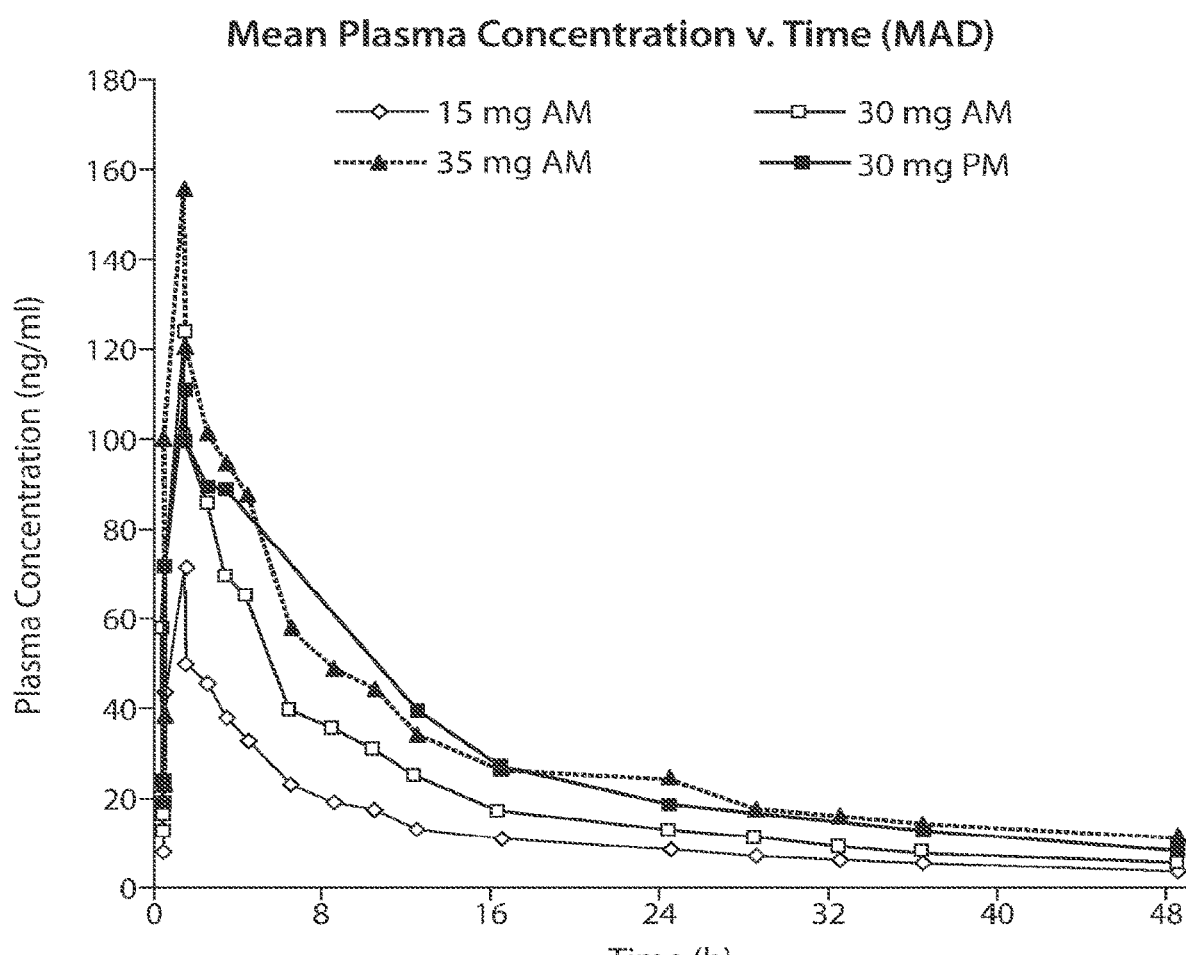
FIG. 6 shows exemplary pharmacokinetics of Compound 9 during Multiple Ascending Dose Study.
Figure 7:
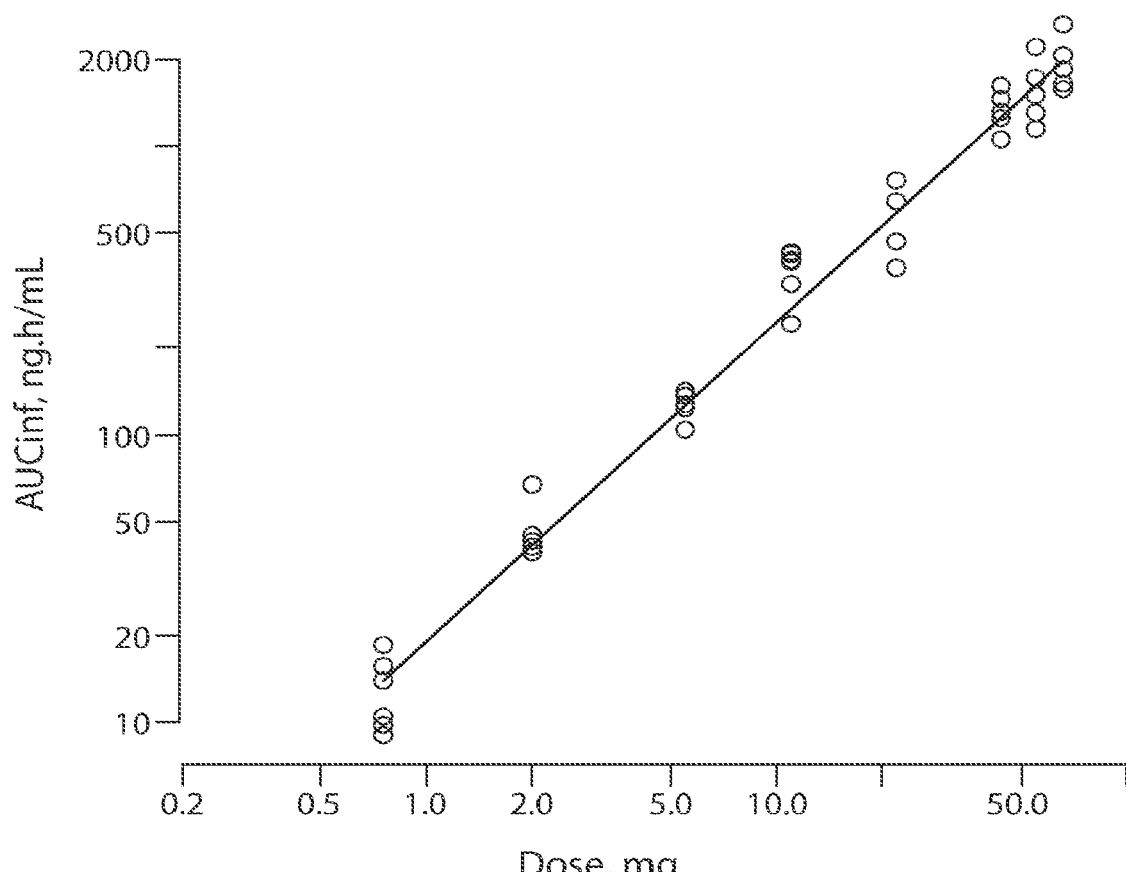
FIG. 7 shows exemplary dose linearity over the Multiple Dose Range Studied.

As generally described herein, the present invention is directed to neuroactive steroids that may act, for example, as GABA modulators. In certain embodiments, such compounds are envisioned to be useful as therapeutic agents for treating a disorder described herein, e.g., tremor (e.g., essential tremor); depression (e.g., postpartum depression, major depressive disorder); an anxiety disorder, comprising administering to the subject an effective amount of a compound of the present invention or a composition thereof. In certain embodiments, the compound is administered by intravenous administration. In certain embodiments, the compound is administered orally.

In some embodiments, a compound disclosed herein, for example, a neuroactive steroid described herein such as allopregnanolone or Compound 9, can be administered as a hormone or steroid replacement therapy in a subject. In an embodiment, a subject described herein has experienced a decrease in a steroid or hormone level prior to treatment with a compound described herein. For example, a subject generally experiences a decrease in allopregnanolone subsequent to delivery of an infant. In an embodiment, the neuroactive steroid is administered to the subject within 3 days, 2 days, 1 day, or 24 hours of delivery of a baby (e.g., within 12 hours, within 6 hours, within 3 hours, within 2 hours, within 1 hour, or within 30 minutes). In an embodiment, a subject can be administered a compound described herein (e.g., allopregnanolone) after experiencing a decrease in steroid or hormone level. In an embodiment, the decrease in hormone or steroid level is at least by a factor of 2 (e.g., at least a factor of 3, 4, 5, 10 or 100).

Also provided herein is a method for treating or preventing a disorder described herein, comprising orally administering a total daily dose of Compound 9, (Compound 9)

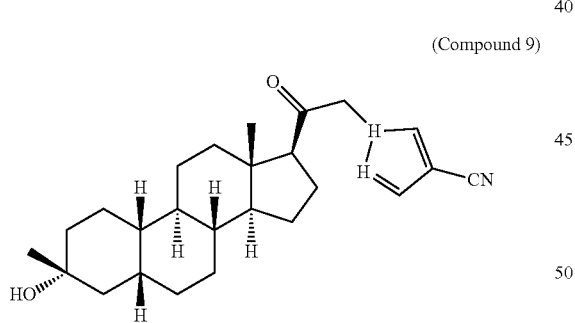

or a pharmaceutically acceptable salt or isotopologue thereof, or a pharmaceutical composition thereof of about 10 mg to about 100 mg to a subject in need thereof.

Compounds of the present invention, as described herein, can modulate GABA function, and therefore can act as neuroactive steroids for the treatment and prevention of CNS-related conditions in a subject. Modulation, as used herein, refers to the inhibition or potentiation of GABA receptor function. Accordingly, the compounds and pharmaceutical compositions provided herein find use as therapeutics for preventing and/or treating CNS conditions in mammals including humans and non-human mammals. Thus, and as stated earlier, the present invention includes within its scope, and extends to, the recited methods of treatment, as well as to the compounds for such methods, and to the use of such compounds for the preparation of medicaments useful for such methods.

Exemplary neuroactive steroid compounds include:

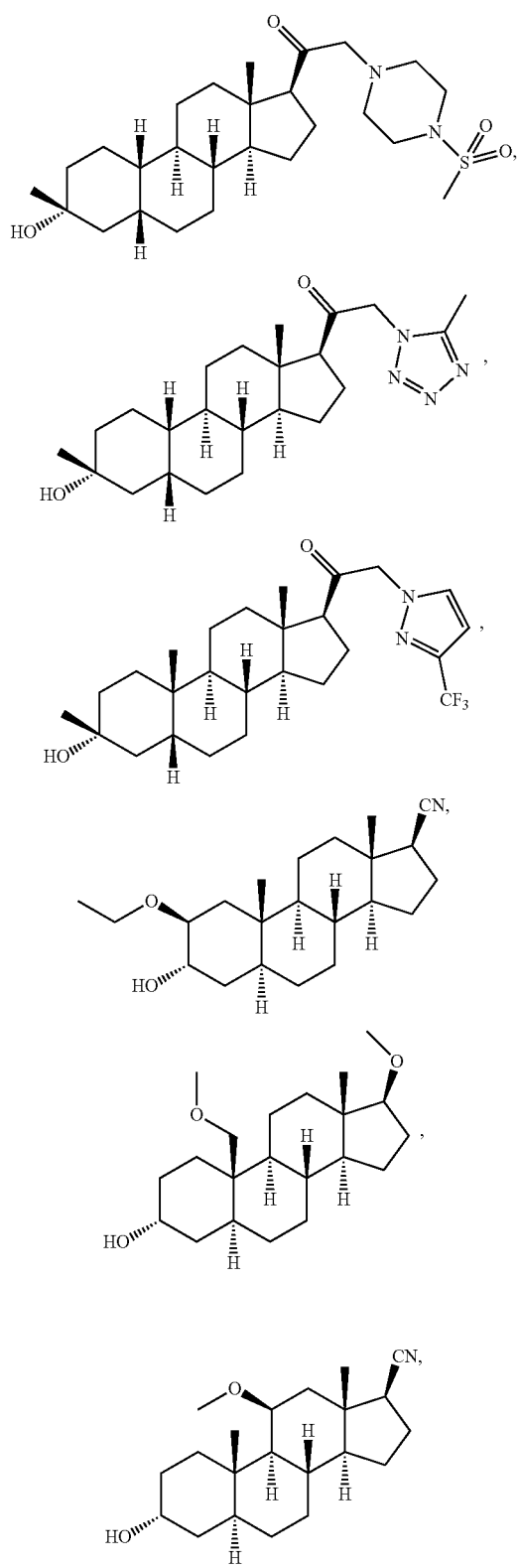

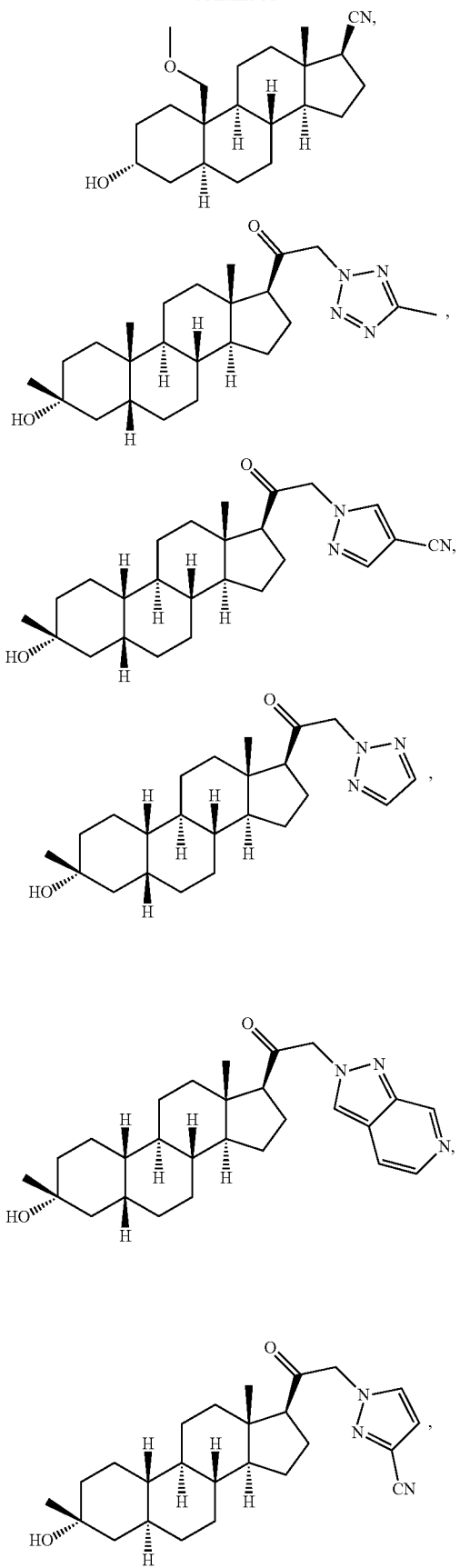
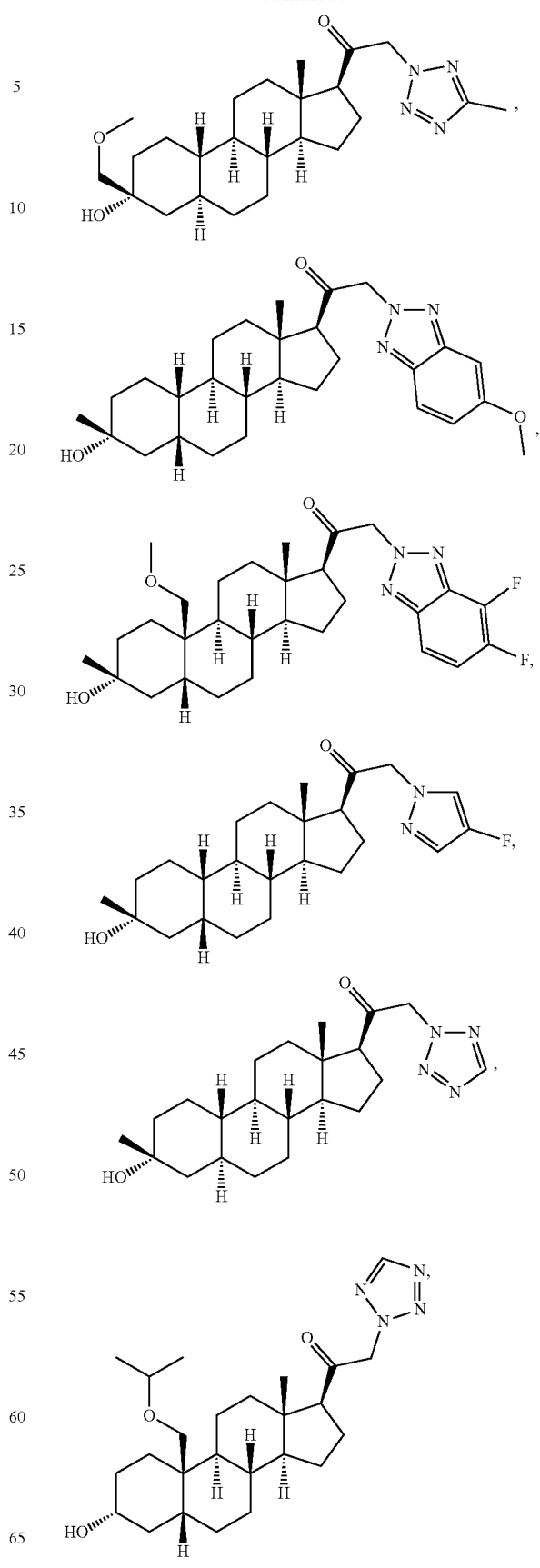

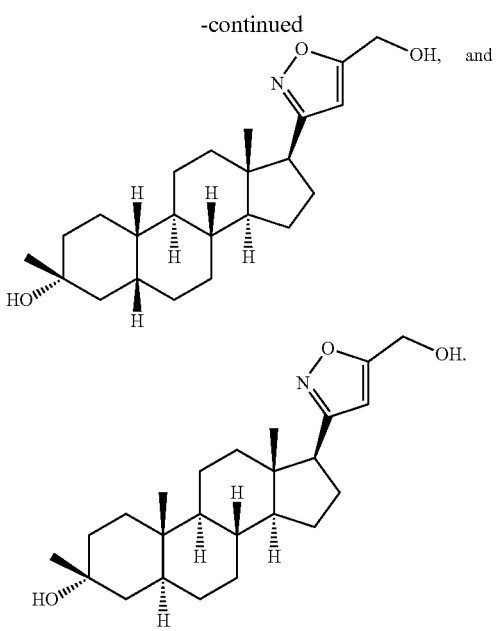

Exemplary CNS conditions related to GABA-modulation include, but are not limited to, sleep disorders [e.g., insomnia], mood disorders [e.g., depression such as PND, major depressive disorder, or perinatal depression, dysthymic disorder (e.g., mild depression), bipolar disorder (e.g., I and/or II), anxiety disorders (e.g., generalized anxiety disorder (GAD), social anxiety disorder), stress, post-traumatic stress disorder (PTSD), compulsive disorders (e.g., obsessive compulsive disorder (OCD))], schizophrenia spectrum disorders [e.g., schizophrenia, schizoaffective disorder], convulsive disorders [e.g., epilepsy (e.g., status epilepticus (SE)), seizures], disorders of memory and/or cognition [e.g., attention disorders (e.g., attention deficit hyperactivity disorder (ADHD)), dementia (e.g., Alzheimer's type dementia, Lewis body type dementia, vascular type dementia], movement disorders [e.g., Huntington's disease, Parkinson's disease], personality disorders [e.g., anti-social personality disorder, obsessive compulsive personality disorder], autism spectrum disorders (ASD) [e.g., autism, monogenetic causes of autism such as synaptophathy's, e.g., Rett syndrome, Fragile X syndrome, Angelman syndrome], pain [e.g., neuropathic pain, injury related pain syndromes, acute pain, chronic pain], traumatic brain injury (TBI), vascular diseases [e.g., stroke, ischemia, vascular malformations], substance abuse disorders and/or withdrawal syndromes [e.g., addition to opiates, cocaine, and/or alcohol], and tinnitus.

In yet another aspect, provided is a combination of a compound of the present invention and another pharmacologically active agent. The compounds provided herein can be administered as the sole active agent or they can be administered in combination with other agents. Administration in combination can proceed by any technique apparent to those of skill in the art including, for example, separate, sequential, concurrent and alternating administration.

In another aspect, provided is a method of treating or preventing brain excitability in a subject susceptible to or afflicted with a condition associated with brain excitability, comprising administering to the subject an effective amount of a compound of the present invention to the subject.

In yet another aspect, provided is a method of treating or preventing tremor in a subject, comprising administering to the subject in need of such treatment an effective amount of a compound of the present invention. In certain embodiments the tremor is essential tremor.

In yet another aspect, provided is a method of treating or preventing mood disorders in a subject, comprising administering to the subject in need of such treatment an effective amount of a compound of the present invention. In certain embodiments the mood disorder is depression. In some embodiments, the mood disorder is postpartum depression. In some embodiments, the mood disorder is major depressive disorder.

In yet another aspect, provided is a method of alleviating or preventing PMS, PND, major depressive disorder, or perinatal depression in a subject, comprising administering to the subject in need of such treatment an effective amount of a compound of the present invention.

In yet another aspect, provided is a method of treating or preventing stress or anxiety in a subject, comprising administering to the subject in need of such treatment an effective amount of a compound of the present invention, or a composition thereof.

In yet another aspect, provided is a method of alleviating or preventing insomnia in a subject, comprising administering to the subject in need of such treatment an effective amount of a compound of the present invention, or a composition thereof.

In yet another aspect, provided is a method of inducing sleep and maintaining substantially the level of REM sleep that is found in normal sleep, wherein substantial rebound insomnia is not induced, comprising administering an effective amount of a compound of the present invention.

In yet another aspect, provided is a method of cognition enhancement or treating memory disorder by administering to the subject a therapeutically effective amount of a compound of the present invention. In certain embodiments, the disorder is Alzheimer's disease. In certain embodiments, the disorder is Rett syndrome.

In yet another aspect, provided is a method of treating attention disorders by administering to the subject a therapeutically effective amount of a compound of the present invention. In certain embodiments, the attention disorder is ADHD.

In some embodiments, the therapeutic agent (e.g., a neuroactive steroid or compound described herein) is administered to the subject within 3 days, 2 days, 1 day, 24 hours of delivery of a baby (e.g., within 12 hours, within 6 hours, within 3 hours, within 2 hours, within 1 hour, within 30 minutes).

In an embodiment, the method includes acute treatment of a disorder described herein. For example, in an embodiment, a method described herein provides relief from a symptom described herein in less than 1 week (e.g., within 6 days, 5 days, 4 days, 3 days, 2 days, 1 day, or 12 horns). In an embodiment, the subject experiences, upon administration of a compound described herein (e.g., allopregnanolone) rapid onset of efficacy of the compound. For example, in an embodiment, a subject experiences relief from a symptom of a disorder described herein within 1 week (e.g., within 6 days, 5 days, 4 days, 3 days, 2 days, 1 day, or 12 hours).

In an embodiment, a method described herein provides for sustained efficacy upon treatment with a compound described herein. For example, in an embodiment, a subject is treated with a compound described herein, wherein the treatment effectively treats a symptom of a disorder described herein and the efficacy is maintained for at least 1 day (e.g., at least 2 days, 3 days, 4 days, 5 days, 6 days, 1 week, 2 weeks, 3 weeks, 1 month, 2 months, 3 months, 4 months, 5 months, or 6 months). In an embodiment, the efficacy is maintained after a single course of treatment of a compound described herein (e.g., allopregnanolone). Course of treatment, as described herein is a treatment regimen administered to a subject so as to provide efficacy of a symptom of a disorder to the subject. In an embodiment, a course of treatment is a single dose. In another embodiment, a course of treatment includes multiple doses of a compound described herein. In another embodiment, a course of treatment includes a cycle of treatment of a compound described herein.

In an embodiment, a method described herein can include a course of treatment with multiple dosages or cycles of treatment, for example, where a first dose or cycle of treatment is a parenteral dose such as an intravenous dose, and a second dose or cycle of treatment is an oral dose. In an embodiment, the first and second dose or cycle of treatment include the same compound described herein. In another embodiment, the first dose or cycle of treatment includes a first compound (e.g., a first compound described herein such as allopregnanolone) and the second dose or cycle of treatment includes a second compound that is different from the first compound.

In an embodiment, a method described herein provides effective treatment without causing a severe adverse event. In an embodiment, a method described herein provides effective treatment without causing a moderate or severe adverse event. In an embodiment, a method described herein provides effective treatment without causing an adverse event.

In certain embodiments, the compound is administered to the subject chronically. In certain embodiments, the compound is administered to the subject orally, subcutaneously, intramuscularly, or intravenously.

Neuroendocrine Disorders and Dysfunction

Provided herein are methods that can be used for treating neuroendocrine disorders and dysfunction. As used herein, "neuroendocrine disorder" or "neuroendocrine dysfunction" refers to a variety of conditions caused by imbalances in the body's hormone production directly related to the brain. Neuroendocrine disorders involve interactions between the nervous system and the endocrine system. Because the hypothalamus and the pituitary gland are two areas of the brain that regulate the production of hormones, damage to the hypothalamus or pituitary gland, e.g., by traumatic brain injury, may impact the production of hormones and other neuroendocrine functions of the brain. In some embodiments, the neuroendocrine disorder or dysfunction is associated with a women's health disorder or condition (e.g., a women's health disorder or condition described herein). In some embodiments, the neuroendocrine disorder or dysfunction is associated with a women's health disorder or condition is polycystic ovary syndrome.

Symptoms of neuroendocrine disorder include, but are not limited to, behavioral, emotional, and sleep-related symptoms, symptoms related to reproductive function, and somatic symptoms; including but not limited to fatigue, poor memory, anxiety, depression, weight gain or loss, emotional lability, lack of concentration, attention difficulties, loss of lipido, infertility, amenorrhea, loss of muscle mass, increased belly body fat, low blood pressure, reduced heart rate, hair loss, anemia, constipation, cold intolerance, and dry skin.

Neurodegenerative Diseases and Disorders

The methods described herein can be used for treating neurodegenerative diseases and disorders. The term "neurodegenerative disease" includes diseases and disorders that are associated with the progressive loss of structure or function of neurons, or death of neurons. Neurodegenerative diseases and disorders include, but are not limited to, Alzheimer's disease (including the associated symptoms of mild, moderate, or severe cognitive impairment); amyotrophic lateral sclerosis (ALS); anoxic and ischemic injuries; ataxia and convulsion (including for the treatment and prevention and prevention of seizures that are caused by schizoaffective disorder or by drugs used to treat schizophrenia); benign forgetfulness; brain edema; cerebellar ataxia including McLeod neuroacanthocytosis syndrome (MLS); closed head injury; coma; contusive injuries (e.g., spinal cord injury and head injury); dementias including multi-infarct dementia and senile dementia; disturbances of consciousness; Down syndrome; drug-induced or medication-induced Parkinsonism (such as neuroleptic-induced acute akathisia, acute dystonia, Parkinsonism, or tardive dyskinesia, neuroleptic malignant syndrome, or medication-induced postural tremor); epilepsy; fragile X syndrome; Gilles de la Tourette's syndrome; head trauma; hearing impairment and loss; Huntington's disease; Lennox syndrome; levodopa-induced dyskinesia; mental retardation; movement disorders including akinesias and akinetic (rigid) syndromes (including basal ganglia calcification, corticobasal degeneration, multiple system atrophy, Parkinsonism-ALS dementia complex, Parkinson's disease, postencephalitic parkinsonism, and progressively supranuclear palsy); muscular spasms and disorders associated with muscular spasticity or weakness including chorea (such as benign hereditary chorea, drug-induced chorea, hemiballism, Huntington's disease, neuroacanthocytosis, Sydenham's chorea, and symptomatic chorea), dyskinesia (including tics such as complex tics, simple tics, and symptomatic tics), myoclonus (including generalized myoclonus and focal cyloclonus), tremor (such as rest tremor, postural tremor, and intention tremor) and dystonia (including axial dystonia, dystonic writer's cramp, hemiplegic dystonia, paroxysmal dystonia, and focal dystonia such as blepharospasm, oromandibular dystonia, and spasmodic dysphonia and torticollis); neuronal damage including ocular damage, retinopathy or macular degeneration of the eye; neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest; Parkinson's disease; seizure; status epilecticus; stroke; tinnitus; tubular sclerosis, and viral infection induced neurodegeneration (e.g., caused by acquired immunodeficiency syndrome (AIDS) and encephalopathies). Neurodegenerative diseases also include, but are not limited to, neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest. Methods of treating or preventing a neurodegenerative disease also include treating or preventing loss of neuronal function characteristic of neurodegenerative disorder.

Epilepsy

The compounds described herein, e.g., the compound of Compound 9, or pharmaceutically acceptable salt, or a pharmaceutically acceptable composition thereof, can be used in a method described herein, for example in the treatment of a disorder described herein such as epilepsy, status epilepticus, or seizure, for example as described in WO2013/112605 and WO/2014/031792, the contents of which are incorporated herein in their entirety.

Epilepsy is a brain disorder characterized by repeated seizures over time. Types of epilepsy can include, but are not limited to generalized epilepsy, e.g., childhood absence epilepsy, juvenile nyoclonic epilepsy, epilepsy with grand-mal seizures on awakening, West syndrome, Lennox-Gastaut syndrome, partial epilepsy, e.g., temporal lobe epilepsy, frontal lobe epilepsy, benign focal epilepsy of childhood.

Status Epilepticus (SE)

Status epilepticus (SE) can include, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges. Convulsive status epilepticus is characterized by the presence of convulsive status epileptic seizures, and can include early status epilepticus, established status epilepticus, refractory status epilepticus, super-refractory status epilepticus. Early status epilepticus is treated with a first line therapy. Established status epilepticus is characterized by status epileptic seizures which persist despite treatment with a first line therapy, and a second line therapy is administered. Refractory status epilepticus is characterized by status epileptic seizures which persist despite treatment with a first line and a second line therapy, and a general anesthetic is generally administered. Super refractory status epilepticus is characterized by status epileptic seizures which persist despite treatment with a first line therapy, a second line therapy, and a general anesthetic for 24 hours or more.

Non-convulsive status epilepticus can include, e.g., focal non-convulsive status epilepticus, e.g., complex partial non-convulsive status epilepticus, simple partial non-convulsive status epilepticus, subtle non-convulsive status epilepticus; generalized non-convulsive status epilepticus, e.g., late onset absence non-convulsive status epilepticus, atypical absence non-convulsive status epilepticus, or typical absence non-convulsive status epilepticus.

The compounds described herein, e.g., the compound of Compound 9, or pharmaceutically acceptable salt, or a pharmaceutically acceptable composition thereof, can also be administered as a prophylactic to a subject having a CNS disorder e.g., a traumatic brain injury, status epilepticus, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges; prior to the onset of a seizure.

Seizure

A seizure is the physical findings or changes in behavior that occur after an episode of abnormal electrical activity in the brain. The term "seizure" is often used interchangeably with "convulsion." Convulsions are when a person's body shakes rapidly and uncontrollably. During convulsions, the person's muscles contract and relax repeatedly.

Based on the type of behavior and brain activity, seizures are divided into two broad categories: generalized and partial (also called local or focal). Classifying the type of seizure helps doctors diagnose whether or not a patient has epilepsy.

Generalized seizures are produced by electrical impulses from throughout the entire brain, whereas partial seizures are produced (at least initially) by electrical impulses in a relatively small part of the brain. The part of the brain generating the seizures is sometimes called the focus.

There are six types of generalized seizures. The most common and dramatic, and therefore the most well known, is the generalized convulsion, also called the grand-mal seizure. In this type of seizure, the patient loses consciousness and usually collapses. The loss of consciousness is followed by generalized body stiffening (called the "tonic" phase of the seizure) for 30 to 60 seconds, then by violent jerking (the "clonic" phase) for 30 to 60 seconds, after which the patient goes into a deep sleep (the "postictal" or after-seizure phase). During grand-mal seizures, injuries and accidents may occur, such as tongue biting and urinary incontinence.

Absence seizures cause a short loss of consciousness (just a few seconds) with few or no symptoms. The patient, most often a child, typically interrupts an activity and stares blankly. These seizures begin and end abruptly and may occur several times a day. Patients are usually not aware that they are having a seizure, except that they may be aware of "losing time."

Myoclonic seizures consist of sporadic jerks, usually on both sides of the body. Patients sometimes describe the jerks as brief electrical shocks. When violent, these seizures may result in dropping or involuntarily throwing objects.

Clonic seizures are repetitive, rhythmic jerks that involve both sides of the body at the same time.

Tonic seizures are characterized by stiffening of the muscles.

Atonic seizures consist of a sudden and general loss of muscle tone, particularly in the arms and legs, which often results in a fall.

Seizures described herein can include epileptic seizures; acute repetitive seizures; cluster seizures; continuous seizures; unremitting seizures; prolonged seizures; recurrent seizures; status epilepticus seizures, e.g., refractory convulsive status epilepticus, non-convulsive status epilepticus seizures; refractory seizures; myoclonic seizures; tonic seizures; tonic-clonic seizures; simple partial seizures; complex partial seizures; secondarily generalized seizures; atypical absence seizures; absence seizures; atonic seizures; benign Rolandic seizures; febrile seizures; emotional seizures; focal seizures; gelastic seizures; generalized onset seizures; infantile spasms; Jacksonian seizures; massive bilateral myoclonus seizures; multifocal seizures; neonatal onset seizures; nocturnal seizures; occipital lobe seizures; post traumatic seizures; subtle seizures; Sylvan seizures; visual reflex seizures; or withdrawal seizures. In some embodiments, the seizure is a generalized seizure associated with Dravet Syndrome, Lennox-Gastaut Syndrome, Tuberous Sclerosis Complex, Rett Syndrome or PCDH19 Female Pediatric Epilepsy.

Movement Disorders

Also described herein are methods for treating a movement disorder. As used herein, "movement disorders" refers to a variety of diseases and disorders that are associated with hyperkinetic movement disorders and related abnormalities in muscle control. Exemplary movement disorders include, but are not limited to, Parkinson's disease and parkinsonism (defined particularly by bradykinesia), dystonia, chorea and Huntington's disease, ataxia, tremor (e.g., essential tremor), myoclonus and startle, tics and Tourette syndrome, Restless legs syndrome, stiff person syndrome, and gait disorders.

Tremor

The methods described herein can be used to treat tremor, for example cerebellar tremor or intention tremor, dystonic tremor, essential tremor, orthostatic tremor, parkinsonian tremor, physiological tremor, psychogenic tremor, or rubral tremor. Tremor includes hereditary, degenerative, and idiopathic disorders such as Wilson's disease, Parkinson's disease, and essential tremor, respectively; metabolic diseases (e.g., thyoid-parathyroid-, liver disease and hypoglycemia); peripheral neuropathies (associated with Charcot-Marie-Tooth, Roussy-Levy, diabetes mellitus, complex regional pain syndrome); toxins (nicotine, mercury, lead, CO, Manganese, arsenic, toluene); drug-induced (narcoleptics, tricyclics, lithium, cocaine, alcohol, adrenaline, bronchodilators, theophylline, caffeine, steroids, valproate, amiodarone, thyroid hormones, vincristine); and psychogenic disorders. Clinical tremor can be classified into physiologic tremor, enhanced physiologic tremor, essential tremor syndromes (including classical essential tremor, primary orthostatic tremor, and task- and position specific tremor), dystonic tremor, parkinsonian tremor, cerebellar tremor, Holmes' tremor (i.e., rubral tremor), palatal tremor, neuropathic tremor, toxic or drug-induced tremor, and psychogenic tremor.

Tremor is an involuntary, at times rhythmic, muscle contraction and relaxation that can involve oscillations or twitching of one or more body parts (e.g., hands, arms, eyes, face, head, vocal folds, trunk, legs).

Cerebellar tremor or intention tremor is a slow, broad tremor of the extremities that occurs after a purposeful movement. Cerebellar tremor is caused by lesions in or damage to the cerebellum resulting from, e.g., tumor, stroke, disease (e.g., multiple sclerosis, an inherited degenerative disorder).

Dystonic tremor occurs in individuals affected by dystonia, a movement disorder in which sustained involuntary muscle contractions cause twisting and repetitive motions and/or painful and abnormal postures or positions. Dystonic tremor may affect any muscle in the body. Dystonic tremors occurs irregularly and often can be relieved by complete rest.

Essential tremor or benign essential tremor is the most common type of tremor. Essential tremor may be mild and nonprogressive in some, and may be slowly progressive, starting on one side of the body but affect both sides within 3 years. The hands are most often affected, but the head, voice, tongue, legs, and trunk may also be involved. Tremor frequency may decrease as the person ages, but severity may increase. Heightened emotion, stress, fever, physical exhaustion, or low blood sugar may trigger tremors and/or increase their severity. Symptoms generally evolve over time and can be both visible and persistent following onset.

Orthostatic tremor is characterized by fast (e.g., greater than 12 Hz) rhythmic muscle contractions that occurs in the legs and trunk immediately after standing. Cramps are felt in the thighs and legs and the patient may shake uncontrollably when asked to stand in one spot. Orthostatic tremor may occurs in patients with essential tremor.

Parkinsonian tremor is caused by damage to structures within the brain that control movement. Parkinsonian tremor is often a precursor to Parkinson's disease and is typically seen as a "pill-rolling" action of the hands that may also affect the chin, lips, legs, and trunk. Onset of parkinsonian tremor typically begins after age 60. Movement starts in one limb or on one side of the body and can progress to include the other side.

Physiological tremor can occur in normal individuals and have no clinical significance. It can be seen in all voluntary muscle groups. Physiological tremor can be caused by certain drugs, alcohol withdrawal, or medical conditions including an overactive thyroid and hypoglycemia. The tremor classically has a frequency of about 10 Hz.

Psychogenic tremor or hysterical tremor can occur at rest or during postural or kinetic movement. Patient with psychogenic tremor may have a conversion disorder or another psychiatric disease.

Rubral tremor is characterized by coarse slow tremor which can be present at rest, at posture, and with intention. The tremor is associated with conditions that affect the red nucleus in the midbrain, classical unusual strokes.

Parkinson's Disease affects nerve cells in the brain that produce dopamine. Symptoms include muscle rigidity, tremors, and changes in speech and gait. Parkinsonism is characterized by tremor, bradykinesia, rigidity, and postural instability. Parkinsonism shares symptoms found in Parkinson's Disease, but is a symptom complex rather than a progressive neurodegenerative disease.

Dystonia is a movement disorder characterized by sustained or intermittent muscle contractions causing abnormal, often repetitive movements or postures. Dystonic movements can be patterned, twisting, and may be tremulous. Dystonia is often initiated or worsened by voluntary action and associated with overflow muscle activation.

Chorea is a neurological disorder characterized by jerky involuntary movements typically affecting the shoulders, hips, and face. Huntington's Disease is an inherited disease that causes nerve cells in the brain to waste away. Symptoms include uncontrolled movements, clumsiness, and balance problems. Huntington's disease can hinder walk, talk, and swallowing.

Ataxia refers to the loss of full control of bodily movements, and may affect the fingers, hands, arms, legs, body, speech, and eye movements.

Myoclonus and Startle is a response to a sudden and unexpected stimulus, which can be acoustic, tactile, visual, or vestibular.

Tics are an involuntary movement usually onset suddenly, brief, repetitive, but non-rhythmical, typically imitating normal behavior and often occurring out of a background of normal activity. Tics can be classified as motor or vocal, motor tics associated with movements while vocal tics associated with sound. Tics can be characterized as simple or complex. For example simple motor tics involve only a few muscles restricted to a specific body part. Tourette Syndrome is an inherited neuropsychiatric disorder with onset in childhood, characterized by multiple motor tics and at least one vocal tic.

Restless Legs Syndrome is a neurologic sensorimotor disorder characterized by an overwhelming urge to move the legs when at rest.

Stiff Person Syndrome is a progressive movement disorder characterized by involuntary painful spasms and rigidity of muscles, usually involving the lower back and legs. Stiff-legged gait with exaggerated lumbar hyperlordosis typically results. Characteristic abnormality on EMG recordings with continuous motor unit activity of the paraspinal axial muscles is typically observed. Variants include "stiff-limb syndrome" producing focal stiffness typically affecting distal legs and feet.

Gait disorders refer to an abnormality in the manner or style of walking, which results from neuromuscular, arthritic, or other body changes. Gait is classified according to the system responsible for abnormal locomotion, and include hemiplegic gait, diplegic gait, neuropathic gait, myopathic gait, parkinsonian gait, choreiform gait, ataxic gait, and sensory gait.

Mood Disorders

Also provided herein are methods for treating a mood disorder, for example clinical depression, postnatal depression or postpartum depression, perinatal depression, atypical depression, melancholic depression, psychotic major depression, cationic depression, seasonal affective disorder, dysthymia, double depression, depressive personality disorder, recurrent brief depression, minor depressive disorder, bipolar disorder or manic depressive disorder, depression caused by chronic medical conditions, treatment-resistant depression, refractory depression, suicidality, suicidal ideation, or suicidal behavior. In some embodiments, the method described herein provides therapeutic effect to a subject suffering from depression (e.g., moderate or severe depression). In some embodiments, the mood disorder is associated with a disease or disorder described herein (e.g., neuroendocrine diseases and disorders, neurodegenerative diseases and disorders (e.g., epilepsy), movement disorders, tremor (e.g., Parkinson's Disease), women's health disorders or conditions).

Clinical depression is also known as major depression, major depressive disorder (MDD), severe depression, unipolar depression, unipolar disorder, and recurrent depression, and refers to a mental disorder characterized by pervasive and persistent low mood that is accompanied by low self-esteem and loss of interest or pleasure in normally enjoyable activities. Some people with clinical depression have trouble sleeping, lose weight, and generally feel agitated and irritable. Clinical depression affects how an individual feels, thinks, and behaves and may lead to a variety of emotional and physical problems. Individuals with clinical depression may have trouble doing day-to-day activities and make an individual feel as if life is not worth living.

Peripartum depression refers to depression in pregnancy. Symptoms include irritability, crying, feeling restless, trouble sleeping, extreme exhaustion (emotional and/or physical), changes in appetite, difficulty focusing, increased anxiety and/or worry, disconnected feeling from baby and/or fetus, and losing interest in formerly pleasurable activities.

Postnatal depression (PND) is also referred to as postpartum depression (PPD), and refers to a type of clinical depression that affects women after childbirth. Symptoms can include sadness, fatigue, changes in sleeping and eating habits, reduced sexual desire, crying episodes, anxiety, and irritability. In some embodiments, the PND is a treatment-resistant depression (e.g., a treatment-resistant depression as described herein). In some embodiments, the PND is refractory depression (e.g., a refractory depression as described herein).

In some embodiments, a subject having PND also experienced depression, or a symptom of depression during pregnancy. This depression is referred to herein as) perinatal depression. In an embodiment, a subject experiencing perinatal depression is at increased risk of experiencing PND.

Atypical depression (AD) is characterized by mood reactivity (e.g., paradoxical anhedonia) and positivity, significant weight gain or increased appetite. Patients suffering from AD also may have excessive sleep or somnolence (hypersomnia), a sensation of limb heaviness, and significant social impairment as a consequence of hypersensitivity to perceived interpersonal rejection.

Melancholic depression is characterized by loss of pleasure (anhedonia) in most or all activities, failures to react to pleasurable stimuli, depressed mood more pronounced than that of grief or loss, excessive weight loss, or excessive guilt.

Psychotic major depression (PMD) or psychotic depression refers to a major depressive episode, in particular of melancholic nature, where the individual experiences psychotic symptoms such as delusions and hallucinations.

Catatonic depression refers to major depression involving disturbances of motor behavior and other symptoms. An individual may become mute and stuporose, and either is immobile or exhibits purposeless or bizarre movements.

Seasonal affective disorder (SAD) refers to a type of seasonal depression wherein an individual has seasonal patterns of depressive episodes coming on in the fall or winter.

Dysthymia refers to a condition related to unipolar depression, where the same physical and cognitive problems are evident. They are not as severe and tend to last longer (e.g., at least 2 years).

Double depression refers to fairly depressed mood (dysthymia) that lasts for at least 2 years and is punctuated by periods of major depression.

Depressive Personality Disorder (DPD) refers to a personality disorder with depressive features.

Recurrent Brief Depression (RBD) refers to a condition in which individuals have depressive episodes about once per month, each episode lasting 2 weeks or less and typically less than 2-3 days.

Minor depressive disorder or minor depression refers to a depression in which at least 2 symptoms are present for 2 weeks.

Bipolar disorder or manic depressive disorder causes extreme mood swings that include emotional highs (mania or hypomania) and lows (depression). During periods of mania the individual may feel or act abnormally happy, energetic, or irritable. They often make poorly thought out decisions with little regard to the consequences. The need for sleep is usually reduced. During periods of depression there may be crying, poor eye contact with others, and a negative outlook on life. The risk of suicide among those with the disorder is high at greater than 6% over 20 years, while self harm occurs in 30-40%. Other mental health issues such as anxiety disorder and substance use disorder are commonly associated with bipolar disorder.

Depression caused by chronic medical conditions refers to depression caused by chronic medical conditions such as cancer or chronic pain, chemotherapy, chronic stress.

Treatment-resistant depression refers to a condition where the individuals have been treated for depression, but the symptoms do not improve. For example, antidepressants or psychological counseling (psychotherapy) do not ease depression symptoms for individuals with treatment-resistant depression. In some cases, individuals with treatment-resistant depression improve symptoms, but come back. Refractory depression occurs in patients suffering from depression who are resistant to standard pharmacological treatments, including tricyclic antidepressants, MAOIs, SSRIs, and double and triple uptake inhibitors and/or anxiolytic drugs, as well as non-pharmacological treatments (e.g., psychotherapy, electroconvulsive therapy, vagus nerve stimulation and/or transcranial magnetic stimulation).

Post-surgical depression refers to feelings of depression that follow a surgical procedure (e.g., as a result of having to confront one's mortality). For example, individuals may feel sadness or empty mood persistently, a loss of pleasure or interest in hobbies and activities normally enjoyed, or a persistent felling of worthlessness or hopelessness.

Mood disorder associated with conditions or disorders of women's health refers to mood disorders (e.g., depression) associated with (e.g., resulting from) a condition or disorder of women's health (e.g., as described herein).

Suicidality, suicidal ideation, suicidal behavior refers to the tendency of an individual to commit suicide. Suicidal ideation concerns thoughts about or an unusual preoccupation with suicide. The range of suicidal ideation varies greatly, from e.g., fleeting thoughts to extensive thoughts, detailed planning, role playing, incomplete attempts. Symptoms include talking about suicide, getting the means to commit suicide, withdrawing from social contact, being preoccupied with death, feeling trapped or hopeless about a situation, increasing use of alcohol or drugs, doing risky or self-destructive things, saying goodbye to people as if they won't be seen again.

Symptoms of depression include persistent anxious or sad feelings, feelings of helplessness, hopelessness, pessimism, worthlessness, low energy, restlessness, difficulty sleeping, sleeplessness, irritability, fatigue, motor challenges, loss of interest in pleasurable activities or hobbies, loss of concentration, loss of energy, poor self-esteem, absence of positive thoughts or plans, excessive sleeping, overeating, appetite loss, insomnia, self-harm, thoughts of suicide, and suicide attempts. The presence, severity, frequency, and duration of symptoms may vary on a case to case basis. Symptoms of depression, and relief of the same, may be ascertained by a physician or psychologist (e.g., by a mental state examination).

In some embodiments, the method provides therapeutic effect (e.g., as measured by reduction in Hamilton Depression Score (HAM-D)) within 4, 3, 2, 1 days; 96, 84, 72, 60, 48, 24, 20, 16, 12, 10, 8 hours or less. In some embodiments, the therapeutic effect is a decrease from baseline in HAM-D score at the end of a treatment period (e.g., 12, 24, 48 hours after administration; 24, 48, 72, 96 hours or more). In some embodiments, the decrease from baseline in HAM-D score is from severe (e.g., HAM-D score of 24 or greater) to symptom-free (e.g., HAM-D score of 7 or lower). In some embodiments, the baseline score is about 10 to 52 (e.g., more than 10, 15, or 20; 10 to 52, 12 to 52, 15 to 52, 17 to 52, 20 to 52, 22 to 52). In some embodiments, the baseline score is at least 10, 15, or 20. In some embodiments, the HAM-D score at the end of the treatment period is about 0 to 10 (e.g., less than 10; 0 to 10, 0 to 6, 0 to 4, 0 to 3, 0 to 2, 1.8). In some embodiments, the HAM-D score at the end of the treatment period is less than 10, 7, 5, or 3. In some embodiments, the decrease in HAM-D score is from a baseline score of about 20 to 30 (e.g., 22 to 28, 23 to 27, 24 to 27, 25 to 27, 26 to 27) to a HAM-D score at the end of the treatment period is about 0 to 10 (e.g., less than 10; 0 to 10, 0 to 6, 0 to 4, 0 to 3, 0 to 2, 1.8). In some embodiments, the decrease in the baseline HAM-D score to HAM-D score at the end of the treatment period is at least 1, 2, 3, 4, 5, 7, 10, 25, 40, 50, or 100 fold). In some embodiments, the percentage decrease in the baseline HAM-D score to HAM-D score at the end of the treatment period is at least 50% (e.g., 60%, 70%, 80%, 90%). In some embodiments, the therapeutic effect is a decrease from baseline in HAM-D score at the end of a treatment period (e.g., 12, 24, 48 hours after administration; 24, 48, 72, 96 hours or more) at least 10, 15, or 20 points. In some embodiments, the therapeutic effect is a decrease from baseline in HAM-D score at the end of a treatment period (e.g., 12, 24, 48 hours after administration; 24, 48, 72, 96 hours or more) at least 5, 7, or 10 points more relative to the therapeutic effect provided by a placebo treatment.

In some embodiments, the method provides therapeutic effect (e.g., as measured by reduction in Montgomery-Asberg Depression Rating Scale (MADRS)) within 4, 3, 2, 1 days; 96, 84, 72, 60, 48, 24, 20, 16, 12, 10, 8 hours or less. The Montgomery-Asberg Depression Rating Scale (MADRS) is a ten-item diagnostic questionnaire (regarding apparent sadness, reported sadness, inner tension, reduced sleep, reduced appetite, concentration difficulties, lassitude, inability to feel, pessimistic thoughts, and suicidal thoughts) which psychiatrists use to measure the severity of depressive episodes in patients with mood disorders. 0-6 indicates normal/symptom absent; 7-19 indicates mild depression; 20-34 indicates moderate depression; and >34 indicates severe depression. In some embodiments, the therapeutic effect is a decrease from baseline in MADRS score at the end of a treatment period (e.g., 12, 24, 48 hours after administration; 24, 48, 60, 72, 96 hours or more). In some embodiments, the decrease from baseline in MADRS score is from severe (e.g., MADRS score of 30 or greater) to symptom-free (e.g., MADRS score of 20 or lower). For example, the mean change from baseline in MADRS total score from treatment with a compound described herein is about −15, −20, −25, −30, while the mean change from baseline in MADRS total score from treatment with placebo is about −15, −10, −5.

In some embodiments, the method provides therapeutic effect (e.g., as measured by reduction in Edinburgh Postnatal Depression Scale (EPDS)) within 4, 3, 2, 1 days; 24, 20, 16, 12, 10, 8 hours or less. In some embodiments, the therapeutic effect is a improvement measured by the EPDS.

In some embodiments, the method provides therapeutic effect (e.g., as measured by reduction in Clinical Global Impression-Improvement Scale (CGI)) within 4, 3, 2, 1 days; 24, 20, 16, 12, 10, 8 hours or less. In some embodiments, the therapeutic effect is a CGI score of 2 or less.

In some embodiments, the method provides therapeutic effect (e.g., as measured by reduction in Generalized Anxiety Disorder 7-Item Scale (GAD-7)) within 4, 3, 2, 1 days; 24, 20, 16, 12, 10, 8 hours or less.

Anxiety Disorders

Provided herein are methods for treating anxiety disorders (e.g., generalized anxiety disorder, panic disorder, obsessive compulsive disorder, phobia, post-traumatic stress disorder). Anxiety disorder is a blanket term covering several different forms of abnormal and pathological fear and anxiety. Current psychiatric diagnostic criteria recognize a wide variety of anxiety disorders.

Generalized anxiety disorder is a common chronic disorder characterized by long-lasting anxiety that is not focused on any one object or situation. Those suffering from generalized anxiety experience non-specific persistent fear and worry and become overly concerned with everyday matters. Generalized anxiety disorder is the most common anxiety disorder to affect older adults.

In panic disorder, a person suffers from brief attacks of intense terror and apprehension, often marked by trembling, shaking, confusion, dizziness, nausea, difficulty breathing. These panic attacks, defined by the APA as fear or discomfort that abruptly arises and peaks in less than ten minutes, can last for several hours and can be triggered by stress, fear, or even exercise; although the specific cause is not always apparent. In addition to recurrent unexpected panic attacks, a diagnosis of panic disorder also requires that said attacks have chronic consequences: either worry over the attacks' potential implications, persistent fear of future attacks, or significant changes in behavior related to the attacks. Accordingly, those suffering from panic disorder experience symptoms even outside of specific panic episodes. Often, normal changes in heartbeat are noticed by a panic sufferer, leading them to think something is wrong with their heart or they are about to have another panic attack. In some cases, a heightened awareness (hypervigilance) of body functioning occurs during panic attacks, wherein any perceived physiological change is interpreted as a possible life threatening illness (i.e. extreme hypochondriasis).

Obsessive compulsive disorder is a type of anxiety disorder primarily characterized by repetitive obsessions (distressing, persistent, and intrusive thoughts or images) and compulsions (urges to perform specific acts or rituals). The OCD thought pattern may be likened to superstitions insofar as it involves a belief in a causative relationship where, in reality, one does not exist. Often the process is entirely illogical; for example, the compulsion of walking in a certain pattern may be employed to alleviate the obsession of impending harm. And in many cases, the compulsion is entirely inexplicable, simply an urge to complete a ritual triggered by nervousness. In a minority of cases, sufferers of OCD may only experience obsessions, with no overt compulsions; a much smaller number of sufferers experience only compulsions.

The single largest category of anxiety disorders is that of phobia, which includes all cases in which fear and anxiety is triggered by a specific stimulus or situation. Sufferers typically anticipate terrifying consequences from encountering the object of their fear, which can be anything from an animal to a location to a bodily fluid.

Post-traumatic stress disorder or PTSD is an anxiety disorder which results from a traumatic experience. Post-traumatic stress can result from an extreme situation, such as combat, rape, hostage situations, or even serious accident. It can also result from long term (chronic) exposure to a severe stressor, for example soldiers who endure individual battles but cannot cope with continuous combat. Common symptoms include flashbacks, avoidant behaviors, and depression.

Women's Health Disorders

Provided herein are methods for treating conditions or disorders related to women's health. Conditions or disorders related to women's health include, but are not limited to, Gynecological health and disorders (e.g., premenstrual syndrome (PMS), premenstrual dysphoric disorder (PMDD)), pregnancy issues (e.g., miscarriage, abortion), infertility and related disorders (e.g., polycystic ovary syndrome (PCOS)), other disorders and conditions, and issues related to women's overall health and wellness (e.g., menopause).

Gynecological health and disorders affecting women include menstruation and menstrual irregularities; urinary tract health, including urinary incontinence and pelvic floor disorders; and such disorders as bacterial vaginosis, vaginitis, uterine fibroids, and vulvodynia.

Premenstrual syndrome (PMS) refers to physical and emotional symptoms that occur in the one to two weeks before a women's period. Symptoms vary but can include bleeding, mood swings, tender breasts, food cravings, fatigue, irritability, acne, and depression.

Premenstrual dysphoric disorder (PMDD) is a severe form of PMS. The symptoms of PMDD are similar to PMS but more severe and may interfere with work, social activity, and relationships. PMDD symptoms include mood swings, depressed mood or feelings of hopelessness, marked anger, increased interpersonal conflicts, tension and anxiety, irritability, decreased interest in usual activates, difficulty concentrating, fatigue, change in appetite, feeling out of control or overwhelmed, sleep problems, physical problems (e.g., bloating, breast tenderness, swelling, headaches, joint or muscle pain).

Pregnancy issues include preconception care and prenatal care, pregnancy loss (miscarriage and stillbirth), preterm labor and premature birth, sudden infant death syndrome (SIDS), breastfeeding, and birth defects.

Miscarriage refers to a pregnancy that ends on its own, within the first 20 weeks of gestation.

Abortion refers to the deliberate termination of a pregnancy, which can be performed during the first 28 weeks of pregnancy.

Infertility and related disorders include uterine fibroids, polycystic ovary syndrome, endometriosis, and primary ovarian insufficiency.

Polycystic ovary syndrome (PCOS) refers to an endocrine system disorder among women of reproductive age. PCOS is a set of symptoms resulting from an elevated male hormone in women. Most women with PCOS grow many small cysts on their ovaries. Symptoms of PCOS include irregular or no menstrual periods, heavy periods, excess body and facial hair, acne, pelvic pain, difficulty getting pregnant, and patches of thick, darker, velvety skin. PCOS may be associated with conditions including type 2 diabetes, obesity, obstructive sleep apnea, heart disease, mood disorders, and endometrial cancer.

Other disorders and conditions that affect only women include Turner syndrome, Rett syndrome, and ovarian and cervical cancers.

Issues related to women's overall health and wellness include violence against women, women with disabilities and their unique challenges, osteoporosis and bone health, and menopause.

Menopause refers to the 12 months after a woman's last menstrual period and marks the end of menstrual cycles. Menopause typically occurs in a woman's 40s or 50s. Physical symptoms such as hot flashes and emotional symptoms of menopause may disrupt sleep, lower energy, or trigger anxiety or feelings of sadness or loss. Menopause includes natural menopause and surgical menopause, which is a type of induced menopause due to an event such as surgery (e.g., hysterectomy, oophorectomy; cancer). It is induced when the ovaries are gravely damaged by, e.g., radiation, chemotherapy, or other medications.

Neuroactive Steroids

Neuroactive steroids (or neurosteroids) are natural, synthetic, or semi-synthetic steroids that rapidly alter neuronal excitability through interaction with neurotransmitter-gated ion channels. Neuroactive steroids effect binding to membrane-bound receptors such as those for inhibitory and (or) excitatory neurotransmitters including GABAA, NMDA, and sigma receptors.

The steroids that may be classified into functional groups according to chemical structure and physiological activity and include estrogenic hormones, progestational hormones, and androgenic hormones. Of particular interest are progestational hormones, referred to herein as "progestins" or "progestogens", and their derivatives and bioactive metabolites. Members of this broad family include steroid hormones disclosed in Remington's Pharmaceutical Sciences, Gennaro et al., Mack Publishing Co. (18th ed. 1990), 990-993. As with all other classes of steroids, stereoisomerism is of fundamental importance with the sex hormones. As used herein, a variety of progestins (e.g., progesterone) and their derivatives, including both synthetic and natural products, can be used, as well as progestin metabolites such as progesterone.

The term "progesterone" as used herein refers to a member of the progestin family and includes a 21 carbon steroid hormone. Progesterone is also known as D4-pregnene-3,20-dione; Δ4-pregnene-3,20-dione; or pregn-4-ene-3,20-dione. As used herein a "synthetic progestin" is a molecule whose structure is related to that of progesterone, is synthetically derived, and retains the biological activity of progesterone.

Representative synthetic progestins include, but are not limited to, substitutions at the 17-position of the progesterone ring to introduce a hydroxyl, acetyl, hydroxyl acetyl, aliphatic, nitro, or heterocyclic group, modifications to produce 17α-OH esters (e.g., 17 α-hydroxyprogesterone caproate), as well as modifications that introduce 6-methyl, 6-ene, and 6-chloro substituents onto progesterone (e.g., medroxyprogesterone acetate, megestrol acetate, and chlomadinone acetate), and which retains the biological activity of progesterone. Such progestin derivatives include 5-dehydroprogesterone, 6-dehydro-retroprogesterone (dydrogesterone), allopregnanolone (allopregnan-3α, or 3β-ol-20-one), ethynodiol diacetate, hydroxyprogesterone caproate (pregn-4-ene-3,20-dione, 17-(1-oxohexy)oxy); levonorgestrel, norethindrone, norethindrone acetate (19-norpregn-4-en-20-yn-3-one, 17-(acetyloxy)-, (17α)-); norethynodrel, norgestrel, pregnenolone, ganaxolone (also referred to as CCD-1042 or INN), and megestrol acetate. In some embodiments, the neuroactive steroid is ganaxolone.

Useful progestins also can include allopregnone-3α or 3β, 20α or 20β-diol (see Merck Index 258-261); allopregnane-3β,21-diol-11,20-dione; allopregnane-3β,17α-diol-20-one; 3,20-allopregnanedione, allopregnane, 3β,11β,17α,20β,21-pentol; allopregnane-3β,17α,20β,21-tetrol; allopregnane-3 a or 3β,11β,17α,21-tetrol-20-one, allopregnane-3β,17α or 20β-triol; allopregnane-3β,17α,21-triol-11,20-dione; allopregnane-3β,11β,21-triol-20-one; allopregnane-3β,17α,21-triol-20-one; allopregnane-3α or 3β-ol-20-one; pregnanediol; 3,20-pregnanedione; pregnan-3α-ol-20-one; 4-pregnene-20,21-diol-3,11-dione; 4-pregnene-11β,17α, 20β,21-tetrol-3-one; 4-pregnene-17α,20β,21-triol-3,11-dione; 4-pregnene-17α,20β,21-triol-3-one, and pregnenolone methyl ether. Further progestin derivatives include esters with non-toxic organic acids such as acetic acid, benzoic acid, maleic acid, malic acid, caproic acid, and citric acid and inorganic salts such as hydrochloride, sulfate, nitrate, bicarbonate and carbonate salts. Other suitable progestins include alphaxalone (also referred to as INN, alfaxolone, and alphaxolone), alphadolone (also referred to as alfadolone), hydroxydione, and minaxolone. In some embodiments, the neuroactive steroid is alphaxolone.

Additional suitable neuroactive steroids are disclosed in WIPO Publication Nos. WO2013/188792, WO 2013/056181, WO2015/010054, WO2014/169832, WO2014/169836, WO2014/169833, WO2014/169831, WO2015/027227, WO 2014/100228, U.S. Pat. Nos. 5,232,917, 8,575, 375 and 8,759,330, which are incorporated herein by reference for the neuroactive steroids described therein.

In some embodiments, the therapeutic agent is a neuroactive steroid (e.g., a neuroactive steroid selected from pregnanolone, ganaxolone, alphadalone, alphaxalone, and allopregnanolone).

Exemplary neuroactive steroid compounds include:

(Compound 1)

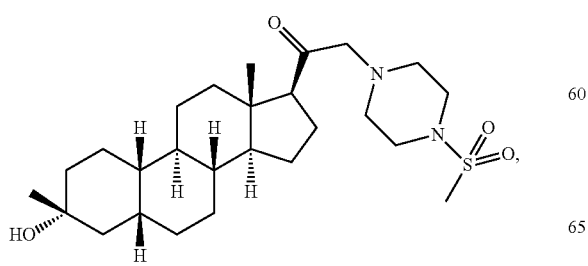

(Compound 2)

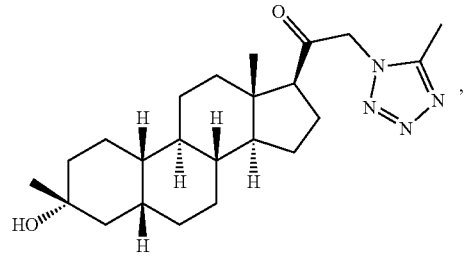

(Compound 3)

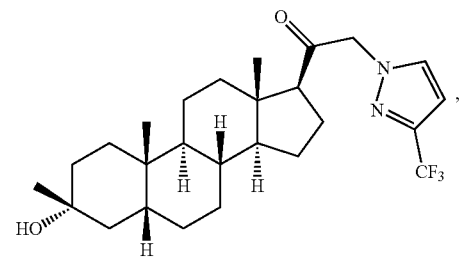

(Compound 4)

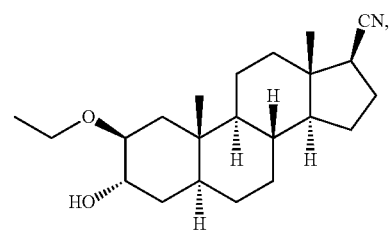

(Compound 5)

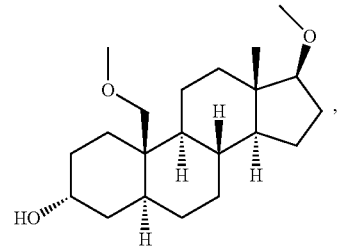

(Compound 6)

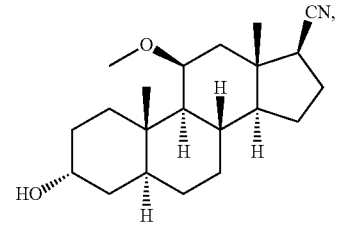

(Compound 7)

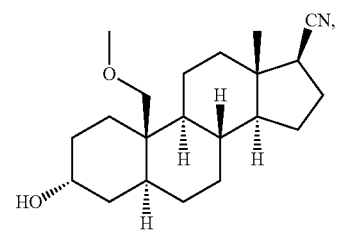

-continued
(Compound 8)
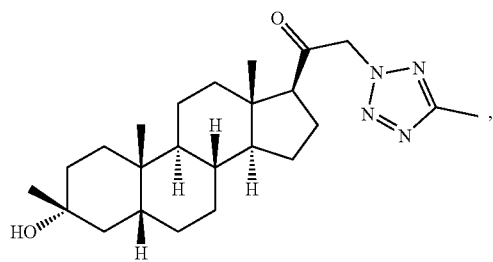
(Compound 9)
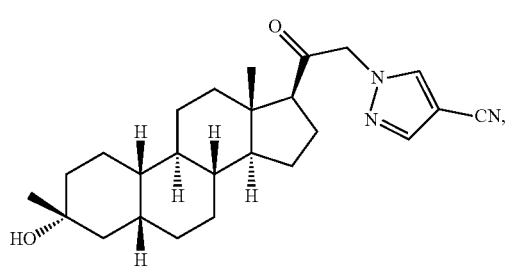
(Compound 10)
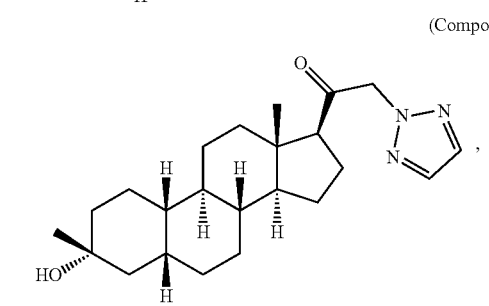
(Compound 11)
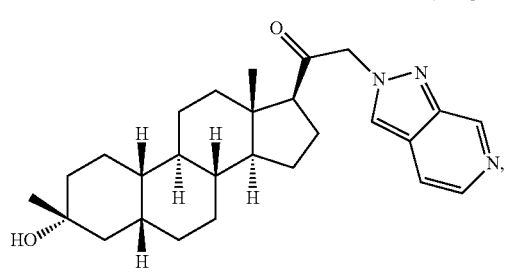
(Compound 12)
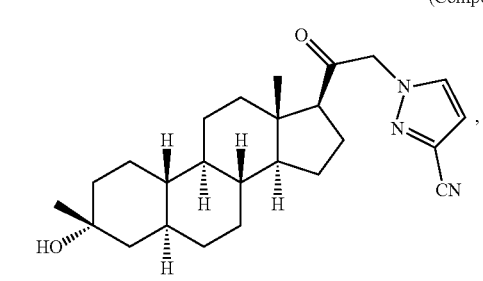
-continued
(Compound 13)
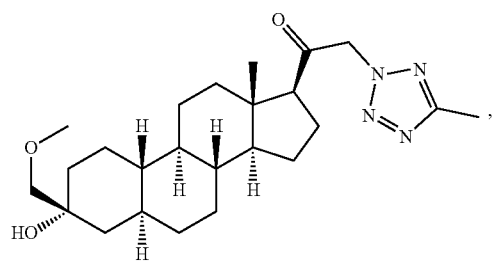
(Compound 14)
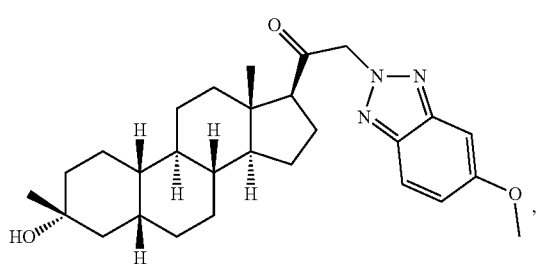
(Compound 15)
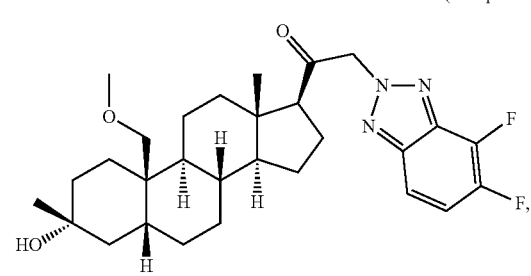
(Compound 16)
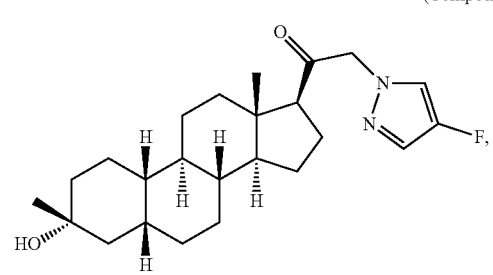
(Compound 17)
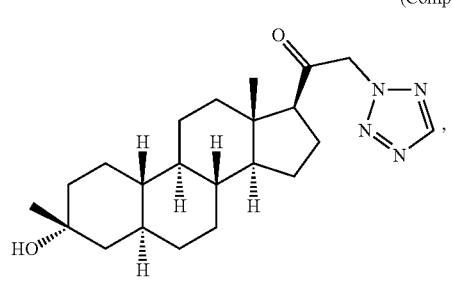

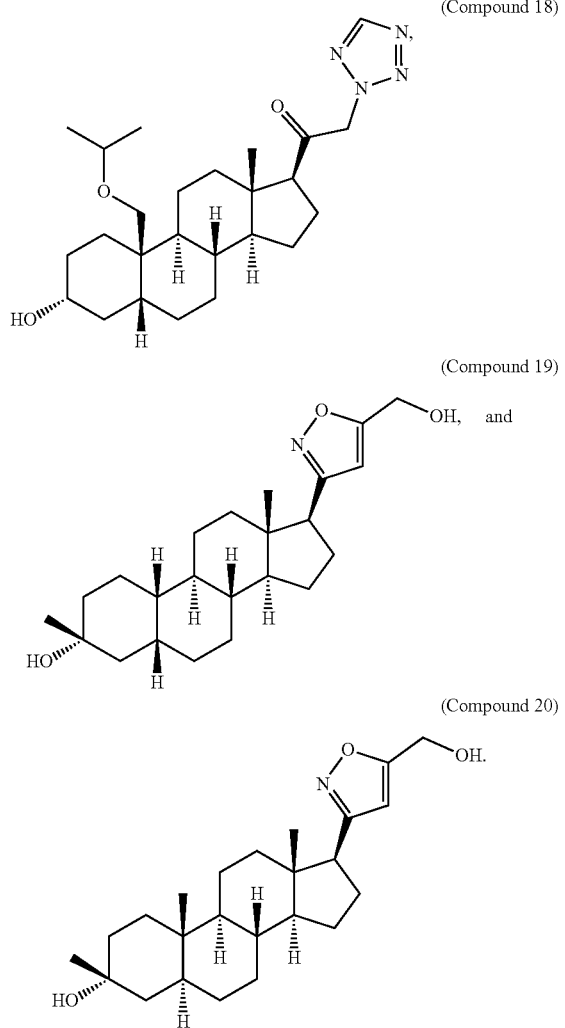

(Compound 18)

(Compound 19)

(Compound 20)

In particular embodiments, the steroids are one or more of a series of sedative-hypnotic 3 alpha-hydroxy ring A-reduced pregnane steroids that include the major metabolites of progesterone and deoxycorticosterone, 3 alpha-hydroxy-5 alpha-pregnan-20-one (allopregnanolone) and 3 alpha,21-dihydroxy-5 alpha-pregnan-20-one (allotetrahydroDOC), respectively. These 3 alpha-hydroxysteroids do not interact with classical intracellular steroid receptors but bind stereoselectively and with high affinity to receptors for the major inhibitory neurotransmitter in the brain, gamma-amino-butyric acid (GABA).

In certain embodiments, the neuroactive steroids are progesterone, pregnanolone, allopregnanolone, alphadalone, ganaxolone, or alphaxolone or other progesterone analogs. In a particular embodiment, the neuroactive steroid is allopregnanolone or a derivative thereof. In some embodiments, the neuroactive steroid is allopregnanolone. Exemplary derivatives include, but are not limited to, (20R)-17beta-(1-hydroxy-2,3-butadienyl)-5alpha-androstane-3alpha-ol (HBAO). Additional derivatives are described in WO 2012/127176.

In some embodiments, the neuroactive steroid is allopregnanolone. In some embodiments, the neuroactive steroid is ganaxolone. In some embodiments, the neuroactive steroid is alphaxolone.

As used herein, the neuroactive steroids described herein, e.g., "allopregnanolone," "ganaxolone," and "alphaxolone," also encompasses pharmaceutically acceptable, pharmacologically active derivatives including individual enantiomers (dextrogyral and levrogyral enantiomers) and their pharmaceutically acceptable salts, mixtures of enantiomers and their pharmaceutically acceptable salts, and active metabolites and their pharmaceutically acceptable salts, unless otherwise noted. It is understood that in some cases dosages of enantiomers, derivatives, and metabolites may need to be adjusted based on relative activity of the racemic mixture of the neuroactive steroid, e.g., pregnanolone, allopregnanolone, alphadalone, ganaxolone, or alphaxolone.

The lipophilic nature of the neuroactive steroid (e.g., pregnanolone, allopregnanolone, alphadalone, ganaxolone, or alphaxolone), can make it different to formulate for in vivo administration. As discussed above, the neuroactive steroid (e.g., pregnanolone, allopregnanolone, alphadalone, ganaxolone, or alphaxolone), can be formulated with a host, such as a cyclodextrin to improve the solubility. Alternatively, or additionally, the neuroactive steroid (e.g., pregnanolone, allopregnanolone, alphadalone, ganaxolone, or alphaxolone), can be modified in an attempt to improve the solubility. For example, polar groups can be introduced onto position 16a with the goal of increasing water solubility, brain accessibility, and potency of neuroactive steroids as described in Kasal et al., *J Med. Chem.*, 52(7), 2119-215 (2009).

Solubilization of Neuroactive Steroids

Some neuroactive steroids possess limited aqueous solubility. In order to provide formulations capable of delivering therapeutically effective dosages, a variety of methods can be employed to enhance the solubility and bioavailability of neuroactive steroids. See, for example, "Water-Insoluble Drug Formulation", 2nd Edition, edited by Rong Liu (CRC Press, Boca Raton, Fla., 2008). Using the techniques described below, a solubilized formulation of one or more neuroactive steroids can be prepared.

Inclusion Complexes

The solubility of neuroactive steroids can be improved by inclusion complexation (e.g., host-guest formulations). Inclusion complexes are formed when a nonpolar molecule (i.e., the guest, such as a drug with poor aqueous stability) or portion of a molecule inserts into a nonpolar cavity of another molecule or group of molecules (i.e., the host). If the host molecule or molecules exhibit water good solubility, the solubility of the host-guest complex will be greater than the solubility of the guest alone.

Inclusion complexes containing or comprising one or more neuroactive steroids can be formed using any suitable host molecule or molecules. For example, the water solubility of neuroactive steroids can be increased by inclusion complexation with cyclodextrins. Steroid-cyclodextrin complexes are known in the art. See, for example, U.S. Pat. No. 7,569,557 to Backensfeld, et al., and U.S. Patent Application Publication No. US 2006/0058262 to Zoppetti, et al.

Dextrans are soluble polysaccharides produced by bacteria and yeasts. They are characterized by a predominance (>95%) of α (1-6) backbone linkages and varying proportions of α(1-2), α(1-3) and α(1-4) linkages typically at branch points 1, 2. Dextrins are partially hydrolyzed glucose homopolymers composed exclusively of α(1-4) backbone linkages.

Cyclodextrins are cyclic oligosaccharides containing or comprising six (α-cyclodextrin), seven (β-cyclodextrin), eight (γ-cyclodextrin), or more α-(1,4)-linked glucose residues. The hydroxyl groups of the cyclodextrins are oriented to the outside of the ring while the glucosidic oxygen and two rings of the non-exchangeable hydrogen atoms are directed towards the interior of the cavity. As a result, cyclodextrins possess a hydrophobic inner cavity combined with a hydrophilic exterior which conveys water solubility. Upon combination with a hydrophobic drug, such as a neuroactive steroid, the neuroactive steroid (i.e., the guest) inserts into the hydrophobic interior of the cyclodextrin (i.e., the host). The host-guest complex retains water solubility as a consequence of the hydrophobic exterior of the cyclodextrin ring.

Neuroactive steroid-cyclodextrin complexes can, as solubility permits, be incorporated into any of the parenteral and non-parenteral formulations described below. If desired, the aqueous solubility of solid neuoractive steroid-cyclodextrin complexes can be further enhanced by isolating the neuoractive steroid-cyclodextrin complex as a solid via lyophilization and/or via micronizing the solid neuoractive steroid-cyclodextrin complex.

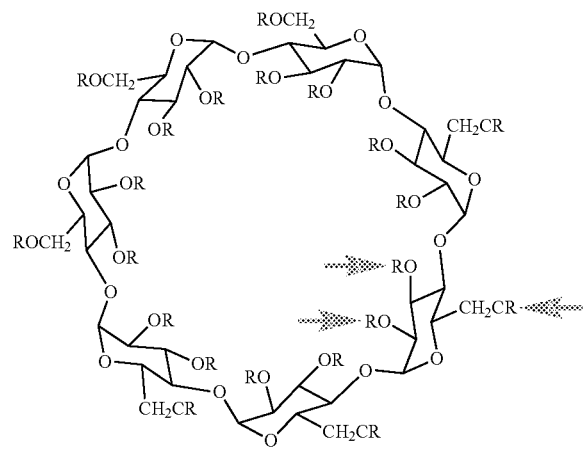

This cyclic orientation provides a truncated cone structure that is hydrophilic on the exterior and lipophilic on the interior. Cyclodextrin complexes are formed when a guest molecule is partially or fully contained in the interior of the cavity. The parent α-, β-, and γ-cyclodextrins (particularly β) have limited aqueous solubility and show toxicity when given parenterally. Therefore, the parent cyclodextrin structure can be chemically modified to generate a parenterally safe CD-derivative. The modifications are typically made at one or more of the 2, 3, or 6 position hydroxyls.

Neuroactive steroid-cyclodextrin complexes are preferably formed from a cyclodextrin selected from the group consisting of α-cyclodextrin, β-cyclodextrin, γ-cyclodextrin, and derivatives thereof. The cyclodextrin may be chemically modified such that some or all of the primary or secondary hydroxyl groups of the macrocycle, or both, are functionalized with a pendant group. Suitable pendant groups include, but are not limited to, sulfinyl, sulfonyl, phosphate, acyl, and $C_1$-$C_{12}$ alkyl groups optionally substituted with one or more (e.g., 1, 2, 3, or 4) hydroxy, carboxy, carbonyl, acyl, oxy, oxo; or a combination thereof. Methods of modifying these alcohol residues are known in the art, and many cyclodextrin derivatives are commercially available, including sulfo butyl ether β-cyclodextrins available under the trade name CAPTISOL® from Ligand Pharmaceuticals (La Jolla, Calif.).

Examples of suitable cyclodextrins for use in neuroactive steroid, e.g., pregnanolone, allopregnanolone, alphadalone, ganaxolone, or alphaxolone formulations, can include cyclodextrins disclosed in U.S. Pat. Nos. 5,874,418; 6,046,177; and 7,635,733, which are herein incorporated by reference. Other examples of suitable cyclodextrins for use in neuroactive steroid formulations non-exclusively include α-cyclodextrin; β-cyclodextrin; γ-cyclodextrin; methyl α-cyclodextrin; methyl β-cyclodextrin; methyl γ-cyclodextrin; ethyl β-cyclodextrin; butyl α-cyclodextrin; butyl β-cyclodextrin; butyl γ-cyclodextrin; pentyl γ-cyclodextrin; hydroxyethyl β-cyclodextrin; hydroxyethyl γ-cyclodextrin; 2-hydroxypropyl α-cyclodextrin; 2-hydroxypropyl β-cyclodextrin; 2-hydroxypropyl γ-cyclodextrin; 2-hydroxybutyl β-cyclodextrin; acetyl α-cyclodextrin; acetyl β-cyclodextrin; acetyl γ-cyclodextrin; propionyl β-cyclodextrin; butyryl β-cyclodextrin; succinyl α-cyclodextrin; succinyl β-cyclodextrin; succinyl γ-cyclodextrin; benzoyl β-cyclodextrin; palmityl β-cyclodextrin; toluenesulfonyl β-cyclodextrin; acetyl methyl β-cyclodextrin; acetyl butyl β-cyclodextrin; glucosyl α-cyclodextrin; glucosyl β-cyclodextrin; glucosyl γ-cyclodextrin; maltosyl α-cyclodextrin; maltosyl β-cyclodextrin; maltosyl γ-cyclodextrin; α-cyclodextrin carboxymethylether; β-cyclodextrin carboxymethylether; γ-cyclodextrin carboxymethylether; carboxymethylethyl β-cyclodextrin; phosphate ester α-cyclodextrin; phosphate ester β-cyclodextrin; phosphate ester γ-cyclodextrin; 3-trimethylammonium-2-hydroxypropyl β-cyclodextrin; sulfobutyl ether β-cyclodextrin; carboxymethyl α-cyclodextrin; carboxymethyl β-cyclodextrin; carboxymethyl γ-cyclodextrin, and combinations thereof.

Preferred cyclodextrins include, but are not limited to, alkyl cyclodextrins, hydroxy alkyl cyclodextrins, such as hydroxy propyl β-cyclodextrin, carboxy alkyl cyclodextrins and sulfoalkyl ether cyclodextrins, such as sulfo butyl ether β-cyclodextrin.

In particular embodiments, the cyclodextrin is a alpha, beta, or gamma cyclodextrin having a plurality of charges (e.g., negative or positive) on the surface. In more particular embodiments, the cyclodextrin is β-cyclodextrin containing or comprising a plurality of functional groups that are negatively charged at physiological pH. Examples of such functional groups include, but are not limited to, carboxylic acid (carboxylate) groups, sulfonate ($RSO_3^-$), phosphonate groups, phosphinate groups, and amino acids that are negatively charged at physiological pH. The charged functional groups can be bound directly to the cyclodextrins or can be linked by a spacer, such as an alkylene chain. The number of carbon atoms in the alkylene chain can be varied, but is generally between about 1 and 10 carbons, preferably 1-6 carbons, more preferably 1-4 carbons. Highly sulfated cyclodextrins are described in U.S. Pat. No. 6,316,613.

In one embodiment, the cyclodextrins is a β-cyclodextrin functionalized with a plurality of sulfobutyl ether groups. Such a cyclodextrins is sold under the trade name CAPTISOL®.

CAPTISOL® is a polyanionic beta-cyclodextrin derivative with a sodium sulfonate salt separated from the lipophilic cavity by a butyl ether spacer group, or sulfobutylether (SBE). CAPTISOL® is not a single chemical species, but comprised of a multitude of polymeric structures of varying degrees of substitution and positional/regional isomers dictated and controlled to a uniform pattern by a patented manufacturing process consistently practiced and improved to control impurities.

CAPTISOL® contains six to seven sulfobutyl ether groups per cyclodextrin molecule. Because of the very low pKa of the sulfonic acid groups, CAPTISOL® carries multiple negative charges at physiologically compatible pH values. The four-carbon butyl chain coupled with repulsion of the end group negative charges allows for an "extension" of the cyclodextrin cavity. This often results in stronger binding to drug candidates than can be achieved using other modified cyclodextrins. It also provides a potential for ionic charge interactions between the cyclodextrin and a positively charged drug molecule. In addition, these derivatives impart exceptional solubility and parenteral safety to the molecule. Relative to beta-cyclodextrin, CAPTISOL® provides higher interaction characteristics and superior water solubility in excess of 100 grams/100 ml, a 50-fold improvement.

In other embodiments, the cyclodextrins has plurality of functional groups that are negatively charged at physiological pH. Suitable positively charged groups include, but are not limited to, quaternary ammonium groups. Exemplary cyclodextrins include, but are not limited to, mono-6(A)-butylammonium-6(A)-deoxy-beta-cyclodextrin tosylate (BuAM-beta-CD) and Amine- and guanidine-derivatised β-cyclodextrin (βCD).

Preferably, the cyclodextrin is present in an amount of from about 0.1% to about 40% w/w of the overall formulation, preferably from about 5% to about 40% w/w, more preferably about 10% to about 40% w/w, most preferably about 10% to about 35% w/w. In certain embodiments, the concentration of the cyclodextrins is from about 15% to about 35% w/w, preferably from about 20% to about 35% w/w, more preferably about 30% to about 35% w/w. In one embodiment, the formulation contains about 1 to about 2, preferably about 1.5 mg neuroactive steroid (e.g., pregnanolone, allopregnanolone, alphadalone, ganaxolone, alphaxolone) per mL of cyclodextrin, e.g., CAPTISOL®.

Pharmaceutical Compositions

In one aspect, the invention provides a pharmaceutical composition comprising a compound of the present invention (also referred to as the "active ingredient") and a pharmaceutically acceptable excipient. In certain embodiments, the pharmaceutical composition comprises an effective amount of the active ingredient. In certain embodiments, the pharmaceutical composition comprises a therapeutically effective amount of the active ingredient. In certain embodiments, the pharmaceutical composition comprises a prophylactically effective amount of the active ingredient.

The pharmaceutical compositions provided herein can be administered by a variety of routes including, but not limited to, oral (enteral) administration, parenteral (by injection) administration, rectal administration, transdermal administration, intradermal administration, intrathecal administration, subcutaneous (SC) administration, intravenous (IV) administration, intramuscular (IM) administration, and intranasal administration.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the onset of a CNS-disorder, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc, or may be continued indefinitely, for example, for the rest of the subject's life. In certain embodiments, the chronic administration is intended to provide a constant level of the compound in the blood, e.g., within the therapeutic window over the extended period of time.

The pharmaceutical compostions of the present invention may be further delivered using a variety of dosing methods. For example, in certain embodiments, the pharmaceutical composition may be given as a bolus, e.g., in order to raise the concentration of the compound in the blood to an effective level. The placement of the bolus dose depends on the systemic levels of the active ingredient desired throughout the body, e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g., by IV drip, to provide maintenance of a steady-state concentration of the active ingredient in the subject's body. Furthermore, in still yet other embodiments, the pharmaceutical composition may be administered as first as a bolus dose, followed by continuous infusion.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses, generally in an amount ranging from about 0.01 to about 20% by weight, preferably from about 0.1 to about 20% by weight, preferably from about 0.1 to about 10% by weight, and more preferably from about 0.5 to about 15% by weight.

Injection dose levels range from about 0.1 mg/kg/hour to at least 20 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 5 g/day for a 40 to 80 kg human patient.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable excipients known in the art. As before, the active compound in such compositions is typically a minor component, often being from about 0.05 to 10% by weight with the remainder being the injectable excipient and the like.

Transdermal compositions are typically formulated as a topical ointment or cream containing the active ingredient (s). When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The compounds of the present invention can also be administered in sustained release forms or from sustained release drug delivery systems. A description of representative sustained release materials can be found in *Remington's Pharmaceutical Sciences.*

The present invention also relates to the pharmaceutically acceptable acid addition salt of a compound of the present invention. The acid which may be used to prepare the pharmaceutically acceptable salt is that which forms a non-toxic acid addition salt, i.e., a salt containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

In another aspect, the invention provides a pharmaceutical composition comprising a compound of the present invention and a pharmaceutically acceptable excipient, e.g., a composition suitable for injection, such as for intravenous (IV) administration.

Pharmaceutically acceptable excipients include any and all diluents or other liquid vehicles, dispersion or suspension aids, surface active agents, isotonic agents, preservatives, lubricants and the like, as suited to the particular dosage form desired, e.g., injection. General considerations in the formulation and/or manufacture of pharmaceutical compositions agents can be found, for example, in *Remington's Pharmaceutical Sciences,* Sixteenth Edition, E. W. Martin (Mack Publishing Co., Easton, Pa., 1980), and *Remington: The Science and Practice of Pharmacy,* 21$^{st}$ Edition (Lippincott Williams & Wilkins, 2005).

For example, injectable preparations, such as sterile injectable aqueous suspensions, can be formulated according to the known art using suitable dispersing or wetting agents and suspending agents. Exemplary excipients that can be employed include, but are not limited to, water, sterile saline or phosphate-buffered saline, or Ringer's solution.

In certain embodiments, the pharmaceutical composition further comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, substituted or unsubstituted methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as Captisol®. See, e.g., U.S. Pat. No. 5,376,645. In certain embodiments, the composition comprises hexapropyl-β-cyclodextrin. In a more particular embodiment, the composition comprises hexapropyl-β-cyclodextrin (10-50% in water).

The injectable composition can be sterilized, for example, by filtration through a bacterial-retaining filter, or by incorporating sterilizing agents in the form of sterile solid compositions which can be dissolved or dispersed in sterile water or other sterile injectable medium prior to use.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, response of the individual patient, the severity of the patient's symptoms, and the like.

The compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include pre-filled, pre-measured ampules or syringes of the liquid compositions. In such compositions, the compound is usually a minor component (from about 0.1% to about 50% by weight or preferably from about 1% to about 40% by weight) with the remainder being various vehicles or carriers and processing aids helpful for forming the desired dosing form.

The compounds provided herein can be administered as the sole active agent, or they can be administered in combination with other active agents. In one aspect, the present invention provides a combination of a compound of the present invention and another pharmacologically active agent. Administration in combination can proceed by any technique apparent to those of skill in the art including, for example, separate, sequential, concurrent, and alternating administration.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of pharmaceutical compositions can be found, for example, in *Remington: The Science and Practice of Pharmacy* 21" ed., Lippincott Williams & Wilkins, 2005.

Buffers

The pharmaceutical compositions described herein (e.g., a pharmaceutical composition formulated for parenteral injection) can comprise a buffer (e.g., a buffer at a pH of between about 3 and about 8 (e.g., between about 5 and about 7, between about 5.5 and about 6.5, between about 5.9 and about 6.1). As used herein, the terms "buffer," "buffer system," or "buffering component" refers to a compound that, usually in combination with at least one other compound, provides a chemical system in solution that exhibits buffering capacity, that is, the capacity to neutralize, within limits, the pH lowering or raising effects of either strong acids or bases (alkali), respectively, with relatively little or no change in the original pH (e.g., the pH before being affected by, e.g., strong acid or base). For example, a buffer described herein maintains or controls the pH of a solution to a certain pH range. For example, "buffering capacity" can refer to the millimoles (mM) of strong acid or base (or respectively, hydrogen or hydroxide ions) required to change the pH by one unit when added to one liter (a standard unit) of the buffer solution. From this definition, it is apparent that the smaller the pH change in a solution caused by the addition of a specified quantity of acid or alkali, the greater the buffer capacity of the solution. See, for example, Remington: The Science and Practice of Pharmacy, Mack Publishing Co., Easton, Pa. (19$^{th}$ Edition, 1995), Chapter 17, pages 225-227. The buffer capacity will depend on the kind and concentration of the buffer components.

According to some embodiments, the buffering components are present from 1 mM, 2 mM, 5 mM, 10 mM, 20 mM, 50 mM, 75 mM, 100 mM, 150 mM, 200 mM, 250 mM or more in solution.

Preferred buffers include 4-2-hydroxyethyl-1-piperazineethanesulfonic acid (HEPES), 2-{[tris(hydroxymethyl)methyl]amino}ethanesulfonic acid (TES), 3-(N-morpholino)propanesulfonic acid (MOPS), piperazine-N,N'-bis(2-ethanesulfonic acid) (PIPES), dimethylarsinic acid (cacodylate), citrate (e.g., saline sodium citrate, potassium citrate, ammonium citrate), 2-(N-morpholino)ethanesulfonic acid (MES), phosphate (e.g., PBS, D-PBS), succinate (i.e., 2(R)-2-(methylamino)succinic acid), acetate, dimethylglutarate, maleate, imidazole, N-(2-Acetamido)-2-aminoethanesulfonic acid (ACES), N,N-bis(2-hydroxyethyl)-2-aminoethanesulfonic acid (BES), Bicine, Bis-Tris, Borate, N-cyclohexyl-3-aminopropanesulfonic acid (CAPS), Glycine, 3-[4-(2-Hydroxyethyl)-1-piperazinyl]propanesulfonic acid (HEPPS or EPPS), N-[Tris(hydroxymethyl)methyl]-3-aminopropanesulfonic acid, [(2-Hydroxy-1,1-bis(hydroxymethyl)ethyl)amino]-1-propanesulfonic acid (TAPS), Tricine, Tris, Tris Base, Tris Buffer, Tris-Glycine, Tris-HCl, collidine, veronal acetate, N-(2-Acetamido)iminodiacetic acid; N-(Carbamoylmethyl)iminodiacetic acid (ADA), β-Hydroxy-4-morpholinepropanesulfonic acid, 3-Morpholino-2-hydroxypropanesulfonic acid (MOPSO), cholamine chloride, 3-(N,N-Bis[2-hydroxyethyl]amino)-2-hydroxypropanesulfonic acid (DIPSO), acetamidoglycine, 3-{[1,3-Dihydroxy-2-(hydroxymethyl)-2-propanyl]amino}-2-hydroxy-1-propanesulfonic acid (TAPSO), Piperazine-N,N'-bis(2-hydroxypropanesulfonic acid) (POPSO), N-(2-Hydroxyethyl)piperazine-N'-(2-hydroxypropanesulfonic acid) (HEPPSO), N-cycloxhexyl-2-aminoethanesulfonic acid (CHES), 2-amino-methyl-1,3-proponediol (AMPd), and glycinamide.

In some embodiments, the buffer comprises a monoprotic acid. In some embodiments, the buffer comprises a polyprotic acid (e.g., citrate or phosphate). In some embodiments, the buffer is a solution of one or more substances (e.g., a salt of a weak acid and a weak base; a mixture of a weak acid and a salt of the weak acid with a strong base). In some embodiments, the buffer comprises a piperazine (e.g., PIPES, HEPES, POPSO, EPPS).

In some embodiments, the buffer comprises a non-metal complexing compound (e.g., MES, MOPS, PIPES).

In some embodiments, the buffer comprises a metal complexing compound (i.e., a metal chelating agent). In some embodiments, the metal chelating agent is citrate.

In some embodiments, the buffer is citrate buffer. In some embodiments, the buffer is phosphate buffer. In some embodiments, the buffer is histidine buffer.

In some embodiments, the buffer is present at a concentration of about 0.01, 0.05, 0.1, 0.5, 1, 5, 10, 20, 50, 100, 200, 250, 500 mM or more. In some embodiments, the buffer is present at a concentration of about 1 to about 500 mM, about 1 to about 300 mM, about 1 to about 200 mM, about 1 to about 100 mM, about 1 to about 50 mM, about 10 to about 500 mM, about 10 to about 300 mM, about 10 to about 200 mM, about 10 to about 100 mM, about 10 to about 50 mM.

In some embodiments, the buffer is present at a concentration of about 0.01 to about 10 mM, about 0.05 to about 5 mM, about 0.05 to about 5 mM, about 0.1 to about 5 mM, about 0.1 to about 3.5 mM.

In some embodiments, the pH of the aqueous solution is at or near physiological pH. Preferably, the pH of the aqueous solution is between about 3 to about 8 (e.g., between about 5 and about 7, between about 5.5 and about 6.5, between about 5.9 and about 6.1), or any specific value within said range. In some embodiments, the pH of the aqueous solution is between about 5 to about 6.5, or any specific value within said range (e.g., 5.5, 5.6, 5.7, 5.8, 5.9, 6, 6.1, 6.2, 6.3, 6.4). In some embodiments, the pH of the aqueous solution is about 6. The skilled artisan would recognize that the pH may be adjusted to a more optimal pH depending on the stability of the neuroactive steroids and sulfoalkylether-β-cyclodextrin included in the solution. The pH can be adjusted, for example, with hydrochloric, phosphoric acid or organic acids, such as citric acid, lactic acid, malic acid, tartaric acid, acetic acid, gluconic acid, succinic acid, and combinations thereof. In some embodiments, the pH is adjusted with base (e.g., 1 N sodium hydroxide) or acid (e.g., 1 N hydrochloric acid).

In some embodiments, the buffer is citrate buffer and the pH is between about 3 to about 8. In some embodiments, the buffer is citrate buffer and the pH is between about 3 to about 7.4. In some embodiments, the buffer is citrate buffer and the pH is between about 5.5 to about 6.2.

In some embodiments, the buffer is phosphate buffer and the pH is between about 3 to about 9. In some embodiments, the buffer is phosphate buffer and the pH is between about 6.2 to about 8.2. In some embodiments, the buffer is phosphate buffer and the pH is about 7.4.

Formulations for Administration, e.g., Parenteral Administration

Compounds (e.g., pregnanolone, allopregnanolone, alphadalone, ganaxolone, alphaxolone) described herein can be formulated for parenteral administration. Preferred doses, dosage forms, or modes of administration are parenteral, e.g., intranasally, buccally, intravenous, intramuscular, subcutaneous, intraparenteral, bucosal, sublingual, intraocular, and topical (e.g., intravenous or intramuscular). In another embodiment, the informational material can include instructions to administer the compound described herein to a suitable subject, e.g., a human, e.g., a human having or at risk for a disorder described herein. In some preferred embodiments, the neuroactive steroid is formulated for parenteral administration.

Parenteral formulations can be prepared as aqueous compositions using techniques known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

In some embodiments, the parenteral formulations are prepared as an injectable formulation, e.g., for intravenous administration. In some embodiments, the parenteral formulation comprises a compound (e.g., a neuroactive steroid as described herein, e.g., pregnanolone, allopregnanolone, alphadalone, ganaxolone, alphaxolone), and a cyclodextrin, e.g., a β-cyclodextrin, e.g., a sulfo butyl ether β-cyclodextrin, e.g., CAPTISOL®). In some embodiments, the parenteral formulation comprises pregnanolone, allopregnanolone, alphadalone, ganaxolone, or alphaxolone and a sulfo butyl ether β-cyclodextrin, e.g., CAPTISOL®.

The carrier can be a solvent or dispersion medium containing or comprising, for example, water (e.g., Water for Injection, USP), ethanol, one or more polyols (e.g., glycerol, propylene glycol, and liquid polyethylene glycol), oils, such as vegetable oils (e.g., peanut oil, corn oil, sesame oil, etc.), and combinations thereof.

The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants may be anionic, cationic, amphoteric or nonionic surface active agents. Suitable anionic surfactants include, but are not limited to, those containing or comprising carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

In some embodiments, a formulation is typically buffered to a pH of 3-9 for parenteral administration upon reconstitution. Suitable buffers include, but are not limited to, phosphate buffers, acetate buffers, citrate buffers, or others described herein.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

The parenteral formulations described herein can be formulated for controlled release including immediate release, delayed release, extended release, pulsatile release, and combinations thereof. In some embodiments, the neuroactive steroid is provided in a composition comprising a cyclodextrin, e.g., β-cyclodextrin, e.g., sulfo butyl ether β-cyclodextrin, e.g., CAPTISOL®.

In some embodiments, the neuroactive steroid is provided at a concentration of 0.1 to 10 mg/mL neuroactive steroid. In some embodiments, the neuroactive steroid is provided at a concentration of 0.1, 0.5, 1, 1.25, 2.5, 3.75, 5, 6.25, 7.5, 8, 9, or 10 mg/mL neuroactive steroid. In some embodiments, the neuroactive steroid is provided at a concentration of 1.25 mg/mL neuroactive steroid. In some embodiments, the neuroactive steroid is provided at a concentration of 2.5 mg/mL neuroactive steroid. In some embodiments, the neuroactive steroid is provided at a concentration of 3.75 mg/mL neuroactive steroid. In some embodiments, the neuroactive steroid is provided at a concentration of 5 mg/mL neuroactive steroid.

In some embodiments, the cyclodextrin is present in the composition at 1-30%, 2-18%, 10-15% by weight of cyclodextrin per volume of composition. In some embodiments, the cyclodextrin is present in the composition at 1, 2.5, 5, 10, 12, 13, 15, 25, or 30% by weight of cyclodextrin per volume of composition. In some embodiments, the cyclodextrin is present in the composition at 12% by weight of cyclodextrin per volume of composition. In some embodiments, the cyclodextrin is present in the composition at 25% by weight of cyclodextrin per volume of composition.

In some embodiments, the cyclodextrin is present in the composition at 1-30%, 2-18%, 10-15%, or 20-30% by weight of cyclodextrin per volume of composition and the neuroactive steroid is provided at a concentration of 0.1, 0.5, 1, 1.25, 2.5, 3.75, 5, 6.25, 7.5, 8, 9, or 10 mg/mL neuroactive steroid. In some embodiments, the cyclodextrin is present in the composition at 1, 2.5, 5, 10, 12, 13, 15, 25, or 30% by weight of cyclodextrin per volume of composition and the neuroactive steroid is provided at a concentration of 0.1, 0.5, 1, 1.25, 2.5, 3.75, 5, 6.25, 7.5, 8, 9, or 10 mg/mL neuroactive steroid. In some embodiments, the cyclodextrin is present in the composition at 12% by weight of cyclodextrin per volume of composition and the neuroactive steroid is provided at a concentration of 5 mg/mL neuroactive steroid. In some embodiments, the cyclodextrin is present in the composition at 25% by weight of cyclodextrin per volume of composition and the neuroactive steroid is provided at a concentration of 5 mg/mL neuroactive steroid. In some embodiments, the cyclodextrin is present in the composition at 12% by weight of cyclodextrin per volume of composition and the neuroactive steroid is provided at a concentration of 3.75 mg/mL neuroactive steroid. In some embodiments, the cyclodextrin is present in the composition at 12% by weight of cyclodextrin per volume of composition and the neuroactive steroid is provided at a concentration of 2.5 mg/mL neuroactive steroid. In some embodiments, the cyclodextrin is present in the composition at 12% by weight of cyclodextrin per volume of composition and the neuroactive steroid is provided at a concentration of 1.25 mg/mL neuroactive steroid.

Dosage and Pharmacokinetics

The compositions described herein include a therapeutically effective amount of a neuroactive steroid, such as pregnanolone, allopregnanolone, alphadalone, ganaxolone, or alphaxolone; and a cyclodextrin, e.g., a β-cyclodextrin, e.g., a sulfo butyl ether β-cyclodextrin, e.g., CAPTISOL®) provided in a dosage form suitable for parenteral administration. The compositions described herein include a therapeutically effective amount of a neuroactive steroid, such as pregnanolone, allopregnanolone, alphadalone, ganaxolone, or alphaxolone; and a cyclodextrin, e.g., a β-cyclodextrin, e.g., a sulfo butyl ether β-cyclodextrin, e.g., CAPTISOL®) provided in a dosage form suitable for oral administration. In some embodiments, the neuroactive steroid is allopregnanolone. In some embodiments, the neuroactive steroid is deuterated allopregnanolone. In some embodiments, the neuroactive steroid is an estrol. In some embodiments, the neuroactive steroid is selected from neuroactive steroids that are disclosed in WIPO Publication Nos. WO2013/188792, WO 2013/056181, WO2015/010054, WO2014/169832, WO2014/169836, WO2014/169833, WO2014/169831, WO2015/027227, WO 2014/100228, U.S. Pat. Nos. 5,232, 917, 8,575,375 and 8,759,330.

Area under the curve (AUC) refers to the area under the curve that tracks the serum concentration (nmol/L) of neuroactive steroid over a given time following the IV administration of the reference neuroactive steroid standard. By "reference neuroactive steroid" is intended the formulation of neuroactive steroid that serves as the basis for determination of the total hourly neuroactive steroid dose to be administered to a human subject with tremor (e.g., essential tremor), depression (e.g., postpartum depression), or an anxiety disorder to achieve the desired positive effect, i.e., a positive therapeutic response that is improved with respect to that observed without administration of neuroactive steroid. In an embodiment, the dose of neuroactive steroid to be administered provides a final serum level of neuroactive steroid of about 100 ng/mL to about 1000 ng/mL, about 1100 ng/mL to about 1450 ng/mL, 100 ng/mL to about 250 ng/mL, about 200 ng/mL to about 350 ng/mL, about 300 ng/mL to about 450 ng/mL, about 350 ng/mL to about 450 ng/mL, about 400 ng/mL to about 550 ng/mL, about 500 ng/mL to about 650 ng/mL, about 600 ng/mL to about 750 ng/mL, about 700 ng/mL to about 850 ng/mL, about 800 ng/mL to about 950 ng/mL, about 900 ng/mL to about 1050 ng/mL, about 1000 ng/mL to about 1150 ng/mL, about 100 ng/mL to about 1250 ng/mL, about 1200 ng/mL to about 1350 ng/mL, about 1300 ng/mL to about 1500 ng/m. In specific embodiments, the serum level of neuroactive steroid is about 100 ng/mL, 250 ng/mL, 300 ng/mL, 350 ng/mL, 360 ng/mL, 370 ng/mL, 380 ng/mL, 390 ng/mL, 400 ng/mL, 410 ng/mL, 420 ng/mL, 430 ng/mL, 440 ng/mL, 450 ng/mL, 500 ng/mL, 750 ng/mL, 900 ng/mL, 1200 ng/mL, 1400 ng/mL, or 1600 ng/mL.

In an embodiment, the dose of neuroactive steroid to be administered provides a final serum level of neuroactive steroid of about 100 nmoles/L to about 5000 nmoles/L, about 100 nmoles/L to about 2500 nmoles/L, about 100 nmoles/L to about 1000 nmoles/L, 100 nmoles/L to about 500 nmoles/L, about 100 nmoles/L to about 250 nmoles/L, about 100 nmoles/L to about 200 nmoles/L, about 125 nmoles/L to about 175 nmoles/L. or about 140 nmoles/L to about 160 nmoles/L. In specific embodiments, the serum level of neuroactive steroid is about 100 nmoles/L, 125 nmoles/L, 150 nmoles/L, 175 nmoles/L, 200 nmoles/L, 250 nmoles/L, 300 nmoles/L, 350 nmoles/L, 500 nmoles/L, 750 nmoles/L, 1000 nmoles/L, 1500 nmoles/L, 2000 nmoles/L, 2500 nmoles/L, or 5000 nmoles/L.

Provided herein are methods of administration, for example, of a therapeutic agent (e.g., a neuroactive steroid described herein) or composition comprising a therapeutic agent, to a subject, for example by IV infusion.

In an embodiment, the infusion occurs over at least 1, 2, 3, 4, 5, 6, or 7 days. In an embodiment, the infusion occurs over the course of 1, 2, 3, 4, 5, 6, or 7 days.

In an embodiment, the infusion is bolus infusion (e.g., single dose, single infusion). In an embodiment, the infusion is a plurality of bolus infusions (e.g., multiple bolus infusions, e.g., more than one bolus infusions, e.g., 2, 3, 4, 5 or more bolus infusions). In an embodiment, the plurality of bolus infusions is administered in 1 day, 2 days, 3 days, 4 days, 5 days, 6 days, 1 week, 2 weeks, 3 weeks, 1 month, 2 months, 3 months, 4 months, 5 months, 6 months or more. In an embodiment, the infusion is an intermittent infusion (e.g., an infusion that occurs at irregular intervals). In an embodiment, the infusion is a continuous infusion. In an embodiment, the method comprises administering a plurality of infusions. In an embodiment, the method comprises administering a first, second, and third infusion. In an embodiment, the administration of the second infusion begins no longer than 90, 60, 30, 10, or 5 minutes after the beginning or end of the administration of the first infusion. In an embodiment, the second infusion begins 0 to 90, 0 to 60, 0 to 30, 0 to 10, or 0 to 5 minutes after the beginning or end of the administration of the first infusion. In an embodiment, the second infusion begins no more than 60, 30, 20, 10, 5, 4, 3, 2, or 1 minute(s) after the end of administration of the first infusion. In an embodiment, the second infusion begins at the end of administration of the first infusion. In an embodiment, the first infusion and the initiation of the second infusion are performed with the same delivery device, e.g., with the same cannula or reservoir.

In an embodiment, the amount of neuroactive steroid delivered/unit time varies during the first infusion. In an embodiment, the first (step-up) infusion delivers a smaller amount of neuroactive steroid/unit time than the second (maintenance) infusion. In an embodiment, the first (step-up) infusion comprises administering a plurality of step doses, wherein each subsequent step dose delivers a larger amount of neuroactive steroid/unit time than the step dose that precedes it.

In an embodiment, said third infusion is administered for a period of time that is between 5 and 20 hours, 8 and 16 hours, 10 and 15 hours, or 10 and 13 hours. In an embodiment, said first infusion is administered for 12+/−2 hours. In an embodiment, said first infusion is administered for 12 hours.

In an embodiment, the amount of neuroactive steroid delivered/unit time varies during the first infusion.

In an embodiment, administering said step-up dose comprises administering a continuously increasing amount of neuroactive steroid or a composition comprising a neuroactive steroid. In an embodiment, administering said step-up dose comprises administering a continuously increasing amount of neuroactive steroid/unit time.

In an embodiment, the method comprises a first, second, and third step dose.

In an embodiment, said first step dose is administered at an amount of neuroactive steroid/unit time of 5-50 µg/kg/hour (e.g., 21.5 µg/kg/hour). In an embodiment, said first step dose is administered at an amount of neuroactive steroid/unit time of 5-50 µg/kg/hour, 10-40 µg/kg/hour, 20-30 µg/kg/hour, 20 µg/kg/hour, 21 µg/kg/hour, 22 µg/kg/hour, or 21.5 µg/kg/hour. In an embodiment, said first step dose is administered at an amount of neuroactive steroid/unit time of 30 µg/kg/hour. In an embodiment, said second step dose is administered at an amount of neuroactive steroid/unit time of 10-100 µg/kg/hour (e.g., 43 µg/kg/hour). In an embodiment, said second step dose is administered at an amount of neuroactive steroid/unit time of 10-100 µg/kg/hour, 20-70 µg/kg/hour, 30-50 µg/kg/hour, 42 µg/kg/hour, 43 µg/kg/hour, or 44 µg/kg/hour. In an embodiment, said second step dose is administered at an amount of neuroactive steroid/unit time of 60 µg/kg/hour. In an embodiment, said third step dose is administered at an amount of neuroactive steroid/unit time of 25-150 µg/kg/hour. In an embodiment, said third step dose is administered at an amount of neuroactive steroid/unit time of 25-150 µg/kg/hour, 40-100 µg/kg/hour, 60-70 µg/kg/hour, 63 µg/kg/hour, 64 µg/kg/hour, 65 µg/kg/hour, or 64.5 µg/kg/hour. In an embodiment, said third step dose is administered at an amount of neuroactive steroid/unit time of 90 µg/kg/hour. In an embodiment, when the neuroactive steroid is allopregnanolone, a first step dose, second step dose, and third step dose are administered by intermittent infusion, wherein said first step dose is administered at an amount of neuroactive steroid/unit time of 30 µg/kg/hour, said second step dose is administered at an amount of neuroactive steroid/unit time of 60 µg/kg/hour, and said third step dose is administered at an amount of neuroactive steroid/unit time of 90 µg/kg/hour. In an embodiment, when the neuroactive steroid is allopregnanolone, a first step dose and second step dose are administered by intermittent infusion, wherein said first step dose is administered at an amount of neuroactive steroid/unit time of 30 µg/kg/hour and said second step dose is administered at an amount of neuroactive steroid/unit time of 60 µg/kg/hour.

In an embodiment, the third (step-down/downward taper) infusion delivers a smaller amount of neuroactive steroid/unit time than the second (maintenance) infusion. In an embodiment, the third (step-down/downward taper) infusion comprises administering a plurality of step doses, wherein each subsequent step dose delivers a lower amount of neuroactive steroid/unit time than the step dose that precedes it. In an embodiment, said third infusion is administered for a period of time that is between 5 and 20 hours, 8 and 16 hours, 10 and 15 hours, or 10 and 13 hours. In an embodiment, said third infusion is administered for 12+/−2 hours. In an embodiment, said third infusion is administered for 12 hours.

In an embodiment, administering said downward taper dose comprises administering a continuously decreasing amount of neuroactive steroid. In an embodiment, administering said downward taper dose comprises administering a continuously decreasing amount of neuroactive steroid/unit time.

In an embodiment, the method comprises a first, second, and third step dose.

In an embodiment, said first step dose is administered at an amount of neuroactive steroid/unit time of 25-150 µg/kg/hour (e.g., 30 µg/kg/hour). In an embodiment, said first step dose is administered at an amount of neuroactive steroid/unit time of 25-150 µg/kg/hour, 40-100 µg/kg/hour, 60-70 µg/kg/hour, 63 µg/kg/hour, 64 µg/kg/hour, 65 µg/kg/hour, or 64.5 µg/kg/hour. In an embodiment, said second step dose is administered at an amount of neuroactive steroid/unit time of 10-100 µg/kg/hour (e.g., 43 µg/kg/hour). In an embodiment, said second step dose is administered at an amount of neuroactive steroid/unit time of 10-100 µg/kg/hour, 20-70 µg/kg/hour, 30-50 µg/kg/hour, 42 µg/kg/hour, 43 µg/kg/hour, or 44 µg/kg/hour. In an embodiment, said third step dose is administered at an amount of neuroactive steroid/unit time of 5-50 µg/kg/hour (e.g., 21.5 µg/kg/hour). In an embodiment, said third step dose is administered at an amount of neuroactive steroid/unit time of 5-50 µg/kg/hour, 10-40 µg/kg/hour, 20-30 µg/kg/hour, 20 µg/kg/hour, 21 µg/kg/hour, 22 µg/kg/hour, or 21.5 µg/kg/hour.

In an embodiment, the method comprises administering a second/maintenance infusion of 50-150 µg/kg/hour (e.g., 86 µg/kg/hour or 60 µg/kg/hour) of the neuroactive steroid. In an embodiment, the second/maintenance infusion is 50-150 µg/kg/hour, 60-100 µg/kg/hour, 70-90 µg/kg/hour, 85 µg/kg/hour, 86 µg/kg/hour, or 87 µg/kg/hour. In an embodiment, said second/maintenance infusion is administered for a period of time that is between 5 and 80 hours, 10 and 70 hours, 20 and 50 hours, or 30 and 40 hours. In an embodiment, said second/maintenance infusion is administered for 36+/−5 hours. In an embodiment, said second/maintenance infusion is administered for 36 hours. In an embodiment, the plasma concentration of said second/maintenance infusion is measured at a preselected time, e.g., at 10, 15, 20, 30, 45, 60 minutes, 2, 3, 4, 5, 6, 8, 10, 12, 24 hours, 2, 3, 4 days after the initiation of said second/maintenance infusion. In an embodiment, said second/maintenance infusion results in a plasma concentration of 150 nM, e.g., as measured at a preselected time, e.g., at 10, 15, 20, 30, 45, 60 minutes, 2, 3, 4, 5, 6, 8, 10, 12, 24 hours, 2, 3, 4 days after the initiation of said second/maintenance infusion. In an embodiment, said second/maintenance infusion is administered at the same amount of neuroactive steroid/unit time over the entire second/maintenance infusion.

In an embodiment, said first step dose is 10 to 40% (e.g., 25%) of the second/maintenance infusion; said second step dose is 30 to 70% (e.g., 50%) of the second/maintenance infusion; and said third step dose is 60 to 90% (e.g., 75%) of the second/maintenance infusion. In an embodiment, said first step dose is 60 to 90% (e.g., 75%) of the second/maintenance infusion; said second step dose is 30 to 70% (e.g., 50%) of the second/maintenance infusion; and said third step dose is 10 to 40% (e.g., 25%) of the second/maintenance infusion. In an embodiment, the amount of neuroactive steroid delivered/unit time in said first step dose is 10 to 40% (e.g., 25%) of the amount of neuroactive steroid delivered/unit time in said second/maintenance infusion; the amount of neuroactive steroid delivered/unit time in said second step dose is 30 to 70% (e.g., 50%) of the amount of neuroactive steroid delivered/unit time in said second/maintenance infusion; and the amount of neuroactive steroid delivered/unit time in said third step dose is 60 to 90% (e.g., 75%) of the amount of neuroactive steroid delivered/unit time in said second/maintenance infusion. In an embodiment, the amount of neuroactive steroid delivered/unit time in said first step dose is 60 to 90% (e.g., 75%) of the amount of neuroactive steroid delivered/unit time in said second/maintenance infusion; the amount of neuroactive steroid delivered/unit time in said second step dose is 30 to 70% (e.g., 50%) of the amount of neuroactive steroid delivered/unit time in said second/maintenance infusion; and the amount of neuroactive steroid delivered/unit time in said third step dose is 10 to 40% (e.g., 25%) of the amount of neuroactive steroid delivered/unit time in said second/maintenance infusion.

EXAMPLES

In order that the invention described herein may be more fully understood, the following examples are set forth. The synthetic and biological examples described in this application are offered to illustrate the compounds, pharmaceutical compositions and methods provided herein and are not to be construed in any way as limiting their scope. In some of the tables that follow (i.e., Table 10, Table 11, Table 12, Table 13, and Table 14), Compound 9 as described herein may also be named as "Formula I."

Example 1. Nonclinical Studies with Compound 9

The GABAA positive allosteric modulator Compound 9, was orally active in preclinical anticonvulsant models, and suppressed seizures arising from a variety of stimuli, including chemoconvulsants, proconvulsant stimuli, and genetic predisposition. Compound 9 caused sedation and ataxia as manifestations of exaggerated pharmacology. The compound was assessed in 14-day rat and dog toxicology studies with daily administration of Compound 9 as a solution in HPBCD in dogs and Labrasol® in rats.

The NOAEL in rats was 3 mg/kg (females) and 22.5 mg/kg (males), and was 2.5 mg/kg in dogs. There were no adverse effects in dogs or rats in the main toxicology studies. A single observation of mortality occurred in one female rat at the high dose in a toxicokinetic study which was suspected to have been related to exaggerated pharmacology.

Example 2. A Phase I, Double-Blind, Placebo-Controlled, Single Ascending Dose Study to Determine the Maximum Tolerated Dose (MTD), Pharmacokinetics and Pharmacodynamics of Compound 9 Oral Solution in Healthy Volunteers and the Safety, Tolerability, and Pharmacokinetics of Compound 9 in Subjects with Essential Tremor Purpose To determine the maximum tolerated dose (MTD) of Compound 9 Oral Solution in healthy volunteers aged 18-55 years. In healthy volunteers:
  To assess the safety and tolerability of Compound 9 Oral Solution;
  To assess the pharmacokinetic (PK) profile of single doses of Compound 9 Oral Solution (with and without food);
  To investigate plasma concentrations of Compound 9 metabolites and urine concentrations of Compound 9;
  To assess the pharmacodynamic effects of Compound 9 Oral Solution MTD using EEG and psychomotor testing; In subjects with Essential Tremor who are otherwise healthy:
  To assess the safety, tolerability and pharmacokinetics (PK) of Compound 9.

Materials and Methods

Compound 9 Oral Solution was prepared as 1 mg/mL and 6 mg/mL stock aqueous solutions of Compound 9 Drug Substance containing 40% HPBCD and 0.0025% sucralose. The 1 mg/mL and 6 mg/mL stock Compound 9 Oral Solutions were compounded from Compound 9 Drug Substance Powder in the Bottle and Excipient(s) in the Bottle (manufactured under cGMP conditions) and further admixed at the clinical site in preparation for dosing. Placebo will be matched to study drug at each dose cohort.

Batch Formula for Stock Compound 9 Oral Solutions 1 mg/mL and 6 mg/mL

Subject doses will be prepared as an approximate 40 mL oral solution to be swallowed all at once, followed by approximately 200 mL of water that has been used to rinse the dosing bottle. The start time of swallowing the approximate 40 mL oral solution is time zero for all assessments.

SAD Cohorts: In each of the SAD cohorts, subjects will be randomly assigned to receive either Compound 9 (six subjects) or placebo (two subjects) in a blinded manner. Cohort 1 will receive Dose 1, Cohort 2 will receive Dose 2, and so on.

Food Cohort: After the Compound 9 single dose MTD has been identified, subjects will be treated with a dose best approximating 50% of the identified MTD in an open-label manner.

EEG Cohorts: After the single dose MTD has been determined, the EEG cohort of subjects will be randomly assigned in a 1:1, blinded manner to receive either Compound 9 oral solution at the MTD or placebo OR the dose from the SAD best approximating 50% MTD or placebo. Subjects will then return to the clinic approximately one week later and cross over to the other treatment within their cohort.

Essential Tremor Cohort: After the single dose MTD has been determined, the Essential Tremor cohort will be assigned to receive Compound 9 Oral Solution at a dose approximating the MTD in an open-label manner.

The maximum recommended starting dose for this Phase I study is 0.25 mg. Doses will be prepared for each cohort based on the dose escalation scheme shown below which may be amended depending on Safety Review Committee (SRC) dose escalation decisions described in the section below.

TABLE 1

Dose Escalation Scheme

| Cohort | Maximum Proposed Escalation from Previous Cohort | Formula (I) Maximum Planned Dose (mg) | HPBCD Dose g (wt %) | Actual Dose Administered (mg) |
|---|---|---|---|---|
| 1 | N/A | 0.25 | 0.113 (0.28%) | 0.25 |
| 2 | 3x | 0.75 | 0.343 (0.86%) | 0.75 |
| 3 | 3x | 2 | 0.910 (2.3%) | 2 |
| 4 | 3x | 6 | 0.460 (1.1%) | 5.5 |
| 5 | 2x | 12 | 0.910 (2.3%) | 11 |
| 6 | 2x | 24 | 1.83 (4.6%) | 22 |
| 7 | 2x | 48 | 3.66 (9.1%) | 44 |
| 8 | 2x | 96 | 7.31 (18.3%) | 66 |
| 9 | N/A | N/A | 4.19 (10.47%) | 55 |
| 10 (Food) | N/A | 50% of MTD | 1.86 (4.6%) | 22 |
| 11A (EEG) | N/A | 50% of MTD | 1.86 (4.6%) | 22 |
| 11B (EEG) | N/A | MTD | 4.19 (10.47%) | 55 |
| 12 (ET) | N/A | MTD | 4.19 (10.47%) | 55 |

Study Design

This four-part study will assess the effects of a single dose of Compound 9. The initial part of the study is a double-blind, placebo-controlled single ascending dose (SAD) design in healthy, adult volunteers with the objective of identifying the maximum tolerated dose (MTD) and pharmacokinetic (PK) profiles of Compound 9 Oral Solution. Escalation to the next dose will be undertaken only after safety and PK data have been reviewed by the Safety Review Committee (SRC) and agreement reached that it is safe to increase the dose. The SRC will not receive any unblinded PK data unless it is agreed upon by the SRC to unblind a subject and/or cohort based on the completed safety review.

The second part of the study will assess food effect by observing the PK profile of the single dose that best approximates 50% of the MTD after consumption of a standard meal in the same cohort that originally tested this dose; this dose level may be adjusted for safety reasons.

In the third part of the study, the pharmacodynamic effects of Compound 9 on the central nervous system (CNS) will be assessed in two cohorts of fasted subjects using electroencephalograph (EEG) and other testing indicative of CNS effects. In one EEG cohort, subjects will receive either the MTD or placebo then return to the clinic to receive the other treatment in crossover fashion. The second EEG cohort will receive either the dose that best approximates 50% of the MTD or placebo, and then return to the clinic to receive the other treatment in crossover fashion. The two EEG cohorts will have approximately one week between crossover periods.

After the single dose MTD has been identified, the fourth part of the study will assess the safety, tolerability and pharmacokinetics of a single dose of Compound 9 in an open label fashion in one cohort of 6 subjects with essential tremor who are otherwise healthy. Subjects will eat a standard clinic breakfast prior to dosing. Enrollment into this cohort will continue until 6 subjects have been dosed.

The SAD and EEG cohorts will consist of eight subjects randomly assigned to active or placebo treatment. Sentinel dosing will be employed for the first SAD cohort, with one subject randomized to receive Compound 9 and the other placebo on the first day. The other six subjects in the first cohort will be dosed approximately 24 hours later. The food effect cohort will be comprised of up to six subjects, all of whom will receive active treatment. Sentinel dosing will be employed for the first cohort, with one subject randomized to receive Compound 9 and the other placebo on the first day. The other six subjects in the first cohort will be dosed approximately 24 hours later. Each cohort will be dosed at approximately weekly intervals in order to allow adequate time for collection and review of safety and PK data. The Essential Tremor cohort will be comprised of 6 subjects assigned to receive a dose approximating the SAD MTD in an open-label fashion.

TABLE 2

Planned Dosing Scheme (Adjustments Possible by the Safety Review Committee)

| | Active Dose: | | | | | | | | | | |
|---|---|---|---|---|---|---|---|---|---|---|---|
| | Dose 1 | Dose 2 | Dose 3 | Dose 4 | Dose 5 | Dose 6 | Dose 7 | Dose 8 | Dose 9 | Dose "50" | MTD |
| Part 1 | | | | | | | | | | | |
| Cohort 1 | 6A 2P | | | | | | | | | | |
| Cohort 2 | | 6A 2P | | | | | | | | | |
| Cohort 3 | | | 6A 2P | | | | | | | | |
| Cohort 4 | | | | 6A 2P | | | | | | | |
| Cohort 5 | | | | | 6A 2P | | | | | | |
| Cohort 6 | | | | | | 6A 2P | | | | | |
| Cohort 7 | | | | | | | 6A 2P | | | | |
| Cohort 8 | | | | | | | | 6A 2P | | | |
| Cohort 9 | | | | | | | | | 6A 2P | | |

TABLE 2-continued

Planned Dosing Scheme (Adjustments Possible by the Safety Review Committee)

| | Active Dose: | | | | | | | | | | |
|---|---|---|---|---|---|---|---|---|---|---|---|
| | Dose 1 | Dose 2 | Dose 3 | Dose 4 | Dose 5 | Dose 6 | Dose 7 | Dose 8 | Dose 9 | Dose "50" | MTD |
| Part 2 | | | | | | | | | | | |
| Cohort Food | | | | | | | | | | 6A | |
| Part 3 | | | | | | | | | | | |
| Cohort EEG-A | | | | | | | | | | | 4A:4P X 4P:4A |
| Cohort EEG-B | | | | | | | | | | 4A:4P X 4P:4A | |
| Part 4 | | | | | | | | | | | |
| Cohort Essential Tremor | | | | | | | | | | | 6A |

Key:
P = subjects on placebo;
A = subjects on active treatment with Compound 9
Dose "50" = the dose that best approximates 50% of the MTD
Cohort Food = the six subjects who previously received the Dose "50" (or nearest dose) in a previous cohort Cohorts Food, EEG-A, EEG-B and Essential Tremor may be conducted concurrently.

Procedure

Single Ascending Dose (SAD) and Determination of MTD

In each of the SAD cohorts, subjects will be randomly assigned to receive either Compound 9 (six subjects) or placebo (two subjects) in a blinded manner. Cohort 1 will receive Dose 1, Cohort 2 will receive Dose 2, and so on. With the exception of the Food cohort, study drug will be administered in a fasting state (no food and only water for the previous 12 hours) and a standard Phase I unit diet will be administered beginning approximately four to five hours after dosing. After the sentinel dosing scheme for the first cohort (two subjects administered blinded study drug on the first day, one receiving Compound 9 and the other placebo, followed by the remainder of the subjects in the cohort administered study drug approximately 24 hours later), all subjects in each cohort will be administered study drug on the same day approximately one week apart to allow time for review of the safety, tolerability, and pharmacokinetic data by the SRC (SRC will not receive unblinded PK data unless formal unblinding procedures are followed), which will determine whether it is acceptable for the dosing scheme to continue as planned. A detailed overview of assessments performed at each visit for this part of the study is provided in the Schedule of Events (Table 6).

Food Effect

After the MTD has been identified, the effects of food on the pharmacokinetics, safety and tolerability of Compound 9 will be determined by having the subjects consume a standard Phase I unit meal followed by Compound 9 at the dose in the SAD that best approximates 50% of the Compound 9 MTD. The same six subjects who received active treatment with Compound 9 Oral Solution at this dose in the SAD portion of the study will receive the same dose in the fed state. Subjects who had received placebo at this dose will not be included in the food effect cohort. See the Schedule of Events (Table 6).

Pharmacodynamics (EEG and Psychomotor Testing)

The pharmacodynamic (PD) effects of the Compound 9 Oral Solution MTD will be assessed via EEG, eye tracking, mood, psychomotor testing and subjective drug effects. The dosing schedule for subjects participating in the EEG portion of the study will be determined in the manner described below. Once the Compound 9 Oral Solution MTD has been determined, the last two cohorts of subjects will be randomly assigned in a blinded manner to receive treatments as shown in Table 2 (Cohorts EEG-A and EEG-B, eight subjects in each cohort). Subjects in Cohort EEG-A will be randomized to either the dose from the SAD that best approximates 50% of MTD or placebo and then crossover to the other treatment after a one-week washout. Subjects in Cohort EEG-B will be randomized to either the MTD or placebo and then crossover to the other treatment after a one-week washout. Subjects in this part of the study will have continuous EEG collected for approximately 24 hours after the start of dosing; standardized eye tracking and psychomotor tests will also be performed (Table 8).

Essential Tremor

The safety, tolerability and pharmacokinetics of Compound 9 will be assessed in six subjects with essential tremor who are otherwise healthy. All six subjects will be assigned to receive a dose approximating the SAD MTD in an open-label manner (Table 9). Subjects in this cohort will perform the clinician-rated TETRAS (Performance subscale) and the accelerometer based Kinesia measure (Great Lakes NeuroTechnologies, Valley View, Ohio) to generate exploratory tremor amplitude data which will be used to inform the design of possible Phase 2 studies in essential tremor. Subjects in the Essential Tremor cohort will be dosed after eating a standard breakfast.

Results

For all safety analyses of the SAD portion of the study, the placebo dose group will be pooled across cohorts. AEs will be coded using MedDRA™ with the version used specified in the clinical study report. The overall incidence of AEs will be displayed by System Organ Class (SOC), preferred term, dose group, and cohort. Incidence of AEs will also be presented by maximum severity and relationship to study drug. Data from vital signs, clinical laboratory measures, ECG, and C-SSRS will be summarized using descriptive statistics by dose group and cohort (where applicable).

Continuous endpoints will be summarized with n, mean, standard deviation, median, minimum and maximum. In addition, change from baseline values will be calculated at each time point and will be summarized using the same summary statistics. Out-of-range safety endpoints may be categorized as low or high where applicable. For all categorical endpoints, summaries will include counts and percentages. Derived PK parameters will include area under the plasma concentration curve (AUC0-inf), the distributional half-life and terminal half-life (t1/2), the maximum concentration (Cmax), the time to reach maximum concentration (Tmax), and the clearance (CL) and urine excretion. PK parameters will be summarized using appropriate descriptive statistics. Time to reach maximum concentration (Tmax) will be summarized using n, mean, standard deviation, median, minimum, and maximum. All other PK parameters will be summarized using n, geometric mean, coefficient of variation, median, minimum, and maximum.

Dose proportionality will be analyzed using an ANCOVA model using the logarithm of PK parameter (AUC and Cmax) as the dependent variable and the logarithm of the dose as the independent variable. Point estimates and the corresponding CIs will be estimated for both AUC and Cmax. For the food effect analysis, the log-transformed AUC and Cmax will be compared across food conditions using a paired t-test. Additional statistical testing may be performed according to the bioanalytical statistical analysis plan.

The pharmacodynamics analysis of EEG endpoints and their relationship to psychomotor testing and eye tracking measures will be described in a separate analysis plan. In addition, PK/PD exploratory analyses will be performed utilizing sedation, mood, EEG and psychomotor data. The secondary endpoints of SSS, MOAA/S, BL-VAS, and DEQ-5 values will be summarized using the same descriptive statistics described above for the safety variables.

Subjects

Up to 94 subjects will be recruited into the study, depending on the number of cohorts studied; this includes 88 healthy subjects and 6 subjects with essential tremor who are otherwise healthy. Subjects will be replaced only if they withdraw/are withdrawn prior to study drug dosing. Note especially that subjects with essential tremor may fail to qualify on the TETRAS after Admission and be withdrawn from the study prior to dosing. These subjects will be replaced to ensure there are 6 subjects dosed in this cohort. Subjects will not be replaced if they withdraw/are withdrawn prior to the second dose planned in the Food cohort or one of the EEG or Essential Tremor cohorts.

Additional cohorts may be considered to accommodate dose repetition or slower dose escalation than planned in the SAD part of the study. Subjects participating in the double-blind, randomized portions of the study will be randomly assigned to either placebo or active treatment with Compound 9 Oral Solution according to a randomization schedule prepared by an independent statistician. The Food cohort subjects will receive study drug at the dose that best approximates 50% of the MTD in an open-label manner once MTD has been determined. The EEG cohort subjects will initially receive either Compound 9 MTD or the dose that best approximates 50% of the MTD or placebo in a 1:1, double-blind fashion and return for the crossover portion of the study to receive the other treatment for that cohort. The Essential Tremor cohort subjects will be assigned to receive a dose approximating the SAD MTD in an open-label manner.

Compound 9 Dosing Regimen

Subjects in each of the SAD cohorts will receive a single dose of study drug, either Compound 9 Oral Solution (6 subjects) or placebo (2 subjects). The proposed dose escalation scheme for the SAD part of the study is presented in Table 3. In the Food cohort, 6 subjects who received the dose that best approximates 50% of the MTD will receive this dose a second time after ingestion of a standard meal. In the EEG part of the study, two cohorts of 8 subjects each will be tested using two dosing periods.

One EEG cohort will receive the MTD; the other EEG cohort will receive the dose that best approximates 50% of the MTD. During the first dosing period of each EEG cohort, subjects will receive either a single dose of Compound 9 or matching placebo (4 subjects per active and placebo treatments). These subjects will return after an approximate one-week washout period to receive the MTD or placebo (Cohort EEG-A) OR the dose that best approximates 50% of the MTD or placebo (Cohort EEG-B) within their cohort in crossover fashion. All 8 subjects will receive active treatment in each of the two EEG cohorts during either the first or second dosing period. The appropriate dose of Compound 9 Oral Solution or placebo will be administered according to the randomization schedule available to the pharmacist. The dose escalation pattern may be modified by the Safety Review Committee.

Subjects in the Essential Tremor cohort will receive a single dose of study drug with Compound 9 Oral Solution at a dose approximating the SAD MTD in an open-label manner.

Doses will be prepared as an approximate 40 mL oral solution to be swallowed all at once, followed by approximately 200 mL of water which has been used to rinse the dosing bottle. The start time of swallowing the approximately 40 mL oral solution is time zero for all assessments. Subjects in the Essential Tremor cohort may have assistance from the clinic staff when taking the study medication. Subjects in this cohort will be dosed following consumption of a standard clinic breakfast.

TABLE 3

Proposed Dose Escalation Schedule for the SAD Part of the Study

| Cohort | Maximum Proposed Escalation from Previous Cohort | Formula (I) Maximum Planned Dose (mg) | HPBCD Dose g (wt %) | Actual Dose Administered (mg) |
|---|---|---|---|---|
| 1 | N/A | 0.25 | 0.113 (0.28%) | 0.25 |
| 2 | 3x | 0.75 | 0.343 (0.86%) | 0.75 |
| 3 | 3x | 2[a] | 0.910 (2.3%) | 2 |
| 4 | 3x | 6 | 0.460 (1.1%) | 5.5 |
| 5 | 2x | 12 | 0.910 (2.3%) | 11 |
| 6 | 2x | 24 | 1.83 (4.6%) | 22 |
| 7 | 2x | 48 | 3.66 (9.1%) | 44 |
| 8 | 2x | 96 | 7.31 (18.3%) | 66 |
| 9 | N/A | N/A | 4.19 (10.47%) | 55 |
| 10 (Food) | N/A | 50% of MTD | 1.86 (4.6%) | 22 |
| 11A (EEG) | N/A | 50% of MTD | 1.86 (4.6%) | 22 |
| 11B (EEG) | N/A | MTD | 4.19 (10.47%) | 55 |
| 12 (ET) | N/A | MTD | 4.19 (10.47%) | 55 |

Dose Rounded for Convenience of Escalation

Dose Escalation and Stopping Rules (SAD Cohorts)

Serious Adverse Event: If any subject in a cohort has a serious adverse event (SAE) that the SRC determines is related to Compound 9, the SRC may stop the SAD phase of the study or may permit ongoing dosing at lower doses of Compound 9 than that at which the event occurred, depending on the nature of the event.

Severe Adverse Event: If three or more active treatment subjects in a cohort have a severe adverse event that the safety committee determines is related to Compound 9, the safety committee may stop the SAD phase of the study or may permit ongoing dosing at the same or lower doses of Compound 9, depending on the nature of the event and the dose(s) at which the events occurred.

MOAA/S Score: If at least one Compound 9-exposed subject within a cohort has a MOAA/S score of two or less (≤2) at any time point during normal waking hours (≥08:00 h to ≤22:00 h) and this score is confirmed, i.e., repeat assessment is the same or lower, or if two or more (≥2) Compound 9-exposed subjects have a confirmed MOAA/S score of three or less (≤3) at any time point during normal waking hours (≥08:00 h to ≤22:00 h) and this score is confirmed, i.e., repeat assessment is the same or lower, dose escalation to the next planned dose will not occur. Additional dosing may be permitted by dosing Compound 9 at a lower dose or by repeating the dose at which these events occurred depending on the extent and duration of the sedation and the dose(s) at which the sedation occurred. The Safety Review Committee will consider MOAA/S scores as qualifying for stopping criteria only when the confirmation score is equal to or lower than the first assessment and when there is congruence with the SSS score at the same time point.

If any of the following findings occur in at least two (2) subjects exposed to Compound 9 Oral Solution within a cohort, the SRC may not allow dose-escalation if at least two subjects report the same finding. However, if each subject reported a different finding, the SRC could allow dose escalation at lower increments than planned. In all circumstances the SRC may allow dose-repetition or dose reduction:

An increase from pre-dose in supine systolic blood pressure of 60 mmHg sustained for at least five minutes, or a decrease from pre-dose in supine systolic blood pressure of 30 mmHg sustained for at least five minutes, or supine systolic blood pressure of ≤70 mmHg or ≥200 mmHg sustained for at least five minutes;

An increase from pre-dose in supine diastolic blood pressure of 40 mmHg sustained for at least five minutes, or a decrease from pre-dose in supine diastolic blood pressure of 30 mmHg sustained for at least five minutes, or supine diastolic blood pressure of ≤40 mmHg or ≥110 mmHg sustained for at least five minutes;

An increase from pre-dose in supine heart rate of 50 bpm sustained for at least five minutes, or a decrease from pre-dose in supine heart rate of 30 bpm sustained for at least five minutes, or supine heart rate of ≤45 bpm or ≥170 bpm sustained for at least five minutes;

QTc prolongation defined as QTcF increasing ≥60 msec and persisting for at least 10 minutes or QTcF >500 msec and persisting for at least 30 minutes;

A sustained increase in alanine aminotransferase (ALT) or aspartate aminotransferase (AST) to >3× upper limit of normal (ULN), which must be confirmed elevated >3×ULN within 48 hours;

Total bilirubin increase to >2×ULN confirmed on repeat testing within 48 hours;

ALT or AST >2×ULN concurrent with total bilirubin >1.5×ULN confirmed on repeat testing within 48 hours;

Serum creatinine >1.5×ULN confirmed on repeat testing within 48 hours;

Leukocyte count <2.5×109/L confirmed on repeat testing within 48 hours;

Neutrophil count <1.0×109/L confirmed on repeat testing within 48 hours;

Platelet count <100×109/L confirmed on repeat testing within 48 hours.

AUC and Cmax: based on the plasma concentration information from previous cohorts, the SRC will consider adjusting the dose (dose reduction, dose repetition, or reduced dose escalation) for the next cohort if the Cmax of >50% of the next cohort is expected to exceed 400 ng/mL (the estimated human Cmax based on the lowest NOAEL Day 14 Cmax in female rats). In addition, the SRC will not allow escalation to doses beyond those predicted to result in an AUC above the lowest NOAEL exposure in toxicology studies (male rat 14-day toxicology, AUC 5,050 ng.h/mL).

Determination of Food-Effect Cohort Dose

The SRC will choose the dose for the food effect cohort based on the doses that have been tolerated within the SAD phase; the dose best approximating 50% of the MTD will be utilized for the Food portion of the study.

Determination of Pharmacodynamic (PD)/EEG Cohort Dose

Two cohorts will be tested during the EEG phase of the study: one cohort will receive the maximum tolerated dose (MTD) or placebo (EEG-A); the other cohort will receive the dose best approximating 50% of the MTD or placebo (EEG-B). Each cohort will return in approximately one week to cross over to the other treatment within that cohort.

Determination of Essential Tremor Cohort Dose

Subjects in the Essential Tremor cohort will receive a single dose of study drug of Compound 9 Oral Solution at the dose best approximating the SAD MTD.

Pharmacokinetic Criteria for Adjustment or Stopping Doses

During the SAD part of the study, the Sponsor PK lead will review the plasma PK data for the first 24 hours post-dose from each dose to determine whether the results indicate a linear increase from the previous dose that is proportionate to the increased dose and whether there are any indications of a compartment syndrome or threshold effect. The Sponsor PK lead will then provide feedback to the Sponsor Study Physician regarding the overall PK results, and the SRC will discuss accordingly. The SRC will not receive any unblinded PK data unless it is agreed upon by the SRC to unblind a subject and/or cohort based on the completed safety review for that cohort.

The SRC will not allow escalation of doses beyond those predicted to result in an AUC above the lowest NOAEL exposure in toxicology studies (male rat 14-day toxicology, AUC 5,050 ng.h/mL). Based on the plasma concentration information from previous cohorts, the SRC will consider adjusting the dose (dose reduction, dose repetition, or reduced dose escalation) for the next cohort if the Cmax of >50% of the next cohort is expected to exceed 400 ng/mL (the estimated human Cmax based on the lowest NOAEL Day 14 Cmax in female rats).

Inclusion Criteria

Signed informed consent before any study-specific procedures are performed;

Non-nicotine or tobacco using, healthy ambulatory male and female subjects ≥18 to ≤55 years of age at the time of screening, with no history or evidence of clinically relevant medical disorders as determined by the investigator, who will consult with the physician if there are questions about eligibility.

Bodyweight ≥60 kg and body mass index (BMI) ≥18.0 and ≤30.0 kg/m2 at screening visit.

Physical and neurological examination, clinical laboratory values (one repeat test allowed), vital signs (normal ranges per the Investigator, one repeat allowed), and electrocardiograms (ECGs) are clinically acceptable to the investigator and Sponsor.

Male subjects must agree to practice an acceptable method of effective birth control while on study, and for 13 weeks after receiving the dose of study drug. Effective methods of birth control include sexual abstinence; vasectomy; or a condom with spermicide (men) in combination with female partner's method, e.g. hormonal birth control, or intrauterine device. Female subjects must be non-childbearing capacity, e.g. postmenopausal (at least 12 months since last menstruation) or surgically sterile (tubal ligation, bilateral oophorectomy, or hysterectomy).

Males must be willing to abstain from sperm donation while on study through 13 weeks after receiving the dose of study drug. Amended for Essential Tremor cohort (must meet above criteria except where amended as indicated)

Diagnosis of Essential Tremor in subjects who are otherwise healthy, with upper limb symptoms clearly present as confirmed by a TETRAS upper limb total score of ≥8 at the Admission visit;

Tremor present for at least three years prior to screening as confirmed by the treating neurologist;

Male or female, ≥18 to ≤75 years of age;

Physical and neurological examination, clinical laboratory values, vital signs (normal ranges per the Investigator), and electrocardiograms (ECGs) are clinically acceptable.

Exclusion Criteria

Clinically significant abnormal values for hematology, clinical chemistry or urinalysis at the screening and admission visits. Abnormalities considered to be non-clinically significant by the investigator are acceptable.

Subject with history of suicidal behavior within two years or who has answered YES to questions 3, 4 or 5 on the C-SSRS at the Screening or Day −1 visits, or is currently at risk of suicide in the opinion of the investigator.

Clinically significant abnormal physical examination OR 12-lead electrocardiogram (ECG) at the screening or admission visits. NOTE: QTc(F) interval of >450 msec in males or >470 msec in females, will be the basis for exclusion from the study. ECG may be repeated for confirmatory purposes if initial values obtained exceed the limits specified.

Significant history and/or presence of hepatic, renal, cardiovascular, pulmonary, gastrointestinal, hematological, immunologic, ophthalmologic, metabolic or oncological disease.

History or presence of psychiatric or neurologic disease or condition (including but not limited to epilepsy, closed head trauma with clinically significant sequelae, partial onset seizures, eating disorders, etc.); the diagnosis of Essential Tremor is not an exclusion for subjects in the Essential Tremor cohort.

Alcohol and Drug Use/Abuse:

Subjects in the SAD, Food and EEG parts of the study are excluded if they have a recent history (within previous 6 months) of alcohol or drug abuse (as judged by the Investigator), or has consumed >2 alcohol drinks/day during the last 3 months prior to screening (1 glass is approximately equivalent to: beer [284 mL], wine [125 mL/4 ounces], or distilled spirits [25 mL/1 ounce]). Subjects that consume 3 glasses of alcoholic beverages per day but less than 14 glasses per week may be enrolled at the discretion of the investigator. Positive screens for alcohol or controlled substances at the screening or admission visits will disqualify a subject from study participation.

Subjects in the Essential Tremor cohort are excluded if there is a recent history (within the previous 6 months) of alcohol or drug abuse (as judged by the Investigator); there are no amounts specified for alcohol consumption for this cohort as it is understood that subjects may be self-medicating with alcohol. A positive result for alcohol or controlled substances at the screening or admission visits will disqualify a subject from study participation.

Tobacco Use:

Subjects in the SAD, Food and EEG parts of the study are excluded if they currently use or have regularly used tobacco or tobacco-containing products (cigarettes, pipes, etc.) for at least one month prior to screening OR positive urine cotinine screen (>400 ng/mL) at the screening or admission visits.

Subjects in the Essential Tremor cohort may be tobacco users and may have a positive urine cotinine screen at the screening or admission visit.

Any subject with a history, presence and/or current evidence of serologic positive results for hepatitis B surface antigen, hepatitis C antibodies, or HIV antibodies 1 and 2.

Donation of one or more units of blood or acute loss of an equivalent amount of blood within 60 days prior to dosing (one unit=450 mL).

Any subject who has received treatment with an investigational drug or device that has not received regulatory approval during the 30 days, or 5 half-lives of the investigational drug, whichever is longer, prior to study drug administration.

Medications:

Subjects in the SAD, Food and EEG parts of the study are excluded if they use or have used any prescription or over-the counter medication, herbal medication, vitamins, or mineral supplements within 14 days prior to administration of the study drug. Acetaminophen up to 3 g per day will be allowed.

Subjects in the Essential Tremor cohort must stop using any medications at least 48 hours or a minimum of 5 half-lives (whichever is longer) prior to study drug administration and they may not take medications sooner than 48 hours after study drug administration, unless approved by the Sponsor Study Physician during the Screening Period. Acetaminophen up to 3 g per day will be allowed as will medications prescribed by the study physician while the subject is confined to the unit.

Use of agents known to affect drug metabolism: use of any known CYP450 inhibitors and/or inducers within the 14 days or 5 halflives (whichever is longer) or consumed grapefruit juice, grapefruit, Seville oranges or St John's Wort or products containing these within 30 days prior to receiving the first dose of study drug.

Any subject who consumes excessive amounts of caffeine, defined as greater than 6 servings (1 serving is approximately equivalent to 120 mg of caffeine) of coffee, tea, cola, or other caffeinated beverages per day within 30 days prior to admission.

Any subject with previous exposure to the study drug or who is known to be allergic to Compound 9 or any of its excipients, including its major excipient HPBCD.

Investigative site personnel or their immediate families (spouse, parent, child or sibling whether biological or legally adopted).

Any subject unwilling or unable to comply with study procedures.

Treatment

Subjects participating in the double-blind, randomized portions of the study will be randomly assigned to either placebo or active treatment with Compound 9 Oral Solution according to a randomization schedule prepared by an independent statistician. The Food cohort subjects will receive study drug at the dose that best approximates 50% of the MTD in an open-label manner once MTD has been determined. The EEG cohort subjects will initially receive either Compound 9 (MTD or the dose that best approximates 50% of the MTD) or placebo in a 1:1, double-blind fashion and return for the crossover portion of the study to receive the other treatment for that cohort. Subjects in each of the SAD cohorts will receive a single dose of study drug, either Compound 9 Oral Solution (6 subjects) or placebo (2 subjects).

In the Food cohort, 6 subjects who received the dose that best approximates 50% of the MTD will receive this dose a second time after ingestion of a standard meal.

In the EEG part of the study, two cohorts of 8 subjects each will be tested using two dosing periods. One EEG cohort will receive the MTD; the other EEG cohort will receive the dose that best approximates 50% of the MTD.

During the first dosing period of each EEG cohort, subjects will receive either a single dose of Compound 9 or matching placebo (4 subjects per active and placebo treatments). These subjects will return after an approximate one week washout period to receive the MTD or placebo (Cohort EEG-A) OR the dose that best approximates 50% of the MTD or placebo (Cohort EEG-B) within their cohort in crossover fashion. All 8 subjects will receive active treatment in each of the two EEG cohorts during either the first or second dosing period.

In the Essential Tremor cohort, 6 subjects will receive a single dose of Compound 9 Oral Solution at the dose best approximating the SAD MTD. Subjects will be dosed after a standard clinic breakfast. Note that subjects with essential tremor may fail to qualify on the TETRAS after Admission and be withdrawn from the study prior to dosing. These subjects will be replaced to ensure there are 6 subjects dosed in this cohort.

The appropriate dose of Compound 9 Oral Solution or placebo will be administered according to the randomization schedule available to the pharmacist. The dose escalation pattern may be modified by the Safety Review Committee.

Procedures/Measurements

The SAD cohorts will consist of up to 6 visits over a period of up to 28 days prior to dosing and 14 days after dosing.

The Food Effect cohort will consist of 9 visits over a period of up to 28 days prior to dosing and 21 days after initial dosing. This cohort will be administered a repeat of the dose that best approximates 50% of the MTD.

The EEG cohorts will consist of 9 visits over a period of up to 28 days prior to dosing and 21 days after initial dosing.

The Essential Tremor cohort will consist of up to 5 visits over a period of up to 28 days prior to dosing and approximately 14 days after dosing.

During each phase of the study, subjects will be admitted to the unit approximately 24 hours prior to the expected time of dosing. During the SAD part of the study, subjects will be confined to the unit for approximately 72 hours after each dose. For the Food effect part of the study, subjects will be confined to the unit for approximately 48 hours after dosing; subjects may be released sooner if it is predicted that plasma concentrations of drug will be below the level of quantification earlier than 48 hours after dosing. During the EEG portion of the study, subjects will be confined to the unit for approximately 36 hours or until the plasma concentration of drug is predicted to be below the level of quantification. Subjects in the Essential Tremor cohort are confined to the unit for 24 hours after dosing.

No subject may be discharged from the unit until the investigator is satisfied that they have no continuing adverse events that could be related to study drug.

Physical examinations, vital signs, laboratory assessments and observations by experienced Phase I personnel will be undertaken throughout the study based on the Schedules of Events for all cohorts. The Stanford Sleepiness Scale (SSS) and Modified Observer's Assessment of Alertness/Sedation Scale (MOAA/S) will be used to assess sedation effects. The Bond-Lader VAS will assess different aspects of self-reported mood; the Drug Effects Questionnaire (DEQ-5) will assess whether the subject "liked" the drug and/or felt "high". Psychomotor testing will be undertaken during the EEG cohorts to assess cognitive function in a variety of domains such as attention, working memory, episodic secondary memory, executive function, and motor skills. A reduced battery of cognitive tests will be applied to subjects in the SAD cohorts.

An EEG with at least 24 channels set for continuous recording will be applied two hours prior to dosing and kept in place for approximately 36 hours after dosing in the EEG phase only. Five-minute relaxation epochs will be conducted during the 36 hours as follows: V2 and V5: −20 to −15 minutes before dosing; post-dose 60 (+1 hour) to 65 minutes; 120 (2 hours) to 125 minutes; 420 (7 hours) to 425 minutes; 1,380 to 1,385 minutes (23 hours) after dosing. A relaxation epoch may be added or the timing of the relaxation epochs adjusted based on Tmax or other findings observed during the SAD part of the study.

Eye tracking will be assessed for the EEG cohorts only.

Dose Adjustment Criteria for the SAD Cohorts

A Safety Review Committee (SRC) will be established comprised of the Principal Investigator, the Sponsor Study Physician and the CRO Drug Safety Physician. Designees may be utilized consistent with the SRC Charter. Optional attendees may participate as required. The roles and responsibilities of the SRC will be described in a SRC Charter which will be agreed and signed prior to the first dose of study drug being administered. The role of the SRC is to assess the safety, tolerability and pharmacokinetic information collected for each dose level and determine that the next cohort should:

advance to the next planned dose level;

advance to a dose lower than the next planned dose level; or repeat the previous dose level.

In addition, the SRC may stop the study for safety reasons at any time and will determine when the MTD has been reached using the pre-defined stopping rules. The committee may overrule these stopping criteria by being more conservative, i.e., next dose lower than planned, but may not rule that the next dose should be higher than planned. The SRC will not receive any unblinded PK data unless it is agreed upon by the SRC to unblind a subject and/or cohort based on the completed safety review.

Dose Escalation and Stopping Rules for the SAD Cohorts

Serious Adverse Event: If any subject in a cohort has a serious adverse event (SAE) that the SRC determines is related to Compound 9, the SRC may stop the SAD phase of the study or may permit ongoing dosing at lower doses of Compound 9 than that at which the event occurred, depending on the nature of the event.

Severe Adverse Event: If three or more active treatment subjects in a cohort have a severe adverse event that the safety committee determines is related to Compound 9, the safety committee may stop the SAD phase of the study or may permit ongoing dosing at the same or lower doses of Compound 9, depending on the nature of the event and the dose(s) at which the events occurred.

MOAA/S Score: If at least one Compound 9-exposed subject within a cohort has a MOAA/S s core of two Or Less (≤2) at anytime point during normal waking hours (≥08:00 h to ≤22:00 h) and this score is confirmed, i.e., repeat assessment is the same or lower, or if two or more (≥2) Compound 9-exposed subjects have a confirmed MOAA/S score of three or less (≤3) at any time point during normal waking hours (≥08:00 h to ≤22:00 h) and this score is confirmed, i.e., repeat assessment is the same or lower, dose escalation to the next planned dose will not occur. Additional dosing may be permitted by dosing Compound 9 at a lower dose or by repeating the dose at which these events occurred depending on the extent and duration of the sedation and the dose(s) at which the sedation occurred. The Safety Review Committee will consider MOAA/S scores as qualifying for stopping criteria only when the confirmation score is equal to or lower than the first assessment and when there is congruence with the SSS score at the same time point.

If any of the following findings occur in at least two (2) subjects exposed to Compound 9 Oral Solution within a cohort, the SRC may not allow dose-escalation if at least two subjects report the same finding. However, if each subject reported a different finding, the SRC could allow dose escalation at lower doses than planned. In all circumstances the SRC may allow dose-repetition or dose reduction:

An increase from pre-dose in supine systolic blood pressure of 60 mmHg sustained for at least five minutes, or a decrease from pre-dose in supine systolic blood pressure of 30 mmHg sustained for at least five minutes, or supine systolic blood pressure of ≤70 mmHg or ≥200 mmHg sustained for at least five minutes;

An increase from pre-dose in supine diastolic blood pressure of 40 mmHg sustained for at least five minutes, or a decrease from pre-dose in supine diastolic blood pressure of 30 mmHg sustained for at least five minutes, or supine diastolic blood pressure of ≤40 mmHg or ≥110 mmHg sustained for at least five minutes;

An increase from pre-dose in supine heart rate of 50 bpm sustained for at least five minutes, or a decrease from pre-dose in supine heart rate of 30 bpm sustained for at least five minutes, or supine heart rate of ≤45 bpm or ≥170 bpm sustained for at least five minutes;

QTc prolongation defined as QTcF increasing ≥60 msec and persisting for at least 10 minutes or QTcF >500 msec and persisting for at least 30 minutes;

A sustained increase in alanine aminotransferase (ALT) or aspartate aminotransferase (AST) to >3×upper limit of normal (ULN), which must be confirmed elevated >3×ULN within 48 hours;

Total bilirubin increase to >2×ULN confirmed on repeat testing within 48 hours;

ALT or AST >2×ULN concurrent with total bilirubin >1.5×ULN confirmed on repeat testing within 48 hours;

Serum creatinine >1.5×ULN confirmed on repeat testing within 48 hours;

Leukocyte count ≤2.5×109/L confirmed on repeat testing within 48 hours;

Neutrophil count ≤1.0×109/L confirmed on repeat testing within 48 hours;

Platelet count <100×109/L confirmed on repeat testing within 48 hours.

AUC and Cmax: based on the plasma concentration information from previous cohorts, the SRC will consider adjusting the dose (dose reduction, dose repetition, or reduced dose escalation) for the next cohort if the Cmax of >50% of the next cohort is expected to exceed 400 ng/mL (the estimated human Cmax based on the lowest NOAEL Day 14 Cmax in female rats). In addition, the SRC will not allow escalation to doses beyond those predicted to result in an AUC above the lowest NOAEL exposure in toxicology studies (male rat 14-day toxicology, AUC 5,050 ng.h/mL).

Pharmacokinetic Assessments

Pharmacokinetic blood samples will be taken and processed for analysis for concentrations of Compound 9. Selected samples may also be analyzed for concentrations of Compound 9 metabolites; urine samples will also be tested for concentrations of Compound 9.

Blood Sample Collection

Plasma samples for PK analysis will be collected according to the sampling collection times specified in Table 4 for the SAD, Food and Essential Tremor cohorts and Table 5 for the EEG cohorts. The start time of study drug administration is time zero and all postdosing sampling times are relative to this time. The Investigator or designee will arrange to have the plasma samples transported as directed for bioanalysis.

Selected samples may also be analyzed for concentrations of metabolites of Compound 9.

An additional PK sample may be collected at any time if clinically indicated and at the discretion of the Investigator (e.g. for unusual or severe AEs). Each sample will be marked with unique identifiers with at least the study number, subject number, and the nominal sample time. The date and actual time that the blood sample was taken will be recorded on the case report form or equivalent.

Urine Sample Collection

During the SAD phase only, all voided urine will be collected and pooled over the following time periods: pre-dose; 0-4 hours; 4-8 hours; 8-12 hours; 12-24 hours; 24-36 hours; 36-48 hours. A sample will be obtained from each pooled sample and processed for analysis of Compound 9 concentrations. Samples may be collected for Compound 9 metabolite concentrations. The predose urine sample is to be collected just prior to dosing. The post-dose collection periods are relative to dosing. If the planned time point is between the hours of ≥22.00 h and ≤08.00 h each day or if the subject has been discharged before the +72 hour time point during the Food, EEG and Essential Tremor phases of the study, the assessment need not be conducted at that time point.

Storage and Shipment of Pharmacokinetic and Urine Samples

The plasma and urine samples should be kept frozen at approximately −70 to −80° C. until analyzed. They should be packed as directed to avoid breakage during transit and with sufficient dry ice to prevent thawing for at least 72 hours. A specimen-identification form or equivalent must be completed and sent to the laboratory with each set of samples. The clinical site will arrange to have the plasma and urine samples transported as directed for bioanalysis as detailed in the PK instructions.

Sample Analysis

Bioanalysis of plasma samples for the determination of Compound 9 levels will be conducted utilizing a validated LC-MS/MS method at Agilux Laboratories, Worcester, Mass. The methodology for urine bioanalysis is in development and will be conducted at a later time by Agilux using the stored samples.

The following lists the laboratory testing that will be done at the appropriate time points:

- Hematology: basophils with differential, eosinophils with differential, lymphocytes with differential, monocytes with differential, neutrophils with differential, reticulocytes, hemoglobin, hematocrit, platelets, red blood cell count, white blood cell count.
- Biochemistry, renal: glucose, calcium, phosphorus, blood urea nitrogen, creatinine, sodium, potassium, chloride, bicarbonate.
- Biochemistry, hepatic: albumin, ALT, AST, total bilirubin, direct bilirubin, indirect bilirubin, alkaline phosphatase, total protein, lactate dehydrogenase, GGT.
- Other: triglycerides, activated partial thromboplastin time (APTT), prothrombin time, INR, HBsAG, antiHCV antibodies, HIV-1 and -2 antibodies.
- Urinalysis: protein, glucose, pH, blood, leukocytes; urobilinogen; bilirubin, ketones, nitrite.
- Other: FSH and serum pregnancy test will be tested during Screening.

Taste Assessment

At approximately one hour after each dose, subjects will be asked to complete a 100 mm visual analogue scale where 0 is "the worst tasting liquid I have ever swallowed" and 100 is "the nicest tasting liquid I have ever swallowed". Subjects will be asked to describe the taste of the medication (using words such as "bitter" or "sweet"). The Taste Assessment scale is provided in Appendix 11.

12-Lead Electrocardiogram (ECG)

A supine 12-lead ECG will be performed at the times specified below and the standard intervals recorded as well as any abnormalities. The 12-lead ECG will be assessed at SAD V1 (Screening and Day −1 [Admission]), SAD V5, Food V1 and V8, EEG V1 and EEG V8. All time points are relative to the time of dosing. If the ECG planned time point is between the hours of ≥22.00 h and ≤08.00 h each day or if the subject has been discharged before the +72 hour time point during the Food and EEG phases of the study, the assessment need not be conducted at that time point.

SAD Cohorts: V1 Admission; post-dose 1, 2, 4, 8, 12, 24, 36, 48, and 72 hours.

Food Cohort: V1 Admission; V5 pre dose and post-dose 1, 2, 4, 8, 12, 24, 36; V7 48 and 72 hours.

EEG Cohorts: V2 through V7—pre-dose; post-dose 1, 2, 4, 8, 12, 24, 36, 48 and 72 hours after dosing.

Essential Tremor Cohort: V1 (Screening and Day −1 [Admission]); V2—pre-dose; post-dose 4, 8, 24 hours; V3—48 h after dosing; V4.

Pulse Oximetry

Continuous pulse oximetry will be recorded at the same time points as the vital signs in all cohorts beginning 30 minutes prior to dosing and continuing for the first 24 h post dose. A pulse oximetry reading will also be taken at V1 (Screening). Continuous pulse oximetry will not be cancelled during the sleeping hours and will continue to be collected at all scheduled time points.

Continuous ECG (cECG)

Continuous ECG monitoring will be conducted from approximately 1 hour pre-dose up to the last assessment time point on discharge days; subjects will have continuous ECG monitoring (telemetry) in order to detect any cardiac rhythm abnormalities. Any such clinically significant Columbia—Suicide Severity Rating Scale (C-SSRS)

The "Baseline/Screening" C-SSRS form will be completed during the Admission visit (lifetime history and past 24 months). The "Since Last Visit" C-SSRS form will be completed at all subsequent scheduled time points as detailed below. The C-SSRS is provided in Appendix 4.

SAD Cohorts: V1 (Day −1 [Admission]); V2 pre-dose, V4 post-dose 72 h, and V5.

Food Cohort: V1 (Day −1 Admission for Food cohort); V7 post-dose 72 h, and V8.

EEG Cohorts: V1 (Day −1 [Admission]); V4 post-dose 72 h, V5 (crossover) pre-dose, V7 post-dose 72 h, and V8.

Essential Tremor Cohort: Baseline/Screening test: V1 (Day −1 [Admission]); Since Last Visit test: V2 post-dose 24 h; V3 post-dose 48 h; V4.

Stanford Sleepiness Scale (SSS)

The SSS will be administered at the time points shown below for each cohort. All time points are relative to the time of dosing. If the planned time point is between the hours of ≥22.00 h and ≤08.00 h each day or if the subject has been discharged before the +72 hour time point during the Food and EEG phases of the study, the assessment need not be conducted at that time point. The SSS is provided in Appendix 5. The SSS should be performed prior to the MOAA/S score.

SAD Cohorts: V2—pre-dose and post-dose 1, 2, 3, 4, 5, 6, 7, 8, 10, 12, 14, 16, 22, and 24 hours; V3—post-dose 28, 32, 36, 40 and 48 hours; V4—post-dose 60 and 72 hours.

Food Cohort: V5—pre-dose and post-dose 1, 2, 3, 4, 5, 6, 7, 8, 10, 12, 14, 16, 22 and 24 hours; V6—post-dose 28, 32, 36, 40, and 48 hours; V7—post-dose 60 and 72 hours.

EEG Cohorts: V2—pre-dose and post-dose 2, 4, 6, 8, 10, 12, 14, 16, and 24 hours; V3—post-dose 36 and 48 hours; V4—post-dose 60 and 72 hours; V5 (crossover)—pre-dose and post-dose 2, 4, 6, 8, 10, 12, 14, 16, and 24 hours; V6—post-dose 36 and 48 hours; V7—post-dose 60 and 72 hours.

Essential Tremor Cohort: V2—pre-dose and post-dose 2, 4, 6, 8, 10, 12, 14, 16 and 24 hours; V3—post-dose 48 hours; V4.

Modified Observer's Assessment of Alertness/Sedation Scale (MOAA/S)

The MOAA/S allows exploration of deeper sedation states than the SSS. The MOAA/S will be administered at the time points shown below for each cohort. All time points are relative to the time of dosing. If the planned time point is between the hours of ≥22.00 h and ≤08.00 h each day or if the subject has been discharged before the +72 hour time point during the Food and EEG phases of the study, the assessment need not be conducted at that time point. If a MOAA/S score of 3 or less (≤3) is observed, confirm the score by waiting approximately 10 minutes and readministering the MOAA/S assessment. Record both the scheduled and unscheduled assessments.

All time points relate to the administration of study drug.
  SAD Cohorts: V2—pre-dose and post dose, 1, 2, 3, 4, 5, 6, 7, 8, 10, 12, 14, 16, 22 and 24 hours; V3—post-dose 28, 32, 36, 40 and 48 hours; V4—post-dose 60 and 72 hours.
  Food Cohort: V5—pre-dose and post-dose, 1, 2, 3, 4, 5, 6, 7, 8, 10, 12, 14, 16, 22 and 24 hours; V6—post-dose 28, 32, 36, 40 and 48 hours; V7—post-dose 60 and 72 hours.
  EEG Cohorts: V2—pre-dose and post-dose, 2, 4, 6, 8, 10, 12, 14, 16, and 24 hours; V3—post-dose 36 and 48 hours; V4—post-dose 60 and 72 hours; V5 (crossover)—pre-dose and post-dose 2, 4, 6, 8, 10, 12, 14, 16 and 24 hours; V6—post-dose 36 and 48 hours; V7—post-dose 60 and 72 hours.
  Essential Tremor Cohort: V2—pre-dose and post-dose 2, 4, 6, 8, 10, 12, 14, 16 and 24 hours; V3—post-dose 48 hours; V4.

Bond-Lader VAS (Mood Rating Scale) (BL-VAS)

Mood will be assessed using the Bond-Lader Mood Rating Scale during the EEG and Essential Tremor cohorts only. This is a 16-part self-administered questionnaire that employs 100 mm visual analogue scales to explore different aspects of self-reported mood. If the planned time point is between the hours of +≥22.00 h and ≤08.00 h each day or if the subject has been discharged before the +72 hour time point during the Food and EEG phases of the study, the assessment need not be conducted at that time point. The BL-VAS is provided in Appendix 7.

The mood scale will be administered at the following time points:
EEG: V2—pre-dose and post-dose 2, 12 and 24 hours; V3—post-dose 36 and 48 hours; V4—postdose 72 hours; V5 (crossover)—pre-dose and post-dose 2, 12 and 24 hours after dosing; V6—postdose 36 and 48 hours; V7—post-dose 72 hours; V8.
  Essential Tremor Cohort: V2—pre-dose and post-dose 2, 12 and 24 hours.

Drug Effects Questionnaire (DEQ-5)

A Drug Effects Questionnaire (DEQ-5) will be administered as follows:
  1. Do you FEEL a drug effect right now?
  2. Are you HIGH right now?
  3. Do you DISLIKE any of the effects that you are feeling right now?
  4. Do you LIKE any of the effects that you are feeling right now?
  5. Would you like MORE of the drug you took, right now?

The answers are recorded on a 100 mm visual analogue scale with the answer for each being "Not at all" and "Extremely" at the extremes. There will be options to record "Not applicable" for questions 3 and 4 if no drug effects are felt and for question 5 prior to administration of study medication.

If the planned time point is between the hours of ≥22.00 h and ≤08.00 h each day or if the subject has been discharged before the +72 hour time point during the Food and EEG phases of the study, the assessment need not be conducted at that time point.

The DEQ5 will be administered at the following time points in all cohorts except the Food cohort:
  SAD Cohorts: V2—pre-dose and post-dose 2, 4, 12 and 24 hours.
  EEG Cohorts: V2—pre-dose and post-dose 2, 4, 12 and 24 hours; V3—post-dose 36 and 48 hours;
V4 —post-dose 72 hours; V5 (crossover)—pre-dose and post-dose 2, 12 and 24 hours; V6—postdose 36 and 48 hours; V7—post-dose 72.
  Essential Tremor Cohort: V2—pre-dose and post-dose 2, 4, 12 and 24 hours.

The DEQ-5 is provided in Appendix 8.

Psychomotor Testing

Psychomotor tests will be conducted to assess cognitive function in a variety of domains such as attention, working memory, episodic secondary memory, executive function, and motor skills. If the planned time point is between the hours of ≥22.00 h and ≤08.00 h each day or if the subject has been discharged before the +72 hour time point during the Food and EEG phases of the study, the assessment need not be conducted at that time point.

SAD Cohorts: V2—pre-dose and post-dose 3, 8 and 24 hours. A reduced battery of cognitive tests will be applied to subjects in the SAD cohorts. EEG Cohorts: V2—pre-dose and post-dose 3, 8 and 24 hours after dosing; V3 post-dose 48 hours; V4—post-dose 72 hours; V5 (crossover)—pre-dose and post-dose 3, 8 and 24 hours; V6—post-dose 48 hours; V7—post-dose 72 hours. Subjects will complete a practice session at admission on Day −1 or at any time prior to the first scheduled time point.

EEG

For the EEG cohorts only, an EEG with a minimum of 24 channels set for continuous recording will be applied approximately two hours prior to dosing and kept in place for approximately 36 hours after dosing. Five-minute relaxation epochs will be conducted at the time points listed below. During these epochs subjects are asked to close their eyes, relax and empty their minds of thoughts. If the relaxation epoch is scheduled at the same time as another assessment, the relaxation epoch takes precedence. If a PK sample is due, the sample should be taken just prior to beginning the relaxation epoch. EEG relaxation epochs: A five-minute relaxation epoch will be undertaken at V2 and V5: −20 to −15 minutes before dosing; post-dose 60 (+1 hour) to 65 minutes; 120 (+2 hours) to 125 minutes (+2 hours); 420 (+7 hours) to 425 minutes; 1,380 to 1,385 minutes (+23 hours) after dosing. A relaxation epoch may be added or the timing of the relaxation epochs adjusted based on Tmax or other findings observed during the SAD part of the study.

Eye Tracking

For the EEG cohorts only, eye tracking will be assessed at the following time points. If the planned time point is between the hours of ≥22.00 h and ≤08.00 h each day or if the subject has been discharged before the +72 hour time point during the Food and EEG phases of the study, the assessment need not be conducted at that time point.

EEG Cohorts: V2 and V5—pre-dose and post-dose 2.5, 7.5, 9.5 and 23.5 hours.

Kinesia (Accelerometer-Based) and TETRAS

For the Essential Tremor cohort, the TRG Essential Tremor Rating Assessment Scale (TETRAS) performance subscale (Appendix 12) and the accelerometer-based Kinesia assessments will be administered at the time points shown below. Note that the TETRAS score for the test conducted during Visit 1 (Admission) will be used to determine eligibility and must be ≥8. The testing performed at Visit 2 just prior to dosing will not disqualify the subject even if any result is <8.

Dosing should occur as soon as possible after completing the third pre-dose TETRAS.

Essential Tremor Cohort Kinesia and TETRAS Testing: V1—Admission (determines eligibility); V2—pre-dose—three tests separated by at least 30 minutes; V2 post-dose 1, 2, 4, 6, 8, 12 and 24 hours after dosing.

Adverse and Serious Adverse Events

Adverse Event (AE)

An AE is the development of an undesirable medical condition or the deterioration of a pre-existing medical condition following or during exposure to a pharmaceutical product, whether or not considered casually related to the product. In clinical studies, an AE can include an undesirable medical condition occurring at any time, including baseline or washout periods, even if no study treatment has been administered.

All AEs that occur after any subject has been enrolled, before treatment, during treatment, or within 14 days following the cessation of treatment, whether or not they are related to the study, must be recorded on forms provided by designee.

Serious Adverse Event (SAE)

A serious adverse event is an AE occurring during any study phase (i.e., baseline, treatment, washout, or follow-up), and at any dose of the investigational product, comparator or placebo, that fulfils one or more of the following:

Results in death

It is immediately life-threatening

It requires in-patient hospitalization or prolongation of existing hospitalization It results in persistent or significant disability or incapacity Results in a congenital abnormality or birth defect It is an important medical event that may jeopardize the subject or may require medical intervention to prevent one of the outcomes listed above.

Recording Sedation as an Adverse Event

Sedation will be assessed using specific rating scales in this study. In order to apply consistency to adverse event reports of sedation, Investigators will not record sedation as an adverse event unless there is a score of ≥5 on the SSS and/or a score of ≤2 on the MOAA/S. Consideration should be given to the most appropriate term to describe the sedation characteristics.

Relationship to Study Drug

An Investigator who is qualified in medicine must make the determination of relationship to the investigational product for each AE (Unrelated, Possibly Related or Probably Related). The Investigator should decide whether, in his or her medical judgment, there is a reasonable possibility that the event may have been caused by the investigational product. If no valid reason exists for suggesting a relationship, then the AE should be classified as "unrelated." If there is any valid reason, even if undetermined, for suspecting a possible cause-and-effect relationship between the investigational product and the occurrence of the AE, then the AE should be considered "related."

Not Related: No relationship between the experience and the administration of study drug; related to other etiologies such as concomitant medications or subject's clinical state.

Possibly Related: A reaction that follows a plausible temporal sequence from administration of the study drug and follows a known response pattern to the suspected study drug. The reaction might have been produced by the subject's clinical state or other modes of therapy administered to the subject, but this is not known for sure.

Probably Related: A reaction that follows a plausible temporal sequence from administration of the study drug and follows a known response pattern to the suspected study drug. The reaction cannot be reasonably explained by the known characteristics of the subject's clinical state or other modes of therapy administered to the subject. If the relationship between the AE/SAE and the investigational product is determined to be "possible" or "probable" the event will be considered to be related to the investigational product for the purposes of expedited regulatory reporting.

Recording Adverse Events

Adverse events spontaneously reported by the subject and/or in response to an open question from the study personnel or revealed by observation will be recorded during the study at the investigational site. Clinically significant changes in laboratory values, blood pressure, and pulse need not be reported as AEs unless they prompt corrective medical action by the investigator, constitute an SAE or lead to discontinuation of administration of study drug.

Information about AEs will be collected from the signing of the consent form until the final visit of the study for that subject. Adverse events that occur after the first administration of study drug will be denoted Treatment Emergent Adverse Events. All AEs will be followed until they are resolved or have reached a clinical plateau with no expectation of future change.

The AE term should be reported in standard medical terminology when possible. For each AE, the investigator will evaluate and report the onset (date and time), resolution or clinical plateau (date and time), intensity, causality, action taken, serious outcome (if applicable), and whether or not it caused the subject to discontinue the study.

Intensity will be assessed according to the following scale:

Mild (awareness of sign or symptom, but easily tolerated)

Moderate (discomfort sufficient to cause interference with normal activities)

Severe (incapacitating, with inability to perform normal activities)

Reporting Serious Adverse Events

All SAEs (related and unrelated) will be recorded from the signing of the consent form until 28 days following the last dose of study drug. Any SAEs considered possibly or probably related to the investigational product and discovered by the Investigator at any time after the study should be reported. All SAEs must be reported to the Sponsor or Sponsor's designee immediately or as soon as possible, but no later than 6 hours by phone and in writing within 24 hours of the first awareness of the event. The Investigator must complete, sign and date the SAE pages, verify the accuracy of the information recorded on the SAE pages with the corresponding source documents to Designee.

Safety Analysis

For all safety analyses of the SAD portion of the study, the placebo dose group will be pooled across cohorts. AEs will be coded using MedDRA™ with the version used specified in the clinical study report. The overall incidence of AEs will be displayed by System Organ Class (SOC), preferred term, dose group, and cohort. Incidence of AEs will also be presented by maximum severity and relationship to study drug. Data from vital signs, clinical laboratory measures, ECG, and C-SSRS will be summarized using descriptive statistics by dose group and cohort, where applicable. Continuous endpoints will be summarized with n, mean, standard deviation, median, minimum and maximum. In addition, change from baseline values will be calculated at each time point and will be summarized using the same summary statistics. Out-of-range safety endpoints may be categorized as low or high, where applicable. For all categorical endpoints, summaries will include counts and percentages.

Pharmacokinetic Analysis

Derived PK parameters will include area under the plasma concentration curve (AUC0-inf), the distributional half-life and terminal half-life (t112), the maximum concentration (Cmax), the time to reach maximum concentration (Tmax), and the clearance (CL) and urine excretion. PK parameters will be summarized using appropriate descriptive statistics. Time to reach maximum concentration (Tmax) will be summarized using n, mean, standard deviation, median, minimum, and maximum.

All other PK parameters will be summarized using n, geometric mean, coefficient of variation, median, minimum, and maximum.

Dose proportionality will be analyzed using an ANCOVA model using the logarithm of PK parameter (AUC and Cmax) as the dependent variable and the logarithm of the dose as the independent variable. Point estimates and the corresponding CIs will be estimated for both AUC and Cmax.

Food Effect Analysis

For the food effect analysis, the log-transformed AUC and Cmax will be compared across food conditions using a paired t-test. Additional statistical testing may be performed according to the bioanalytical statistical analysis plan.

Other Endpoint Analyses

The secondary endpoints of SSS, MOAA/S, BL-VAS, and DEQ-5 values will be summarized using the same descriptive statistics described above for the safety variables. The pharmacodynamics analysis of EEG endpoints and their relationship to psychomotor testing and eye tracking measures will be described in a separate analysis plan. In addition, PK/PD exploratory analyses will be performed utilizing sedation, mood, EEG and psychomotor data. For the Essential Tremor cohort, the exploratory endpoints of the TRG Essential Tremor Rating Assessment Scale (TETRAS) performance subscale and accelerometer-based Kinesia scores will be summarized as described for safety and secondary endpoints.

Statistical Considerations

The Safety Population is defined as all subjects who are administered study drug. The Pharmacokinetic (PK) Population is defined as all subjects who are administered Compound 9 and have at least one bioanalysis result for the plasma concentration of Compound 9.

No formal sample size calculations have been undertaken for this safety and tolerability study. The number of subjects in each cohort and at each dose level is thought to be sufficient to assess preliminary safety and tolerability following single doses of Compound 9. No efficacy parameters are being collected or analyzed for this Phase I study.

For all safety analyses of the SAD portion of the study, the placebo dose group will be pooled across cohorts. AEs will be coded using MedDRA™ with the version used specified in the clinical study report. The overall incidence of AEs will be displayed by System Organ Class (SOC), preferred term, dose group, and cohort. Incidence of AEs will also be presented by maximum severity and relationship to study drug. Data from vital signs, clinical laboratory measures, ECG, and C-SSRS will be summarized using descriptive statistics by dose group and cohort, where applicable. Continuous endpoints will be summarized with n, mean, standard deviation, median, minimum and maximum. In addition, change from baseline values will be calculated at each time point and will be summarized using the same summary statistics. Out-of-range safety endpoints may be categorized as low or high, where applicable. For all categorical endpoints, summaries will include counts and percentages. PK parameters will be summarized using appropriate descriptive statistics.

Time to reach maximum concentration (Tmax) will be summarized using n, mean, standard deviation, median, minimum, and maximum. All other PK parameters will be summarized using n, geometric mean, coefficient of variation, median, minimum, and maximum.

Dose proportionality will be analyzed using an ANCOVA model using the logarithm of PK parameter (AUC and Cmax) as the dependent variable and the logarithm of the dose as the independent variable. Point estimates and the corresponding CIs will be estimated for both AUC and Cmax.

For the food effect analysis, the log-transformed AUC and Cmax will be compared across food conditions using a paired t-test. Additional statistical testing may be performed according to the bioanalytical statistical analysis plan.

The secondary endpoints of SSS, MOAA/S, BL-VAS, and DEQ-5 values will be summarized using the same descriptive statistics described above for the safety variables. The pharmacodynamics analysis of EEG endpoints and their relationship to psychomotor testing and eye tracking measures will be described in a separate analysis plan. In addition, PK/PD exploratory analyses will be performed utilizing sedation, mood, EEG and psychomotor data.

Pharmacokinetic Exemplary Schedule

TABLE 4

SAD, Food Effect and Essential Tremor Cohorts - all sampling times in hours relative to dosing
Visit 2 for SAD and Essential Tremor/Visit 5 for Food-Effect

| Pre-Dose | 0.25 | 0.5 | 1 | 1.5 | 2 | 2.5 | 3 | 3.5 | 4 | 4.5 | 5 | 5.5 | 6 | 7 | 8 | 10 | 12 | 16 | 24 |
|---|---|---|---|---|---|---|---|---|---|---|---|---|---|---|---|---|---|---|---|

The following additional time point is to be collected for the Essential Tremor cohort:

| Visit 3 |
|---|
| 48 |

The following additional time point is to be collected for the SAD and Food Effect cohorts:

| Visit 3/Visit 6 | | | |
|---|---|---|---|
| 28 | 32 | 36 | 48 |

TABLE 5

| EEG Cohort - all sampling times in hours relative to dosing | | | | | | | | | | | | |
|---|---|---|---|---|---|---|---|---|---|---|---|---|
| | | | | | | | | | | | | Visit |
| Visit 2 and Visit 5 for PD/EEG* | | | | | | | | | | | | 3/6 |
| Pre-Dose | 2 | 2.5 | 3 | 6 | 7.5 | 8 | 9 | 9.5 | 23 | 23.5 | 24 | 36 |

*Blood samples for plasma concentrations of Compound 9 should be taken just prior to any scheduled relaxation epoch

TABLE 6

Schedule of Events SAD Cohorts

| | Visit | | | | | |
|---|---|---|---|---|---|---|
| | V1 | V2 | V3 | V4 | V5 | V6 |
| | | | Visit Window | | | |
| | D −28 to D −1 | 0 to +24 h | +24 h to +48 h | +48 h to +72 h | V2 + 7 d (±1 d) | V2 + 14 d (±1 d) |
| | | | Visit Days | | | |
| | Screen | D 1 | D 2 | D 3 | Follow Up | End of Study |
| Informed Consent | X | | | | | |
| Inclusion/Exclusion | X | | | | | |
| Demographics | X | | | | | |
| Medical History | X | | | | | |
| Physical Examination | X | | | | | X |
| Body Weight/Height | X | | | | | |
| CBC/Serum Chemistry[1] | X | X | | X | X | |
| Urinalysis[1] | X | X | | X | X | |
| Drug/Alcohol Screen[10] | X | X | | | | |
| Hepatitis & HIV Screen | X | | | | | |
| Genetic Sample | | X | | | | |
| Vital Signs[2] | X | X | X | X | X | |
| Pulse oximetry | X | X | | | | |
| 12-Lead ECG[3] | X | X | X | X | X | |
| cECG | | X | X | X | | |
| C-SSRS[4] | X | X | | | X | X |
| SSS[5] | | X | X | X | | |
| MOAA/S[6] | | X | X | X | | |
| DEQ5[7] | | X | | | | |
| Psychomotor Testing[8] | | X | | | | |
| Plasma PK Samples[9] | | X | X | | | |
| Urine PK Samples | | X | X | | | |
| Confined to Unit | | X | X | X | | |
| Administer Study Drug | | X | | | | |
| Taste Assessment | | X | | | | |
| Adverse Events[11] | X | X | X | X | X | X |
| Concomitant Meds[11] | X | X | X | X | X | X |
| Study Completion | | | | | | X |

[1]Screening and Safety Laboratory Tests SAD Cohorts: V1 (Screening and Day −1 [Admission]); V2 pre-dose; V4 72 h post-dose; V5
[2]Vital Signs SAD Cohorts: V1 (Screening and Day −1 [Admission]), V2 pre-dose and post-dose 15, 30, 60, 90, and 120 minutes, and 2.5, 3, 3.5, 4, 4.5, 5, 5.5, 6, 7, 8, 10, 12, 14, 16, 22, and 24 hours; V3 - post-dose 28, 32, 36, and 48 hours after dosing, V4 - 60 and 72 hours after dosing; V5.
[3]12-Lead ECG SAD Cohorts V1: V1 Screening and Day −1 (Admission), pre-dose and post-dose 1, 2, 4, 8, 12, 24, 36, 48, and 72 hours.
[4]C-SSRS SAD Cohorts: Screening and Day −1 (admission), V4 post-dose 72 h, and V5.
[5]SSS SAD Cohorts: V2 - pre-dose and post-dose 1, 2, 3, 4, 5, 6, 7, 8, 10, 12, 14, 16, 22, and 24; V3 - post-dose 28, 32, 36, 40 and 48 hours; V4 - post-dose 60 and 72 hours.
[6]MOAA/S SAD Cohorts: V2 - pre-dose and post-dose 1, 2, 3, 4, 5, 6, 7, 8, 10, 12, 14, 16, 22, and 24; V3 - post-dose 28, 32, 36, 40 and 48 hours; V4 - post-dose 60 and 72 hours.
[7]DEQ5 SAD Cohorts: V2 - pre-dose and post dose 2, 12 and 24 hours.
[8]Psychomotor testing SAD Cohorts: V2 - pre-dose and post-dose 3, 8 and 24 hours. Subjects will complete a practice session during Screening prior to their Day −1 (Admission) assessment.
[9]See Appendix 2
[10]Urine drug screen and alcohol breathalyzer will be conducted at Visit 1 during Screening and Day −1 (Admission)
[11]Adverse Events and concomitant medications (new or changed) will be collected during Visit 1 at both Screening and Day −1 (Admission) in addition to the other time points noted in the Schedule of Events.

TABLE 7

Schedule of Events Food Cohort
Note that subjects will have already completed the SAD portion of the study and are returning for the "fed" part of the study; Screening assessments completed prior to admission for the SAD portion do not need to be repeated even if more than 28 days have elapsed prior to the "V1 Admission for Food cohort" visit.

| | V1 Admission for Food | V5 Food | V6 Food | V7 Food | V8 Follow Up | V9 End Study |
|---|---|---|---|---|---|---|
| | | | Visit Window | | | |
| | D −1 | 0 to +24 h | V5 + 24 h to +48 h | V5 + 48 h to +72 h | V5 + 7 d (±1 d) | V5 + 14 d (±1 d) |
| Inclusion/Exclusion | X | | | | | |
| Physical Examination | X | | | | X | |
| Body Weight/Height | X | | | | | |
| CBC/Serum Chemistry[1] | X | | | X | X | |
| Urinalysis | X | | | X | X | |
| Drug/Alcohol Screen | X | | | | | |
| Vital Signs[2] | X | X | X | X | X | |
| Pulse oximetry | | X | | | | |
| 12-Lead ECG[3] | X | X | X | X | X | |
| cECG | | X | X | X | | |
| C-SSRS[4] | X | | | X | X | |
| SSS[5] | | X | X | X | | |
| MOAA/S[6] | | X | X | X | | |
| Plasma PK Samples[7] | | X | X | | | |
| Confined to Unit | X | X | X | X | | |
| Administer Study Drug | | X | | | | |
| Taste Assessment | | X | | | | |
| Adverse Events | X | X | X | X | X | X |
| Concomitant Meds | X | X | X | X | X | X |
| Study Completion | | | | | | X |

[1]Screening and Safety Laboratory Tests Food Cohorts: Visit 1 (Admission for Food cohort), V7 72 h post-dose; V8
[2]Vital Signs Food Cohort: V1 (Admission for Food cohort), V5 pre-dose and post-dose 15, 30, 60, 90, and 120 minutes, and 2.5, 3, 3.5, 4, 4.5, 5, 5.5, 6, 7, 8, 10, 12, 14, 16, 22, and 24 hours after dosing; V6 - 28, 32, 36, and 48 hours after dosing, V7 - 60 and 72 hours after dosing; V8.
[3]12-Lead ECG Food Cohort: V1 (Admission for Food cohort), V5 pre-dose and post-dose 1, 2, 4, 8, 12, 24; V6 36, 48; V7 72 hours; V8.
[4]C-SSRS Food Cohort: V1 Admission for Food; V7 post-dose, and V8.
[5]SSS Food Cohort: V5 - pre-dose and post-dose 1, 2, 3, 4, 5, 6, 7, 8, 10, 12, 14, 16, 22, and 24; V6 - post-dose 28, 32, 36, 40 and 48 hours; V4 - post-dose 60 and 72 hours.
[6]MOAA/S Food Cohort: V5 - pre-dose and post-dose 1, 2, 3, 4, 5, 6, 7, 8, 10, 12, 14, 16, 22, and 24; V6 - post-dose 28, 32, 36, 40 and 48 hours; V7 - post-dose 60 and 72 hours.
[7]See Appendix 2

TABLE 8

Schedule of Events EEG Cohort

| | V1 Screen | V2 EEG | V3 EEG | V4 EEG | V5 EEG | V6 EEG | V7 EEG | V8 Follow Up | V9 End Study |
|---|---|---|---|---|---|---|---|---|---|
| | | | | | Visit Window | | | | |
| | D −28 to D −1 | 0-+24 h | V2 + 24 h to +48 h | V2 + 48 h to +72 h | V2 + 7 d 0 to +24 h | V5 + 24 h to +48 h | V5 + 48 h to +72 h | V2 + 14 d (±1 d) | V2 + 21 d (±1 d) |
| Informed Consent | X | | | | | | | | |
| Inclusion/Exclusion | X | | | | | | | | |
| Demographics | X | | | | | | | | |
| Medical History | X | | | | | | | | |
| Physical Examination | X | | | | | | | X | |
| Body Weight/Height | X | | | | | | | | |
| CBC/Serum Chemistry[1] | X | X | | X | X | | X | X | |
| Urinalysis | X | X | | X | X | | X | X | |
| Drug/Alcohol Screen | X | X | | | X | | | | |
| Hepatitis & HIV Screen | X | | | | | | | | |
| Genetic Sample | | X | | | | | | | |
| Vital Signs[2] | X | X | X | X | X | X | X | X | |
| Pulse oximetry | X | X | | | | | | | |
| 12-Lead ECG[3] | X | X | X | X | X | X | X | X | |
| cECG | | X | X | X | X | X | X | | |
| C-SSRS[4] | X | | | | X | X | | X | X |

TABLE 8-continued

Schedule of Events EEG Cohort

|  | Visit | | | | | | | | |
|---|---|---|---|---|---|---|---|---|---|
|  | V1 Screen | V2 EEG | V3 EEG | V4 EEG | V5 EEG | V6 EEG | V7 EEG | V8 Follow Up | V9 End Study |
|  | | | | | Visit Window | | | | |
|  | D −28 to D −1 | 0−+24 h | V2 + 24 h to +48 h | V2 + 48 h to +72 h | V2 + 7 d 0 to +24 h | V5 + 24 h to +48 h | V5 + 48 h to +72 h | V2 + 14 d (±1 d) | V2 + 21 d (±1 d) |
| SSS[5] | | X | X | X | X | X | X | | |
| MOAA/S[6] | | X | X | X | X | X | X | | |
| Bond-Lader Mood Scale[7] | | X | X | X | X | X | X | X | |
| DEQ5[8] | | X | X | X | X | X | X | | |
| Psychomotor Testing[9] | X | X | X | X | X | X | X | | |
| EEG[10] | | X | X | | X | X | | | |
| Eye Tracking[11] | | X | | | X | | | | |
| Plasma PK Samples[12] | | X | X | | X | X | | | |
| Confined to Unit | | X | X | X | X | X | X | | |
| Administer Study Drug | | X | | | X | | | | |
| Taste Assessment | | X | | | | | | | |
| Adverse Events | X | X | X | X | X | X | X | X | X |
| Concomitant Meds | X | X | X | X | X | X | X | X | X |
| Study Completion | | | | | | | | | X |

[1]Screening and Safety Laboratory Tests EEG Cohorts: V1 (Screening and Day −1 [Admission]); V2 pre-dose; V4 72 h post-dose; V5 (crossover) pre-dose; V7 72 h post-dose; V8
[2]Vital Signs EEG Cohorts: V1 (Screeening and Day −1 [Admission], V2 pre-dose and post-dose 1, 2, 3, 4, 6, 8, 12, 14, 16, 22, and 24 hours after dosing; V4-60 and 72 hours after dosing; V5 (crossover) - pre-dose and post-dose 1, 2, 3, 4, 5, 6, 7, 8, 10, 12, 14, 16, 22, and 24 hours after dosing; V6 - 28, 32, 36, and 48 hours after dosing, V7 - 60 and 72 hours after dosing; V8.
[3]12-Lead ECG EEG Cohort: V1 (Screening and Day −1 [Admission]; V2 - pre-dose; post-dose 4, 8, 24; V5 48 and Visit 7 72 hours after dosing.
[4]C-SSRS EEG Cohorts: V1 (Day −1 [Admission]); V4 post-dose 72 h, V5 (crossover) pre-dose, V7 post-dose 72 h, and V8.
[5]SSS EEG Cohorts: V2 - pre-dose and post-dose 2, 4, 6, 8, 10, 12, 14, 16, 22, and 24 hours; V3 - post-dose 36 and 48 hours; V4 - post-dose 60 and 72 hours; V5 (crossover) - pre-dose and post-dose 2, 4, 6, 8, 10, 12, 14, 16, 22, and 24 hours; V6 - post-dose 36 and 48 hours; V7 - post-dose 60 and 72 hours.
[6]MOAA/S EEG Cohorts: V2 - pre-dose and post-dose 2, 4, 6, 8, 10, 12, 14, 16, 22, and 24 hours; V3 - post-dose 36 and 48 hours; V4 - post-dose 60 and 72 hours. V5 (crossover) - pre-dose and post-dose 2, 4, 6, 8, 10, 12, 14, 16, 22, and 24 hours; V6 - post-dose 36 and 48 hours; V7 - post-dose 60 and 72 hours.
[7]BL-VAS EEG Cohorts: V2 - pre-dose and post-dose 2, 12 and 24 hours; V3 - post-dose 36 and 48 hours; V4 - post-dose 72 hours; V5 (crossover) - pre-dose and post-dose dose 2, 12 and 24 hours after dosing; V6 - post-dose 36 and 48 hours; V7 - post-dose 72 hours; V8.
[8]DEQ5 EEG Cohorts: V2 - pre-dose and post-dose 2, 12 and 24 hours; V3 - post-dose 36 and 48 hours; V4 - post-dose 72 hours; V5 (crossover) - pre-dose and post-dose dose 2, 12 and 24 hours; V6 - post-dose 36 and 48 hours; V7 - post-dose 72 hours.
[9]Psychomotor testing EEG Cohorts: V2 - pre-dose and post-dose 3, 8 and 24 hours. V3 post-dose 48 hours; V4 - post-dose 72 hours; V5 (crossover) - pre-dose and post-dose 3, 8 and 24 hours; V6 post-dose 48 hours; V7 - post-dose 72 hours. Subjects will complete a practice session during Screening and on Day −1 (Admission).
[10]EEG relaxation epochs EEG Cohorts: V2 and V5: −20 to −15 minutes before dosing post-dose 60 (1 hour) to 65 minutes; 120 (2 hours) to 125 minutes; 420 (7 hours) to 425 minutes; 1,380 to 1,385 minutes (23 hours) after dosing. A relaxation epoch may be added or the timing of the relaxation epochs adjusted based on $T_{max}$ or other findings observed during the SAD part of the study.
[11]Eye Tracking EEG Cohorts: V2 and V5 - pre-dose and post-dose 2.5, 7.5, 9.5 and 23.5 hours.
[12]See Appendix 2.

TABLE 9

Schedule of Events Essential Tremor Cohort

|  | Visit | | | | |
|---|---|---|---|---|---|
|  | V1 | V2 | V3 | V4 | V5 |
|  | | | Visit Window | | |
|  | −28 d to −24 h | −24 h to 0 h | 0 h to +24 h | +24 h to +48 h | V2 + 7 d (±1 d) | V2 + 14 d (±1 d) |
|  | | | Visit Days | | |
|  | Screen | Admit | D 1 | D 2 | Follow Up | End Study |
| Informed Consent | X | | | | | |
| Inclusion/Exclusion | X | | | | | |
| Demographics | X | | | | | |
| Medical History | X | | | | | |
| Physical Examination | X | | | | X | |
| Body Weight/Height | X | | | | | |
| CBC/Serum Chemistry[1] | X | | X | | X | |
| Urinalysis | X | | X | | X | |
| Drug/Alcohol Screen | X | X | | | | |
| Hepatitis & HIV Screen | X | | | | | |
| Genetic Sample | | X | | | | |
| Vital Signs[2] | X | X | X | X | X | |
| Pulse oximetry[3] | X | | X | | | |
| 12-Lead ECG[3] | X | X | X | X | X | |
| C-SSRS[4] | | X | X | X | X | |
| SSS[5] | | X | X | X | | |

TABLE 9-continued

Schedule of Events Essential Tremor Cohort

| | V1 | V2 | V3 | V4 | V5 | |
| --- | --- | --- | --- | --- | --- | --- |
| | \-28 d to \-24 h | \-24 h to 0 h | 0 h to +24 h | +24 h to +48 h | V2 + 7 d (±1 d) | V2 + 14 d (±1 d) |
| | Screen | Admit | D 1 | D 2 | Follow Up | End Study |
| MOAA/S[6] | | | X | X | X | |
| Bond-Lader Mood Scale[7] | | | X | | | |
| DEQ5[8] | | | X | | | |
| Kinesia | | X | X | | | |
| TETRAS Performance Subscale[9] | | X | X | | | |
| Plasma PK Samples[10] | | | X | X | | |
| Confined to Unit | | X | X | | | |
| Administer Study Drug | | | X | | | |
| Adverse Events | X | X | X | X | X | X |
| Concomitant Meds | X | X | X | X | X | X |
| Study Completion | | | | | | X |

[1]Screening and Safety Laboratory Tests Essential Tremor Cohort: V1 (Screening and Day −1 [Admission]); V2 pre-dose; V4.
[2]Vital Signs Essential Tremor Cohort: V1 (Screening and Day −1 [Admission]); V2 pre-dose and post-dose 1, 2, 3, 4, 6, 8, 12, 14, 16 and 24 hours; V3 48 hours after dosing; V4. Continuous pulse oximetry beginning 30 minutes pre-dose and through 24 h post-dose.
[3]12-Lead ECG: V1 (Screening and Day −1 [Admission]); V2 pre-dose; post-dose 4, 8, 24; V3 48; V4.
[4]C-SSRS Essential Tremor Cohort: V1 (Day −1 [Admission]); V2 post-dose 24 h; V3 post-dose 48 h; V4.
[5]SSS Essential Tremor Cohort: V2 pre-dose and post-dose 2, 4, 6, 8, 10, 12, 14, 16 and 24 hours; V3 48 hours; V4..
[6]MOAA/S Essential Tremor Cohort: V2 pre-dose and post-dose 2, 4, 6, 8, 10, 12, 14, 16 and 24 hours; V3 48 hours; V4.
[7]BL-VAS Essential Tremor Cohort: V2 pre-dose and post-dose 2, 12 and 24 hours.
[8]DEQ5 Essential Tremor Cohort: V2 pre-dose and post-dose 2, 12 and 24 hours.
[9]Kinesia and TETRAS Testing Essential Tremor Cohort: V1 (Admission/Eligibility); V2 - pre-dose (3 assessments separated by at least 30 min) and post-dose 1, 2, 4, 6, 8, 12 and 24 hours after dosing.
[10]PK sampling times: See Appendix 2.

Five cohorts in this single ascending dose study have been dosed and this study is ongoing. The following adverse events have been reported to date and deemed by the investigator as possibly or probably related to the study drug; mild drowsiness, mild confusion, somnolence, headache, orthostatic heart rate increase, aloofness, anxiety, sore throat and mild abdominal discomfort.

Expected risks are those identified during the toxicology and safety pharmacology studies for Compound 9 and clinical study Example 2. The most common drug-related effect seen across species, studies and doses was dose-related sedation. This will be monitored in the clinical study using two scales, one designed to monitor "sleepiness" (Stanford Sleepiness Scale) and one to monitor deeper sedation (Modified Observer's Assessment of Alertness/Sedation).

Other effects were noted in toxicology studies but were determined to be non-adverse, reversible and possibly related to Compound 9 administration. In both male and female rats, a slight prolongation of APTT without microscopic correlates, a slight increase in urine pH without microscopic correlates, and slight increases (<2-fold) in AST/ALT in high dose male and female rats with microscopic correlates (increased incidence of minimal hepatocellular vacuolation) were found. In dogs, transient decreases in core body temperature, transient increases in heart rate, and minimal renal tubular vacuolation (a well-documented vehicle effect (Stella and He, 2008)) were observed.

A Safety Review Committee will be employed to review available data from each cohort and to determine the dose selection for the subsequent cohort, not to exceed the maximum proposed dose for each cohort. The protocol also includes clear stopping rules with regard to sedation and other medical events of interest, as well as seriousness and severity of adverse events.

The ability to monitor for most of these effects and the careful consideration of safety data before increasing the dose for the next cohort, and the pre-specified escalation and stopping rules mitigate the risk of these effects.

Figure 8:
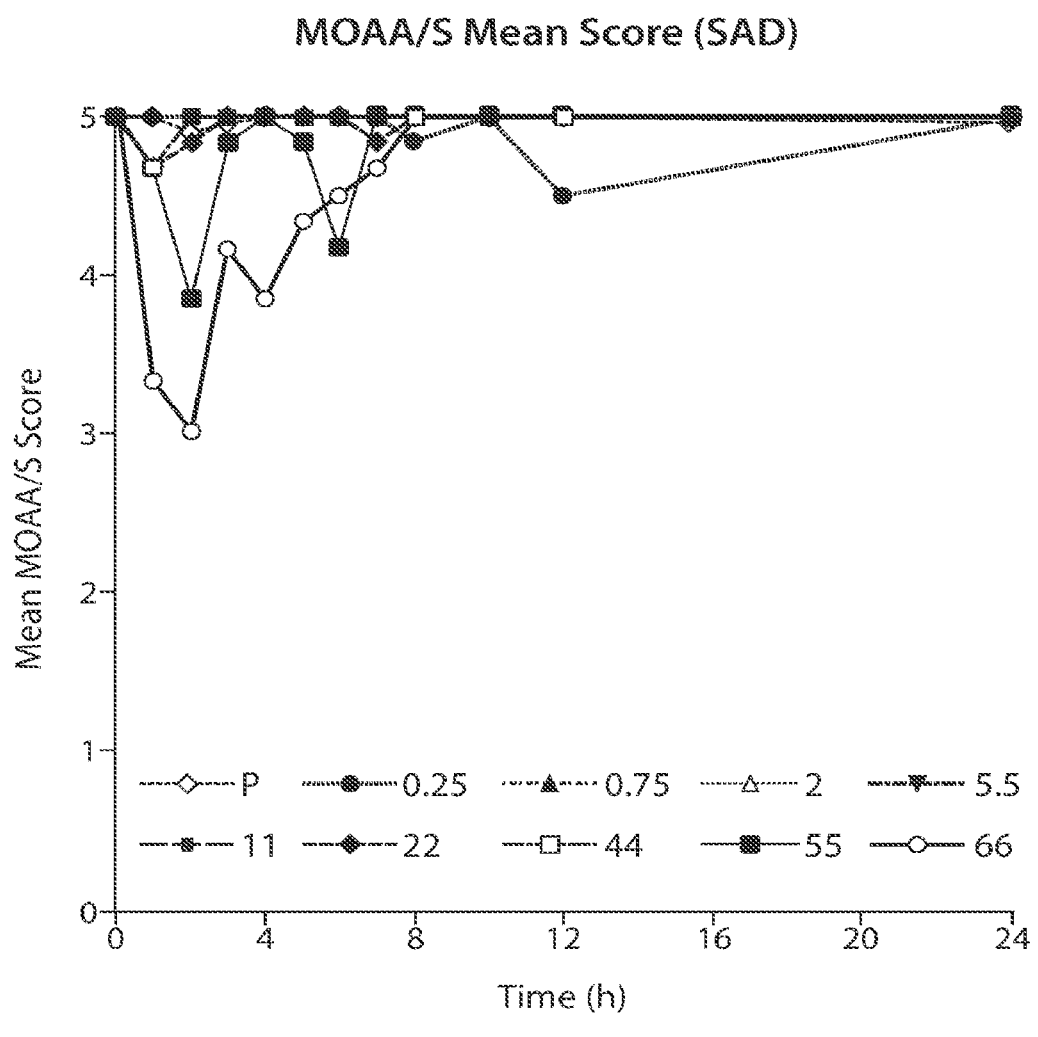
FIG. 8 shows exemplary MOAA/S Mean Score for Single Ascending Dose Study.

As seen in FIG. 8, MOAA/S≤2 was one of the stopping criteria for dose escalation. 2 subjects in the 66 mg dose of SAD (stopping criteria met); 2 subjects in the 55 mg dose of SAD (stopping criteria not met). 2 subjects had a MOAA/S score of ≤2, which upon repeat one subject had a value of >2.

MOAA/S Scale: 0, No response after painful trapezius squeeze; 1, Responds only after painful trapezius squeeze; 2, Responds only after mild prodding or shaking; 3, Responds only after name is called loudly and/or repeatedly; 4, Lethargic response to name spoken in normal tone; 5, Responds readily to name spoken in normal tone.

Figure 9:
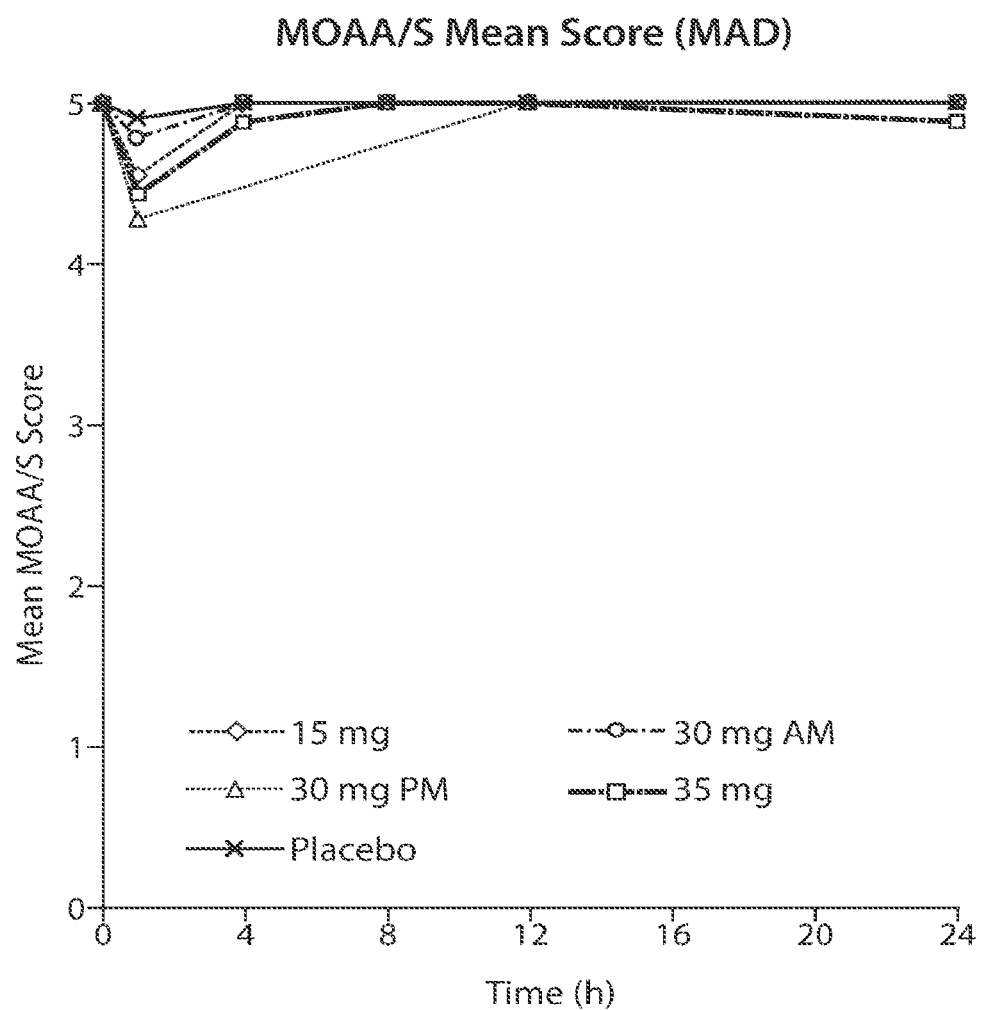
FIG. 9 shows exemplary MOAA/S Mean Score for Multiple Ascending Dose Study.

As shown in FIG. 9, Scores of 1 or 2 (deep sedation) only observed for two subjects in 35 mg group; all occurred at 1 hour post-dose. By 4 hours post-dose, mean MOAA/S approached baseline values.

Example 3. Phase I, Double-Blind, Placebo-Controlled, Multiple Ascending Dose Study to Determine Safety, Tolerability, Pharmacokinetics and Pharmacodynamics of Compound 9 Oral Solution in Healthy Volunteers Purpose To determine the safety and tolerability of multiple doses of Compound 9 Oral Solution in healthy volunteers aged 18-55 years as assessed by spontaneously reported adverse events, physical examination, vital sign measurements, laboratory testing, 12-lead ECGs, the Stanford Sleepiness Scale (SSS), Modified Observer's Assessment of Alertness/Sedation Scale (MOAA/S), and the Columbia-Suicide Severity Rating Scale (C-SSRS).

To determine the pharmacokinetic (PK) profile of multiple doses of Compound 9 Oral Solution as assessed by the calculation of standard PK parameters;

To investigate concentrations of Compound 9 metabolites in plasma and urine after multiple oral dosing;

To investigate the pharmacodynamic effects of multiple doses of Compound 9 Oral Solution as assessed by psychomotor testing (Cogstate Early Phase Battery consisting of Detection Task, Identification Task, One Card Learning Task, and Groton Maze Learning Test), mood, anxiety and depression (the Bond-Lader VAS and Hospital Anxiety and Depression Scale), drug likeability (the Drug Effects Questionnaire—5), and electroencephalography (EEG) with eye tracking;

To investigate whether Compound 9 Oral Solution induces the metabolism of drugs metabolized via the CYP3A4 and CYP2B6 pathways as assessed by dosing simvastatin and bupropion before and after exposure to Compound 9 in the Drug-Drug-Interaction (DDI) Cohort.

Materials

Compound 9 Oral Solution is available as 1 mg/mL and 6 mg/mL stock aqueous solutions of Compound 9 Drug Substance containing 40% HPBCD (Kleptose®) and 0.0025% sucralose which is further diluted with Sterile Water for Injection to achieve the selected dosages. The 1 mg/mL and 6 mg/mL stock Compound 9 Oral Solutions will be compounded from Compound 9 Drug Substance Powder in the Bottle and Excipient (s) in the Bottle (manufactured under cGMP conditions at Pharmatek) and further admixed at the clinical site in preparation for dosing. Placebo will be matched to study drug at each dose cohort. Detailed instructions for study drug preparation will be provided in the Pharmacy Manual. The PAREXEL clinical Phase I unit will be responsible for procuring the CYP induction drugs (bupropion and simvastatin). For the bupropion dosing, Wellbutrin IR® is preferred but a generic may be substituted with permission from the Sponsor. The generic equivalent of Zocor® is acceptable for simvastatin.

The composition and pharmaceutical quality of the investigational product will be maintained according to the current Good Manufacturing Practice (GMP) and Good Clinical Practice (GCP) guidelines and available for review in the study medication documentation. Compound 9 will be provided to the Phase 1 unit as powder in the bottle and excipient (s) in the bottle and compounded in the pharmacy at a volume of 125 mL of either a 1 mg/mL or 6 mg/mL stock solution and then further diluted to approximately 40 mL at the identified doses. Study drug labels with all required information and conforming to all applicable CFR and GMP/GCP guidelines will be prepared by the Phase I unit.

The study medication must be carefully stored at the temperature specified in the pharmacy manual (e.g., clinical dosing solutions stored at approximately 2-8° C. or room temperature for up to 24 hours after preparation), safely and separately from other drugs.

Treatment Protocol

This study comprises a double blind, placebo-controlled multiple ascending dose (MAD) study followed by an open-label drug-drug interaction study (DDI) without placebo in healthy, adult volunteers. Four cohorts of 12 subjects each will be recruited for a total of 48 subjects. Subjects in Cohorts 1, 2, and 3 will participate in the multiple-ascending-dose (MAD) part of the study, and subjects in Cohort 4 will participate in the drug-drug-interaction (DDI) part of the study.

The objective of the MAD part of the study is to determine the safety, tolerability, pharmacokinetics (PK), and pharmacodynamic (PD) profile of seven days of dosing with Compound 9 Oral Solution (henceforth referred to as Compound 9).

Safety will be assessed utilizing physical examination, vital sign measurements, safety laboratory testing, 12-lead ECGs, sedation scores (the Stanford Sleepiness Scale (SSS) and Modified Observer's Assessment of Alertness/Sedation Scale (MOAA/S), and the Columbia-Suicide Severity Rating Scale (C-SSRS). Tolerability will be assessed by spontaneously reported adverse events.

The pharmacodynamic (PD) effects of multiple days of dosing with Compound 9 will be assessed in Cohorts 1-3. Pharmacodynamic effects on the central nervous system (CNS) will be assessed using psychomotor testing (Cogstate Early Phase Battery or similar consisting of Detection Task, Identification Task, One Card Learning Task, and Groton Maze Learning Test), mood, anxiety and depression (the Bond-Lader VAS for self-reported mood assessment and the Hospital Depression and Anxiety Scale [HADS]), a drug likeability questionnaire (Drug Effects Questionnaire [DEQ-5[), and electroencephalography (EEG) with eye tracking. Sleep quality will be assessed via a subject-rated questionnaire in Cohort 3 Part 2 (nighttime dosing).

The planned total daily dose for each MAD cohort is based on information obtained during the ongoing single, ascending dose (SAD) study (Example 2). Information such as the half-life of a single dose of Compound 9 will be reviewed to determine whether to dose once-daily (QD) or twice-daily (BID) dosing. The planned total daily dose for each cohort in Example 3 based on the SAD study is provided below:

Cohort 1: Dose from the Phase I SAD study that achieved an AUC of approximately 400 ng*h/mL Cohort 2: Approximately 2 to 4 times the dose tested in Cohort 1

Cohort 3: Approximately the MTD from the SAD study

If dosing QD during the MAD part of the study, the total daily dose of Compound 9 or placebo for each cohort will be administered in the morning for 7 days.

If dosing is twice daily (BID), the total daily dose will be equally divided and 50% administered in the morning and 50% in the evening for six days; 50% of the total daily dose will be administered in the morning only on Day 7 to allow for a full PK profile. Morning dosing will be between the hours of approximately 08:00 h and 09:00 h and evening dosing will be between the hours of approximately 19:00 h and 20:00 h. Compound 9 will be administered in the morning to fasted subjects after a minimum of an 8 hour fast with a standard diet beginning approximately 4 hours after dosing.

Fasting is not required prior to any evening dosing. Note that the time of dosing in each cohort may be staggered/adjusted depending on timing of other assessments, e.g., EEG. The doses for each regimen will be selected based on information from the single ascending dose (SAD) Phase 1 study using the following criteria:

Cohort 1: the Compound 9 total daily dose will approximate the SAD dose that resulted in a median AUC of approximately 400 ng*h/mL;

Cohort 2: the Compound 9 total daily dose will approximate a two-to-four-fold increase from the Cohort 1 MAD dose based on clinical observations from Cohort 1;

Cohort 3: the Compound 9 total daily dose will approximate the SAD study MTD. If once daily dosing is employed, Part 1 of Cohort 3 will be administered the total daily dose of Compound 9/placebo between approximately 08:00 h and 09.00 h each morning and Part 2 of Cohort 3 will be administered the total daily dose of Compound 9/placebo between approximately 19:00 h and 20:00 h. If twice daily dosing is employed, Cohort 3 may have only one part.

If Cohort 3 Part 2 is not utilized for evening dosing, the SRC may use the second part of Cohort 3 for exploratory doses or dosing regimens as long as the total daily dose does not exceed the total daily dose used in the MAD part of the study.

Of the 12 subjects in the MAD cohorts, nine will be randomized to Compound 9 and three will be randomized to placebo. If dosing is QD for this study, subjects participating in Cohort 3 will be dosed in the morning for seven days (Part 1), then after a suitable washout period of at least seven days return for a second period of seven days' dosing in the evening (Cohort 3 Part 2). If Cohort 3 Part 2 subjects return for evening dosing, they will receive the same study drug (active or placebo) for the evening dosing as they did for the morning dosing. If BID dosing is employed, Cohort 3 will not return for a second period of dosing, unless the Safety Review Committee decides to utilize Cohort 3 Part 2 to explore a lower dose than that administered in the first part of Cohort 3, or to evaluate a different dosing regimen. The total daily dose will not exceed those evaluated during the earlier parts of the MAD part of the study. Concentrations of Compound 9 in plasma and urine will be assessed after multiple days of oral dosing. Pharmacokinetics will be assessed based on parameters derived from frequent sampling for bioanalysis of Compound 9 concentrations. Metabolite concentrations of Compound 9 in plasma and in urine will also be investigated.

CYP Drug-Drug Interaction Dosing Regimen

The DDI part of the study (Cohort 4) will investigate whether multiple dosing with Compound 9 induces the metabolism of either the CYP3A4 or CYP2B6 enzyme. All 12 subjects in the DDI part of the study will receive Compound 9 in an open-label fashion with the total daily dose of Compound 9 approximating the maximum well-tolerated single dose administered in the MAD part of the study.

As with the MAD part of the study, it may be required to administer Compound 9 using a BID regimen. The DDI cohort dosing schedule is provided below. Compound 9 dosing is with subjects in fasted state unless it is decided to administer Compound 9 BID in which case only the morning dose would be administered with subjects in a fasted state; subjects may have a standard breakfast prior to dosing with bupropion or simvastatin. The dosing regimen for the DDI part of the study is presented below:

Day 1: Bupropion 100 mg (Wellbutrin IR® or generic equivalent)

Day 2: Simvastatin 20 mg (Zocor® or generic equivalent)

Days 3-9: Compound 9 at approximately the MAD MTD

Day 10: Simvastatin 20 mg (Zocor® or generic equivalent)

Day 11: Bupropion 100 mg (Wellbutrin IR® or generic equivalent)

Plasma samples will be obtained to fully characterize the concentrations of simvastatin, bupropion, and Compound 9 and comparisons made for simvastatin and bupropion concentrations before and after Compound 9 administration.

Dose Escalation and Stopping Rules

The SRC may stop dose escalation and may permit ongoing dosing at the same or lower total daily doses if any of the following occur:

Serious Adverse Event: If any subject in a cohort has a serious adverse event (SAE) that the SRC determines is related to Compound 9, the SRC may stop the MAD phase of the study or may permit ongoing dosing at lower doses of Compound 9 than that at which the event occurred, depending on the nature of the event.

Severe Adverse Event: If three or more active treatment subjects in a cohort have a severe adverse event that the safety committee determines is related to Compound 9, the safety committee may stop the MAD phase of the study or may permit ongoing dosing at the same or lower doses of Compound 9, depending on the nature of the event and the dose(s) at which the events occurred.

MOAA/S Score: If at least one Compound 9-exposed subject within a cohort has a MOAA/S score of two or less ($\leq 2$) at any time point during normal waking hours ($\geq 08:00$ h to $\leq 22:00$ h) and this score is confirmed i.e., repeat assessment is the same or lower, or if two or more ($\geq 2$) Compound 9-exposed subjects have a confirmed MOAA/S score of three or less ($\leq 3$) at any time point during normal waking hours ($\geq 08:00$ h to $\leq 22:00$ h), dose escalation to the next planned dose will not occur.

Additional dosing may be permitted by dosing Compound 9 at a lower dose or by repeating the dose at which these events occurred depending on the extent and duration of the sedation and the dose(s) at which the sedation occurred. The Safety Review Committee will consider MOAA/S scores as qualifying for stopping criteria only when the confirmation score is equal to or lower than the first assessment and when there is congruence with the SSS score at the same time point.

If any of the following findings occur in at least two (2) subjects exposed to Compound 9 Oral Solution within a cohort and the findings are confirmed (if applicable), the SRC may not allow dose-escalation if at least two subjects report the same finding. However, if each subject reported a different finding, the SRC could allow dose escalation at lower doses than planned. In all circumstances the SRC may allow dose repetition or dose reduction:

An increase from pre-dose in supine systolic blood pressure of 60 mmHg sustained for at least five minutes, or a decrease from pre-dose in supine systolic blood pressure of 30 mmHg sustained for at least five minutes, or supine systolic blood pressure of ≤70 mmHg or ≥200 mmHg sustained for at least five minutes;

An increase from pre-dose in supine diastolic blood pressure of 40 mmHg sustained for at least five minutes, or a decrease from pre-dose in supine diastolic blood pressure of 30 mmHg sustained for at least five minutes, or supine diastolic blood pressure of ≤40 mmHg or ≥110 mmHg sustained for at least five minutes;

An increase from pre-dose in supine heart rate of 50 bpm sustained for at least five minutes, or a decrease from pre-dose in supine heart rate of 30 bpm sustained for at least five minutes, or supine heart rate of ≤45 bpm or ≥170 bpm sustained for at least five minutes;

QTc prolongation defined as QTcF increasing >60 msec and persisting for at least 10 minutes or QTcF >500 msec and persisting for at least 30 minutes;

A sustained increase in alanine aminotransferase (ALT) or aspartate aminotransferase (AST) to >3×upper limit of normal (ULN), which must be confirmed elevated >3×ULN within 48 hours (Guideline of Liver Safety Assessment Best Practices Workshop 2014 [Avigan et al., 2014]);

Total bilirubin increase to >2×ULN confirmed on repeat testing in fed condition within 48 hours;

ALT or AST >2×ULN concurrent with total bilirubin >1.5×ULN confirmed on repeat testing within 48 hours;

Serum creatinine >1.5×ULN confirmed on repeat testing within 48 hours;

Leukocyte count <2.5×109/L confirmed on repeat testing within 48 hours;

Neutrophil count <1.0×109/L confirmed on repeat testing within 48 hours;

Platelet count <100×109/L confirmed on repeat testing within 48 hours.

AUC and Cmax: based on the plasma concentration information from previous cohorts, the SRC will consider adjusting the dose (dose reduction, dose repetition, or reduced dose escalation) for the next cohort if the Cmax of ≥50% of the next cohort is expected to exceed 400 ng/mL (the estimated human Cmax based on the lowest NOAEL Day 14 Cmax in female rats). In addition, the SRC will not allow escalation to doses beyond those predicted to result in a median AUC above the lowest NOAEL exposure in toxicology studies (male rat 14-day toxicology, AUC 5,050 ng.h/mL).

Statistical Considerations

The Safety Population is defined as all subjects who are administered study drug.

The Pharmacokinetic (PK) Population is defined as all subjects who are administered Compound 9 and have at least one bioanalysis result for the plasma concentration of Compound 9.

No formal sample size calculations have been undertaken for this safety and tolerability study. The number of subjects in each cohort and at each dose level is thought to be sufficient to assess preliminary safety and tolerability following multiple doses of Compound 9. No efficacy parameters are being collected or analyzed for this Phase I study.

For all safety analyses of the MAD portion of the study, the placebo dose group will be pooled across cohorts. AEs will be coded using MedDRA™ with the version used specified in the clinical study report. The overall incidence of AEs will be displayed by System Organ Class (SOC), preferred term, dose group, and cohort. Incidence of AEs will also be presented by maximum severity and relationship to study drug. Data from vital signs, clinical laboratory measures, ECG, and C-SSRS will be summarized using descriptive statistics by dose group and cohort, where applicable. Continuous endpoints will be summarized with n, mean, standard deviation, median, minimum and maximum. In addition, change from baseline values will be calculated at each time point and will be summarized using the same summary statistics. Out-of-range safety endpoints may be categorized as low or high, where applicable. For all categorical endpoints, summaries will include counts and percentages.

PK parameters will be summarized using appropriate descriptive statistics. Time to reach maximum concentration (Tmax) will be summarized using n, mean, standard deviation, median, minimum, and maximum. All other PK parameters will be summarized using n, geometric mean, coefficient of variation, median, minimum, and maximum.

Dose proportionality will be analyzed using an ANCOVA model using the logarithm of PK parameter (AUC and Cmax) as the dependent variable and the logarithm of the dose as the independent variable. Point estimates and the corresponding CIs will be estimated for both AUC and Cmax.

To evaluate the effect of administration of Compound 9 on the plasma PK profile of the test drug simvastatin and the test drug bupropion, PK parameters for AUC and Cmax for simvastatin and bupropion will be natural log-transformed and evaluated using a linear mixed effects model with fixed effects terms for treatment. An unstructured covariance matrix will be used to allow for unequal treatment variances and to model the correlation between the treatment measurements within each subject via the REPEATED statement in SAS PEOC MIXED. Kenward and Roger's method will be used to calculate the denominator degrees of freedom for the fixed effects (DDFM=KR).

A ninety percent (90%) confidence interval (CI) will be constructed for the difference in least squares means on the log scale for each of AUC and Cmax.

Exponentiating the log-scale 90% CI will provide a 90% CI for the geometric mean ratios (simvastatin+Compound 9/simvastatin alone or bupropion+Compound 9/bupropion alone).

The secondary endpoints of SSS, MOAA/S, BL-VAS, HADS and DEQ-5 values will be summarized using the same descriptive statistics described above for the safety variables. The pharmacodynamics analysis of EEG endpoints and their relationship to psychomotor testing and eye tracking measures will be described in a separate analysis plan. In addition, PK/PD exploratory analyses will be performed utilizing sedation, mood, anxiety, depression, EEG and psychomotor data.

Further details of the above analyses will be provided in the statistical analysis plan.

Placebo will be matched to study drug for each multiple ascending dose (MAD) cohort. The drug-drug interaction (DDI) part of the study will be conducted in an open-label manner with Compound 9, bupropion and simvastatin.

Procedures/Measurements

Cohorts 1 and 2 of the MAD part of the study will consist of up to 14 visits over a period of up to 28 days prior to dosing, approximately 11 days confined to unit (admission, 7 days of dosing with Compound 9 and up to 3 days of follow up) and approximately 14 days after the last dose of Compound 9.

Cohort 3 (Parts 1 and 2 assuming QD dosing) will consist of up to 25 visits over a period of up to 28 days prior to dosing, approximately 22 days confined to unit (two 11-day periods of [admission 7 days of dosing with Compound 9 and up to 3 days of follow up with each Compound 9 dosing period] separated by approximately 7 days) and approximately 14 days after the last dose of Compound 9. If MAD dosing is determined to be BID, Cohort 3 will either not take place or will have a dosing regimen determined by the SRC with total daily dose not exceeding the maximum total daily dose tested during the previous cohorts.

The DDI cohort will consist of up to 16 visits over a period of up to 28 days prior to CYP-induction drug dosing, approximately 13 days confined to the unit (admission, 2 days of CYP-induction drug dosing, 7 days of dosing with Compound 9, a 3-day in-house follow up after last dose of Compound 9 (which includes 2 days of CYP-induction drug dosing) and 14 days after the last dose of Compound 9. During each phase of the study, subjects will be admitted to the unit approximately 24 hours prior to the first dose of study drug (either Compound 9 [Cohorts 1, 2 and 3] or CYP-induction drug [Cohort 4]). During the MAD and DDI parts of the study, subjects will be confined to the unit for approximately 72 hours after the last dose of Compound 9 (or placebo in the MAD part of the study); subjects may be released sooner if it is predicted that plasma concentrations of Compound 9 will be below the level of quantification earlier than 72 hours after dosing. No subject may be discharged from the unit until the Investigator is satisfied that it is safe for the subject to be discharged from the unit.

Physical examinations, vital signs, laboratory assessments and observations by experienced Phase I personnel will be undertaken throughout the study based on the Schedules of Events. The Stanford Sleepiness Scale (SSS) and Modified Observer's Assessment of Alertness/Sedation Scale (MOAA/S) will be used to assess sedation effects. The Bond-Lader VAS and the Hospital Anxiety and Depression Scale (HADS) will assess different aspects of self-reported mood, anxiety and depression; the Drug Effects Questionnaire (DEQ-5) will assess whether the subject "liked" the drug and/or felt "high". Psychomotor testing will be undertaken in the MAD cohorts to assess cognitive function in a variety of domains such as attention, working memory, episodic secondary memory, executive function, and motor skills. Sleep will be assessed in Cohort 3 Part 2 if dosing is QD.

An EEG with at least 24 channels set for continuous recording will be applied approximately 1 hour prior to dosing and kept in place for approximately 9 hours after Compound 9/placebo dosing for Cohorts 1, 2 and 3 Part 1 on Days 1 and 7.

EEG relaxation epochs and eye tracking will be completed at approximately 30 minutes pre-dose and at approximately 2 and 8 hours post-dose.

See the Schedule of Events tables for each cohort for the full list of study assessments and timings.

Subjects

Approximately 48 healthy subjects will be recruited into the study.

Inclusion Criteria

1. Signed informed consent before any study-specific procedures are performed;
2. Healthy ambulatory male and female subjects ≥18 to ≤55 years of age at the Screening visit, with no history or evidence of clinically relevant medical disorders as determined by the Investigator in consultation with the Sponsor.
3. Bodyweight ≥50 kg and body mass index (BMI) ≥18.0 and ≤32.0 kg/m2 at the screening visit.
4. Physical and neurological examination, clinical laboratory values, vital signs (normal ranges per the Investigator), and electrocardiograms (ECGs) are clinically acceptable to the Investigator.
5. Male subjects must agree to practice an acceptable method of highly effective birth control from the Screening visit, while on study and for 13 weeks after receiving the last dose of study drug. Highly effective methods of birth control include sexual abstinence; vasectomy; or a condom with spermicide (men) in combination with a highly effective female partner's method, e.g. hormonal birth control, or intrauterine device. Female subjects must be non-childbearing capacity, e.g. postmenopausal (at least 12 months since last menstruation) or surgically sterile (tubal ligation, bilateral oophorectomy, hysterectomy).
6. Males must be willing to abstain from sperm donation from the Screening visit, while on study and through 13 weeks after receiving the last dose of study drug.

Key Exclusion Criteria

1. Clinically significant abnormal values for hematology, clinical chemistry or urinalysis at the screening and admission visits. Abnormalities considered to be non-clinically significant by the Investigator are acceptable.
2. Subject with history of suicidal behavior within two years or who has answered YES to questions 3, 4 or 5 on the C-SSRS at the screening or admission visits, or is currently at risk of suicide in the opinion of the Investigator.
3. Clinically significant abnormal physical examination OR 12-lead electrocardiogram (ECG) at the screening or admission visits. NOTE: QTcF interval of ≥450 msec in males or ≥470 msec in females, will be the basis for exclusion from the study. ECG may be repeated for confirmatory purposes if initial values obtained exceed the limits specified.
4. Significant history and/or presence of hepatic, renal, cardiovascular, pulmonary, gastrointestinal, hematological, immunologic, ophthalmologic, metabolic or oncological disease.
5. History or presence of psychiatric or neurologic disease or condition (including but not limited to epilepsy, closed head trauma with clinically significant sequelae, partial onset seizures, eating disorders, etc.).
6. Recent history (within previous six months prior to screening) of alcohol or drug abuse (as judged by the Investigator), or has consumed >2 alcohol drinks/day during the last three months prior to screening (one glass is approximately equivalent to: beer [284 mL], wine [125 mL/4 ounces], or distilled spirits [25 mL/1 ounce]). Subjects that consume three glasses of alcoholic beverages per day but less than 14 glasses per week may be enrolled at the discretion of the Investigator. Positive screens for alcohol or controlled substances at the screening or admission visits will disqualify a subject from study participation.
7. Any subject who currently uses or has regularly used tobacco or tobacco containing products (cigarettes, pipes, etc.) for at least 30 days prior to screening OR positive urine cotinine screen (>400 ng/mL) at the screening or admission visits.
8. Any subject with a history, presence and/or current evidence of serologic positive results for hepatitis B surface antigen, hepatitis C antibodies, or HIV antibodies 1 or 2.

9. Donation of blood or acute loss of blood within 60 days prior to the Screening visit.
10. Any subject who has received treatment with an investigational drug during the 30 days, or 5 half-lives, whichever is longer, prior to the Screening visit. Exposure to an investigational medical device within 30 days of the Screening visit.
11. Use of any prescription or over-the-counter medication, herbal medication, vitamins, or mineral supplements within 14 days prior to first administration of the study drug.
12. Use of agents known to affect drug metabolism: use of any known CYP3A4 or CYP2B6 inhibitors and/or inducers within 14 days prior to first administration of study drug, or 5 half-lives (whichever is longer) or consumed grapefruit juice, grapefruit, Seville oranges or St John's Wort or products containing these within 30 days prior to first administration of study drug.
13. Any subject who consumes excessive amounts of caffeine, defined as greater than 6 servings (1 serving is approximately equivalent to 120 mg of caffeine) of coffee, tea, cola, or other caffeinated beverages per day within 30 days prior to the Screening visit.
14. Any subject with previous exposure to Compound 9 or who is known to be allergic to Compound 9 or any of its excipients, including its major excipient HPBCD, or for Cohort 4 has known allergy to bupropion or simvastatin. Previous exposure to simvastatin and/or bupropion is allowed.
15. Investigative site personnel or their immediate families (spouse, parent, child or sibling whether biological or legally adopted).
16. Any subject unwilling or unable to comply with study procedures.

Pharmacokinetic Assessments

Pharmacokinetic blood samples will be taken and processed for analysis for concentrations of Compound 9 at the time points described. Selected samples may also be analyzed for concentrations of Compound 9 metabolites; urine samples will also be tested for concentrations of Compound 9. Samples from subjects participating in Cohort 4 will also be tested for concentrations of simvastatin, simvastatin acid, bupropion and hydroxyl-bupropion.

Blood Sample Collection

Plasma samples for PK analysis will be collected according to the sampling collection times specified for the MAD and the DDI cohorts. The time of study drug administration is time zero and all post-dosing sampling times are relative to this time. The Investigator or designee will arrange to have the plasma samples processed, stored and transported as directed for bioanalysis.

Selected samples may also be analyzed for concentrations of metabolites of Compound 9.

An additional PK sample may be collected at any time if clinically indicated and at the discretion of the Investigator (e.g. for unusual or severe AEs).

Each sample will be marked with unique identifiers such as the study number, subject number, and the nominal sample time. The date and actual time that the blood sample was taken Urine Sample Collection During the MAD phase only (Cohorts 1 and 2; Cohort 3 Part 1) on Days 1 and 7 all voided urine will be collected and pooled over the following time periods: pre-dose; 0-4 hours; 4-8 hours; and 8-12 hours. A sample will be obtained from each pooled sample and processed for analysis of Compound 9 concentrations. Urine samples may also be analyzed for Compound 9 metabolite concentrations. The pre-dose urine sample is to be collected within approximately 60 minutes prior to dosing. The post-dose collection periods are relative to dosing.

Storage and Shipment of Pharmacokinetic and Urine Samples

The plasma and urine samples should be kept frozen at approximately −70° C. to −80° C. until analyzed. They should be packed as directed to avoid breakage during transit and with sufficient dry ice to prevent thawing for at least 72 hours. A specimen-identification form must be completed and sent to the laboratory with each set of samples. The clinical site will arrange to have the plasma and urine samples transported as directed for bioanalysis as detailed in the PK instructions.

Sample Analysis

Bioanalysis of plasma samples for the determination of Compound 9 will be performed utilizing a validated LC-MS/MS method at Agilux Laboratories, Worcester, Mass.; bioanalysis of plasma samples for the determination of simvastatin, simvastatin acid, bupropion, and hydroxylbupropion levels will be conducted at a qualified laboratory. The methodology for urine bioanalysis is in development and will be conducted at a later time using the stored samples.

Genomics Samples

Plasma samples will be taken from consenting participants in all cohorts on Day −1 (Admission) (timing on Day 1 is flexible and will be determined by PAREXEL) and retained for possible future genomics studies. The genomics samples will be stored at PAREXEL until the Sponsor identifies a suitable laboratory. Note that providing this sample is optional for subjects under a separate consent form.

Safety Parameters

The safety and tolerability of multiple doses of Compound 9 will be assessed via adverse event reporting, vital sign measurement, laboratory data, ECG parameters, sedation scores and assessment of suicidal ideation using the Columbia-Suicide Severity Rating Scale (C-SSRS).

During each phase of the study, subjects will be admitted to the unit approximately 24 hours prior to the expected time of dosing with Compound 9/placebo or CYP-interaction drug. Subjects will be confined to the unit for approximately 72 hours after completion of the Compound 9 7-day dosing period for all cohorts; subjects may be released sooner if it is predicted that plasma concentrations of drug will be below the level of quantification earlier than 72 hours after Compound 9 dosing. No subjects may be discharged from the unit until the Investigator is satisfied that it is safe for the subject to be discharged from the unit.

Physical examinations, vital signs, laboratory assessments and observations by experienced Phase I personnel will be undertaken throughout the study based on the following sections and Schedules of Events. All study assessments may be performed by suitably trained personnel, but the results must be reviewed and signed off by medical personnel.

PK samples and safety and pharmacodynamic assessments are currently planned to coincide with Tmax, but sample timing may be adjusted depending on the PK data observed earlier in the clinical development program.

Compound 9 daytime dosing days are Days 1-7 for Cohorts 1, 2 and 3 and Days 3-9 for Cohort 4.
Compound 9 evening dosing days are Days 1-7 for Cohort 3 Part 2 (if applicable).
Compound 9 non-dosing days include: Day −1 (Admission) for all cohorts; Days 8, 9 and 10 for Cohorts 1, 2 and 3; and Days 1, 2, 10, 11 for Cohort 4.

Compound 9 "frequent sampling days" are Days 1 and 7 in Cohorts 1, 2 and 3 and Days 3 and 9 for Cohort 4.

12-Lead Electrocardiogram (ECG)

The 12-lead ECG assessments will be performed after the subject has been supine for at least approximately 5 minutes and the standard intervals recorded as well as any abnormalities. All time points are relative to the time of dosing. If the ECG planned time point is between the hours of approximately ≥22:00 h and ≤08:00 h each day or if the subject has been discharged before the last time point, the assessment need not be conducted at that time point. Timing for this assessment may be adjusted depending on Tmax timing observed in the Example 2 SAD study. Timing is presented below.

On daytime PK frequent sampling days (relative days 1 and 7): if once daily dosing obtain predose and 2, 4, 8 and 12 hours post dose, or if twice daily dosing obtain pre-dose and 2, 4, 8, 12 hours post the morning dose, and 2 hours after the evening dose.

On daytime Compound 9/placebo dosing days (relative days 2-6): if once daily dosing obtain predose and 2 and 4 hours post-dose, or if twice daily dosing obtain pre-dose and 2 and 4 hours post the morning dose, and 2 hours post the evening dose.

On evening dosing days (Cohort 3 Part 2 Days 1-7): pre-dose and 12 hours post-dose.

Continuous ECG (cECG)

While confined to the unit, subjects will have continuous ECG monitoring (telemetry) for Days 1 and 7 of Compound 9/placebo dosing with cECG records printed out every four hours. Any clinically significant abnormalities will be recorded as adverse events, with the corresponding cECG record kept in the source documents for the study.

Columbia—Suicide Severity Rating Scale (C-SSRS)

This scale will be assessed during the MAD cohorts only. The "Baseline/Screening" C-SSRS form will be completed during Screening. The "Since Last Visit" C-SSRS form will be completed on Compound 9/placebo dosing day Day 7. See Appendix 4.

Stanford Sleepiness Scale (SSS)

This scale measures level of alertness/sedation, see Appendix 5. All time points are relative to the time of dosing. If the planned time point is between the hours of approximately 22:00 h and 08:00 h each day or if the subject has been discharged before the last scheduled time point, the assessment need not be conducted at that time point.

On the first and last Compound 9/placebo daytime dosing days in each cohort (e.g., Cohort 1 Days 1 and 7, and Cohort 4 Days 3 and 9): if once daily dosing obtain pre-dose and 1, 2, 4, 6, 8, 12, and 24 hours after dosing, or if twice daily dosing obtain pre-dose and 1, 2, 4, 6, 8, 12 hours after the morning dose, and 1, 2 and 3 hours after the evening dose.

On all other daytime Compound 9 dosing days: if once daily dosing obtain pre-dose and 1, 4, 8, 12 and 24 hours after dosing, or if twice daily dosing obtain pre-dose and 1, 4, 8, 12 hours after the morning dose and 2 and 12 hours after the evening dose.

On Compound 9/placebo evening dosing days (Cohort 3 Part 2, if applicable): pre-dose and 1, 2, 3, 12, 14, 16 and 20 hours after dosing.

Modified Observer's Assessment of Alertness/Sedation Scale (MOAA/S)

The MOAA/S allows exploration of deeper sedation states than the SSS. All time points are relative to the time of dosing. If the planned time point is between the hours of 22:00 h and 08:00 h each day or if the subject has been discharged before the +72 hour time point, the assessment need not be conducted at that time point. If a subject is difficult to awaken, an additional MOAA/S assessment may be performed at the discretion of the PI. Any MOAA score of 3 or less must be repeated. The MOAA/S assessment should be conducted after other assessments that are scheduled at the same time point. All time points relate to the administration of study drug.

On the first and last daytime Compound 9/placebo dosing day in each cohort: if once daily dosing obtain pre-dose and 1, 2, 4, 6, 8 and 12 hours after dosing, or if twice daily dosing obtain pre-dose and 1, 2, 4, 6, 8 and 12 hours after the morning dose, and 2 hours after the evening dose.

On all other daytime Compound 9/placebo dosing days: if once daily dosing obtain pre-dose and 1, 4, 8, 12 hours after dosing, or if twice daily dosing obtain pre-dose and 1, 4, 8, 12 hours after the morning dose, and 2 hours after the evening dose.

On evening Compound 9/placebo dosing days (Cohort 3, second dosing period): pre-dose and 1, 2, 3, 12, 14, 16, and 20 hours after dosing.

Bond-Lader VAS (Mood Rating Scale)

Mood will be assessed using the Bond-Lader Mood Rating Scale (Appendix 7). This is a 16-part self-administered questionnaire that employs 100 mm visual analogue scales to explore different aspects of self-reported mood. The mood scale will be administered at the following time points:

On the first and last daytime Compound 9/placebo dosing (relative Days 1 and 7): if once daily dosing obtain pre-dose, and at approximately 2, 4 and 12 hours post-dose; or if twice daily dosing obtain pre-dose, and at approximately 2, 4, 8 and 12 hours post the morning dose, and 2 hours post the evening dose (post-dose assessment timing may be adjusted depending on Example 2 SAD Tmax).

On Compound 9 evening dosing Days 1 and 7: pre-dose and approximately 12 hours post-dose.

Hospital Anxiety and Depression Scale

Anxiety will be assessed using the Hospital Anxiety and Depression Scale (HADS) (Zigmond and Snaith, 1983) at the following time points:

On the first and last daytime Compound 9/placebo dosing (relative Days 1 and 7): if once daily dosing obtain pre-dose, and at approximately 2, 4 and 12 hours post-dose; or if twice daily dosing obtain pre-dose, and at approximately 2, 4, 8 and 12 hours post the morning dose and 2 hours post the evening dose (post-dose assessment timing may be adjusted depending on Example 2 SAD Tmax).

On Compound 9/placebo evening dosing Days 1 and 7: pre-dose and approximately 12 hours postdose.

Blood Sample Collection for Pharmacokinetic Assessments

Plasma samples for analysis of Compound 9 concentrations will be collected at the time points relative to dosing as shown.

The time of study drug administration is time zero and all post-dosing sampling times are relative to dosing time. The investigator will arrange to have the plasma samples processed and transported as directed for bioanalysis as directed by the Sponsor. Selected samples may be analyzed for concentrations of metabolites of Compound 9. An additional sample for analysis of Compound 9 concentrations may be collected at any time if clinically indicated and at the discretion of the investigator (e.g. for unusual or severe AEs). Samples for CYP induction drugs will be processed and transported as directed by the Sponsor. Timing for sample draw times may be adjusted for each cohort based on earlier PK results.

Each sample will be marked with unique identifiers as determined by the CRO and agreed by the Sponsor.

Blood samples for plasma concentrations of Compound 9 should be taken just prior to any scheduled relaxation epoch when the sample time coincides with an EEG time point.

Urine Sample Collection for Pharmacokinetic Assessments

During the MAD daytime dosing cohorts (1, 2 and 3 [Part 1]), all voided urine will be collected and pooled over the following time periods on Day 1 and Day 7: pre-dose; 0-4 hours; 4-8 hours; and 8-12 hours. A sample will be obtained from each pooled sample and processed for analysis of Compound 9 concentrations. Urine samples may also be analyzed for Compound 9 metabolite concentrations. The pre-dose urine sample is to be collected just prior to dosing. The post-dose collection periods are relative to dosing.

Drug Effects Questionnaire (DEQ-5)

A Drug Effects Questionnaire (DEQ-5) (see Appendix 8) will be administered as follows:
1. Do you FEEL a drug effect right now?
2. Are you HIGH right now?
3. Do you DISLIKE any of the effects that you are feeling right now?
4. Do you LIKE any of the effects that you are feeling right now?
5. Would you like MORE of the drug you took, right now?
   The answers are recorded on a 100 mm visual analogue scale with the answer for each being "Not at all" and "Extremely" at the extremes. There will be options to record "Not applicable" for questions 3 and 4 if no drug effects are felt and for question 5 prior to administration of study medication.

The DEQ5 will be administered at the following time points during the MAD part of the study:

On the first and last Compound 9/placebo daytime dosing (relative Days 1 and 7): if once daily dosing obtain pre-dose and 2, 4, 8 and 12 hours post-dose, or if twice daily dosing obtain predose and 2, 4, 8 and 12 hours post the morning dose, and 2 hours post the evening dose.

On Compound 9/placebo evening dosing days 1 and 7: pre-dose and 12 hours post-dose.

Psychomotor Testing

Psychomotor testing will be undertaken to assess cognitive function in a variety of domains such as attention, working memory, episodic secondary memory, executive function, and motor skills. Examples of psychomotor testing include the Detection Task, Identification Task, One Card Learning Task, and Groton Maze Learning Test. The actual tests performed may vary depending on the vendor chosen. Psychomotor testing will be conducted during the MAD cohorts only.

On Compound 9 daytime dosing days (Day 1 and Day 7): pre-dose and 3 hours post-dose (post the morning dose if twice daily dosing). Psychomotor testing will not be performed for Cohort 3 Part 2.

EEG with Eye Tracking

Measures of brain electrical activity will indicate any direct impact on the nervous system and are used as a critical adjunct to behavioral assessment. Findings can be used to investigate subclinical behavioral effects of Compound 9 and can be easily quantified and compared to changes in pharmacokinetic measures. The samples will be cleaned for EMG, eye motion, head movement or other non-cerebral artifacts; cleaned data will then be submitted to power spectral analysis to quantitatively assess impact on the brain over time. Previous studies with the benzodiazepine midazolam have shown significant dose-dependent slowing of peak velocity, peak acceleration, peak deceleration, reduced saccade acceleration/deceleration ratio and saccade accuracy, as well as increased sedation self-rating. The current study will use measures of saccadic velocity to assess sedative effects of Compound 9. An EEG with at least 24 channels set for continuous recording will be applied approximately 1 hour prior to dosing and kept in place for approximately 9 hours after dosing for subjects participating in MAD cohorts 1, 2 and 3 (Part 1 only) on Days 1 and 7. EEG relaxation epochs and eye tracking will completed at approximately 30 minutes pre-dose and at approximately 2 and 8 hours post-dose. The post-dose assessment timing may be adjusted depending on earlier PK results from the SAD study Example 2 or previous MAD cohorts. During the relaxation epochs subjects are asked to close their eyes, relax and empty their minds of thoughts. Eye tracking will be assessed at the same time as the EEG is being recorded.

Sleep Questionnaire

A 6-item subject-rated sleep quality questionnaire created for internal use will be administered to subjects in Cohort 3 Part 2 (nighttime dosing) upon awakening in the morning the mornings of Days 16 to 22.

Window Allowance Document

A "Window Allowance Document" document will be prepared which will outline acceptable windows for intervals between nominal times and actual times for study procedures, e.g. ±5 minutes for PK sampling times. This will allow flexibility when multiple procedures are scheduled for the same time point, e.g., PK sampling and vital signs both taken at "1 h after dosing".

Adverse Event (AE)

An AE is the development of an undesirable medical condition or the deterioration of a pre-existing medical condition following or during exposure to a pharmaceutical product, whether or not considered casually related to the product. In clinical studies, an AE can include an undesirable medical condition occurring at any time, including baseline or washout periods, even if no study treatment has been administered.

All AEs that occur after any subject/subject has been enrolled, before treatment, during treatment, or within 14 days following the cessation of treatment, whether or not they are related to the study, must be recorded on forms provided by designee.

Serious Adverse Event (SAE)

A serious adverse event is an AE occurring during any study phase (i.e., baseline, treatment, washout, or follow-up), and at any dose of the investigational product, comparator or placebo, that fulfils one or more of the following:

Results in death

It is immediately life-threatening

It requires in-subject hospitalization or prolongation of existing hospitalization It results in persistent or significant disability or incapacity Results in a congenital abnormality or birth defect It is an important medical event that may jeopardize the subject or may require medical intervention to prevent one of the outcomes listed above.

All SAEs that occur after any subject/subject has been enrolled, before treatment, during treatment, or within 28 days following the cessation of treatment, whether or not they are related to the study, must be recorded on forms provided by designee.

Recording Sedation as an Adverse Event

Sedation will be assessed using specific rating scales in this study. In order to apply consistency to adverse event reports of sedation and taking into consideration the frequent assessment of sedation using the scoring scales, Investigators need not record sedation as an adverse event unless there is a score of ≥5 on the SSS and/or a score of <2 on the MOAA/S. Consideration should be given to the most appropriate term to describe the sedation characteristics.

Relationship to Study Drug

An Investigator who is qualified in medicine must make the determination of relationship to the investigational product for each AE (Unrelated, Possibly Related or Probably Related). The Investigator should decide whether, in his or her medical judgment, there is a reasonable possibility that the event may have been caused by the investigational product. If no valid reason exists for suggesting a relationship, then the AE should be classified as "unrelated." If there is any valid reason, even if undetermined, for suspecting a possible cause-and-effect relationship between the investigational product and the occurrence of the AE, then the AE should be considered "related."

Not Related: No relationship between the experience and the administration of study drug; related to other etiologies such as concomitant medications or subject's clinical state.

Possibly Related: A reaction that follows a plausible temporal sequence from administration of the study drug and follows a known response pattern to the suspected study drug.

The reaction might have been produced by the subject's clinical state or other modes of therapy administered to the subject, but this is not known for sure.

Probably Related: A reaction that follows a plausible temporal sequence from administration of the study drug and follows a known response pattern to the suspected study drug.

The reaction cannot be reasonably explained by the known characteristics of the subject's clinical state or other modes of therapy administered to the subject.

If the relationship between the AE/SAE and the investigational product is determined to be "possible" or "probable" the event will be considered to be related to the investigational product for the purposes of expedited regulatory reporting.

Recording Adverse Events

Adverse events spontaneously reported by the subject/ subject and/or in response to an open question from the study personnel or revealed by observation will be recorded during the study at the investigational site. Clinically significant changes in laboratory values, blood pressure, and pulse need not be reported as AEs unless they prompt corrective medical action by the Investigator, constitute an SAE or lead to discontinuation of administration of study drug.

Information about AEs will be collected from the signing of the consent form until the final visit of the study for that subject. Adverse events that occur after the first administration of study drug will be denoted Treatment Emergent Adverse Events.

All AEs will be followed until they are resolved or have reached a clinical plateau with no expectation of future change.

The AE term should be reported in standard medical terminology when possible. For each AE, the Investigator will evaluate and report the onset (date and time), resolution or clinical plateau (date and time), intensity, causality, action taken, outcome, and whether or not it caused the subject to discontinue the study.

Intensity will be assessed according to the following scale:

Mild (awareness of sign or symptom, but easily tolerated)

Moderate (discomfort sufficient to cause interference with normal activities)

Severe (incapacitating, with inability to perform normal activities)

Reporting Serious Adverse Events

All SAEs (regardless of causality) will be recorded from the signing of the consent form until 28 days following the last dose of study drug. Any SAEs considered possibly or probably related to the investigational product and discovered by the Investigator at any time after the study should be reported. All SAEs must be reported to the Sponsor or Sponsor's designee immediately by phone and in writing within 24 hours of the first awareness of the event.

Safety Analysis

For all safety analyses of the MAD portion of the study, the placebo dose group will be pooled across cohorts. AEs will be coded using MedDRA™ with the version used specified in the clinical study report. The overall incidence of AEs will be displayed by System Organ Class (SOC), preferred term, and dose group. Incidence of AEs will also be presented by maximum severity and relationship to study drug. Data from vital signs, clinical laboratory measures, ECG, and C-SSRS will be summarized using descriptive statistics by dose group and time point, where applicable.

Continuous endpoints will be summarized with n, mean, standard deviation, median, minimum and maximum. In addition, change from baseline values will be calculated at each time point and will be summarized using descriptive statistics. Out-of-range safety endpoints may be categorized as low or high, where applicable. For all categorical endpoints, summaries will include counts and percentages.

Pharmacokinetic Analysis

Derived PK parameters will include area under the plasma concentration curve (AUC0-inf), the distribution half-life and terminal half-life (t1/2), the maximum concentration (Cmax), the time to reach maximum concentration (Tmax), and the clearance (CL) and urine excretion. PK parameters will be summarized using appropriate descriptive statistics. Time to reach maximum concentration (Tmax) will be summarized using n, median, minimum, and maximum. All other PK parameters will be summarized using n, geometric mean, coefficient of variation, median, minimum, and maximum.

Dose proportionality of Compound 9 will be analyzed using a linear regression model with the logarithm of PK parameter (AUC and Cmax) as the dependent variable and the logarithm of the dose as the independent variable. Point estimates of the slope coefficient and the corresponding CIs will be provided for both AUC and Cmax.

Exemplary Pharmacokinetic Sampling Schedule

TABLE 10

MAD Cohorts PK Sampling Schedule (times in hours relative to dosing)

Formula I MAD Cohorts 1, 2, and 3 (Part 1)

| | Formula I Daytime Dosing (Days 1 and 7) | | | | | | | | | | | | Formula I Follow up (Day 8) | | | |
|---|---|---|---|---|---|---|---|---|---|---|---|---|---|---|---|---|
| Pre-Dose | 0.25 | 0.5 | 1 | 1.5 | 2 | 3 | 4 | 6 | 8 | 10 | 12 | 16* | 24* | 28 | 32 | 36 48 |

Formula I MAD Evening Dosing (Cohort 3 Part 2) (If applicable)

| | Formula I Evening Dosing (Days 1 and 7) | | | | | | | | Formula I Follow up (Day 8) | |
|---|---|---|---|---|---|---|---|---|---|---|
| Pre-Dose | 0.25 | 0.5 | 1 | 1.5 | 2 | 3 | 12 | 16 | 24 | 36 48 |

*If dosing BID, obtain on Day 7 only.

TABLE 11

DDI Cohort PK Sampling Schedule (times in hours relative to dosing)

Days 1 and 2 CYP Induction Drugs Prior to Formula I Dosing:

Simvastatin (Day 1) and Bupropion (Day 2)

| Pre-Dose | 1 | 2 | 3 | 4 | 5 | 6 | 8 | 10 | 12 | 16 | 24 |
|---|---|---|---|---|---|---|---|---|---|---|---|

Days 3-9 Formula I Dosing:

| | Formula I Daytime Dosing (Days 3 and 9) | | | | | | | | | | | | Formula I Follow-Up (Day 10) | | |
|---|---|---|---|---|---|---|---|---|---|---|---|---|---|---|---|
| Pre-Dose | 0.25 | 0.5 | 1 | 1.5 | 2 | 3 | 4 | 6 | 8 | 10 | 12 | 16 | 24 | 28 | 32 36 48 |

Days 10 and 11 CYP Induction Drugs Following Formula I Dosing:

Bupropion (Day 10) and Simvastatin (Day 11)

| Pre-Dose | 1 | 2 | 3 | 4 | 5 | 6 | 8 | 10 | 12 | 16 | 24 |
|---|---|---|---|---|---|---|---|---|---|---|---|

Drug-Drug Interaction (DDI) Analysis

To evaluate the effect of administration of Compound 9 on the plasma PK profile of the test drug simvastatin and the test drug bupropion, PK parameters for AUC and Cmax for simvastatin and bupropion will be natural log-transformed and evaluated using a linear mixed effects model with fixed effects terms for treatment. An unstructured covariance matrix will be used to allow for unequal treatment variances and to model the correlation between the treatment measurements within each subject via the REPEATED statement in SAS PEOC MIXED. Kenward and Roger's method will be used to calculate the denominator degrees of freedom for the fixed effects (DDFM=KR).

A ninety percent (90%) confidence interval (CI) will be constructed for the difference in least squares means on the log scale for each of AUC and Cmax. Exponentiating the log-scale 90% CI will provide a 90% CI for the geometric mean ratios (simvastatin+Compound 9/simvastatin alone or bupropion+Compound 9/bupropion alone).

Further details of the above DDI analysis will be provided in the statistical analysis plan.

Other Endpoint Analyses

The secondary endpoints of SSS, MOAA/S, BL-VAS, HADS, and DEQ-5 values and the exploratory sleep quality data will be summarized using the same descriptive statistics described above for the safety variables. The pharmacodynamics analysis of EEG endpoints and their relationship to psychomotor testing and eye tracking measures will be described in a separate analysis plan. In addition, PK/PD exploratory analyses will be performed utilizing sedation, mood, anxiety, depression, EEG and psychomotor data. Sleep quality will be assessed by a self administered sleep questionnaire PK/PD analysis will consist of descriptive figures plotting PK concentrations versus numeric ratings or scores associated with SSS, MOAA/S, BL-VAS, HADS and DEQ-5 outcomes.

TABLE 12

Cohorts 1, 2 and 3 Part 1 Schedule of Events

| | Cohorts 1 and 2 Visit | | | | | | | |
|---|---|---|---|---|---|---|---|---|
| | V1 | V2 | V3 | V4 | V5 | V6 | V7 | V8 |
| | | | | | Visit Window | | | |
| | V2 − 1-28 d | V3 − 1 d | 0 h-+24 h | +24 h-+48 h | +48 h-+72 h | +72 h-+96 h | +96 h-+120 h | +120 h-+144 h |
| | | | | | Visit Days | | | |
| | Screen | Admit | D 1 | D 2 | D 3 | D 4 | D 5 | D 6 |
| Informed Consent | X | | | | | | | |
| Inclusion/Exclusion | X | X | | | | | | |
| Demographics | X | | | | | | | |
| Medical History | X | | | | | | | |
| Physical Examination | X | | | | | | | |
| Body Weight/Height | X | | | | | | | |
| CBC/Serum Chemistry | X | X | | | X | | | |
| Urinalysis | X | X | | | X | | | |
| Drug/Alcohol Screen | X | X | | | | | | |
| Hepatitis & HIV Screen | X | | | | | | | |
| Genetic Sample | | X | | | | | | |
| Vital Signs[1] | X | X | X | X | X | X | X | X |
| 12-Lend ECG[2] | X | X | X | X | X | X | X | X |
| cECG[3] | | X | | | | | | |
| C-SSRS[4] | X | | | | | | | |
| SSS[5] | | | X | X | X | X | X | X |
| MOAA/S[5] | | | X | X | X | X | X | X |
| DEQ5[6] | | | X | | | | | |
| Bond-Lader Mood Score[7] | | | X | | | | | |
| HADS[8] | | | X | | | | | |
| Psychomotor Testing[9] | | | X | | | | | |
| EEG & Eye Tracking[10] | | | X | | | | | |
| Plasma PK Samples[11] | | | X | | | | | |
| Urine PK Samples[12] | | | X | | | | | |
| Confined to Unit | | X | X | X | X | X | X | X |
| Administer Formulation 1[13] | | | X | X | X | X | X | X |
| Adverse Events | | X | X | X | X | X | X | X |

| | Cohorts 1 and 2 Visit | | | | | |
|---|---|---|---|---|---|---|
| | V9 | V10 | V11 | V12 | V13 | V14 |
| | | | Visit Window | | | |
| | +144 h-+168 h | +168 h-+196 h | +196 h-+220 h | +220 h-+244 h | V9 + 7 d (±1 d) | V9 + 14 d (±1 d) |
| | | | Visit Days | | | |
| | D 7 | D 8 | D 9 | D 10 | Follow Up | Study End |
| Informed Consent | | | | | | |
| Inclusion/Exclusion | | | | | | |
| Demographics | | | | | | |
| Medical History | | | | | | |
| Physical Examination | | | | | X | |
| Body Weight/Height | | | | | | |
| CBC/Serum Chemistry | X Wt only | | | | X | |
| Urinalysis | X | | | | X | |
| Drug/Alcohol Screen | | | | | | |
| Hepatitis & HIV Screen | | | | | | |
| Genetic Sample | | | | | | |
| Vital Signs[1] | X | X | X | X | X | |
| 12-Lend ECG[2] | X | X | X | X | X | |
| cECG[3] | | | | | | |
| C-SSRS[4] | | | | | | |
| SSS[5] | X | | | | | |
| MOAA/S[5] | X | | | | | |
| DEQ5[6] | X | | | | | |
| Bond-Lader Mood Score[7] | X | | | | | |
| HADS[8] | X | | | | | |
| Psychomotor Testing[9] | X | | | | | |
| EEG & Eye Tracking[10] | X | | | | | |
| Plasma PK Samples[11] | X | X | | | | |
| Urine PK Samples[12] | X | | | | | |

TABLE 12-continued

Cohorts 1, 2 and 3 Part 1 Schedule of Events

| | | | | | | | | | | | | | | |
|---|---|---|---|---|---|---|---|---|---|---|---|---|---|---|
| Confined to Unit | | X | | X | | X | | X | | | | | | |
| Administer Formulation 1[13] | | X | | | | | | | | | | | | |
| Adverse Events | | X | | X | | X | | X | | X | | X | | |
| Cohorts 1 and 2 Visit | V1 | V2 | V3 | V4 | V5 | V6 | V7 | V8 | V9 | V10 | V11 | V12 | V13 | V14 |
| Concomitant Meds | X | X | X | X | X | X | X | X | X | X | X | X | X | X |

If discrepancies are noted between the Schedule of Events and the text sections, the text sections take precedence.

TABLE 13

Cohort 3 Part 2 Schedule of Events
This Schedule of Events (SoE) assumes QD dosing; if dosing is BID then this SoE is not needed.

| | Cohort 3 Part 2 Visit | | | | | | |
|---|---|---|---|---|---|---|---|
| | V13 | V14 | V15 | V16 | V17 | V18 | V19 | V20 |

| | Visit Window | | | | | | | |
|---|---|---|---|---|---|---|---|---|
| | V14 − 1 d | 0 h-+24 h | +24 h-+48 | +48 h-+72 h | +72 h-+96 h | +96 h-+120 h | +120 h-+144 h | +144 h-+168 h |

| | Visit Days | | | | | | | |
|---|---|---|---|---|---|---|---|---|
| | D 14 Admit | D 15 | D 16 | D 17 | D 18 | D 19 | D 20 | D 21 |
| Informed Consent | | | | | | | | |
| Inclusion/Exclusion | | | | | | | | |
| Demographics | | | | | | | | |
| Medical History | | | | | | | | |
| Physical Examination | | | | | | | | |
| Body Weight/Height | | | | | | | | X Wt only |
| CBC/Serum Chemistry | X | | | X | | | | X |
| Urinalysis | X | | | X | | | | X |
| Drug/Alcohol Screen | X | | | | | | | |
| Vital Signs[1] | X | X | X | X | X | X | X | X |
| 12-Lend ECG[2] | X | X | X | X | X | X | X | X |
| cECG[3] | X | X | | | | | | X |
| C-SSRS[4] | | | | | | | | X |
| SSS[5] | | X | X | X | X | X | X | X |
| MOAA/S[5] | | X | X | X | X | X | X | X |
| DEQ[6] | | | | | | | | |
| Bond Lader Mood Score[6] | | X | | | | | | X |
| HADS[6] | | X | | | | | | X |
| Plasma PK Samples[7] | | X | | | | | | X |
| Sleep Quality Questionnaire[8] | | | X | X | X | X | X | X |
| Confined to Unit | X | X | X | X | X | X | X | X |
| Administer Formula 1 | | X | X | X | X | X | X | X |

| | Cohort 3 Part 2 Visit | | | | |
|---|---|---|---|---|---|
| | V21 | V22 | V23 | V24 | V25 |

| | Visit Window | | | | |
|---|---|---|---|---|---|
| | +168 h-+196 h | +196 h-+220 h | +220 h-+240 h | V20 + 7 d (±1 d) | V20 + 14 d (±1 d) |

| | Visit Days | | | | |
|---|---|---|---|---|---|
| | D 22 | D 23 | D 24 | Follow Up | Study End |
| Informed Consent | | | | | |
| Inclusion/Exclusion | | | | | |
| Demographics | | | | | |
| Medical History | | | | | |
| Physical Examination | | | | X | |
| Body Weight/Height | | | | | |
| CBC/Serum Chemistry | | | | X | |
| Urinalysis | | | | X | |
| Drug/Alcohol Screen | | | | | |
| Vital Signs[1] | X | X | X | | |
| 12-Lend ECG[2] | X | X | X | X | |
| cECG[3] | | | | | |
| C-SSRS[4] | | | | | |
| SSS[5] | | | | | |

TABLE 13-continued

Cohort 3 Part 2 Schedule of Events
This Schedule of Events (SoE) assumes QD dosing; if dosing is BID then this SoE is not needed.

| | | | | | | | | | | | | | |
|---|---|---|---|---|---|---|---|---|---|---|---|---|---|
| MOAA/S[5] | | | | | | | | | | | | | |
| DEQ[6] | | | | | | | | | | | | | |
| Bond Lader Mood Score[6] | | | | | | | | | | | | | |
| HADS[6] | | | | | | | | | | | | | |
| Plasma PK Samples[7] | | X | | X | | X | | | | | | | |
| Sleep Quality Questionnaire[8] | | X | | | | | | | | | | | |
| Confined to Unit | | X | | X | | X | | | | | | | |
| Administer Formula 1 | | | | | | | | | | | | | |

| Cohorts 3 Part 2 Visit | V13 | V14 | V15 | V16 | V17 | V18 | V19 | V20 | V21 | V22 | V23 | V24 | V25 |
|---|---|---|---|---|---|---|---|---|---|---|---|---|---|
| Adverse Events | X | X | X | X | X | X | X | X | X | X | X | X | X |
| Concomitant Meds | X | X | X | X | X | X | X | X | X | X | X | X | X |

If the protocol text and Schedule of Events differ, the protocol text takes precedence.
*Visit days may be adjusted of washout period duration of 7 days is adjusted. By the SRC.

TABLE 14

Cohort 4 Schedule of Events

| | V1 | V2 | V3 | V4 | V5 | V6 | V7 | V8 | V9 |
|---|---|---|---|---|---|---|---|---|---|
| Visit Window | V2 − 1-28 d | V3 − 1 d | 0 h-+24 h | +24 h-+48 | +48 h-+72 h | +72 h-+96 h | +96 h-+120 h | +120 h-+144 h | +144 h-+168 h |
| Visit Days | Screen | Admit | D 1 | D 2 | D 3 | D 4 | D 5 | D 6 | D 7 |
| Informed Consent | X | | | | | | | | |
| Inclusion/Exclusion | X | | | | | | | | |
| Demographics | X | | | | | | | | |
| Medical History | X | | | | | | | | |
| Physical Examination | X | | | | | | | | |
| Body Weight/Height | X | | | | | | | | |
| CBC/Serum Chemistry | X | X | | | | | X | | |
| Urinalysis | X | X | | | | | X | | |
| Drug/Alcohol Screen | X | X | | | | | | | |
| Hepatitis & HIV Screen | X | | | | | | | | |
| Genetic Sample | | X | | | | | | | |
| Vital Signs[1] | X | X | X | X | X | X | X | X | X |
| 12-Lend ECG[2] | X | X | X | X | X | X | X | X | X |
| cECG[3] | | | | | X | | | | |
| SSS[4] | | | | | X | X | X | X | X |
| MOAA/S[5] | | | | | X | X | X | X | X |
| Plasma PK Samples[6] | | | X | X | X | | | | |
| Confined to Unit | | X | X | X | X | X | X | X | X |
| Administer Formula 1 | | | | | X | X | X | X | X |
| Induction Test Drug | | | X | X | | | | | |
| Adverse Events | | X | X | X | X | X | X | X | X |
| Concomitant Meds | X | X | X | X | X | X | X | X | X |

| | V10 | V11 | V12 | V13 | V14 | V15 | V16 |
|---|---|---|---|---|---|---|---|
| Visit Window | +168 h-+196 h | +196 h-+220 h | +220 h-+244 h | +244 h-+268 h | +268 h-+282 h | V11 + 7 d | V11 + 14 d |
| Visit Days | D 8 | D 9 | D 10 | D 11 | D 12 | Follow Up | Study End |
| Informed Consent | | | | | | | |
| Inclusion/Exclusion | | | | | | | |
| Demographics | | | | | | | |
| Medical History | | | | | | | |

TABLE 14-continued

Cohort 4 Schedule of Events

| | | | | | | | |
|---|---|---|---|---|---|---|---|
| Physical Examination | | | | | | X | |
| Body Weight/Height | | | | | | | |
| CBC/Serum Chemistry | | X | | | | X | |
| | | Wt only | | | | | |
| Urinalysis | | X | | | | X | |
| Drug/Alcohol Screen | | | | | | | |
| Hepatatis & HIV Screen | | | | | | | |
| Genetic Sample | | | | | | | |
| Vital Signs[1] | X | X | X | X | X | X | |
| 12-Lend ECG[2] | X | X | X | X | X | X | |
| cECG[3] | | X | | | | | |
| SSS[4] | X | X | X | X | | | |
| MOAA/S[5] | X | X | X | X | | | |
| Plasma PK Samples[6] | | X | X | | | | |
| Confined to Unit | X | X | X | X | X | | |
| Administer Formula 1 | X | X | | | | | |
| Induction Test Drug | | | X | X | | | |
| Adverse Events | X | X | X | X | X | X | X |
| Concomitant Meds | X | X | X | X | X | X | X |

If the protocol text and Schedule of Events differ, the protocol takes precedence.

Example 4. A Double-Blind, Randomized, Placebo-Controlled, Phase 2 Registration Study of Brexanolone in 21 Hospital Inpatient Women with Severe PPD Materials and Methods
Study Design and Participants This multicenter, randomized, double-blind, parallel-group, placebo-controlled trial (NCT02614547) was conducted at 11 sites in the United States with IRB approval from each study site. Sage Therapeutics, Inc. collaborated with the principal investigator (SMB) in the design of the trial and all investigators in the execution of the trial and collection of data. All authors vouch for the accuracy and completeness of the data, data analyses, and the fidelity of this report to the study protocol. Additional study conduct details are provided in the Supplementary Appendix.

Study Population

Enrollment required written informed consent. Eligible subjects were required to have had a major depressive episode that began no earlier than the third trimester and no later than the first four weeks following delivery and to be within six months postpartum at the time of enrollment. PPD diagnoses were confirmed by the Structured Clinical Interview for DSM-W Axis I Disorders (SCID-I). Enrollment required a 17-item Hamilton Rating Scale for Depression (HAM-D) total score of ≥26. Subjects remained as in-patients during the 60-hour study infusion period.

Exclusion criteria included: active psychosis; attempted suicide associated with index case of PPD; history of seizures, bipolar disorder, schizophrenia and/or schizoaffective disorder, and/or alcoholism or drug addiction (including benzodiazepines) in the 12 months prior to screening. Additional inclusion/exclusion details are available in the Supplementary Appendix.

Randomization and Masking

Each subject was provided the next randomization number in sequence by a blinded study monitor. Subjects were then randomized, according to a computer-generated randomization schedule, 1:1 to brexanolone or placebo. The randomization schedule was produced by an independent statistician at Applied Statistics and Consulting (Spruce Pine, N.C.). Subjects, clinicians, and study teams were blinded to treatment allocation. Subjects in the placebo group received equivalent infusion rates, and both treatments were identical in appearance. The pharmacist at each site, who prepared the infusion bags according to the randomization schedule, and an unblinded monitor, who performed drug accountability during the study, were unblinded. No other study personnel were unblinded until after formal locking of the study database. Only the clinic pharmacist was given a copy of the randomization schedule. In the event of a medical emergency, the pharmacist was to reveal actual infusion contents to the primary investigator, who was to alert the Sponsor of the emergency. In all cases, if the study drug allocation for a subject had been unblinded, pertinent information (including the reason for unblinding) was to be documented in the subject's records and on the eCRF. If the subject or study center personnel were unblinded, the subject was to be terminated from the study. No such unblinding occurred during the study.

Procedures

Brexanolone is a sterile solution of 5 mg/mL allopregnanolone in 250 mg/mL sulfobutylether-β-cyclodextrin (SBECD) buffered with citrate, which is diluted with sterile water for injection to render it isotonic for IV infusion. Each subject received a single continuous W infusion of blinded study drug for 60 hours during inpatient care under the following schedule: 30 μg/kg/hour (0-4 hours); 60 μg/kg/hour (4-24 hours); 90 μg/kg/hour (24-52 hours); 60 μg/kg/hour (52-56 hours); 30 μg/kg/hour (56-60 hours). Infusion rate adjustments were allowed based on tolerability, side effects, and pre-determined protocol rules. Dosing was based on both a prior open-label exploratory trial in PPD (Kanes et al., 2016; *Human Psychopharmacology*, in press) and on pharmacokinetic (PK) modelling. After dosing was complete, subjects were followed through Day 30, with clinical and safety assessments obtained at 7 and 30 days.

Outcomes

The primary outcome measure was the change from baseline in the HAM-D total score (brexanolone vs. placebo) at the end of the treatment period (60 hours). Secondary analyses included changes in the HAM-D from baseline at 2 hours through 30 days. Secondary HAM-D endpoints included remission rates (total score ≤7), response rates (≥50% reduction in total score), change from baseline in the Bech-6 subscore, which assesses the core symptoms of major depression, and changes in the HAM-D Depressed Mood Item Score. Additional, pre-specified secondary and exploratory endpoints are detailed in Table 17, including the Montgomery Asberg Depression Rating Scale (MADRS) Total Score, Clinical Global Impression-Global Improvement (CGI-I), Generalized Anxiety Disorder Questionnaire (GAD-7), Edinburgh Postnatal Depression Scale (EPDS), Patient Health Questionnaire-9 (PHQ-9), and Barkin Index of Maternal Function (BIMF).

The safety and tolerability of brexanolone were evaluated by collecting and summarizing adverse events (AEs), clinical laboratory measures, vital signs, and ECGs (including changes from baseline); concomitant medication usage was also assessed. Emergent suicidal ideation and behaviors were assessed using the Columbia-Suicide Severity Rating scale (C-SSRS); subject-reported sedation/sleepiness was assessed using the Stanford Sleepiness Scale (SSS). Plasma was collected to assay for allopregnanolone, allopregnanolone metabolites, and SBECD.

Statistical Analysis

The Safety Population included all randomized subjects who started infusion of study drug or placebo. The Efficacy (EFF) Population included the subset of the Safety Population who had a completed baseline HAM-D assessment and at least one post-baseline HAM-D assessment. The change from baseline in HAM-D and MADRS total score was analyzed using a mixed effects model for repeated measures (MMRM). The model included center, treatment, baseline HAM-D total score, assessment time point, and time point-by-treatment as explanatory variables. Center was treated as a random effect, while all other explanatory variables were treated as fixed effects. Model based point estimates (i.e., LS means, 95% confidence intervals, and p-values) were reported for each time point. The primary comparison was between brexanolone and placebo at the 60-hour time point. Other changes from baseline endpoints were analyzed using similar methods. The HAM-D response and remission rates at each time point were analyzed using Fisher's Exact Test. Model-based point estimates (i.e., odds ratios), 95% confidence intervals, and p-values were reported.

Assuming a two-sided test at an alpha level of 0.10, a sample size of 10 evaluable subjects per group provided 80% power to detect an effect size of 1.2 between the brexanolone and placebo groups with regard to the primary outcome variable of change from baseline in HAM-D total score. An effect size of 1.2 corresponds to a placebo-adjusted difference of 12 points in the change from baseline in HAM-D total score at 60 hours with an assumed standard deviation of ten points. By including two treatment groups and using a 1:1 randomization ratio, a total of 20 evaluable subjects were required. Based on the results of the interim analysis, the sample size could have been increased to a maximum of 32 randomized subjects. This adjustment to the sample size would have allowed for an effect size of 1.0 to be detected.

Results

Figure 10:
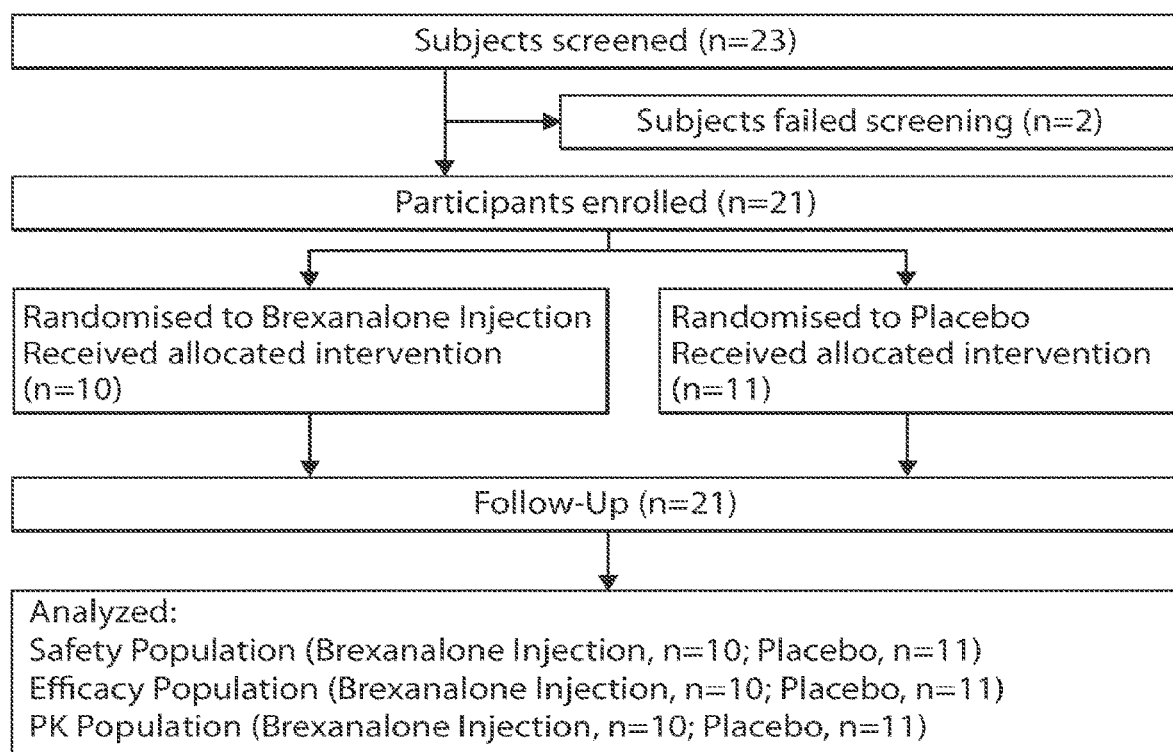
FIG. 10 shows an outline of an exemplary double-blind, randomized, placebo-controlled, Phase 2 registration study of brexanolone in 21 hospital inpatient women with severe PPD.

Twenty-three subjects with severe PPD (HAM-D≥26) enrolled in this study, which was conducted from Dec. 15, 2015 to May 19, 2016. Twenty-one were subsequently randomized (10 brexanolone, 11 placebo), and all completed the 60-hour in-patient dosing protocol and full trial (FIG. 10, Table 15). The mean age (SD) was 28.8 (4.58) for placebo and 27.4 (5.34) for brexanolone groups. The percentage of subjects with a prior history of psychiatric conditions was comparable between treatment groups, with the exception of anxiety (20.0% brexanolone, 45.5% placebo). The percentage of subjects with at least one previous episode of PPD was 36.3% in the placebo group treatment group and 70.0% in the brexanolone group. Antidepressant medication use was balanced between the brexanolone and placebo treatment groups (30.0% and 27.3%, respectively). Demographic characteristics are summarized in Table 15.

Figure 11A:
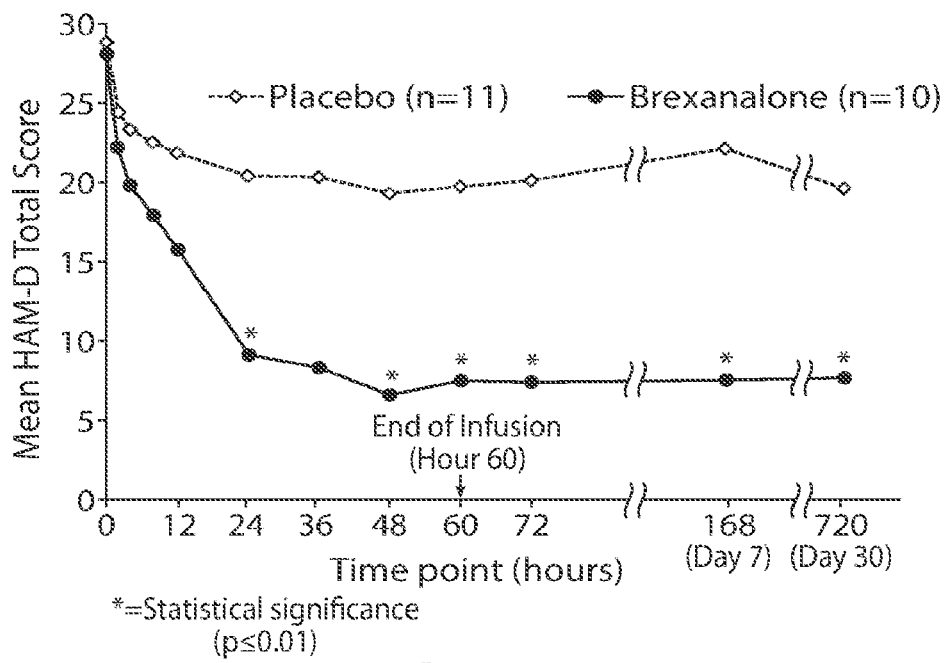
FIG. 11A shows effects of brexanolone or placebo on mean HAM-D total score over time in 21 hospital inpatient women with severe PPD participating in an exemplary double-blind, randomized, placebo-controlled, Phase 2 registration study of brexanolone.
Figure 11B:
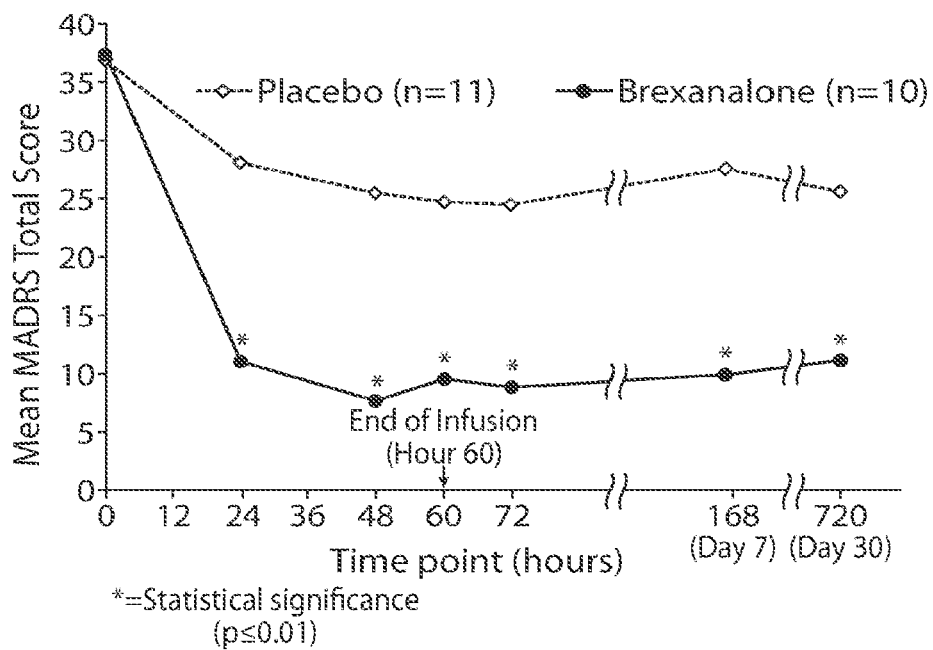
FIG. 11B shows effects of brexanolone or placebo on mean MADRS total score over time in 21 hospital inpatient women with severe PPD participating in an exemplary double-blind, randomized, placebo-controlled, Phase 2 registration study of brexanolone.

The primary endpoint was achieved; at the end of the 60-hour infusion, brexanolone-treated subjects demonstrated a mean reduction in HAM-D total score of 20.97 points, a 12.2 [95% CI, −3.67 to −20.77] point difference from placebo (p=0.008). Pre-specified secondary analyses demonstrated an 11.9 [−3.65 to −18.86] point mean difference at 24 hours (p=0.006), with statistically significant improvements also observed for the brexanolone group at 36, 48, and 72 hours, as well as Days 7 and 30 (FIG. 11). The effect size for the clinical efficacy of brexanolone at 60 hours was 1.2, and the effect was statistically significant by 24 hours. Assessment using the MADRS total score and change from baseline showed similar results to those obtained using HAM-D (FIGS. 11A, 11B and Table 16).

Figure 12:
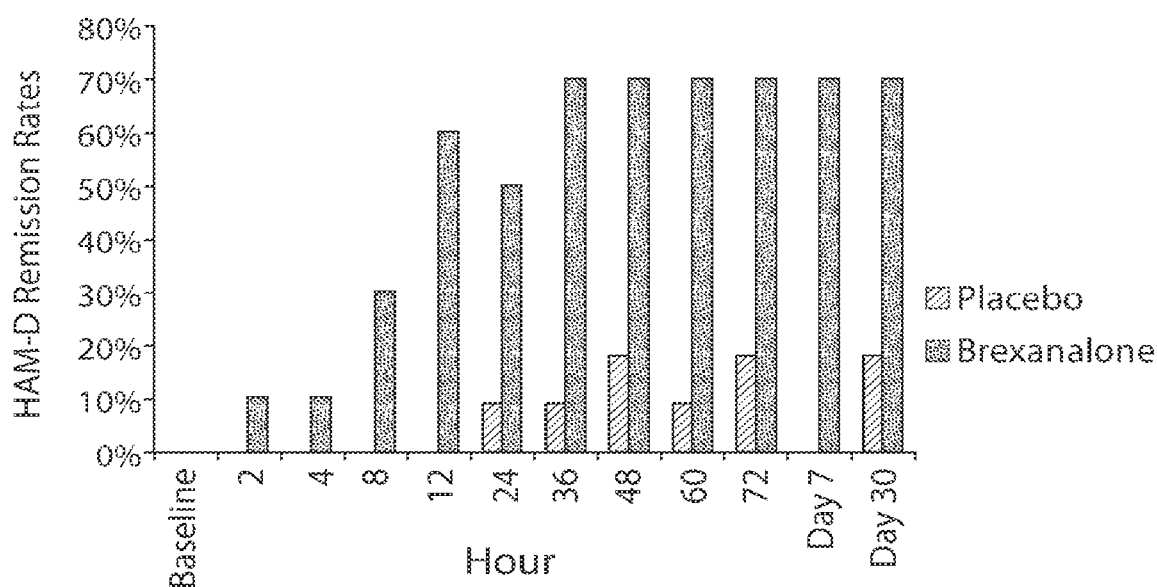
FIG. 12 shows exemplary HAM-D Remission Rates Over Time in 21 hospital inpatient women with severe PPD participating in an exemplary double-blind, randomized, placebo-controlled, Phase 2 registration study of brexanolone.

Remission from depression (HAM-D≤7) was observed in 7 of 10 brexanolone-treated subjects and 1 of 11 placebo-treated subjects at 60 hours (OR-23.33; CI-1.56, 1152.71, p=0.008; FIG. 12). This difference was observed at 24 hours (1 placebo vs. 6 brexanolone; OR 15, 95% CI 1.07 to 756.72, p=0.024) and a difference was maintained through the 30-day follow-up (2 placebo vs. 7 brexanolone; OR 10., 95% CI 1.01 to 140.57, p=0.030). Additional secondary measures and categorical response measures were supportive of the primary endpoint of the trial, showing improvements in favor of brexanolone relative to placebo (Table 17).

Brexanolone was generally well tolerated. There were no deaths, serious adverse events (SAEs), or discontinuations. Overall, fewer subjects who received brexanolone experienced AEs compared with placebo (4 of 10 subjects on brexanolone and 8 of 11 subjects on placebo; Table 18). The most commonly reported AEs in the brexanolone group were dizziness (2 brexanolone-treated subjects; 3 placebo-treated subjects) and somnolence (2 brexanolone-treated subjects; 0 placebo-treated subjects). Sedation was reported in one brexanolone-treated subject and in no placebo-treated subjects.

At baseline, mean SSS scores were similar in the brexanolone and placebo groups (2.7 vs. 2.6) as measured by SSS. There were no differences in sleepiness between treatment groups. One subject who was taking a standing clonazepam dose (6 mg) experienced sleepiness on brexanolone, requiring dose reduction of the study drug and, after dose reduction, completed participation in the study (Table 19).

Improvements in C-SSRS suicidal ideation items were noted in both treatment groups; of note, two subjects in the brexanolone group reported active suicidal ideation with a specific plan and intent at baseline but not at the post-treatment assessment. No individuals experienced worsening of suicidal ideation or behavior during the treatment or follow-up period (Table 20).

This trial demonstrates that a study of postpartum, lactating, depressed women with PPD is feasible and that complex trial designs are not necessarily required to overcome presumed placebo responses, especially with the large effect size we observed with brexanolone. Furthermore, trials in such a clearly defined and previously understudied patient population are crucial to develop novel treatments for PPD. Due to the large effect size and rapid response, the study was adequately powered, with remission durable in the treatment group to at least 30 days post treatment.

TABLE 15

Demographics and Characteristics. Demographic parameters included date of birth, age, race, and ethnicity. Age was derived from the birth date and screening date. Body weight and height were measured at screening. Body mass index was programmatically calculated in the eCRF. Medical histories were coded according to the Medical Dictionary for Regulatory Activities (MedDRA) version 17 or higher.
Table 15: Demographics and Characteristics

| Characteristics | | Placebo | Brexanolone | Overall |
|---|---|---|---|---|
| Age | Mean | 28.8 | 27.4 | 28.1 |
| | SD | 4.6 | 5.3 | 28.1 |
| | Median | 28 | 27 | 27 |
| Sex | Male | 0 | 0 | 0 |
| | Female | 11 | 10 | 21 |
| Ethnicity | Hispanic or Latino | 0 | 0 | 0 |
| | Not Hispanic or Latino | 11 | 10 | 21 |
| Race | Black or African American | 6 | 7 | 13 |
| | White | 5 | 3 | 8 |
| Height (cm) | Mean | 161.7 | 162.4 | 162.0 |
| | SD | 6.7 | 7.1 | 6.7 |
| | Median | 162.0 | 163.5 | 162.0 |
| Weight (kg) | Mean | 77.0 | 86.7 | 81.6 |
| | SD | 22.3 | 28.8 | 25.4 |
| | Median | 73.5 | 76.5 | 73.9 |
| BMI (kg/m$^2$) | Mean | 29.3 | 32.7 | 30.9 |
| | SD | 7.8 | 9.9 | 8.8 |
| | Median | 28.2 | 30.5 | 30.1 |
| Personal history | | | | |
| Psychiatric Disorder | Depression (non-PPD) | 6 (54.5%) | 6 (60.0%) | 12 (57.1%) |
| | Anxiety | 5 (45.5%) | 2 (20.0%) | 7 (33.3%) |
| | Other | 2 (18.2%) | 1 (10.0%) | 3 (14.3%) |
| Prior PPD episodes | | 4 (36.4%) | 7 (70.0%) | 11 (52.3%) |
| Family history | | | | |
| Perinatal Psychiatric Conditions | Mother | 2 (18.2%) | 2 (20.0%) | 4 (19.0%) |
| | Sister(s) | 1 (9.1%) | 1 (10.0%) | 2 (9.5%) |

SD = standard deviation.

TABLE 16

Study Drug vs. Placebo, HAM-D and MADRS Total Score Change From Baseline. The changes from baseline for HAM-D and MADRS mean total scores are summarized. The change from baseline of the HAM-D mean total score and MADRS mean total score was analyzed using a mixed effects model for repeated measures. MADRS was not assessed at 2, 4, 8, 12, or 36 hours.
Table 16: Study Drug vs. Placebo, Differences in HAM-D and MADRS scores

| | HAM-D | (SE) | p-value | MADRS | (SE) | p-value |
|---|---|---|---|---|---|---|
| Hour 2 | −2.16 | 2.342 | 0.369 | | | |
| Hour 4 | −3.47 | 2.905 | 0.248 | | | |
| Hour 8 | −4.64 | 3.131 | 0.155 | | | |
| Hour 12 | −6.01 | 3.656 | 0.116 | | | |
| Hour 24 | −11.26 | 3.636 | 0.006 | −17.53 | 5.363 | 0.004 |
| Hour 36 | −11.97 | 4.026 | 0.008 | | | |
| Hour 48 | −12.67 | 3.959 | 0.005 | −18.4 | 5.287 | 0.003 |
| Hour 60 | −12.22 | 4.081 | 0.008 | −15.86 | 5.536 | 0.010 |
| Hour 72 | −12.68 | 4.272 | 0.008 | −16.2 | 5.525 | 0.009 |
| Day 7 | −12.91 | 3.907 | 0.004 | −15.96 | 5.448 | 0.009 |
| Day 30 | −11.93 | 4.129 | 0.010 | −15.07 | 5.213 | 0.010 |

SE = standard error.

TABLE 17

Efficacy Measures, Change from Baseline at Day 30.
Table 17: Efficacy Measures, Change from Baseline at Day 30

| Measure | Placebo | Brexanolone | p-value |
|---|---|---|---|
| HAM-D Total Score | −9.2 | −20.4 | 0.010 |
| HAM-D Bech 6 Subscale Score | −3.5 | −10.0 | 0.018 |
| HAM-D Depressed Mood Item Score | −1.2 | −2.3 | 0.080 |
| MADRS Total Score | −11.3 | −26.2 | 0.010 |
| GAD-7 Total Score | −8.1 | −8.7 | 0.470 |
| EPDS Total Score | −5.3 | −13.5 | 0.024 |
| PHQ-9 Total Score | −8.3 | −11.0 | 0.470 |
| BIMF Total Score | 12.1 | 24.4 | 0.240 |
| BIMF Mom's Competency Subscore | 4.9 | 8.0 | 0.390 |
| BIMF Mom's Needs Subscore | 5.1 | 11.9 | 0.450 |
| Categorical Response Measures, Day 30 | | | |
| CGI-I response (1 or 2) | 3 (27.3%) | 8 (80.0%) | 0.030 |
| GAD-7 minimal anxiety (0 to 4) | 1 (9.1%) | 6 (60.0%) | 0.024 |
| PHQ-9 minimal to no depression (0 to 4) | 1 (9.1%) | 6 (60.0%) | 0.024 |

HAM-D: Hamilton Rating Scale for Depression. MADRS: Montgomery-Åsberg Depression Rating Scale. CGI-I: Clinical Global Impression - Improvement. GAD-7: Generalized Anxiety Disorder 7-item Scale. EPDS: Edinburgh Postnatal Depression Scale. PHQ-9: Patient Health Questionnaire. BIMF: Barkin's Index of Maternal Functioning. All baseline calculations based on a mixed effects model for repeated measures (MMRM).

TABLE 18

Treatment Emergent Adverse Events in at Least 1 Brexanolone Subject: A TEAE was defined as an AE with onset after the start of study drug, or any worsening of a pre-existing medical condition/AE with onset after the start of study drug and until the Day 7 follow-up visit (ie, approximately 4 days after the end of the infusion). AEs were coded according to MedDRA ® version 18.0.
Table 18: Treatment Emergent Adverse Events in at Least 2 Subjects in Either Group

| Adverse Event | Placebo (N = 11), Number of Subjects Reporting | Brexanolone (N = 10), Number of Subjects Reporting |
|---|---|---|
| Any AE | 8 | 4 |
| Dizziness | 3 | 2 |
| Somnolence | 0 | 2 |
| Nausea | 3 | 1 |
| Abnormal Dreams | 2 | 0 |
| Headache | 2 | 0 |
| Infusion Site Pain | 2 | 0 |
| Insomnia | 2 | 0 |

TABLE 19

Stanford Sleepiness Scale. The Stanford Sleepiness Scale (SSS) was administered to monitor sedation. Although greater mean increases from baseline in SSS score were noted in the brexanolone group compared with the placebo group, none of the treatment group differences were clinically or statistically significant.
Table 19: Stanford Sleepiness Scale

| Time (hours) | Mean Placebo (n = 11) | Mean Brexanolone (n = 10) |
|---|---|---|
| 0 | 2.6 | 2.7 |
| 2 | 3 | 2.8 |
| 4 | 2.3 | 3 |
| 8 | 2.6 | 2.2 |
| 12 | 2.5 | 3.6 |
| 24 | 2.6 | 1.9 |
| 30 | 1.4 | 2 |

TABLE 19-continued

Stanford Sleepiness Scale. The Stanford Sleepiness Scale (SSS) was administered to monitor sedation. Although greater mean increases from baseline in SSS score were noted in the brexanolone group compared with the placebo group, none of the treatment group differences were clinically or statistically significant.
Table 19: Stanford Sleepiness Scale

| Time (hours) | Mean Placebo (n = 11) | Mean Brexanolone (n = 10) |
|---|---|---|
| 36 | 2.1 | 2 |
| 48 | 1.8 | 1.5 |
| 54 | 1.5 | 1.3 |
| 60 | 2 | 1.4 |
| 72 | 1.7 | 1.4 |

1 = Feeling active, vital, alert, or wide awake; 2 = Feeling active, vital, alert, or wide awake; 3 = Awake, but relaxed; responsive but not fully alert; 4 = Somewhat foggy, let down; 5 = Foggy; losing interest in remaining awake; slowed down; 6 = Sleepy, woozy, fighting sleep; prefer to lie down, 7 = No longer fighting sleep, sleep onset soon; having dream-like thoughts, X = Asleep.

TABLE 20

Columbia Suicide Severity Rating Scale: Suicidality was monitored during the study using the C-SSRS. This scale consists of a pre-dose evaluation that assesses the lifetime and recent experience of the subject with suicidal ideation and behavior, and a post-baseline evaluation that focuses on suicidality since the last study visit.
Table 20: Columbia Suicide Severity Rating Scale

| | | Pre-treatment | | Post-treatment | |
|---|---|---|---|---|---|
| | | Placebo (N = 11) | Brexanolone (N = 10) | Placebo (N = 11) | Brexanolone (N = 10) |
| Suicidal ideation | Wish to be dead | 2 | 3 | 2 | 2 |
| | Non-specific active sucicidal thoughts | 1 | 3 | 0 | 2 |
| | Active suicidal ideation with any methods (not plan) without intent to act | 2 | 2 | 0 | 1 |
| | Active suicidal ideation with some intent to act, without specific plan | 1 | 2 | 0 | 0 |
| | Active suicidal ideation with specific plan and intent | 0 | 2 | 0 | 0 |
| Sucicidal behavior | Actual attempt | 0 | 0 | 0 | 0 |
| | Has subject engaged in non-suicidal self-injurious behavior | 2 | 1 | 0 | 0 |

Example 5. Effects of Brexanolone or Placebo on Mean HAM-D Total Score (FIG. 11A) and Mean MADRS Total Score (FIG. 11b) Over Time in the Study Described in Example 4

For panel A: mean total score was assessed for the HAM-D at each time point and in Day 7 and Day 30 follow-ups, as indicated. The HAM-D is a 17-item diagnostic questionnaire used to measure the severity of depressive episodes in patients with mood disorders. It is comprised of individual ratings related to the following symptoms: depressed mood (sadness, hopeless, helpless, worthless), feelings of guilt, suicide, insomnia (early, middle, late), work and activities, retardation (slowness of thought and speech; impaired ability to concentrate; decreased motor activity), agitation, anxiety (psychic and somatic), somatic symptoms (gastrointestinal and general), genital symptoms, hypochondriasis, loss of weight, and insight. Higher HAMD-D scores indicate more severe depression. For panel B: mean total score was assessed for the MADRS at each time point and in Day 7 and Day 30 follow-ups, as indicated. The MADRS is a ten-item diagnostic questionnaire used to measure the severity of depressive episodes in patients with mood disorders. Higher MADRS scores indicate more severe depression, and each item yields a score of 0 to 6, producing total score ranges from 0 to 60. * denotes statistical significance versus placebo, *=p≤0.01.

Example 6. HAM-D Remission Rates Over Time in the Study Described in Example 4 (FIG. 12)

Remission was defined as having a HAM-D total score of <7. The remission rates at each time point were calculated. A larger percentage of subjects in the brexanolone group than the placebo group achieved HAM-D remission at each time point after +2 hours. The difference was statistically significant at 24 (p=0.024), 48 (p=0.030), 60 (p=0.008), and 72 hours (p=0.030), as well as Days 7 (p=0.003) and 30 (p=0.030).

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control.

In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

APPENDIX 1. THE ESSENTIAL TREMOR RATING ASSESSMENT SCALE (TETRAS)

TRG ESSENTIAL TREMOR RATING ASSESSMENT SCALE (TETRAS©) V 3.1

Activities of Daily Living Subscale

Rate tremor's impact on activities of daily living (0 - 4 scoring).

1. Speaking
0 = Normal.
1 = Slight voice tremulousness, only when "nervous".
2 = Mild voice tremor. All words easily understood.
3 = Moderate voice tremor. Some words difficult to understand.
4 = Severe voice tremor. Most words difficult to understand.

2. Feeding with a spoon
0 = Normal
1 = Slightly abnormal. Tremor is present but does not interfere with feeding with a spoon.
2 = Mildly abnormal. Spills a little.
3 = Moderately abnormal. Spills a lot or changes strategy to complete task such as using two hands or leaning over.
4 = Severely abnormal. Cannot feed with a spoon.

3. Drinking from a glass
0 = Normal.
1 = Slightly abnormal. Tremor is present but does not interfere with drinking from a glass.
2 = Mildly abnormal. Spills a little.
3 = Moderately abnormal. Spills a lot or changes strategy to complete task such as using two hands or leaning over.
4 = Severely abnormal. Cannot drink from a glass or uses straw or sippy cup.

4. Hygiene
0 = Normal.
1 = Slightly abnormal. Tremor is present but does not interfere with hygiene.
2 = Mildly abnormal. Some difficulty but can complete task.
3 = Moderately abnormal. Unable to do most fine tasks such as putting on lipstick or shaving unless changes strategy such as using two hands or using the less affected hand.
4 = Severely abnormal. Cannot complete hygiene activities independently.

5. Dressing
0 = Normal.
1 = Slightly abnormal. Tremor is present but does not interfere with dressing.
2 = Mildly abnormal. Able to do everything but has difficulty due to tremor.
3 = Moderately abnormal. Unable to do most dressing unless uses strategy such as using Velcro, buttoning shirt before putting it on or avoiding shoes with laces.
4 = Severely abnormal. Cannot dress independently.

6. Pouring
0 = Normal.
1 = Slightly abnormal. Tremor is present but does not interfere with pouring.
2 = Mildly abnormal. Must be very careful to avoid spilling but may spill occasionally.
3 = Moderately abnormal. Must use two hands or uses other strategies to avoid spilling.
4 = Severely abnormal. Cannot pour.

7. Carrying food trays, plates or similar items
0 = Normal
1 = Slightly abnormal. Tremor is present but does not interfere with carrying food trays, plates or similar items.
2 = Mildly abnormal. Must be very careful to avoid spilling items on food tray.
3 = Moderately abnormal. Uses strategies such as holding tightly against body to carry.
4 = Severely abnormal. Cannot carry food trays or similar items.

8. Using Keys
0 = Normal
1 = Slightly abnormal. Tremor is present but can insert key with one hand without difficulty.
2 = Mildly abnormal. Commonly misses target but still routinely puts key in lock with one hand.
3 = Moderately abnormal. Needs to use two hands or other strategies to put key in lock.
4 = Severely abnormal. Cannot put key in lock.

9. Writing
0 = Normal
1 = Slightly abnormal. Tremor present but does not interfere with writing.
2 = Mildly abnormal. Difficulty writing due to the tremor
3 = Moderately abnormal. Cannot write without using strategies such as holding the writing hand with the other hand, holding pen differently or using large pen.
4 = Severely abnormal. Cannot write.

10. Working. If patient is retired, ask as if they were still working. If the patient is a housewife, ask the question as it relates to housework:
0 = Normal .
1 = Slightly abnormal. Tremor is present but does not affect performance at work or at home.
2 = Mildly abnormal. Tremor interferes with work; able to do everything, but with errors. .
3 = Moderately abnormal. Unable to continue working without using strategies such as changing jobs or using special equipment.
4 = Severely abnormal. Cannot perform any job or household work.

11. Overall disability with the most affected task (Name task, e.g. using computer mouse, writing, etc)
        Task _____
0 = Normal.
1 = Slightly abnormal. Tremor present but does not affect task.
2 = Mildly abnormal. Tremor interferes with task but is still able to perform task.
3 = Moderately abnormal. Can do task but must use strategies.
4 = Severely abnormal. Cannot do the task.

12. Social Impact
0 = None
1 = Aware of tremor, but it does not affect lifestyle or professional life.
2 = Feels embarrassed by tremor in some social situations or professional meetings.
3 = Avoids participating in some social situations or professional meetings because of tremor.
4 = Avoids participating in most social situations or professional meetings because of tremor.

Performance Subscale

Instructions

Scoring is 0 – 4. For most items, the scores are defined only by whole numbers, but 0.5 increments may be used if you believe the rating is between two whole number ratings and cannot be reconciled to a whole number. Each 0.5 increment in rating is specifically defined for the assessment of upper limb postural and kinetic tremor and the dot approximation task (items 4 and 8). All items of the examination, except standing tremor, are performed with the patient seated comfortably. For each item, score the highest amplitude seen at any point during the exam. Instruct patients not to attempt to suppress the tremor, but to let it come out.

1. Head tremor: The head is rotated fully left and right and then observed for 10s in mid position. Patient then is instructed to gaze fully to the left and then to the right with the head in mid position. The nose should be used as the landmark to assess and rate the largest amplitude excursions during the examination.

0 = no tremor
    1 = slight tremor (< 0.5 cm)
    2 = mild tremor (0.5- < 2.5 cm)
    3 = moderate tremor (2.5-5 cm)
    4 = severe or disfiguring tremor (> 5 cm)

2. Face (including jaw) tremor: Smile, close eyes, open mouth, purse lips. The highest amplitude of the most involved facial anatomy is scored, regardless of whether it occurs during rest or activation. Repetitive blinking or eye fluttering should not be considered as part of facial tremor.

0 = no tremor
    1 = slight; barely perceptible tremor
    2 = mild: noticeable tremor
    3 = moderate: obvious tremor, present in most voluntary facial contractions
    4 = severe: gross disfiguring tremor 3. Voice tremor: First ask subject to produce an extended "aaah" sound and eee" sound for 5 seconds each. Then assess speech during normal conversation by asking patients "How do you spend your average day?".

0 = no tremor
    1 = slight: tremor during aaah, and eee and no tremor during speech
    2 = mild: tremor in "aaah" and "eee" and minimal tremor in speech
    3 = moderate: obvious tremor in speech that is fully intelligible
    4 = severe: some words difficult to understand 4. Upper limb tremor: Tremor is assessed during three maneuvers: forward horizontal reach posture, lateral "wing beating" posture and finger-nose-finger testing. Each upper limb is assessed and scored individually. The forward horizontal reach posture is held for 5 seconds.

The lateral wing beating posture is held for 20 seconds. The finger-nose-finger movement is executed three times. Amplitude assessment should be estimated using the maximally displaced point of the hand at the point of greatest displacement along any single plane. For example, the amplitude of a pure supination-pronation tremor, pivoting around the wrist would be assessed at either the thumb or fifth digit.

a. Forward outstretched postural tremor: Subjects should bring their arms forward, slightly lateral to midline and parallel to the ground. The wrist should also be straight and the fingers abducted so that they do not touch each other.

b. Lateral "wing beating" postural tremor: Subjects will abduct their arms parallel to the ground and flex the elbows so that the two hands do not quite touch each other and are at the level of the nose. The fingers are abducted so that they do not touch each other. The posture should be held for 20 seconds.

c. Kinetic tremor: Subjects extend only their index finger. They then touch a set object or the examiners finger located to the full extent of their reach, which is located at the same height (parallel to the ground) and slightly lateral to the midline. Subjects then touch their own nose (or chin if the tremor is severe) and repeat this back and forth three times. Only the position along the trajectory of greatest tremor amplitude is assessed. This will typically be either at the nose or at the point of full limb extension.

For all three hand tremor ratings
- 0 = no tremor
- 1 = tremor is barely visible
- 1.5 = tremor is visible, but less than 1 cm
- 2 = tremor is 1- < 3 cm amplitude
- 2.5 = tremor is 3- < 5 cm amplitude
- 3 = tremor is 5- < 10 cm amplitude
- 3.5 = tremor is 10- < 20 cm amplitude
- 4 = tremor is $\geq$ 20 cm amplitude 5. Lower limb tremor: Raise each lower limb horizontally parallel to the ground for 5 seconds each. Then perform a standard heel to shin maneuver with each leg, three times. The maximum tremor in either maneuver is scored, and only the limb with the largest tremor is scored. Tremor may exist in any part of the limb, including foot.
   - 0 = no tremor
   - 1 = slight: barely perceptible
   - 2 = mild, less than 1 cm at any point
   - 3 = moderate tremor, less than 5 cm at any point
   - 4 = severe tremor, greater than 5 cm 6. Archimedes spirals: Demonstrate how to draw Archimedes spiral that approximately fills ¼ of an unlined page of standard (letter) paper. The lines of the spiral should be approximately 1.3 cm (0.5 inch) apart. Then ask the subject to copy the spiral. Test and score each hand separately. Use a ballpoint pen. The pen should be held such that no part of the limb touches the table. Secure the paper on the table in a location that is suitable for the patient's style of drawing. Score the tremor in the spiral, not the movement of the limb.

0 = normal
   1 = slight: tremor barely visible.
   2 = mild: obvious tremor
   3 = moderate: portions of figure not recognizable.
   4 = severe: figure not recognizable 7. Handwriting: Have patient write the standard sentence "This is a sample of my best handwriting" using the dominant hand only. Patients must write cursively (i.e., no printing). They cannot hold or stabilize their hand with the other hand.. Use a ballpoint pen. Secure the paper on the table in a location that is suitable for the patient's style of writing. Score the tremor in the writing, not the movement of the limb.

0 = normal
   1 = slight: untidy due to tremor that is barely visible.
   2 = mild: legible, but with considerable tremor.
   3 = moderate: some words illegible.
   4 = severe: completely illegible 8. Dot approximation task: The examiner makes a dot or X and instructs the subject to hold the tip of the pen "as close as possible to the dot (or center of an X) without touching it, (ideally approximately 1 mm) for 10 seconds ". Each hand is score separately.

0 = no tremor
   1 = tremor is barely visible
   1.5 = tremor is visible, but less than 1 cm
   2 = tremor is 1- < 3 cm amplitude
   2.5 = tremor is 3- < 5 cm amplitude
   3 = tremor is 5- < 10 cm amplitude
   3.5 = tremor is 10- < 20 cm amplitude
   4 = tremor is $\geq$ 20 cm amplitude 9. Standing tremor: Subjects are standing, unaided if possible. The knees are 10-20 cm apart and are flexed 10-20°. The arms are down at the subject's side. Tremor is assessed at any point on the legs or trunk
   0 = no tremor
   1 = barely perceptible tremor
   2 = obvious but mild tremor, does not cause instability
   3 = moderate tremor, impairs stability of stance
   4 = severe tremor, unable to stand without assistance

APPENDIX 2.  COLUMBIA - SUICIDE SEVERITY RATING SCALE (C-SSRS)

COLUMBIA-SUICIDE SEVERITY RATING SCALE (C-SSRS)

Baseline/Screening Version

Phase 1 study

Version 1/14/09

*Posner, K.; Brent, D.; Lucas, C.; Gould, M.; Stanley, B.; Brown, G.; Fisher, P.; Zelazny, J.; Burke, A.; Oquendo, M.; Mann, J.*

*Disclaimer:*

*This scale is intended to be used by individuals who have received training in its administration. The questions contained in the Columbia-Suicide Severity Rating Scale are suggested probes. Ultimately, the determination of the presence of suicidal ideation or behavior depends on the judgment of the individual administering the scale.*

*Definitions of behavioral suicidal events in this scale are based on those used in* The Columbia Suicide History Form, *developed by John Mann, MD and Maria Oquendo, MD, Conte Center for the Neuroscience of Mental Disorders (CCNMD), New York State Psychiatric Institute, 1051 Riverside Drive, New York, NY, 10032. (Oquendo M. A., Halberstam B. & Mann J. J., Risk factors for suicidal behavior: utility and limitations of research instruments. In M.B. First [Ed.] Standardized Evaluation in Clinical Practice, pp. 103-130, 2003.)*

*For reprints of the C-SSRS contact Kelly Posner, Ph.D., New York State Psychiatric Institute, 1051 Riverside Drive, New York, New York, 10032; inquiries and training requirements contact posnerk@childpsych.columbia.edu*

© 2008 The Research Foundation for Mental Hygiene, Inc.

| *SUICIDAL IDEATION* | Lifetime: Time He/She Felt Most Suicidal | Past 6 Months |
|---|---|---|
| *Ask questions 1 and 2. If both are negative proceed to "Suicidal Behavior" section. If the answer to question 2 is "yes", ask questions 3, 4 and 5. If the answer to question 1 and/or 2 is "yes", complete "Intensity of Ideation" section below.* | | |
| 1. Wish to be Dead<br>Subject endorses thoughts about a wish to be dead or not alive anymore, or wish to fall asleep and not wake up.<br>*Have you wished you were dead or wished you could go to sleep and not wake up?*<br><br>If yes, describe: | Yes ☐ No ☐ | Yes ☐ No ☐ |
| 2. Non-Specific Active Suicidal Thoughts<br>General non-specific thoughts of wanting to end one's life/commit suicide (e.g. *"I've thought about killing myself"*) without thoughts of ways to kill oneself/associated methods, intent, or plan during the assessment period.<br>*Have you actually had any thoughts of killing yourself?*<br><br>If yes, describe: | Yes ☐ No ☐ | Yes ☐ No ☐ |
| 3. Active Suicidal Ideation with Any Methods (Not Plan) without Intent to Act<br>Subject endorses thoughts of suicide and has thought of at least one method during the assessment period. This is different than a specific plan with time, place or method details worked out (e.g., thought of method to kill self but not a specific plan). Includes person who would say, *"I thought about taking an over dose but I never made a specific plan as to when, where or how I would actually do it... and I would never go through with it."*<br>*Have you been thinking about how you might do this?*<br><br>If yes, describe: | Yes ☐ No ☐ | Yes ☐ No ☐ |
| 4. Active Suicidal Ideation with Some Intent to Act, without Specific Plan<br>Active suicidal thoughts of killing oneself and subject reports having some intent to act on such thoughts, as opposed to *"I have the thoughts but I definitely will not do anything about them."*<br>*Have you had these thoughts and had some intention of acting on them?*<br><br>If yes, describe: | Yes ☐ No ☐ | Yes ☐ No ☐ |
| 5. Active Suicidal Ideation with Specific Plan and Intent<br>Thoughts of killing oneself with details of plan fully or partially worked out and subject has some intent to carry it out.<br>*Have you started to work out or worked out the details of how to kill yourself? Do you intend to carry out this plan?*<br><br>If yes, describe: | Yes ☐ No ☐ | Yes ☐ No ☐ |
| *INTENSITY OF IDEATION* | | |
| *The following features should be rated with respect to the most severe type of ideation (i.e. 1-5 from above, with 1 being the least severe and 5 being the most severe). Ask about time he/she was feeling the most suicidal.*<br><br>Lifetime- *Most Severe Ideation:* _____ _____<br>　　　　　　　　　　　　　　*Type # (1-5)　Description of Ideation*<br><br>Past 6 Months - *Most Severe Ideation:* _____ _____<br>　　　　　　　　　　　　　　　*Type # (1-5)　Description of Ideation* | Most Severe | Most Severe |
| Frequency<br>*How many times have you had these thoughts?*<br>(1) Less than once a week　(2) Once a week　(3) 2-5 times in week　(4) Daily or almost daily　(5) Many times each day | ____ | ____ |
| Duration<br>*When you have the thoughts how long do they last?*<br>(1) Fleeting - few seconds or minutes　　(4) 4-8 hours/most of day<br>(2) Less than 1 hour/some of the time　　(5) More than 8 hours/persistent or continuous<br>(3) 1-4 hours/a lot of time | ____ | ____ |
| Controllability<br>*Could/can you stop thinking about killing yourself or wanting to die if you want to?*<br>(1) Easily able to control thoughts　　(4) Can control thoughts with a lot of difficulty<br>(2) Can control thoughts with little difficulty　　(5) Unable to control thoughts<br>(3) Can control thoughts with some difficulty　　(0) Does not attempt to control thoughts | ____ | ____ |
| Deterrents<br>*Are there things - anyone or anything (e.g., family, religion, pain of death) - that stopped you from wanting to die or acting on thoughts of committing suicide?*<br>(1) Deterrents definitely stopped you from attempting suicide　　(4) Deterrents most likely did not stop you<br>(2) Deterrents probably stopped you　　(5) Deterrents definitely did not stop you<br>(3) Uncertain that deterrents stopped you　　(0) Does not apply | ____ | ____ |
| Reasons for Ideation<br>*What sort of reasons did you have for thinking about wanting to die or killing yourself? Was it to end the pain or stop the way you were feeling (in other words you couldn't go on living with this pain or how you were feeling) or was it to get attention, revenge or a reaction from others? Or both?*<br>(1) Completely to get attention, revenge or a reaction from others　　(4) Mostly to end or stop the pain (you couldn't go on living with the pain or how you were feeling)<br>(2) Mostly to get attention, revenge or a reaction from others<br>(3) Equally to get attention, revenge or a reaction from others and to end/stop the pain　　(5) Completely to end or stop the pain (you couldn't go on living with the pain or how you were feeling)<br>　　(0) Does not apply | ____ | ____ |

Version 1/14/09

| | Lifetime |
|---|---|
| *SUICIDAL BEHAVIOR*<br>*(Check all that apply, so long as these are separate events; must ask about all types)* | |
| Actual Attempt:<br>A potentially self-injurious act committed with at least some wish to die, *as a result of act*. Behavior was in part thought of as method to kill oneself. Intent does not have to be 100%. If there is *any* intent/desire to die associated with the act, then it can be considered an actual suicide attempt. *There does not have to be any injury or harm,* just the potential for injury or harm. If person pulls trigger while gun is in mouth but gun is broken so no injury results, this is considered an attempt.<br>Inferring Intent: Even if an individual denies intent/wish to die, it may be inferred clinically from the behavior or circumstances. For example, a highly lethal act that is clearly not an accident so no other intent but suicide can be inferred (e.g., gunshot to head, jumping from window of a high floor/story). Also, if someone denies intent to die, but they thought that what they did could be lethal, intent may be inferred.<br>Have you made a suicide attempt?<br>Have you done anything to harm yourself?<br>Have you done anything dangerous where you could have died?<br>   What did you do?<br>   Did you_____ as a way to end your life?<br>   Did you want to die (even a little) when you_____?<br>   Were you trying to end your life when you_____?<br>   Or Did you think it was possible you could have died from_____?<br>Or did you do it purely for other reasons / without ANY intention of killing yourself (like to relieve stress, feel better, get sympathy, or get something else to happen)? (Self-Injurious Behavior without suicidal intent)<br>If yes, describe: | Yes No<br>☐ ☐<br><br>Total # of Attempts<br>_____<br><br>Yes No<br>☐ ☐ |
| Has subject engaged in Non-Suicidal Self-Injurious Behavior? | |
| Interrupted Attempt:<br>When the person is interrupted (by an outside circumstance) from starting the potentially self-injurious act *(if not for that, actual attempt would have occurred)*.<br>Overdose: Person has pills in hand but is stopped from ingesting. Once they ingest any pills, this becomes an attempt rather than an interrupted attempt. Shooting: Person has gun pointed toward self, gun is taken away by someone else, or is somehow prevented from pulling trigger. Once they pull the trigger, even if the gun fails to fire, it is an attempt. Jumping: Person is poised to jump, is grabbed and taken down from ledge. Hanging: Person has noose around neck but has not yet started to hang - is stopped from doing so.<br>*Has there been a time when you started to do something to end your life but someone or something stopped you before you actually did anything?*<br>If yes, describe: | Yes No<br>☐ ☐<br><br><br>Total # of interrupted<br>_____ |
| Aborted Attempt:<br>When person begins to take steps toward making a suicide attempt, but stops themselves before they actually have engaged in any self-destructive behavior. Examples are similar to interrupted attempts, except that the individual stops him/herself, instead of being stopped by something else.<br>*Has there been a time when you started to do something to try to end your life but you stopped yourself before you actually did anything?*<br>If yes, describe: | Yes No<br>☐ ☐<br><br>Total # of aborted<br>_____ |
| Preparatory Acts or Behavior:<br>Acts or preparation towards imminently making a suicide attempt. This can include anything beyond a verbalization or thought, such as assembling a specific method (e.g., buying pills, purchasing a gun) or preparing for one's death by suicide (e.g., giving things away, writing a suicide note).<br>*Have you taken any steps towards making a suicide attempt or preparing to kill yourself (such as collecting pills, getting a gun, giving valuables away or writing a suicide note)?*<br>If yes, describe: | Yes No<br>☐ ☐ |
| Suicidal Behavior:<br>Suicidal behavior was present during the assessment period? | Yes No<br>☐ ☐ |

| *Answer for Actual Attempts Only* | Most Recent Attempt Date | Most Lethal Attempt Date | Initial/First Attempt Date |
|---|---|---|---|
| Actual Lethality/Medical Damage:<br>0. No physical damage or very minor physical damage (e.g., surface scratches).<br>1. Minor physical damage (e.g., lethargic speech; first-degree burns; mild bleeding; sprains).<br>2. Moderate physical damage; medical attention needed (e.g., conscious but sleepy, somewhat responsive; second-degree burns; bleeding of major vessel).<br>3. Moderately severe physical damage; *medical* hospitalization and likely intensive care required (e.g., comatose with reflexes intact; third-degree burns less than 20% of body, extensive blood loss but can recover; major fractures).<br>4. Severe physical damage; *medical* hospitalization with intensive care required (e.g., comatose without reflexes; third-degree burns over 20% of body, extensive blood loss with unstable vital signs; major damage to a vital area).<br>5. Death | *Enter Code*<br><br>_____ | *Enter Code*<br><br>_____ | *Enter Code*<br><br>_____ |
| Potential Lethality: Only Answer if Actual Lethality= 0<br>Likely lethality of actual attempt if no medical damage (the following examples, while having no actual medical damage, had potential for very serious lethality: put gun in mouth and pulled the trigger but gun fails to fire so no medical damage; laying on train tracks with oncoming train but pulled away before run over).<br><br>0 = Behavior not likely to result in injury<br>1 = Behavior likely to result in injury but not likely to cause death<br>2 = Behavior likely to result in death despite available medical care | *Enter Code*<br><br><br><br>_____ | *Enter Code*<br><br><br><br>_____ | *Enter Code*<br><br><br><br>_____ |

COLUMBIA-SUICIDE SEVERITY RATING SCALE (C-SSRS)

Since Last Visit

Version 1/14/09

*Posner, K.; Brent, D.; Lucas, C.; Gould, M.; Stanley, B.; Brown, G.; Fisher, P.; Zelazny, J.; Burke, A.; Oquendo, M.; Mann, J.*

*Disclaimer:*

*This scale is intended to be used by individuals who have received training in its administration. The questions contained in the Columbia-Suicide Severity Rating Scale are suggested probes. Ultimately, the determination of the presence of suicidal ideation or behavior depends on the judgment of the individual administering the scale.*

*Definitions of behavioral suicidal events in this scale are based on those used in* The Columbia Suicide History Form*, developed by John Mann, MD and Maria Oquendo, MD, Conte Center for the Neuroscience of Mental Disorders (CCNMD), New York State Psychiatric Institute, 1051 Riverside Drive, New York, NY, 10032. (Oquendo M. A., Halberstam B. & Mann J. J., Risk factors for suicidal behavior: utility and limitations of research instruments. In M.B. First [Ed.] Standardized Evaluation in Clinical Practice, pp. 103-130, 2003.)*

*For reprints of the C-SSRS contact Kelly Posner, Ph.D., New York State Psychiatric Institute, 1051 Riverside Drive, New York, New York, 10032; inquiries and training requirements contact posnerk@nyspi.columbia.edu*

© 2008 The Research Foundation for Mental Hygiene, Inc.

| SUICIDAL IDEATION | Since Last Visit |
|---|---|
| *Ask questions 1 and 2. If both are negative proceed to "Suicidal Behavior" section. If the answer to question 2 is "yes", ask questions 3, 4 and 5. If the answer to question 1 and/or 2 is "yes", complete "Intensity of Ideation" section below.* | |
| 1. Wish to be Dead<br>Subject endorses thoughts about a wish to be dead or not alive anymore, or wish to fall asleep and not wake up.<br>*Have you wished you were dead or wished you could go to sleep and not wake up?*<br><br>If yes, describe: | Yes ☐  No ☐ |
| 2. Non-Specific Active Suicidal Thoughts<br>General non-specific thoughts of wanting to end one's life/commit suicide (e.g. *"I've thought about killing myself"*) without thoughts of ways to kill oneself/associated methods, intent, or plan during the assessment period.<br>*Have you actually had any thoughts of killing yourself?*<br><br>If yes, describe: | Yes ☐  No ☐ |
| 3. Active Suicidal Ideation with Any Methods (Not Plan) without Intent to Act<br>Subject endorses thoughts of suicide and has thought of at least one method during the assessment period. This is different than a specific plan with time, place or method details worked out (e.g., thought of method to kill self but not a specific plan). Includes person who would say, *"I thought about taking an overdose but I never made a specific plan as to when, where or how I would actually do it... and I would never go through with it."*<br>*Have you been thinking about how you might do this?*<br><br>If yes, describe: | Yes ☐  No ☐ |
| 4. Active Suicidal Ideation with Some Intent to Act, without Specific Plan<br>Active suicidal thoughts of killing oneself and subject reports having <u>some intent to act on such thoughts</u>, as opposed to *"I have the thoughts but I definitely will not do anything about them."*<br>*Have you had these thoughts and had some intention of acting on them?*<br><br>If yes, describe: | Yes ☐  No ☐ |
| 5. Active Suicidal Ideation with Specific Plan and Intent<br>Thoughts of killing oneself with details of plan fully or partially worked out and subject has some intent to carry it out.<br>*Have you started to work out or worked out the details of how to kill yourself? Do you intend to carry out this plan?*<br><br>If yes, describe: | Yes ☐  No ☐ |

| INTENSITY OF IDEATION | |
|---|---|
| *The following features should be rated with respect to the most severe type of ideation (i.e. 1-5 from above, with 1 being the least severe and 5 being the most severe).*<br><br>Most Severe Ideation: _____   _____<br>　　　　　　　　　　　*Type # (1-5)*　　　　*Description of Ideation* | Most Severe |
| Frequency<br>*How many times have you had these thoughts?*<br>(1) Less than once a week  (2) Once a week  (3) 2-5 times in week  (4) Daily or almost daily  (5) Many times each day | ____ |
| Duration<br>*When you have the thoughts, how long do they last?*<br>(1) Fleeting - few seconds or minutes　　　　(4) 4-8 hours/most of day<br>(2) Less than 1 hour/some of the time　　　　 (5) More than 8 hours/persistent or continuous<br>(3) 1-4 hours/a lot of time | ____ |
| Controllability<br>*Could/can you stop thinking about killing yourself or wanting to die if you want to?*<br>(1) Easily able to control thoughts　　　　　(4) Can control thoughts with a lot of difficulty<br>(2) Can control thoughts with little difficulty　(5) Unable to control thoughts<br>(3) Can control thoughts with some difficulty　(0) Does not attempt to control thoughts | ____ |
| Deterrents<br>*Are there things - anyone or anything (e.g., family, religion, pain of death) - that stopped you from wanting to die or acting on thoughts of committing suicide?*<br>(1) Deterrents definitely stopped you from attempting suicide　(4) Deterrents most likely did not stop you<br>(2) Deterrents probably stopped you　　　　　　　　　　　(5) Deterrents definitely did not stop you<br>(3) Uncertain that deterrents stopped you　　　　　　　　　(0) Does not apply | ____ |
| Reasons for Ideation<br>*What sort of reasons did you have for thinking about wanting to die or killing yourself? Was it to end the pain or stop the way you were feeling (in other words you couldn't go on living with this pain or how you were feeling) or was it to get attention, revenge or a reaction from others? Or both?*<br>(1) Completely to get attention, revenge or a reaction from others　(4) Mostly to end or stop the pain (you couldn't go on<br>(2) Mostly to get attention, revenge or a reaction from others　　　　living with the pain or how you were feeling)<br>(3) Equally to get attention, revenge or a reaction from others　　(5) Completely to end or stop the pain (you couldn't go on<br>　　and to end/stop the pain　　　　　　　　　　　　　　　　　　living with the pain or how you were feeling)<br>　　　　　　　　　　　　　　　　　　　　　　　　　　　　　　　(0) Does not apply | ____ |

Version 1/14/09

| | Since Last Visit |
|---|---|
| *SUICIDAL BEHAVIOR*<br>*(Check all that apply, so long as these are separate events; must ask about all types)* | |
| Actual Attempt:<br>A potentially self-injurious act committed with at least some wish to die, *as a result of act*. Behavior was in part thought of as method to kill oneself. Intent does not have to be 100%. If there is *any* intent/desire to die associated with the act, then it can be considered an actual suicide attempt. *There does not have to be any injury or harm,* just the potential for injury or harm. If person pulls trigger while gun is in mouth but gun is broken so no injury results, this is considered an attempt.<br>Inferring Intent: Even if an individual denies intent/wish to die, it may be inferred clinically from the behavior or circumstances. For example, a highly lethal act that is clearly not an accident so no other intent but suicide can be inferred (e.g., gunshot to head, jumping from window of a high floor/story). Also, if someone denies intent to die, but they thought that what they did could be lethal, intent may be inferred.<br>*Have you made a suicide attempt?*<br>*Have you done anything to harm yourself?*<br>*Have you done anything dangerous where you could have died?*<br>    *What did you do?*<br>    *Did you_____ as a way to end your life?*<br>    *Did you want to die (even a little) when you_____?*<br>    *Were you trying to end your life when you _____?*<br>    *Or did you think it was possible you could have died from_____?*<br>*Or did you do it purely for other reasons / without ANY intention of killing yourself (like to relieve stress, feel better, get sympathy, or get something else to happen)?* (Self-Injurious Behavior without suicidal intent)<br>If yes, describe: | Yes No<br>☐ ☐<br><br><br>Total # of Attempts<br>_____ |
| Has subject engaged in Non-Suicidal Self-Injurious Behavior? | Yes No<br>☐ ☐ |
| Interrupted Attempt:<br>When the person is interrupted (by an outside circumstance) from starting the potentially self-injurious act *(if not for that, actual attempt would have occurred)*.<br>Overdose: Person has pills in hand but is stopped from ingesting. Once they ingest any pills, this becomes an attempt rather than an interrupted attempt. Shooting: Person has gun pointed toward self, gun is taken away by someone else, or is somehow prevented from pulling trigger. Once they pull the trigger, even if the gun fails to fire, it is an attempt. Jumping: Person is poised to jump, is grabbed and taken down from ledge. Hanging: Person has noose around neck but has not yet started to hang - is stopped from doing so.<br>*Has there been a time when you started to do something to end your life but someone or something stopped you before you actually did anything?*<br>If yes, describe: | Yes No<br>☐ ☐<br><br><br>Total # of interrupted<br>_____ |
| Aborted Attempt:<br>When person begins to take steps toward making a suicide attempt, but stops themselves before they actually have engaged in any self-destructive behavior. Examples are similar to interrupted attempts, except that the individual stops him/herself, instead of being stopped by something else.<br>*Has there been a time when you started to do something to try to end your life but you stopped yourself before you actually did anything?*<br>If yes, describe: | Yes No<br>☐ ☐<br><br>Total # of aborted<br>_____ |
| Preparatory Acts or Behavior:<br>Acts or preparation towards imminently making a suicide attempt. This can include anything beyond a verbalization or thought, such as assembling a specific method (e.g., buying pills, purchasing a gun) or preparing for one's death by suicide (e.g., giving things away, writing a suicide note).<br>*Have you taken any steps towards making a suicide attempt or preparing to kill yourself (such as collecting pills, getting a gun, giving valuables away or writing a suicide note)?*<br>If yes, describe: | Yes No<br>☐ ☐ |
| Suicidal Behavior:<br>Suicidal behavior was present during the assessment period? | Yes No<br>☐ ☐ |
| Suicide: | Yes No<br>☐ ☐ |
| *Answer for Actual Attempts Only* | Most Lethal Attempt Date: |
| Actual Lethality/Medical Damage:<br>0. No physical damage or very minor physical damage (e.g., surface scratches).<br>1. Minor physical damage (e.g., lethargic speech; first-degree burns; mild bleeding; sprains).<br>2. Moderate physical damage; medical attention needed (e.g., conscious but sleepy, somewhat responsive; second-degree burns; bleeding of major vessel).<br>3. Moderately severe physical damage; *medical* hospitalization and likely intensive care required (e.g., comatose with reflexes intact; third-degree burns less than 20% of body, extensive blood loss but can recover; major fractures).<br>4. Severe physical damage; *medical* hospitalization with intensive care required (e.g., comatose without reflexes; third-degree burns over 20% of body, extensive blood loss with unstable vital signs; major damage to a vital area).<br>5. Death | *Enter Code*<br><br>_____ |
| Potential Lethality: Only Answer if Actual Lethality= 0<br>Likely lethality of actual attempt if no medical damage (the following examples, while having no actual medical damage, had potential for very serious lethality: put gun in mouth and pulled the trigger but gun fails to fire so no medical damage, laying on train tracks with oncoming train but pulled away before run over).<br><br>0 = Behavior not likely to result in injury<br>1 = Behavior likely to result in injury but not likely to cause death<br>2 = Behavior likely to result in death despite available medical care | *Enter Code*<br><br>_____ |

APPENDIX 3.

Edinburgh Postnatal Depression Scale[1] (EPDS)

Name: _____   Address: _____

Your Date of Birth: _____

Baby's Date of Birth: _____   Phone: _____

---

As you are pregnant or have recently had a baby, we would like to know how you are feeling. Please check the answer that comes closest to how you have felt IN THE PAST 7 DAYS, not just how you feel today.

Here is an example, already completed.

I have felt happy:
- ☐ Yes, all the time
- ☒ Yes, most of the time    This would mean: "I have felt happy most of the time" during the past week.
- ☐ No, not very often        Please complete the other questions in the same way.
- ☐ No, not at all In the past 7 days:

1. I have been able to laugh and see the funny side of things
   - ☐ As much as I always could
   - ☐ Not quite so much now
   - ☐ Definitely not so much now
   - ☐ Not at all 2. I have looked forward with enjoyment to things
   - ☐ As much as I ever did
   - ☐ Rather less than I used to
   - ☐ Definitely less than I used to
   - ☐ Hardly at all

*3. I have blamed myself unnecessarily when things went wrong
   - ☐ Yes, most of the time
   - ☐ Yes, some of the time
   - ☐ Not very often
   - ☐ No, never 4. I have been anxious or worried for no good reason
   - ☐ No, not at all
   - ☐ Hardly ever
   - ☐ Yes, sometimes
   - ☐ Yes, very often

*5. I have felt scared or panicky for no very good reason
   - ☐ Yes, quite a lot
   - ☐ Yes, sometimes
   - ☐ No, not much
   - ☐ No, not at all

*6. Things have been getting on top of me
   - ☐ Yes, most of the time I haven't been able to cope at all
   - ☐ Yes, sometimes I haven't been coping as well as usual
   - ☐ No, most of the time I have coped quite well
   - ☐ No, I have been coping as well as ever

*7. I have been so unhappy that I have had difficulty sleeping
   - ☐ Yes, most of the time
   - ☐ Yes, sometimes
   - ☐ Not very often
   - ☐ No, not at all

*8. I have felt sad or miserable
   - ☐ Yes, most of the time
   - ☐ Yes, quite often
   - ☐ Not very often
   - ☐ No, not at all

*9. I have been so unhappy that I have been crying
   - ☐ Yes, most of the time
   - ☐ Yes, quite often
   - ☐ Only occasionally
   - ☐ No, never

*10. The thought of harming myself has occurred to me
   - ☐ Yes, quite often
   - ☐ Sometimes
   - ☐ Hardly ever
   - ☐ Never Administered/Reviewed by _____   Date _____

[1] Source: Cox, J.L., Holden, J.M., and Sagovsky, R. 1987. Detection of postnatal depression: Development of the 10-item Edinburgh Postnatal Depression Scale. *British Journal of Psychiatry* 150:782-786.

[2] Source: K. L. Wisner, B. L. Parry, C. M. Piontek, Postpartum Depression N Engl J Med vol. 347, No 3, July 18, 2002, 194-199

Users may reproduce the scale without further permission providing they respect copyright by quoting the names of the authors, the title and the source of the paper in all reproduced copies.

Edinburgh Postnatal Depression Scale[1] (EPDS)

Postpartum depression is the most common complication of childbearing.[2] The 10-question Edinburgh Postnatal Depression Scale (EPDS) is a valuable and efficient way of identifying patients at risk for "perinatal" depression. The EPDS is easy to administer and has proven to be an effective screening tool.

Mothers who score above 13 are likely to be suffering from a depressive illness of varying severity. The EPDS score should not override clinical judgment. A careful clinical assessment should be carried out to confirm the diagnosis. The scale indicates how the mother has felt *during the previous week*. In doubtful cases it may be useful to repeat the tool after 2 weeks. The scale will not detect mothers with anxiety neuroses, phobias or personality disorders.

Women with postpartum depression need not feel alone. They may find useful information on the web sites of the National Women's Health Information Center <www.4women.gov> and from groups such as Postpartum Support International <www.chss.iup.edu/postpartum> and Depression after Delivery <www.depressionafterdelivery.com>.

SCORING

**QUESTIONS 1, 2, & 4 (without an *)**
Are scored 0, 1, 2 or 3 with top box scored as 0 and the bottom box scored as 3.

**QUESTIONS 3, 5-10 (marked with an *)**
Are reverse scored, with the top box scored as a 3 and the bottom box scored as 0.

Maximum score:       30
   Possible Depression: 10 or greater
   Always look at item 10 (suicidal thoughts)

Users may reproduce the scale without further permission, providing they respect copyright by quoting the names of the authors, the title, and the source of the paper in all reproduced copies.

Instructions for using the Edinburgh Postnatal Depression Scale:

1. The mother is asked to check the response that comes closest to how she has been feeling in the previous 7 days.

2. All the items must be completed.

3. Care should be taken to avoid the possibility of the mother discussing her answers with others. (Answers come from the mother or pregnant woman.)

4. The mother should complete the scale herself, unless she has limited English or has difficulty with reading.

[1] Source: Cox, J.L., Holden, J.M., and Sagovsky, R. 1987. Detection of postnatal depression. Development of the 10-item Edinburgh Postnatal Depression Scale. *British Journal of Psychiatry* 150:782-786.

[2] Source: K. L. Wisner, B. L. Parry, C. M. Piontek, Postpartum Depression N Engl J Med vol. 347, No 3, July 18, 2002, 194-199.

APPENDIX 4. HAMILTON RATING SCALE FOR DEPRESSION (17-ITEMS) (HAM-D-17)

Study ID: _____  Date: _____

Hamilton Rating Scale for Depression (17-items)

Instructions. For each item select the "cue" which best characterizes the patient during the past week.

1. Depressed Mood
   (sadness, hopeless, helpless, worthless)
   0 Absent
   1 These feeling states indicated only on questioning
   2 These feeling states spontaneously reported verbally
   3 Communicates feeling states nonverbally, i.e., through facial expression, posture, voice and tendency to weep
   4 Patient reports VIRTUALLY ONLY these feeling states in his spontaneous verbal and nonverbal communication 2. Feelings of Guilt
   0 Absent
   1 Self-reproach, feels he has let people down
   2 Ideas of guilt or rumination over past errors or sinful deeds
   3 Present illness is a punishment. Delusions of guilt
   4 Hears accusatory or denunciatory voices and/or experiences threatening visual hallucinations 3. Suicide
   0 Absent
   1 Feels life is not worth living
   2 Wishes he were dead or any thoughts of possible death to self
   3 Suicide ideas or gesture
   4 Attempts at suicide (any serious attempt rates 4)

4. Insomnia - Early
   0 No difficulty falling asleep
   1 Complains of occasional difficulty falling asleep i.e., more than ½ hour
   2 Complains of nightly difficulty falling asleep 5. Insomnia - Middle
   0 No difficulty
   1 Patient complains of being restless and disturbed during the night
   2 Waking during the night – any getting out of bed rates 2 (except for purposes of voiding)

6. Insomnia - Late
   0 No difficulty
   1 Waking in early hours of the morning but goes back to sleep
   2 Unable to fall asleep again if gets out of bed 7. Work and Activities
   0 No difficulty
   1 Thoughts and feelings of incapacity, fatigue or weakness related to activities; work or hobbies
   2 Loss of interest in activity; hobbies or work – either directly reported by patient, or indirect in listlessness, indecision and vacillation (feels he has to push self to work or activities)
   3 Decrease in actual time spent in activities or decrease in productivity. In hospital, rate 3 if patient does not spend at least three hours a day in activities (hospital job or hobbies) exclusive of ward chores.
   4 Stopped working because of present illness. In hospital, rate 4 if patient engages in no activities except ward chores, or if patient fails to perform ward chores unassisted.

8. Retardation
   (slowness of thought and speech; impaired ability to concentrate; decreased motor activity)
   0 Normal speech and thought
   1 Slight retardation at interview
   2 Obvious retardation at interview
   3 Interview difficult
   4 Complete stupor 9. Agitation
   0 None
   1 "Playing with" hands, hair, etc.
   2 Hand-wringing, nail-biting, biting of lips 10. Anxiety - Psychic
    0 No difficulty
    1 Subjective tension and irritability
    2 Worrying about minor matters
    3 Apprehensive attitude apparent in face or speech
    4 Fears expressed without questioning 11. Anxiety - Somatic
    0 Absent      Physiological concomitants of anxiety such as
    1 Mild        Gastrointestinal - dry mouth, wind, indigestion,
    2 Moderate    diarrhea, cramps, belching
    3 Severe      Cardiovascular – palpitations, headaches
    4 Incapacitating Respiratory - hyperventilation, sighing
                  Urinary frequency
                  Sweating 12. Somatic Symptoms - Gastrointestinal
    0 None
    1 Loss of appetite but eating without staff encouragement. Heavy feelings in abdomen.
    2 Difficulty eating without staff urging. Requests or requires laxatives or medications for bowels or medication for G.I. symptoms.

13. Somatic Symptoms - General
    0 None
    1 Heaviness in limbs, back or head, backaches, headache, muscle aches, loss of energy and fatigability
    2 Any clear-cut symptom rates 2

14. Genital Symptoms
    0 Absent      0 Not ascertained
    1 Mild        Symptoms such as loss of libido,
    2 Severe      menstrual disturbances 15. Hypochondriasis
    0 Not present
    1 Self-absorption (bodily)
    2 Preoccupation with health
    3 Frequent complaints, requests for help, etc.
    4 Hypochondriacal delusions 16. Loss of Weight
    A. When Rating by History:
    0 No weight loss
    1 Probable weight loss associated with present illness
    2 Definite (according to patient) weight loss B. On Weekly Ratings by Ward Psychiatrist, When Actual Changes are Measured:
    0 Less than 1 lb. weight loss in week
    1 Greater than 1 lb. weight loss in week
    2 Greater than 2 lb. weight loss in week 17. Insight
    0 Acknowledges being depressed and ill
    1 Acknowledges illness but attributes cause to bad food, climate, overwork, virus, need for rest, etc.
    2 Denies being ill at all Total Score: _____

APPENDIX 5. STANFORD SLEEPINESS SCALE

Stanford Sleepiness Scale

This is a quick way to assess how alert you are feeling. If it is during the day when you go about your business, ideally you would want a rating of a one. Take into account that most people have two peak times of alertness daily, at about 9 a.m. and 9 p.m. Alertness wanes to its lowest point at around 3 p.m.; after that it begins to build again. Rate your alertness at different times during the day. If you go below a three when you should be feeling alert, this is an indication that you have a serious sleep debt and you need more sleep.

An Introspective Measure of Sleepiness
The Stanford Sleepiness Scale (SSS)

| Degree of Sleepiness | Scale Rating |
|---|---|
| Feeling active, vital, alert, or wide awake | 1 |
| Functioning at high levels, but not at peak; able to concentrate | 2 |
| Awake, but relaxed; responsive but not fully alert | 3 |
| Somewhat foggy, let down | 4 |
| Foggy; losing interest in remaining awake; slowed down | 5 |
| Sleepy, woozy, fighting sleep; prefer to lie down | 6 |
| No longer fighting sleep, sleep onset soon; having dream-like thoughts | 7 |
| Asleep | X |

APPENDIX 6. MODIFIED OBSERVER'S ASSESSMENT OF ALERTNESS/SEDATION SCALE (MOAA/S)

Table 1. Modified Observer's Assessment of Alertness/Sedation Scale

| Score | Responsiveness |
|---|---|
| 5 | Responds readily to name spoken in normal tone |
| 4 | Lethargic response to name spoken in normal tone |
| 3 | Responds only after name is called loudly and/or repeatedly |
| 2 | Responds only after mild prodding or shaking |
| 1 | Responds only after painful trapezius squeeze |
| 0 | No response after painful trapezius squeeze |

APPENDIX 7. BOND-LADER VAS (MOOD RATING SCALE) (BL-VAS)

BOND-LADER VAS (MOOD RATING SCALE) (BL-VAS)

1. Please rate the way you feel in terms of the dimensions given below.
2. Regard the line as representing the full range of each dimension.
3. Rate your feelings as they are at the moment.
4. Mark clearly and perpendicularly across each line.

| | |
|---|---|
| Alert | Drowsy |
| Calm | Excited |
| Strong | Feeble |
| Muzzy | Clear-headed |
| Well-coordinated | Clumsy |
| Lethargic | Energetic |
| Contented | Discontented |
| Troubled | Tranquil |
| Mentally Slow | Quick-witted |
| Tense | Relaxed |
| Attentive | Dreamy |
| Incompetent | Proficient |
| Happy | Sad |
| Antagonistic | Amicable |
| Interested | Bored |
| Withdrawn | Gregarious |

APPENDIX 8. DRUG EFFECTS QUESTIONNAIRE (DEQ-5)

DRUG EFFECTS QUESTIONNAIRE (DEQ-5)

Instructions: This questionnaire asks about how you are feeling after taking the substance that was given to you. Please draw a mark on the line to show how strongly you are feeling each of the following effects *right now*. You can mark anywhere on the line, but please draw a vertical line (one that goes straight up and down).

Let's look at an example first.

EXAMPLE: Do you feel dizzy right now?
If you do not feel dizzy, draw a line at NOT AT ALL. If you feel very dizzy, draw a line at EXTREMELY. If you feel somewhere in between, you can draw a mark anywhere along the line between NOT AT ALL and EXTREMELY to indicate how dizzy you are. For example, if you feel a little dizzy, you might draw a line that looks something like the example below.

NOT AT ALL                        EXTREMELY

1. Do you FEEL a drug effect right now?

NOT AT ALL                        EXTREMELY

2. Are you HIGH right now?

NOT AT ALL                        EXTREMELY

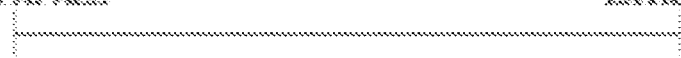

3. Do you DISLIKE any of the effects you are feeling right now?

NOT AT ALL                        EXTREMELY

4. Do you LIKE any of the effects you are feeling right now?

NOT AT ALL                        EXTREMELY

5. Would you like MORE of the drug you took, right now?

NOT AT ALL                        EXTREMELY

APPENDIX 9. HOSPITAL ANXIETY AND DEPRESSION SCALE

Hospital Anxiety and Depression Scale (HADS)

Tick the box beside the reply that is closest to hoe you have been feeling in the past week.
Don't take too long over you replies: your immediate is best.

| D | A | | D | A | |
|---|---|---|---|---|---|
| | | I feel tense or 'wound up': | | | I feel as if I am slowed down: |
| | 3 | Most of the time | 3 | | Most of the time |
| | 2 | A lot of the time | 2 | | A lot of the time |
| | 1 | From time to time, occasionally | 1 | | From time to time, occasionally |
| | 0 | Not at all | 0 | | Not at all |
| | | I still enjoy the things I used to enjoy: | | | I get a sort of frightened feeling like 'butterflies' in the stomach: |
| 0 | | Definitely as much | | 0 | Not at all |
| 1 | | Not quite so much | | 1 | Occasionally |
| 2 | | Only a little | | 2 | Quite Often |
| 3 | | Hardly at all | | 3 | Very Often |
| | | I get a sort of frightened feeling as if something awful is about to happen: | | | I have lost interest in my appearance: |
| | 3 | Very definitely and quite badly | 3 | | Definitely |
| | 2 | Yes, but not too badly | 2 | | I don't take as much care as I should |
| | 1 | A little, but it doesn't worry me | 1 | | I may not take quite as much care |
| | 0 | Not at all | 0 | | I take just as much care as ever |
| | | I can laugh and see the funny side of things: | | | I feel restless as I have to be on the move: |
| 0 | | As much as I always could | | 3 | Very much indeed |
| 1 | | Not quite so much now | | 2 | Quite a lot |
| 2 | | Definitely not so much now | | 1 | Not very much |
| 3 | | Not at all | | 0 | Not at all |
| | | Worrying thoughts go through my mind: | | | I look forward with enjoyment to things: |
| | 3 | A great deal of the time | 0 | | As much as I ever did |
| | 2 | A lot of the time | 1 | | Rather less than I used to |
| | 1 | From time to time, but not too often | 2 | | Definitely less than I used to |
| | 0 | Only occasionally | 3 | | Hardly at all |
| | | I feel cheerful: | | | I get sudden feelings of panic: |
| 3 | | Not at all | | 3 | Very often indeed |
| 2 | | Not often | | 2 | Quite often |
| 1 | | Sometimes | | 1 | Not very often |
| 0 | | Most of the time | | 0 | Not at all |
| | | I can sit at ease and feel relaxed: | | | I can enjoy a good book or radio or TV program: |
| | 0 | Definitely | 0 | | Often |
| | 1 | Usually | 1 | | Sometimes |
| | 2 | Not often | 2 | | Not often |
| | 3 | Not at all | 3 | | Very seldom |

Please check you have answered all the questions

APPENDIX 10. SLEEP QUALITY QUESTIONNAIRE

Sage Sleep Quality Questionnaire

Subject Number: _____ Subject Initials: _____ Date: _____

Please indicate the most appropriate response for each question.

| | | | | | |
|---|---|---|---|---|---|
| 1. How satisfying was your sleep? | Very Satisfying | Somewhat Satisfying | Satisfying | Somewhat Dissatisfying | Very Dissatisfying |
| 2. How easily did you fall asleep? | Very easy | Somewhat easy | Easy | Some Difficulty | Very Difficult |
| 3. Did you wake up during the night? | Not at all | Once or twice | Several times | Hardly slept | Did not sleep at all |
| 4. How long were you awake during your longest wakeful period? | Did not wake up | Less than 30 minutes | 30 to 60 minutes | 1 to 2 hours | >2 hours |
| 5. Were you aware of your dreams? | Very aware of my dreams | | Somewhat aware of my dreams | | I was not aware of my dreams |
| 6. How did you feel when you woke up? | Refreshed | | Somewhat Refreshed | | Not Refreshed |

APPENDIX 11 TASTE ASSESSMENT

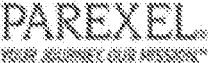

INSTRUCTIONS

This questionnaire asks about what the substance that was given to you tastes like to you.

Please draw a mark on the line to show how much you like or dislike the taste of the substance. You can mark anywhere on the line to indicate how much you like or dislike the substance, but please draw a vertical line (one that goes straight up and down as in the example below).

The worst tasting liquid I have ever swallowed   The nicest tasting liquid I have ever swallowed

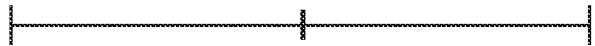

1. How much did you like the substance that was given to you?

The worst tasting liquid I have ever swallowed   The nicest tasting liquid I have ever swallowed

2. What does the substance taste like to you?
(a) Bitter
(b) Sweet
(c) Salty
(d) Sour
(e) Other (describe the taste in your own words):

Rater Signature: Date: D D/ MMM/ YYYY

Stop Time (24-hour Clock):

HH :MM

APPENDIX 12. TETRAS PERFORMANCE SUBSCALE

Performance Subscale

Instructions

Scoring is 0 – 4. For most items, the scores are defined only by whole numbers, but 0.5 increments may be used if you believe the rating is between two whole number ratings and cannot be reconciled to a whole number. Each 0.5 increment in rating is specifically defined for the assessment of upper limb postural and kinetic tremor and the dot approximation task (Items 4 and 8). All items of the examination, except standing tremor, are performed with the patient seated comfortably. For each item, score the highest amplitude seen at any point during the exam. Instruct patients not to attempt to suppress the tremor, but to let it come out.

1. Head tremor: The head is rotated fully left and right and then observed for 10s in mid position. Patient then is instructed to gaze fully to the left and then to the right with the head in mid position. The nose should be used as the landmark to assess and rate the largest amplitude excursions during the examination.

0 = no tremor
    1 = slight tremor (< 0.5 cm)
    2 = mild tremor (0.5- < 2.5 cm)
    3 = moderate tremor (2.5-5 cm)
    4 = severe or disfiguring tremor (> 5 cm)

2. Face (including jaw) tremor: Smile, close eyes, open mouth, purse lips. The highest amplitude of the most involved facial anatomy is scored, regardless of whether it occurs during rest or activation. Repetitive blinking or eye fluttering should not be considered as part of facial tremor.

0 = no tremor
    1 = slight, barely perceptible tremor
    2 = mild: noticeable tremor
    3 = moderate: obvious tremor, present in most voluntary facial contractions
    4 = severe: gross disfiguring tremor 3. Voice tremor: First ask subject to produce an extended "aaah" sound and "eee" sound for 5 seconds each. Then assess speech during normal conversation by asking patients "How do you spend your average day?".

0 = no tremor
    1 = slight: tremor during aaah, and eee and no tremor during speech
    2 = mild: tremor in "aaah" and "eee" and minimal tremor in speech
    3 = moderate: obvious tremor in speech that is fully intelligible
    4 = severe: some words difficult to understand 4. Upper limb tremor. Tremor is assessed during three maneuvers: forward horizontal reach posture, lateral "wing beating" posture and finger-nose-finger testing. Each upper limb is assessed and scored individually. The forward horizontal reach posture is held for 5 seconds.

The lateral wing beating posture is held for 20 seconds. The finger-nose-finger movement is executed three times. Amplitude assessment should be estimated using the maximally displaced point of the hand at the point of greatest displacement along any single plane. For example, the amplitude of a pure supination-pronation tremor, pivoting around the wrist would be assessed at either the thumb or fifth digit.

a. Forward outstretched postural tremor: Subjects should bring their arms forward, slightly lateral to midline and parallel to the ground. The wrist should also be straight and the fingers abducted so that they do not touch each other.
  b. Lateral "wing beating" postural tremor: Subjects will abduct their arms parallel to the ground and flex the elbows so that the two hands do not quite touch each other and are at the level of the nose. The fingers are abducted so that they do not touch each other. The posture should be held for 20 seconds.
  c. Kinetic tremor: Subjects extend only their index finger. They then touch a set object or the examiners finger located to the full extent of their reach, which is located at the same height (parallel to the ground) and slightly lateral to the midline. Subjects then touch their own nose (or chin if the tremor is severe) and repeat this back and forth three times. Only the position along the trajectory of greatest tremor amplitude is assessed. This will typically be either at the nose or at the point of full limb extension.

For all three hand tremor ratings
   0 = no tremor
   1 = tremor is barely visible
   1.5 = tremor is visible, but less than 1 cm
   2 = tremor is 1- < 3 cm amplitude
   2.5 = tremor is 3- < 5 cm amplitude
   3 = tremor is 5- < 10 cm amplitude
   3.5 = tremor is 10- < 20 cm amplitude
   4 = tremor is ≥ 20 cm amplitude 5. Lower limb tremor: Raise each lower limb horizontally parallel to the ground for 5 seconds each. Then perform a standard heel to shin maneuver with each leg, three times. The maximum tremor in either maneuver is scored, and only the limb with the largest tremor is scored. Tremor may exist in any part of the limb, including foot.
   0 = no tremor
   1 = slight: barely perceptible
   2 = mild, less than 1 cm at any point
   3 = moderate tremor, less than 5 cm at any point
   4 = severe tremor, greater than 5 cm 6. Archimedes spirals: Demonstrate how to draw Archimedes spiral that approximately fills ½ of an unlined page of standard (letter) paper. The lines of the spiral should be approximately 1.3 cm (0.5 inch) apart. Then ask the subject to copy the spiral. Test and score each hand separately. Use a ballpoint pen. The pen should be held such that no part of the limb touches the table. Secure the paper on the table in a location that is suitable for the patient's style of drawing. Score the tremor in the spiral, not the movement of the limb.

0 = normal
   1 = slight: tremor barely visible.
   2 = mild: obvious tremor
   3 = moderate: portions of figure not recognizable.
   4 = severe: figure not recognizable 7. Handwriting: Have patient write the standard sentence "This is a sample of my best handwriting" using the dominant hand only. Patients must write cursively (i.e., no printing). They cannot hold or stabilize their hand with the other hand. Use a ballpoint pen. Secure the paper on the table in a location that is suitable for the patient's style of writing. Score the tremor in the writing, not the movement of the limb.

0 = normal
   1 = slight: untidy due to tremor that is barely visible.
   2 = mild: legible, but with considerable tremor.
   3 = moderate: some words illegible.
   4 = severe: completely illegible 8. Dot approximation task: The examiner makes a dot or X and instructs the subject to hold the tip of the pen "as close as possible to the dot (or center of an X) without touching it, (ideally approximately 1 mm) for 10 seconds". Each hand is score separately.

0 = no tremor
   1 = tremor is barely visible
   1.5 = tremor is visible, but less than 1 cm
   2 = tremor is 1- < 3 cm amplitude
   2.5 = tremor is 3- < 5 cm amplitude
   3 = tremor is 5- < 10 cm amplitude
   3.5 = tremor is 10- < 20 cm amplitude
   4 = tremor is $\geq$ 20 cm amplitude 9. Standing tremor: Subjects are standing, unaided if possible. The knees are 10-20 cm apart and are flexed 10-20°. The arms are down at the subject's side. Tremor is assessed at any point on the legs or trunk
   0 = no tremor
   1 = barely perceptible tremor
   2 = obvious but mild tremor, does not cause instability
   3 = moderate tremor, impairs stability of stance
   4 = severe tremor, unable to stand without assistance

We claim:

1. A method for treating essential tremor in a human subject in need thereof, the method comprising administering allopregnanolone at a dosing regimen over a time period of about 60 hours, wherein the dosing regimen comprises a continuous infusion of:
- 30 μg/kg/hour of allopregnanolone from about hour 0 to about hour 4;
- 60 μg/kg/hour of allopregnanolone from about hour 4 to about hour 24;
- 90 μg/kg/hour of allopregnanolone from about hour 24 to about hour 52;
- 60 μg/kg/hour of allopregnanolone from about hour 52 to about hour 56; and
- 30 μg/kg/hour of allopregnanolone from about hour 56 to about hour 60.

2. The method of claim 1, wherein allopregnanolone is in a sterile aqueous solution comprising allopregnanolone and sulfobutylether-β-cyclodextrin.

3. The method of claim 2, wherein the sterile aqueous solution is buffered with citrate.

4. The method of claim 3, wherein the sterile aqueous solution comprises about 0.1 mg/mL to about 10 mg/mL of allopregnanolone.

5. The method of claim 4, wherein the sterile aqueous solution comprises about 0.1 mg/mL to about 5 mg/mL of allopregnanolone.

6. The method of claim 5, wherein the sterile aqueous solution comprises about 1 mg/mL of allopregnanolone.

7. The method of claim 3, wherein the sterile aqueous solution comprises about 1% to about 30% by weight of sulfobutylether-β-cyclodextrin per volume of sterile aqueous solution.

8. The method of claim 7, wherein the sterile aqueous solution comprises about 1% to about 15% by weight of sulfobutylether-β-cyclodextrin per volume of sterile aqueous solution.

9. The method of claim 8, wherein the sterile aqueous solution comprises about 1% to about 5% by weight of sulfobutylether-β-cyclodextrin per volume of sterile aqueous solution.

10. The method of claim 9, wherein the sterile aqueous solution comprises about 5% by weight of sulfobutylether-β-cyclodextrin per volume of sterile aqueous solution.

* * * * *